(12) United States Patent
Mikesell et al.

(10) Patent No.: US 7,723,479 B2
(45) Date of Patent: May 25, 2010

(54) BSL3 POLYPEPTIDES

(75) Inventors: Glen Eugene Mikesell, Pacifica, CA (US); Han Chang, Princeton Junction, NJ (US); Joshua N. Finger, Spring City, PA (US); Guchen Yang, Princeton, NJ (US); Robert James Peach, San Diego, CA (US); Henry Shen, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 306 days.

(21) Appl. No.: 11/900,026

(22) Filed: Sep. 6, 2007

(65) Prior Publication Data

US 2009/0215995 A1 Aug. 27, 2009

Related U.S. Application Data

(62) Division of application No. 10/944,824, filed on Nov. 22, 2004, now Pat. No. 7,279,567.

(51) Int. Cl.
C07K 14/705 (2006.01)
(52) U.S. Cl. ..................................... 530/350
(58) Field of Classification Search ....................... None
See application file for complete search history.

(56) References Cited

U.S. PATENT DOCUMENTS

| | | |
|---|---|---|
| 6,630,575 B2 | 10/2003 | Coyle et al. |
| 6,635,750 B1 | 10/2003 | Coyle et al. |
| 7,030,219 B2 | 4/2006 | Pardoll et al. |
| 7,368,531 B2 | 5/2008 | Rosen et al. |
| 7,411,051 B2 | 8/2008 | Rosen et al. |
| 7,414,122 B2 | 8/2008 | Fox et al. |
| 7,432,059 B2 | 10/2008 | Freeman et al. |
| 7,432,062 B2 | 10/2008 | Coyle et al. |
| 7,560,540 B2 | 7/2009 | Pardoll et al. |
| 2002/0091246 A1 | 7/2002 | Pardoll et al. |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0164600 A1 | 11/2002 | Freeman et al. |
| 2004/0137577 A1 | 7/2004 | Coyle et al. |
| 2004/0162236 A1 | 8/2004 | Alsobrook et al. |
| 2005/0228170 A1 | 10/2005 | Fox et al. |
| 2006/0292593 A1 | 12/2006 | Pardoll et al. |
| 2008/0118511 A1 | 5/2008 | Freeman et al. |
| 2008/0226662 A1 | 9/2008 | Pardoll et al. |
| 2008/0241175 A1 | 10/2008 | Pardoll et al. |
| 2009/0004237 A1 | 1/2009 | Fox et al. |
| 2009/0269783 A1 | 10/2009 | Coyle et al. |

FOREIGN PATENT DOCUMENTS

| | | |
|---|---|---|
| EP | 1074617 | 7/2000 |
| EP | 1067182 | 1/2001 |
| EP | 1074617 | 2/2001 |
| EP | 1130094 | 9/2001 |
| WO | WO9819706 | 5/1998 |
| WO | WO98/58965 | 12/1998 |
| WO | WO9946281 | 3/1999 |
| WO | WO 99/46281 | 9/1999 |
| WO | WO9947558 | 9/1999 |
| WO | WO 00/55375 | 9/2000 |
| WO | WO0053756 | 9/2000 |
| WO | WO 00/61612 | 10/2000 |
| WO | WO 00/68266 | 11/2000 |
| WO | WO0068266 | 11/2000 |
| WO | WO 01/14557 | 3/2001 |
| WO | WO 01/18021 | 3/2001 |
| WO | WO 01/18022 | 3/2001 |
| WO | WO 01/18204 | 3/2001 |
| WO | WO0114556 | 3/2001 |
| WO | WO0114566 | 3/2001 |
| WO | WO0114577 | 3/2001 |
| WO | WO0121631 | 3/2001 |
| WO | WO0134629 | 5/2001 |
| WO | WO0134768 | 5/2001 |
| WO | WO0139722 | 6/2001 |

(Continued)

OTHER PUBLICATIONS

Gerstmayer, et al., "Costimulation of T-cell proliferation by a chimeric B7-antibody fusion protein", Cancer Immunol. Immunother., vol. 45, pp. 156-158 (1997).
Henry, et al., "Structure and evolution of the extended B7 family", Immunol. Today, vol. 20, No. 6, pp. 285-288 (1999).
Stammers, et al., "BTL-II: a polymorphic locus with homology to the butyrophilin gene family, located at the border of the major histocompatibility complex class II and class III regions in human and mouse", Immunogenetics, vol. 51, pp. 373-382 (2000).
NCBI Entrez Accession No. AF329193 (gi:13569409), Tseng, et al., Apr. 10, 2001.
NCBI Entrez Accession No. AF344424 (gi:13183882), Latchman, et al., Apr. 8, 2002.
NCBI Entrez Accession No. AL162253 (gi:13677203), Clark, G., May 6, 2008.

(Continued)

Primary Examiner—Ilia Ouspenski
(74) Attorney, Agent, or Firm—Stephen C. D'Amico

(57) ABSTRACT

The present invention provides nucleic acids encoding B7-related factors that modulate the activation of immune or inflammatory response cells, such as T-cells. Also provided are expression vectors and fusion constructs comprising nucleic acids encoding B7-related polypeptides, including BSL1, BSL2, and BSL3. The present invention further provides isolated B7-related polypeptides, isolated fusion proteins comprising B7-related polypeptides, and antibodies that are specifically reactive with B7-related polypeptides, or portions thereof. In addition, the present invention provides assays utilizing B7-related nucleic acids, polypeptides, or peptides. The present invention further provides compositions of B7-related nucleic acids, polypeptides, fusion proteins, or antibodies that are useful for the immunomodulation of a human or animal subject.

16 Claims, 37 Drawing Sheets

FOREIGN PATENT DOCUMENTS

Figure 7D:
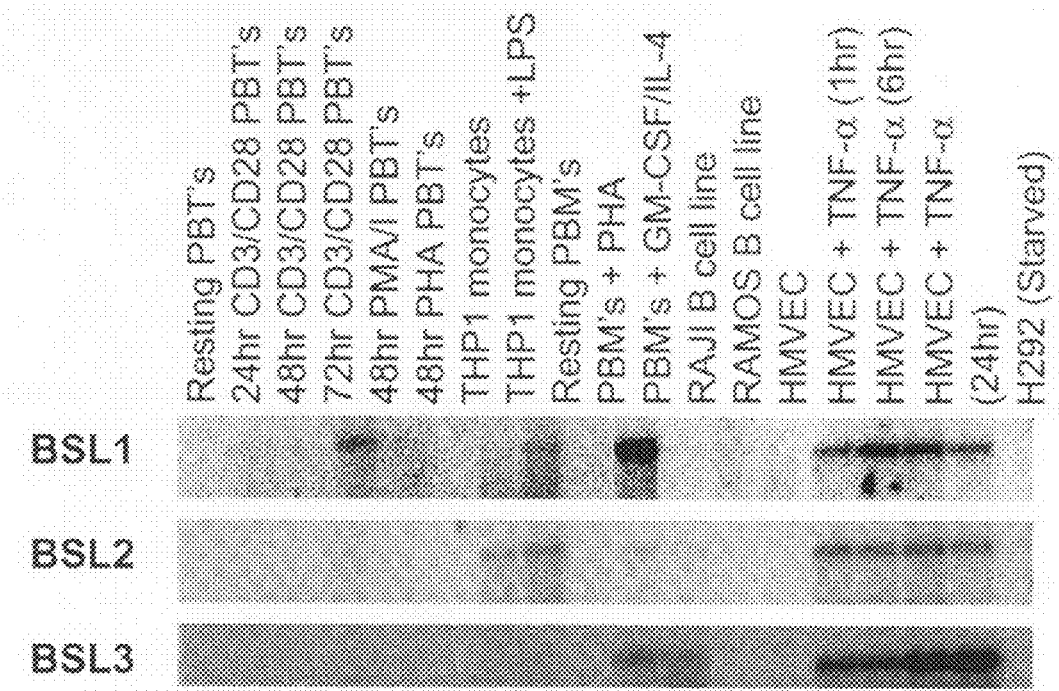

| WO | WO 01/53312 | 7/2001 |
| --- | --- | --- |
| WO | WO0168848 | 9/2001 |
| WO | WO 01/77137 | 10/2001 |
| WO | WO 01/83750 | 11/2001 |
| WO | WO0183750 | 11/2001 |
| WO | WO 02/02587 | 1/2002 |
| WO | WO0200692 | 1/2002 |
| WO | WO0200730 | 1/2002 |
| WO | WO0208279 | 1/2002 |
| WO | WO0210187 | 2/2002 |
| WO | WO 02/24891 | 3/2002 |
| WO | WO0222683 | 3/2002 |
| WO | WO02097046 A2 | 12/2002 |
| WO | WO03/014293 A2 | 2/2003 |
| WO | WO03085124 A2 | 10/2003 |
| WO | WO2004093894 A2 | 11/2004 |

OTHER PUBLICATIONS

NCBI Entrez Accession No. Q9WUL5 (gi:68606058), Tseng, et al., Nov. 25, 2008.
NCBI Entrez Accession No. AAK15370 (gi:13183883), Latchman, et al., Apr. 8, 2002.
NCBI Entrez Accession No. AAK31105 (gi:13569410), Tseng, et al., Apr. 10, 2001.
NCBI Entrez Accession No. AAK15438(gi:13194193), Chapoval, et al., Mar. 3, 2001.
Ellison, et al., "The nucleotide sequence of a human immunoglobulin $C_\gamma 1$ gene", Nucleic Acids Res., vol. 10(13), pp. 4071-4079 (1982).
Castriconi, et al., "Identification of 4Ig-B7-H3 as a neuroblastoma-associated molecule that exerts a protective role from an NK cell-mediated lysis", PNAS, vol. 101(34), pp. 12640-12645 (2004).
Collins, et al., "The B7 family of immune-regulatory ligands", Genome Biol., vol. 6, pp. 223.1-223.7 (2005).
Dong, et al., "Immune Regulation by Novel Costimulatory Molecules", Immunologic Res., vol. 28(1), pp. 39-48 (2003).
Ferlazzo, et al., "T lymphocytes express B7 family molecules following interaction with dendritic cells and acquire bystander costimulatory properties", Eur. J. Immunol., vol. 32, pp. 3092-3101 (2002).
Greenwald, et al., "The B7 Family Revisited", Annu. Rev. Immunol., vol. 23, pp. 515-548 (2005).
Kim, et al., "Constitutive and Inducible Expression of B7 Family of Ligands by Human Airway Epithelial Cells", Am. J. Respir. Cell Mol. Biol., vol. 33, pp. 280-289 (2005).
Lane, et al., "mRNA For Genes Associated with Antigen Presentation are Expressed by Human Middle Meatal Epithelial Cells in Culture", The Laryngoscope, vol. 114, pp. 1827-1832 (2004).
Ling, et al., "Duplication of primate and rodent B7-H3 immunoglobulin V- and C- like domains: divergent history of functional redundancy and exon loss", Genomics, vol. 82, pp. 365-377 (2003).
Loke, et al., Emerging mechanisms of immune regulation: the extended B7 family and regulatory T cell, Arthritis Res. Therapy, vol. 6(5), pp. 208-214 (2004).
Luo, et al., "B7-H3 Enhances Tumor Immunity In Vivo by Costimulating Rapid Clonal Expansion of Antigen-Specific $CD8^+$Cytolytic T Cells", J. Immunol., vol. 173, pp. 5445-5450 (2004).
Petroff, et al., "The Immunomodulatory Proteins B7-DC, B7-H2, and B7-H3 Are Differentially Expressed across Gestation in the Human Placenta", Amer. J. Pathology, vol. 167(2), pp. 465-473 (2005).
Prasad, et al., "Murine B7-H3 Is a Negative Regulator of T Cells", J. Immunol., vol. 173, pp. 2500-2506 (2004).
Saatian, et al., "Expression of genes for B7-H3 and other T cell ligands by nasal epithelial cells during differentiation and activation", Am. J. Physiol. Lung Cell Mol. Physiol., vol. 287, pp. L127-L225 (2004).
Steinberger, et al., "Molecular Characterization of Human 4Ig-B7-H3, a Member of the B7 Family with Four Ig-Like Domains", J. Immunol., vol. 172, pp. 2352-2359 (2004).

Suh, et al., The B7 family member B7-H3 preferentially down-regulates T helper type 1-mediated immune responses, Nature Immunol., vol. 4, pp. 899-906 (2003).
Suh, et al., "The immune regulatory protein B7-H3 promotes osteoblast differentiation and bone mineralization", PNAS, vol. 101(35), pp. 12969-12973 (2004).
Sun, et al., "Mouse B7-H3 induces antitumor immunity", Gene Therapy, vol. 10, pp. 1728-1734 (2003).
Thomas, et al., "A Cell-Based Artificial Antigen-Presenting Cell Coated with Anti-CD3 and CD28 Antibodies Enables Rapid Expansion and Long-Term Growth of CD4 T Lymphocytes", Clinical Immunol., vol. 105(3), pp. 259-272 (2002).
Wang, et al., "Co-signaling molecules of the B7-CD28 family in positive and negative regulation of T lymphocyte responses", Microbes Infection, vol. 6, pp. 759-766 (2004).
Wang, et al., "B7-H13 promotes acute and chronic allograft rejection", Eur. J. Immunol., vol. 35, pp. 428-438 (2005).
Zhang, et al., "Human Recombinant B7-H3 Expressed in *E. coli* Enhances T Lymphocyte Proliferation and IL-10 Secretion in Vitro", Acta Biochimica Biophysica Sinica, vol. 36(6), pp. 430-436 (2004).
NCBI Entrez Accession No. gi|7023409, T. Isogai et al., Feb. 22, 2000.
NCBI Entrez Accession No. gi|13376850, Y. Latchman et al., Mar. 18, 2001.
NCBI Entrez Accession No. gi|13376852, A.I. Chapoval et al., Mar. 18, 2001.
NCBI Entrez Accession No. gi|13640665, NCBI Annotation Project, Oct. 16, 2001.
NCBI Entrez Accession No. gi|14741794, NCBI Annotation Project, Aug. 27, 2001.
NCBI Entrez Accession No. gi|16160937, NCBI Annotation Project, Oct. 16, 2001.
NCBI Entrez Accession No. gi|22760560, T. Isogai et al., Sep. 3, 2002.
NCBI Entrez Accession No. gi|22761770, T. Ota et al., Sep. 3, 2002.
M.W. Biggs et al., "Suppression of immune surveillance in melanoma", Medical Hypotheses, vol. 56, No. 6, pp. 648-652 (2001).
C.C. Bleul et al., "Laser capture microdissection-based expression profiling identifies PD1-ligand as a target of the nude locus gene product", Eur. J. Immunol., vol. 31, pp. 2497-2503 (2001).
L.L. Carter et al., "PD-1:PD-L inhibitory pathway affects both $CD4^+$and $CD8^+$T cells and is overcome by IL-2", Eur. J. Immunol., vol. 32, pp. 634-643 (2002).
H. Dong et al., "B7-H1, a third member of the B7 family, co-stimulates T-cell proliferation and interleukin-10 secretion", Nature Medicine, vol. 5, No. 12, pp. 1365-1369 (1999).
M.J. Eppihimer et al., "Expression and Regulation of the PD-L1 Immunoinhibitory Molecule on Microvascular Endothelial Cells", Microcirculation, vol. 9, pp. 133-145 (2002).
R.J. Greenwald et al., "Negative co-receptors on lymphocytes", Current Opinion in Immunology, vol. 14, pp. 391-396 (2002).
L. Liang et al., "The right place at the right time: novel B7 family members regulate effector T cell responses", Current Opinion in Immunology, vol. 14, pp. 384-390 (2002).
M.G. Petroff et al., "B7 Family Molecules: Novel Immunomodulators at the Maternal-Fetal Interface", Placenta, vol. 23, Supp. A, Trophoblast Research, vol. 16, pp. S95-S101 (2002).
M. Sun et al., "Character of Mouse and Human B7-H3 Genes", The Journal of Immunology, vol. 168, pp. 6294-6297 (2002).
Dong et al., GenBank Accession No. AF177937, National Center for Biotechnology Information, National Library of Medicine, NIH (Bethesda, MD, USA), Jan. 18, 2000, encodes instant SEQ ID No. 2.
Dong et al., Nature Medicine, 5(12): 1365-1369, Dec. 1999.
NCBI Entrez Accession No. gi:14741794 (Oct. 16, 2001).
NCBI Entrez Accession No. gi:22761770 (Sep. 3, 2002).
NCBI Entrez Accession No. gi:22760560 (Sep. 3, 2002).
NCBI Entrez Accession No. gi:16160937 (Oct. 16, 2001).
NCBI Entrez Accession No. gi:13376852 (Mar. 18, 2001).
NCBI Entrez Accession No. gi:13376850 (Mar. 18, 2001).
NCBI Entrez Accession No. gi:13640665 (Oct. 16, 2001).
Dong et al., Nature Medicine, vol. 5, No. 12, pp. 1365-1369 (1999).
Carter et al., Eur. J. Immunol. 32:634-643 (2002).
Conrad et al., Eur. J. Immunol. 31:2497-2503 (2001).

Petroff et al., Placenta 23 Suppl.A:S95-S101 (2002).
Biggs et al., Med. Hypotheses 56(6):648-652 (2001).
Sun et al., J. Immunol. 168(12): 6294-7 (2002).
Liang et al., Current Opinions in Immunology 14:384-90 (2002).
Greenwald et al., Current Opinions in Immunology 14:391-96 (2002).
Eppihimer et al., Microcirculation 9:133-145 (2002).
NCBI Entrez Accession No. gi:7023409, 2008.
NCBI Entrez Accession No. gi:14741814, 2001.
NCBI Entrez Accession No. gi:7023409.
NCBI Entrez Accession No. gi:14741814.
Freeman GJ, Long AJ, Iwai Y, Bourque K, Chernova T, Nishimura H, Fitz LJ, Malenkovich N, Okazaki T, Byrne MC, Horton HF, Fouser L, Carter L, Ling V, Bowman MR, Carreno BM, Collins M, Wood CR, Honjo T., "Engagement of the PD-1 immunoinhibitory receptor by a novel B7 family member leads to negative regulation of lymphocyte activation." *J Exp Med*. Oct. 2, 2000;192(7):1027-34.
Nishimura H, Honjo T, Minato N., "Facilitation of beta selection and modification of positive selection in the thymus of PD-1-deficient mice." *J Exp Med*. Mar. 6, 2000;191(5):891-8.
S.K. Yoshinaga, J.S. Whoriskey, S.D. Khare, U. Sarmiento, J. Guo, T. Horan, G. Shih, M. Zhang, M.A. Coccia, T. Kohno, A. Tafuri-Bladt, D. Brankow, P. Campbell, D. Chang, L. Chiu, T. Dai, G. Duncan, G.S. Elliot, A. Hui, S.M. McCabe, S. Scully, A. Shahinian, C.L. Shaklee, G. Van, T.W. Mak, G. Senaldi, 1999, *Nature*, 402:827-832.
Nishimura H, Nose M, Hiai H, Minato N, Honjo T., "Development of lupus-like autoimmune diseases by disruption of the PD-1 gene encoding an ITIM motif-carrying immunoreceptor." *Immunity*. Aug. 1999;11(2):141-51.
Nishimura H, Minato N, Nakano T, Honjo T., "Immunological studies on PD-1 deficient mice: implication of PD-1 as a negative regulator for B cell responses." *Int Immunol*. Oct. 1998;10(10):1563-72.
Finger LR, Pu J, Wasserman R, Vibhakar R, Louie E, Hardy RR, Burrows PD, Billips LG., "The human PD-1 gene: complete cDNA, genomic organization, and developmentally regulated expression in B cell progenitors." *Gene*. Sep. 15, 1997;197(12-):177-87.
Nishimura H, Agata Y, Kawasaki A, Sato M, Imamura S, Minato N, Yagita H, Nakano T, Honjo T., "Developmentally regulated expression of the PD-1 protein on the surface of double-negative (CD4-CD8-)thymocytes." *Int Immunol*. May 1996;8(5):773-80.
Agata Y, Kawasaki A, Nishimura H, Ishida Y, Tsubata T, Yagita H, Honjo T., "Expression of the PD-1 antigen on the surface of stimulated mouse T and B lymphocytes." *Int Immunol*. May 1996;8(5):765-72.
Shinohara T, Taniwaki M, Ishida Y, Kawaichi M, Honjo T., "Structure and chromosomal localization of the human PD-1 gene (PDCD1)." *Genomics*. Oct. 1994;23(3):704-6.
Ishida Y, Agata Y, Shibahara K, Honjo T., "Induced expression of PD-1, a novel member of the immunoglobulin gene superfamily, upon programmed cell death." *EMBO J*. Nov. 1992;11(11):3887-95.
Batra SK, Metzgar RS, Hollingsworth MA., "Isolation and characterization of a complementary DNA (PD-1) differentially expressed by human pancreatic ductal cell tumors." *Cell Growth Differ*. Aug. 1991;2(8):385-90.

Dong H, Zhu G, Tamada K, Chen L., "B7-H1, a third member of the B7 family, co-stimulates T-cell proliferation and interleukin-10 secretiion." *Nat Med*. Dec. 1995;5(12):1365-9.
Wang S, Zhu G, Chapoval AI, Dong H, Tamada K, Ni J, Chen L., "Costimulation of T cells by B7-H2, a B7-like molecule that binds ICOS." *Blood*. Oct. 15, 2000;96(8):2808-13.
Mages HW, Hutloff A, Heuck C, Buchner K, Hummelbauer H, Oliveri F, Kroczek RA., "Molecular cloning and characterization of murine ICOS and identification of B7h as ICOS ligand." *Eur J Immunol*. Apr. 2000;30(4):1040-7.
Ling V, Wu PW, Finnerty HF, Bean KM, Spaulding V, Fouser LA, Leonard JP, Hunter SE, Zollner R, Thomas JL, Miyashiro JS, Jacobs KA, Collins M., "Cutting edge: identification of GL50, a novel B7-like protein that functionally binds to ICOS receptor." *J Immunol*. Feb. 15, 2000;164(4):1653-7.
Swallow MM, Wallin JJ, Sha WC., "B7h, a novel costimulatory homolog of B7.1 and B7.2, is induced by TNFalpha." *Immunity*. Oct. 1999;11(4):423-32.
Chapoval AI, Ni J, Lau JS, Wilcox RA, Flies DB, Liu D, Dong H, Sica GL, Zhu G, Tamada K, Chen L., "B7-H3: a costimulatory molecule for T cell activation and IFN-gamma production." *Nat Immunol*. Mar. 2001;2(3):269-74.
Nishimura H, Honjo T. "PD-1: an inhibitory immunoreceptor involved in peripheral tolerance" *Trends Immunol*. May 2001;22(5):265-8.
Nishimura H, Okazaki T, Tanaka Y, Nakatani K, Hara M, Matsumori A, Sasayama S, Mizoguchi A, Hiai H, Minato N, Honjo T. "Autoimmune dilated cardiomyopathy in PD-1 receptor-deficient mice" *Science*. Jan. 12, 2001;291(5502):319-22.
Tseng SY, Otsuji M, Gorski K, Huang X, Slansky JE, Pai SI, Shalabi A, Shin T, Pardoll DM, Tsuchiya H. B7-DC, a new dendritic cell molecule with potent costimulatory properties for T cells. *J Exp Med*. Apr. 2, 2001;193(7):839-46.
Tamura H, Dong H, Zhu G, Sica GL, Flies DB, Tamada K, Chen L., "B7-H1 costimulation preferentially enhances CD28-independent T-helper cell function." *Blood*. Mar. 15, 2001;97(6):1809-16.
Wallin JJ, Liang L, Bakardjiev A, Sha WC., "Enhancement of cd8(+) t cell responses by icos/b7h costimulation." *J Immunol*. Jul. 1, 2001;167(1):132-9.
Ling V, Wu PW, Miyashiro JS, Marusic S, Finnerty HF, Collins M., "Differential expression of inducible costimulator-ligand splice variants: lymphoid regulation of mouse g150-b and human g150 molecules." *J Immunol*. Jun. 15, 2001;166(12):7300-8.
Y. Latchman, C.R. Wood, T. Chernova, D. Chaudhary, M. Borde, I. Chernova, Y. Iwai, A.J. Long, J.A. Brown, R, Nunes, E.A. Greenfield, K. Bourque, V.A. Boussiotis, L.L. Carter, B.M. Carreno, N. Malenkovich, H. Nishimura, T. Okazaki, T. Honjo, A.H. Sharpe, G.J. Freeman, 2001, "PD-L2 is a second ligand for PD-1 and inhibits T cell activation" *Nature Immunol*. 2:261-268.
Amendment and Response to Non-Final Office Action, In re: Freeman, et al., U.S. Appl. No. 11/765,838, filed Jun. 20, 2007, submitted Jan. 12, 2009 attaching Declaration Under 37 C.F.R. §1.131.
Supplemental Response to Non-Final Office Action, In re: Freeman, et al., U.S. Appl. No. 11/765,838, filed Jun. 20, 2007, submitted Feb. 19, 2009 attaching Declaration Under 37 C.F.R. §1.131.

FIG. 1A

```
   1    acgcggggggt gccgcgcggc cccagttctg cgcagcttcc cgaggctccg
  51    caccagccgc gcttctgtcc gcctgcaggg cattccagaa agatgaggat
 101    atttgctgtc tttatattca tgacctactg gcatttgctg aacgcattta
 151    ctgtcacggt tcccaaggac ctatatgtgg tagagtatgg tagcaatatg
 201    acaattgaat gcaaattccc agtagaaaaa caattagacc tggctgcact
 251    aattgtctat tgggaaatgg aggataagaa cattattcaa tttgtgcatg
 301    gagaggaaga cctgaaggtt cagcatagta gctacagaca gagggcccgg
 351    ctgttgaagg accagctctc cctgggaaat gctgcacttc agatcacaga
 401    tgtgaaattg caggatgcag gggtgtaccg ctgcatgatc agctatggtg
 451    gtgccgacta caagcgaatt actgtgaaag tcaatgcccc atacaacaaa
 501    atcaaccaaa gaattttggt tgtggatcca gtcacctctg aacatgaact
 551    gacatgtcag gctgagggct accccaaggc cgaagtcatc tggacaagca
 601    gtgaccatca agtcctgagt ggtaagacca ccaccaccaa ttccaagaga
 651    gaggagaagc ttttcaatgt gaccagcaca ctgagaatca acacaacaac
 701    taatgagatt ttctactgca cttttaggag attagatcct gaggaaaacc
 751    atacagctga attggtcatc ccagaactac ctctggcaca tcctccaaat
 801    gaaaggactc acttggtaat tctgggagcc atcttattat gccttggtgt
 851    agcactgaca ttcatcttcc gtttaagaaa agggagaatg atggatgtga
 901    aaaaatgtgg catccaagat acaaactcaa agaagcaaag tgatacacat
 951    ttggaggaga cgtaatccag cattggaact tctgatcttc aagcagggat
1001    tctcaacctg tggtttaggg gttcatcggg gctgagcgtg acaagaggaa
1051    ggaatgggcc cgtgggatgc aggcaatgtg ggacttaaaa ggcccaagca
1101    ctgaaaatgg aacctgcgaa agcagaggag gagaatgaag aaagatggag
1151    tcaaacaggg agcctggagg gagaccttga tactttcaaa tgcctgaggg
1201    gctcatcgac gcctgtgaca gggagaaagg atacttctga acaaggagcc
1251    tccaagcaaa tcatccattg ctcatcctag gaagacgggt tgagaatccc
1301    taatttgagg gtcagttcct gcagaagtgc cctttgcctc cactcaatgc
1351    ctcaatttct tttctgcatg actgagagtc tcagtgttgg aacgggacag
1401    tatttatgta tgagtttttc ctatttattt tgagtctgtg aggtcttctt
1451    gtcatgtgag tgtggttgtg aatgatttct tttgaagata tattgtagta
1501    gatgttacaa ttttgtcgcc aaactaaact tgctgcttaa tgatttgctc
1551    acatctagta aaacatggag tattcaaaaa aaaaaaaaaa aaaaaaaaaa
1601    aaaa
```

FIG. 1B

```
  1  MRIFAVFIFMTYWHLLNAFTVTVPKDLYVVEYGSNMTIECKFPVEKQLDLAALIVYWEME
 61  DKNIIQFVHGEEDLKVQHSSYRQRARLLKDQLSLGNAALQITDVKLQDAGVYRCMISYGG
121  ADYKRITVKVNAPYNKINQRILVVDPVTSEHELTCQAEGYPKAEVIWTSSDHQVLSGKTT
181  TTNSKREEKLFNVTSTLRINTTTNEIFYCTFRRLDPEENHTAELVIPELPLAHPPNERTH
241  LVILGAILLCLGVALTFIFRLRKGRMMDVKKCGIQDTNSKKQSDTHLEET
```

FIG. 1C

```
   1   acgcggggt  gccgcgcggc  cccagttctg  cgcagcttcc  cgaggctccg
  51   caccagccgc  gcttctgtcc  gcctgcaggg  cattccagaa  agatgaggat
 101   atttgctgtc  tttatattca  tgacctactg  gcatttgctg  aacgcattta
 151   ctgtcacggt  tcccaaggac  ctatatgtgg  tagagtatgg  tagcaatatg
 201   acaattgaat  gcaaattccc  agtagaaaaa  caattagacc  tggctgcact
 251   aattgtctat  tgggaaatgg  aggataagaa  cattattcaa  tttgtgcatg
 301   gagaggaaga  cctgaaggtt  cagcatagta  gctacagaca  gagggcccgg
 351   ctgttgaagg  accagctctc  cctggaaat   gctgcacttc  agatcacaga
 401   tgtgaaattg  caggatgcag  gggtgtaccg  ctgcatgatc  agctatggtg
 451   gtgccgacta  caagcgaatt  actgtgaaag  tcaatgcccc  atacaacaaa
 501   atcaaccaaa  gaattttggt  tgtggatcca  gtcacctctg  aacatgaact
 551   gacatgtcag  gctgagggct  accccaaggc  cgaagtcatc  tggacaagca
 601   gtgaccatca  agtcctgagt  ggtaagacca  ccaccaccaa  ttccaagaga
 651   gaggagaagc  ttttcaatgt  gaccagcaca  ctgagaatca  acacaacaac
 701   taatgagatt  ttctactgca  cttttaggag  attagatcct  gaggaaaacc
 751   atacagctga  attggtcatc  ccagaactac  ctctggcaca  tcctccaaat
 801   gaaaggactc  acttggtaat  tctgggagcc  atcttattat  gccttggtgt
 851   agcactgaca  ttcatcttcc  gtttaagaaa  agggagaatg  atggatgtga
 901   aaaaatgtgg  catccaagat  acaaactcaa  agaagcaaag  tgatacacat
 951   ttggaggaga  cgtaatccag  cattggaact  tctgatcttc  aagcagggat
1001   tctcaacctg  tggtttaggg  gttcatcggg  gctgagcgtg  acaagaggaa
1051   ggaatgggcc  cgtgggatgc  aggcaatgtg  ggacttaaaa  ggcccaagca
1101   ctgaaaatgg  aacctgcgaa  agcagaggag  gagaatgaag  aaagatggag
1151   tcaaacaggg  agcctggagg  gagaccttga  tactttcaaa  tgcctgaggg
1201   gctcatcgac  gcctgtgaca  gggagaaagg  atacttctga  caaggagcc
1251   tccaagcaaa  tcatccattg  ctcatcctag  gaagacgggt  tgagaatccc
1301   taatttgagg  gtcagttcct  gcagaagtgc  cctttgcctc  cactcaatgc
1351   ctcaatttct  tttctgcatg  actgagagtc  tcagtgttgg  aacgggacag
1401   tatttatgta  tgagttttc   ctatttattt  tgagtctgtg  aggtcttctt
1451   gtcatgtgag  tgtggttgtg  aatgatttct  tttgaagata  tattgtagta
1501   gatgttacaa  ttttgtcgcc  aaactaaact  tgctgcttaa  tgatttgctc
1551   acatctagta  aaacatggag  tatttgtaag  gtgcttggtc  tcctctataa
1601   ctacaagtat  acattggaag  cataaagatc  aaaccgttgg  ttgcatagga
1651   tgtcaccttt  atttaaccca  ttaatactct  ggttgaccta  atcttattct
1701   cagacctcaa  gtgtctgtgc  agtatctgtt  ccatttaaat  atcagcttta
1751   caattatgtg  gtagcctaca  cacataatct  catttcatcg  ctgtaaccac
1801   cctgttgtga  taaccactat  tattttaccc  atcgtacagc  tgaggaagca
1851   aacagattaa  gtaacttgcc  caaaccagta  aatagcagac  ctcagactgc
1901   cacccactgt  cctttataa   tacaatttac  agctatattt  tactttaagc
1951   aattctttta  ttcaaaaacc  atttattaag  tgcccttgca  atatcaatcg
2001   ctgtgccagg  cattgaatct  acagatgtga  gcaagacaaa  gtacctgtcc
2051   tcaaggagct  catagtataa  tgaggagatt  aacaagaaaa  tgtattatta
2101   caatttagtc  cagtgtcata  gcataaggat  gatgcgaggg  gaaaacccga
2151   gcagtgttgc  caagaggagg  aaataggcca  atgtggtctg  ggacggttgg
2201   atatacttaa  acatcttaat  aatcagagta  attttcattt  acaaagagag
2251   gtcggtactt  aaaataaccc  tgaaaaataa  cactggaatt  ccttttctag
2301   cattatattt  attcctgatt  tgcctttgcc  atataatcta  atgcttgttt
```

FIG. 1C (CON'T)

```
2351  atatagtgtc tggtattgtt taacagttct gtcttttcta tttaaatgcc
2401  actaaatttt aaattcatac ctttccatga ttcaaaattc aaaagatccc
2451  atgggagatg gttggaaaat ctccacttca tcctccaagc cattcaagtt
2501  tcctttccag aagcaactgc tactgccttt cattcatatg ttcttctaaa
2551  gatagtctac atttggaaat gtatgttaaa agcacgtatt tttaaaattt
2601  ttttcctaaa tagtaacaca ttgtatgtct gctgtgtact ttgctatttt
2651  tatttatttt agtgtttctt atatagcaga tggaatgaat ttgaagttcc
2701  cagggctgag gatccatgcc ttctttgttt ctaagttatc tttcccatag
2751  cttttcatta tctttcatat gatccagtat atgttaaata tgtcctacat
2801  atacatttag acaaccacca tttgttaagt atttgctcta ggacagagtt
2851  tggatttgtt tatgtttgct caaaaggaga cccatgggct ctccagggtg
2901  cactgagtca atctagtcct aaaaagcaat cttattatta actctgtatg
2951  acagaatcat gtctggaact tttgttttct gctttctgtc aagtataaac
3001  ttcactttga tgctgtactt gcaaaatcac atttTctttc tggaaattcc
3051  ggcagtgtac cttgactgct agctaccctg tgccagaaaa gcctcattcg
3101  ttgtgcttga acccttgaat gccaccagct gtcatcacta cacagccctc
3151  ctaagaggct tcctggaggt ttcgagattc agatgccctg ggagatccca
3201  gagtttcctt tccctcttgg ccatattctg tgtcaatga caaggagtac
3251  cttggctttg ccacatgtca aggctgaaga aacagtgtct ccaacagagc
3301  tccttgttat ctgtttgtac atgtgcattt gtacagtaat tggtgtgaca
3351  gtgttctttg tgtgaattac aggcaagaat tgtggctgag caaggcacat
3401  agtctactca gtctattcct aagtcctaac tcctccttgt ggtgttggat
3451  ttgtaaggca ctttatccct tttgtctcat gtttcatcgt aaatggcata
3501  ggcagagatg atacctaatt ctgcatttga ttgtcacttt ttgtacctgc
3551  attaatttaa taaatattc ttatttattt tgttacttgg taaaaaaaaa
3601  aaaaaaaaaa aaaaaaaaa a
```

FIG. 2A

```
   1  atgcccatggggtctctgcaaccgctggccaccttgtacctgctggggatgctggtcgct
  61  tcctgcctcggaactagtgttcccaaggacctatatgtggtagagtatggtagcaatatg
 121  acaattgaatgcaaattcccagtagaaaaacaattagacctggctgcactaattgtctat
 181  tgggaaatggaggataagaacattattcaatttgtgcatggagaggaagacctgaaggtt
 241  cagcatagtagctacagacagagggcccggctgttgaaggaccagctctccctgggaaat
 301  gctgcacttcagatcacagatgtgaaattgcaggatgcaggggtgtaccgctgcatgatc
 361  agctatggtggtgccgactacaagcgaattactgtgaaagtcaatgccccatacaacaaa
 421  atcaaccaaagaattttggttgtggatccagtcacctctgaacatgaactgacatgtcag
 481  gctgagggctaccccaaggccgaagtcatctggacaagcagtgaccatcaagtcctgagt
 541  ggtaagaccaccaccaccaattccaagagagaggagaagcttttcaatgtgaccagcaca
 601  ctgagaatcaacacaacaactaatgagattttctactgcacttttaggagattagatcct
 661  gaggaaaaccatacagctgaattggtcatcccagaactacctctggcacatcctccaaat
 721  gaaaggactcgaggagatcccgaggagcccaaatcttgtgacaaaactcacacatgccca
 781  ccgtgcccagcacctgaactcctgggggaccgtcagtcttcctcttccccccaaaaccc
 841  aaggacaccctcatgatctcccggacccctgaggtcacatgcgtggtggtggacgtgagc
 901  cacgaagaccctgaggtcaagttcaactggtacgtggacggcgtggaggtgcataatgcc
 961  aagacaaagccgcgggaggagcagtacaacagcacgtaccgtgtggtcagcgtcctcacc
1021  gtcctgcaccaggactggctgaatggcaaggagtacaagtgcaaggtctccaacaaagcc
1081  ctcccagcccccatcgagaaaaccatctccaaagccaaagggcagccccgagaaccacag
1141  gtgtacaccctgcccccatcccgggatgagctgaccaagaaccaggtcagcctgacctgc
1201  ctggtcaaaggcttctatcccagcgacatcgccgtggagtgggagagcaatgggcagccg
1261  gagaacaactacaagaccacgcctcccgtgctggactccgacggctccttcttcctctac
1321  agcaagctcaccgtggacaagagcaggtggcagcaggggaacgtcttctcatgctccgtg
1381  atgcatgaggctctgcacaaccactacacgcagaagagcctctccctgtctccgggtaaa
1441  tga
```

FIG. 2B

```
  1   MPMGSLQPLATLYLLGMLVASCLGTSVPKDLYVVEYGSNMTIECKFPVEKQLDLAALIVY
 61   WEMEDKNIIQFVHGEEDLKVQHSSYRQRARLLKDQLSLGNAALQITDVKLQDAGVYRCMI
121   SYGGADYKRITVKVNAPYNKINQRILVVDPVTSEHELTCQAEGYPKAEVIWTSSDHQVLS
181   GKTTTTNSKREEKLFNVTSTLRINTTTNEIFYCTFRRLDPEENHTAELVIPELPLAHPPN
241   ERTRGDPEEPKSCDKTHTCPPCPAPELLGGPSVFLFPPKPKDTLMISRTPEVTCVVVDVS
301   HEDPEVKFNWYVDGVEVHNAKTKPREEQYNSTYRVVSVLTVLHQDWLNGKEYKCKVSNKA
361   LPAPIEKTISKAKGQPREPQVYTLPPSRDELTKNQVSLTCLVKGFYPSDIAVEWESNGQP
421   ENNYKTTPPVLDSDGSFFLYSKLTVDKSRWQQGNVFSCSVMHEALHNHYTQKSLSLSPGK
```

FIG. 3A

```
   1    attcggctcg agggcgactg agccaggctg ggccgcgtcc ctgagtccca
  51    gagtcggcgc ggcgcggcag gggcagcctt ccaccacggg gagcccagct
 101    gtcagccgcc tcacaggaag atgctgcgtc ggcggggcag ccctggcatg
 151    ggtgtgcatg tgggtgcagc cctgggagca ctgtggttct gcctcacagg
 201    agccctggag gtccaggtcc ctgaagaccc agtggtggca ctggtgggca
 251    ccgatgccac cctgtgctgc tccttctccc ctgagcctgg cttcagcctg
 301    gcacagctca acctcatctg gcagctgaca gataccaaac agctggtgca
 351    cagctttgct gagggccagg accagggcag cgcctatgcc aaccgcacgg
 401    ccctcttccc ggacctgctg cacagggca  acgcatccct gaggctgcag
 451    cgcgtgcgtg tggcggacga gggcagcttc acctgcttcg tgagcatccg
 501    ggatttcggc agcgctgccg tcagcctgca ggtggccgct ccctactcga
 551    agcccagcat gaccctggag cccaacaagg acctgcggcc aggggacacg
 601    gtgaccatca cgtgctccag ctaccagggc taccctgagg ctgaggtgtt
 651    ctggcaggat gggcagggtg tgccctgac  tggcaacgtg accacgtcgc
 701    agatggccaa cgagcagggc ttgtttgatg tgcacagcat cctgcgggtg
 751    gtgctgggtg caaatggcac ctacagctgc ctggtgcgca accccgtgct
 801    gcagcaggat gcgcacagct ctgtcaccat cacacccag  agaagcccca
 851    caggagccgt ggaggtccag gtccctgagg accggtggt  ggccctagtg
 901    ggcaccgatg ccaccctgcg ctgctccttc tcccccgagc ctggcttcag
 951    cctggcacag ctcaacctca tctggcagct gacagacacc aaacagctgg
1001    tgcacagttt caccgaaggc cgggaccagg gcagcgccta tgccaaccgc
1051    acggccctct tcccggacct gctggcacaa gcaatgcat  ccctgaggct
1101    gcagcgcgtg cgtgtggcgg acgagggcag cttcacctgc ttcgtgagca
1151    tccgggattt cggcagcgct gccgtcagcc tgcaggtggc cgctccctac
1201    tcgaagccca gcatgaccct ggagcccaac aaggacctgc ggccagggga
1251    cacggtgacc atcacgtgct ccagctaccg ggctaccct  gaggctgagg
1301    tgttctggca ggatgggcag ggtgtgcccc tgactggcaa cgtgaccacg
1351    tcgcagatgg ccaacgagca gggcttgttt gatgtgcaca gcgtcctgcg
1401    ggtggtgctg ggtgcgaatg gcacctacag ctgcctggtg cgcaaccccg
1451    tgctgcagca ggatgcgcac ggctctgtca ccatcacagg gcagcctatg
1501    acattccccc cagaggccct gtgggtgacc gtgggctgt  ctgtctgtct
1551    cattgcactg ctggtggccc tggctttcgt gtgctggaga aagatcaaac
1601    agagctgtga ggaggagaat gcaggagctg aggaccagga tggggaggga
1651    gaaggctcca agacagccct gcagcctctg aaacactctg acagcaaaga
1701    agatgatgga caagaaatag cctgaccatg aggaccaggg agctgctacc
1751    cctccctaca gctcctaccc tctggctgca atggggctgc actgtgagcc
1801    ctgccccaa cagatgcatc ctgctctgac aggtgggctc cttctccaaa
1851    ggatgcgata cacagaccac tgtgcagcct tatttctcca atggacatga
1901    ttcccaagtc atcctgctgc ctttttctt  atagacacaa tgaacagacc
1951    acccacaacc ttagttctct aagtcatcct gcctgctgcc ttatttcaca
2001    gtacatacat ttcttaggga cacagtacac tgaccacatc accaccctct
```

FIG. 3A (CON'T)

```
2051  tcttccagtg ctgcgtggac catctggctg cctttttct  ccaaaagatg
2101  caatattcag actgactgac cccctgcctt atttcaccaa agacacgatg
2151  catagtcacc ccggccttgt ttctccaatg gccgtgatac actagtgatc
2201  atgttcagcc ctgcttccac ctgcatagaa tcttttcttc tcagacaggg
2251  acagtgcggc ctcaacatct cctggagtct agaagctgtt tcctttcccc
2301  tccttcctcc tcttgctcta gccttaatac tggccttttc cctccctgcc
2351  ccaagtgaag cagggcact  ctgcgccac  cacatgcaca gctgtgcatg
2401  gagacctgca ggtgcacgtg ctggaacacg tgtggttccc ccctggccca
2451  gcctcctctg cagtgcccct ctccctgcc  catcctcccc acggaagcat
2501  gtgctggtca cactggttct caggggtct  gtgatggggc cctgggggt
2551  cagcttctgt ccctctgcct tctcacctct ttgttccttt cttttcatgt
2601  atccattcag ttgatgttta ttgagcaact acagatgtca gcactgtgtt
2651  aggtgctggg ggccctgcgt gggaagataa agttcctccc tcaaggactc
2701  cccatccagc tgggagacag acaactaact acactgcacc ctgcggtttg
2751  caggggctc  ctgcctggct ccctgctcca cacctcctct gtggctcaag
2801  gcttcctgga tacctcaccc ccatcccacc cataattctt acccagagca
2851  tggggttggg gcggaaacct ggagagaggg acatagcccc tcgccacggc
2901  tagagaatct ggtggtgtcc aaaatgtctg tccaggtgtg ggcaggtggg
2951  caggcaccaa ggccctctgg acctttcata gcagcagaaa aggcagagcc
3001  tggggcaggg cagggccagg aatgctttgg ggacaccgag gggactgccc
3051  cccaccccca ccatggtgct attctggggc tggggcagtc ttttcctggc
3101  ttgcctctgg ccagctcctg gcctctggta gagtgagact tcagacgttc
3151  tgatgccttc cggatgtcat ctctccctgc cccaggaatg gaagatg
```

FIG. 3B

```
  1    MLRRRGSPGM  GVHVGAALGA  LWFCLTGALE  VQVPEDPVVA  LVGTDATLCC
 51    SFSPEPGFSL  AQLNLIWQLT  DTKQLVHSFA  EGQDQGSAYA  NRTALFPDLL
101    AQGNASLRLQ  RVRVADEGSF  TCFVSIRDFG  SAAVSLQVAA  PYSKPSMTLE
151    PNKDLRPGDT  VTITCSSYQG  YPEAEVFWQD  GQGVPLTGNV  TTSQMANEQG
201    LFDVHSILRV  VLGANGTYSC  LVRNPVLQQD  AHSSVTITPQ  RSPTGAVEVQ
251    VPEDPVVALV  GTDATLRCSF  SPEPGFSLAQ  LNLIWQLTDT  KQLVHSFTEG
301    RDQGSAYANR  TALFPDLLAQ  GNASLRLQRV  RVADEGSFTC  FVSIRDFGSA
351    AVSLQVAAPY  SKPSMTLEPN  KDLRPGDTVT  ITCSSYRGYP  EAEVFWQDGQ
401    GVPLTGNVTT  SQMANEQGLF  DVHSVLRVVL  GANGTYSCLV  RNPVLQQDAH
451    GSVTITGQPM  TFPPEALWVT  VGLSVCLIAL  LVALAFVCWR  KIKQSCEEEN
501    AGAEDQDGEG  EGSKTALQPL  KHSDSKEDDG  QEIA
```

FIG. 3C

```
  1   atgctgcgtc ggcggggcag ccctggcatg ggtgtgcatg tgggtgcagc
 51   cctgggagca ctgtggttct gcctcacagg agccctggag gtccaggtcc
101   ctgaagaccc agtggtggca ctggtgggca ccgatgccac cctgcgctgc
151   tccttctccc ccgagcctgg cttcagcctg gcacagctca acctcatctg
201   gcagctgaca gacaccaaac agctggtgca cagtttcacc gaaggccggg
251   accagggcag cgcctatgcc aaccgcacgg ccctcttccc ggacctgctg
301   gcacaaggca atgcatccct gaggctgcag cgcgtgcgtg tggcggacga
351   gggcagcttc acctgcttcg tgagcatccg ggatttcggc agcgctgccg
401   tcagcctgca ggtggccgct ccctactcga agcccagcat gaccctggag
451   cccaacaagg acctgcggcc aggggacacg gtgaccatca cgtgctccag
501   ctaccggggc taccctgagg ctgaggtgtt ctggcaggat gggcagggtg
551   tgccctgac  tggcaacgtg accacgtcgc agatggccaa cgagcagggc
601   ttgtttgatg tgcacagcgt cctgcgggtg gtgctgggtg cgaatggcac
651   ctacagctgc ctggtgcgca ccccgtgct  gcagcaggat gcgcacggct
701   ctgtcaccat cacagggcag cctatgacat tcccccaga  ggccctgtgg
751   gtgaccgtgg ggctgtctgt ctgtctcatt gcactgctgg tggccctggc
801   tttcgtgtgc tggagaaaga tcaaacagag ctgtgaggag gagaatgcag
851   gagctgagga ccaggatggg gagggagaag gctccaagac agccctgcag
901   cctctgaaac actctgacag caaagaagat gatggacaag aaatagcctg
951   a
```

FIG. 3D

```
  1    MLRRRGSPGM  GVHVGAALGA  LWFCLTGALE  VQVPEDPVVA  LVGTDATLRC
 51    SFSPEPGFSL  AQLNLIWQLT  DTKQLVHSFT  EGRDQGSAYA  NRTALFPDLL
101    AQGNASLRLQ  RVRVADEGSF  TCFVSIRDFG  SAAVSLQVAA  PYSKPSMTLE
151    PNKDLRPGDT  VTITCSSYRG  YPEAEVFWQD  GQGVPLTGNV  TTSQMANEQG
201    LFDVHSVLRV  VLGANGTYSC  LVRNPVLQQD  AHGSVTITGQ  PMTFPPEALW
251    VTVGLSVCLI  ALLVALAFVC  WRKIKQSCEE  ENAGAEDQDG  EGEGSKTALQ
301    PLKHSDSKED  DGQEIA*
```

FIG. 3E

```
1    atgctgcgtc ggcggggcag ccctggcatg ggtgtgcatg tgggtgcagc
51   cctgggagca ctgtggttct gcctcacagg agccctggag gtccaggtcc
101  ctgaagaccc agtggtggca ctggtgggca ccgatgccac cctgtgctgc
151  tccttctccc ctgagcctgg cttcagcctg gcacagctca acctcatctg
201  gcagctgaca gataccaaac agctggtgca cagctttgct gagggccagg
251  accagggcag cgcctatgcc aaccgcacgg ccctcttccc ggacctgctg
301  gcacaaggca atgcatccct gaggctgcag cgcgtgcgtg tggcggacga
351  gggcagcttc acctgcttcg tgagcatccg ggatttcggc agcgctgccg
401  tcagcctgca ggtggccgct ccctactcga agcccagcat gaccctggag
451  cccaacaagg acctgcggcc agggacacg gtgaccatca cgtgctccag
501  ctaccggggc taccctgagg ctgaggtgtt ctggcaggat gggcagggtg
551  tgccctgac tggcaacgtg accacgtcgc agatggccaa cgagcagggc
601  ttgtttgatg tgcacagcgt cctgcgggtg gtgctgggtg cgaatggcac
651  ctacagctgc ctggtgcgca accccgtgct gcagcaggat gcgcacggct
701  ctgtcaccat cacagggcag cctatgacat tcccccagga ggccctgtgg
751  gtgaccgtgg ggctgtctgt ctgtctcatt gcactgctgg tggccctggc
801  tttcgtgtgc tggagaaaga tcaaacagag ctgtgaggag gagaatgcag
851  gagctgagga ccaggatggg gagggagaaa gctccaagac agccctgcag
901  cctctgaaac actctgacag caaagaagat gatggacaag aaatagccga
```

FIG. 3F

```
1    MLRRRGSPGM GVHVGAALGA LWFCLTGALE VQVPEDPVVA LVGTDATLCC
51   SFSPEPGFSL AQLNLIWQLT DTKQLVHSFA EGQDQGSAYA NRTALFPDLL
101  AQGNASLRLQ RVRVADEGSF TCFVSIRDFG SAAVSLQVAA PYSKPSMTLE
151  PNKDLRPGDT VTITCSSYRG YPEAEVFWQD GQGVPLTGNV TTSQMANEQG
201  LFDVHSVLRV VLGANGTYSC LVRNPVLQQD AHGSVTITGQ PMTFPPEALW
251  VTVGLSVCLI ALLVALAFVC WRKIKQSCEE ENAGAEDQDG EGESSKTALQ
301  PLKHSDSKED DGQEIA
```

FIG. 4A

```
   1  atgctgcgtc ggcggggcag ccctggcatg ggtgtgcatg tgggtgcagc
  51  cctgggagca ctgtggttct gcctcacagg agccctggag gtccaggtcc
 101  ctgaagaccc agtggtggca ctggtgggca ccgatgccac cctgtgctgc
 151  tccttctccc ctgagcctgg cttcagcctg cacagctca  acctcatctg
 201  gcagctgaca gataccaaac agctggtgca cagctttgct gagggccagg
 251  accagggcag cgcctatgcc aaccgcacgg ccctcttccc ggacctgctg
 301  gcacagggca acgcatccct gaggctgcag cgcgtgcgtg tggcggacga
 351  gggcagcttc acctgcttcg tgagcatccg ggatttcggc agcgctgccg
 401  tcagcctgca ggtggccgct ccctactcga agcccagcat gaccctggag
 451  cccaacaagg acctgcggcc aggggacacg gtgaccatca cgtgctccag
 501  ctaccagggc taccctgagg ctgaggtgtt ctggcaggat gggcagggtg
 551  tgccctgac  tggcaacgtg accacgtcgc agatggccaa cgagcaggc
 601  ttgtttgatg tgcacagcat cctgcgggtg gtgctgggtg caaatggcac
 651  ctacagctgc ctggtgcgca ccccgtgct  gcagcaggat gcgcacagct
 701  ctgtcaccat cacacccag  agaagcccca caggagccgt ggaggtccag
 751  gtccctgagg acccggtggt ggccctagtg ggcaccgatg ccaccctgcg
 801  ctgctccttc tcccccgagc ctggcttcag cctggcacag ctcaacctca
 851  tctggcagct gacagacacc aaacagctgg tgcacagttt caccgaaggc
 901  cgggaccagg gcagcgccta tgccaaccgc acggccctct cccggacct
 951  gctggcacaa ggcaatgcat ccctgaggct gcagcgcgtg cgtgtggcgg
1001  acgagggcag cttcacctgc ttcgtgagca tccgggattt cggcagcgct
1051  gccgtcagcc tgcaggtggc cgctccctac tcgaagccca gcatgaccct
1101  ggagcccaac aaggacctgc ggccagggga cacggtgacc atcacgtgct
1151  ccagctaccg ggctaccct  gaggctgagg tgttctggca ggatgggcag
1201  ggtgtgcccc tgactggcaa cgtgaccacg tcgcagatgg ccaacgagca
1251  gggcttgttt gatgtgcaca gcgtcctgcg ggtggtgctg ggtgcgaatg
1301  gcacctacag ctgcctggtg cgcaacccg  tgctgcagca ggatgcgcac
1351  ggctctgtca ccatcacagg gcagcctatg acattccccc agaattcga
1401  gcccaaatct tgtgacaaaa ctcacacatg cccaccgtgc ccagcacctg
1451  aactcctggg gggaccgtca gtcttcctct tccccccaaa acccaaggac
1501  accctcatga tctcccggac ccctgaggtc acatgcgtgg tggtggacgt
1551  gagccacgaa gaccctgagg tcaagttcaa ctggtacgtg gacggcgtgg
1601  aggtgcataa tgccaagaca aagccgcggg aggagcagta acagcacg
1651  taccgtgtgg tcagcgtcct caccgtcctg caccaggact ggctgaatgg
1701  caaggagtac aagtgcaagg tctccaacaa agccctccca gcccccatcg
1751  agaaaaccat ctccaaagcc aagggcagc  ccgagaacc  acaggtgtac
1801  accctgcccc catcccggga tgagctgacc aagaaccagg tcagcctgac
1851  ctgcctggtc aaaggcttct atcccagcga catcgccgtg gagtgggaga
1901  gcaatgggca gccggagaac aactacaaga ccacgcctcc cgtgctggac
1951  tccgacggct ccttcttcct ctacagcaag ctcaccgtgg acaagagcag
2001  gtggcagcag gggaacgtct tctcatgctc cgtgatgcat gaggctctgc
2051  acaaccacta cacgcagaag agcctctccc tgtctccggg taaatga
```

FIG. 4B

```
  1  MLRRRGSPGM GVHVGAALGA LWFCLTGALE VQVPEDPVVA LVGTDATLCC
 51  SFSPEPGFSL AQLNLIWQLT DTKQLVHSFA EGQDQGSAYA NRTALFPDLL
101  AQGNASLRLQ RVRVADEGSF TCFVSIRDFG SAAVSLQVAA PYSKPSMTLE
151  PNKDLRPGDT VTITCSSYQG YPEAEVFWQD GQGVPLTGNV TTSQMANEQG
201  LFDVHSILRV VLGANGTYSC LVRNPVLQQD AHSSVTITPQ RSPTGAVEVQ
251  VPEDPVVALV GTDATLRCSF SPEPGFSLAQ LNLIWQLTDT KQLVHSFTEG
301  RDQGSAYANR TALFPDLLAQ GNASLRLQRV RVADEGSFTC FVSIRDFGSA
351  AVSLQVAAPY SKPSMTLEPN KDLRPGDTVT ITCSSYRGYP EAEVFWQDGQ
401  GVPLTGNVTT SQMANEQGLF DVHSVLRVVL GANGTYSCLV RNPVLQQDAH
451  GSVTITGQPM TFPPEFEPKS CDKTHTCPPC PAPELLGGPS VFLFPPKPKD
501  TLMISRTPEV TCVVVDVSHE DPEVKFNWYV DGVEVHNAKT KPREEQYNST
551  YRVVSVLTVL HQDWLNGKEY KCKVSNKALP APIEKTISKA KGQPREPQVY
601  TLPPSRDELT KNQVSLTCLV KGFYPSDIAV EWESNGQPEN NYKTTPPVLD
651  SDGSFFLYSK LTVDKSRWQQ GNVFSCSVMH EALHNHYTQK SLSLSPGK*
```

FIG. 5A

```
   1  gctttcgtca gttcctcaga actagttctg gtttgactca ctctcatgtt
  51  acggcaaacc ttaagctgaa tgaacaactt ttcttctctt gaatatatct
 101  taacgccaaa ttttgagtgc ttttttgtta cccatcctca tatgtcccag
 151  ctggaaagaa tcctgggttg gagctactgc atgttgattg ttttgttttt
 201  ccttttggct gttcattttg gtggctacta taaggaaatc taacacaaac
 251  agcaactgtt ttttgttgtt tacttttgca tctttacttg tggagctgtg
 301  gcaagtcctc atatcaaata cagaacatga tcttcctcct gctaatgttg
 351  agcctggaat tgcagcttca ccagatagca gctttattca cagtgacagt
 401  ccctaaggaa ctgtacataa tagagcatgg cagcaatgtg accctggaat
 451  gcaactttga cactggaagt catgtgaacc ttggagcaat aacagccagt
 501  ttgcaaaagg tggaaaatga tacatcccca caccgtgaaa gagccacttt
 551  gctggaggag cagctgcccc tagggaaggc ctcgttccac atacctcaag
 601  tccaagtgag ggacgaagga cagtaccaat gcataatcat ctatggggtc
 651  gcctgggact acaagtacct gactctgaaa gtcaaagctt cctacaggaa
 701  aataaacact cacatcctaa aggttccaga aacagatgag gtagagctca
 751  cctgccaggc tacaggttat cctctggcag aagtatcctg gccaaacgtc
 801  agcgttcctg ccaacaccag ccactccagg accoctgaag cctctacca
 851  ggtcaccagt gttctgcgcc taaagccacc ccctggcaga aacttcagct
 901  gtgtgttctg gaatactcac gtgagggaac ttactttggc cagcattgac
 951  cttcaaagtc agatggaacc caggacccat ccaacttggc tgcttcacat
1001  tttcatcccc tcctgcatca ttgctttcat tttcatagcc acagtgatag
1051  ccctaagaaa acaactctgt caaaagctgt attcttcaaa agacacaaca
1101  aaaagacctg tcaccacaac aaagagggaa gtgaacagtg ctatctgaac
1151  ctgtggtctt gggagccagg gtgacctgat atgacatcta aagaagcttc
1201  tggactctga acaagaattc ggtggcctgc agagcttgcc atttgcactt
1251  ttcaaatgcc tttggatgac ccagcacttt aatctgaaac ctgcaacaag
1301  actagccaac acctggccat gaaacttgcc ccttcactga tctggactca
1351  cctctggagc ctatggcttt aagcaagcac tactgcactt tacagaatta
1401  ccccactgga tcctggaccc acagaattcc ttcaggatcc ttcttgctgc
1451  cagactgaaa gcaaaggaa ttatttcccc tcaagttttc taagtgattt
1501  ccaaaagcag aggtgtgtgg aaatttccag taacagaaac agatgggttg
1551  ccaatagagt tattttttat ctatagcttc ctctgggtac tagaagaggc
1601  tattgagact atgagctcac agacagggct tcgcacaaac tcaaatcata
1651  attgacatgt tttatggatt actggaatct tgatagcata atgaagttgt
1701  tctaattaac agagagcatt taaatataca ctaagtgcac aaattgtgga
1751  gtaaagtcat caagctctgt ttttgaggtc taagtcacaa agcatttgtt
1801  ttaacctgta atggcaccat gtttaatggt ggttttttt ttgaactaca
1851  tctttccttt aaaaattatt ggtttctttt tatttgtttt taccttagaa
1901  atcaattata tacagtcaaa aatatttgat atgctcatac gttgtatctg
1951  cagcaatttc agataagtag ctaaaatggc caaagcccca aactaagcct
2001  ccttttctgg ccctcaatat gactttaaat ttgactttc agtgcctcag
2051  tttgcacatc tgtaatacag caatgctaag tagtcaaggc ctttgataat
2101  tggcactatg gaaatcctgc aagatcccac tacatatgtg tggagcagaa
2151  gggtaactcg gctacagtaa cagcttaatt ttgttaaatt tgttctttat
2201  actggagcca tgaagctcag agcattagct gacccttgaa ctattcaaat
2251  gggcacatta gctagtataa cagacttaca taggtgggcc taaagcaagc
2301  tccttaactg agcaaaattt ggggcttatg agaatgaaag ggtgtgaaat
2351  tgactaacag acaaatcata catctcagtt tctcaattct catgtaaatc
2401  agagaatgcc tttagaaatt accaaagtgt tccat
```

FIG. 5B

```
  1    MIFLLLMLSL  ELQLHQIAAL  FTVTVPKELY  IIEHGSNVTL  ECNFDTGSHV
 51    NLGAITASLQ  KVENDTSPHR  ERATLLEEQL  PLGKASFHIP  QVQVRDEGQY
101    QCIIIYGVAW  DYKYLTLKVK  ASYRKINTHI  LKVPETDEVE  LTCQATGYPL
151    AEVSWPNVSV  PANTSHSRTP  EGLYQVTSVL  RLKPPPGRNF  SCVFWNTHVR
201    ELTLASIDLQ  SQMEPRTHPT  WLLHIFIPSC  IIAFIFIATV  IALRKQLCQK
251    LYSSKDTTKR  PVTTTKREVN  SAI*
```

FIG. 6A

```
   1  atgatcttcc tcctgctaat gttgagcctg gaattgcagc ttcaccagat
  51  agcagcttta ttcacagtga cagtccctaa ggaactgtac ataatagagc
 101  atggcagcaa tgtgaccctg gaatgcaact ttgacactgg aagtcatgtg
 151  aaccttggag caataacagc cagtttgcaa aaggtggaaa atgatacatc
 201  cccacaccgt gaaagagcca ctttgctgga ggagcagctg cccctaggga
 251  aggcctcgtt ccacatacct caagtccaag tgagggacga aggacagtac
 301  caatgcataa tcatctatgg ggtcgcctgg gactacaagt acctgactct
 351  gaaagtcaaa gcttcctaca ggaaaataaa cactcacatc ctaaaggttc
 401  cagaaacaga tgaggtagag ctcacctgcc aggctacagg ttatcctctg
 451  gcagaagtat cctggccaaa cgtcagcgtt cctgccaaca ccagccactc
 501  caggacccct gaaggcctct accaggtcac cagtgttctg cgcctaaagc
 551  cacccctgg cagaaacttc agctgtgtgg tctggaatac tcacgtgagg
 601  gaacttactt tggccagcat tgaccttcaa agtcagatgg aacccaggac
 651  cgaattcgag cccaaatctt gtgacaaaac tcacacatgc ccaccgtgcc
 701  cagcacctga actcctgggg ggaccgtcag tcttcctctt ccccccaaaa
 751  cccaaggaca ccctcatgat ctcccggacc cctgaggtca catgcgtggt
 801  ggtggacgtg agccacgaag accctgaggt caagttcaac tggtacgtgg
 851  acggcgtgga ggtgcataat gccaagacaa agccgcggga ggagcagtac
 901  aacagcacgt accgtgtggt cagcgtcctc accgtcctgc accaggactg
 951  gctgaatggc aaggagtaca agtgcaaggt ctccaacaaa gccctcccag
1001  cccccatcga gaaaaccatc tccaaagcca agggcagcc cgagaaccaa
1051  caggtgtaca ccctgccccc atcccgggat gagctgacca gaaccaggt
1101  cagcctgacc tgcctggtca aaggcttcta tcccagcgac atcgccgtgg
1151  agtgggagag caatgggcag ccggagaaca actacaagac cacgcctccc
1201  gtgctggact ccgacggctc cttcttcctc tacagcaagc tcaccgtgga
1251  caagagcagg tggcagcagg ggaacgtctt ctcatgctcc gtgatgcatg
1301  aggctctgca caaccactac acgcagaaga cctctccct gtctccgggt
1351  aaatga
```

FIG. 6B

```
  1  MIFLLLMLSL ELQLHQIAAL FTVTVPKELY IIEHGSNVTL ECNFDTGSHV
 51  NLGAITASLQ KVENDTSPHR ERATLLEEQL PLGKASFHIP QVQVRDEGQY
101  QCIIIYGVAW DYKYLTLKVK ASYRKINTHI LKVPETDEVE LTCQATGYPL
151  AEVSWPNVSV PANTSHSRTP EGLYQVTSVL RLKPPPGRNF SCVVWNTHVR
201  ELTLASIDLQ SQMEPRTEFE PKSCDKTHTC PPCPAPELLG GPSVFLFPPK
251  PKDTLMISRT PEVTCVVVDV SHEDPEVKFN WYVDGVEVHN AKTKPREEQY
301  NSTYRVVSVL TVLHQDWLNG KEYKCKVSNK ALPAPIEKTI SKAKGQPREP
351  QVYTLPPSRD ELTKNQVSLT CLVKGFYPSD IAVEWESNGQ PENNYKTTPP
401  VLDSDGSFFL YSKLTVDKSR WQQGNVFSCS VMHEALHNHY TQKSLSLSPG
451  K*
```

FIG. 7A

```
  1    agcttttcaa  tgtgaccagc  acactgagaa  tcaacacaac  aactaatgag
 51    attttctact  gcacttttag  gagattagat  cctgaggaaa  accatacagc
101    tgaattggtc  atcccagaac  tacctctggc  acatcctcca  aatgaaagga
151    ctcacttggt  aattctggga  gccatcttat  tatgccttgg  tgtagcactg
201    acattcatct  tccgtttaag  aaaagggaga  atgatggatg  tgaaaaaatg
251    tggcatccaa  gatacaaact  caaagaagca  aagtgataca  catttggagg
301    agacgtaatc  cagcattgga  acttctgatc  ttcaagcagg  gattctcaac
351    ctgtggttta  ggggttcatc  ggggctgagc  gtgacaagag  gaaggaatgg
401    gcccgtggga  tgcaggcaat  gtgggactta  aaaggcccaa  gcactgaaaa
451    tggaacctgg  cgaaacagag  gaggagaatg  aagaaagatg  gagtcaaaca
501    gggagcctgg  agggagacct  tgatactttc  aaatgcctga  ggggctcatc
551    gacgcctgtg  acagggagaa  aggatacttc  tgaacaagga  gcctccaagc
601    aaatcatcca  ttgctcatcc  taggaagacg  ggttgagaat  ccctaatttg
651    agggtcagtt  cctgca
```

FIG. 7B

```
   1    attcggctcg agggcgactg agccaggctg ggccgcgtcc ctgagtccca
  51    gagtcggcgc ggcgcggcag gggcagcctt ccaccacggg gagcccagct
 101    gtcagccgcc tcacaggaag atgctgcgtc ggcggggcag ccctggcatg
 151    ggtgtgcatg tgggtgcagc cctgggagca ctgtggttct gcctcacagg
 201    agccctggag gtccaggtcc ctgaagaccc agtggtggca ctggtgggca
 251    ccgatgccac cctgtgctgc tccttctccc tgagcctgg cttcagcctg
 301    gcacagctca acctcatctg gcagctgaca gataccaaac agctggtgca
 351    cagctttgct gagggccagg accagggcag cgcctatgcc aaccgcacgg
 401    ccctcttccc ggacctgctg gcacagggca acgcatccct gaggctgcag
 451    cgcgtgcgtg tggcggacga gggcagcttc acctgcttcg tgagcatccg
 501    ggatttcggc agcgctgccg tcagcctgca ggtggccgct ccctactcga
 551    agcccagcat gaccctggag cccaacaagg acctgcggcc aggggacacg
 601    gtgaccatca cgtgctccag ctaccagggc taccctgagg ctgaggtgtt
 651    ctggcaggat gggcagggtg tgcccctgac tggcaacgtg accacgtcgc
 701    agatggccaa cgagcagggc ttgtttgatg tgcacagcat cctgcgggtg
 751    gtgctgggtg caaatggcac ctacagctgc tggtgcgca ccccgtgct
 801    gcagcaggat gcgcacagct ctgtcaccat cacccccag agaagcccca
 851    caggagccgt ggaggtccag gtccctgagg acccggtggt ggccctagtg
 901    ggcaccgatg ccaccctgcg ctgctccttc tcccccgagc ctggcttcag
 951    cctggcacag ctcaacctca tctggcagct gacagacacc aaacagctgg
1001    tgcacagttt caccgaaggc cgggaccagg gcagcgccta tgccaaccgc
1051    acggccctct tcccggacct gctggcacaa ggcaatgcat ccctgaggct
1101    gcagcgcgtg cgtgtggcgg acgagggcag cttcacctgc ttcgtgagca
1151    tccgggattt cggcagcgct gccgtcagcc tgcaggtggc cgctccctac
1201    tcgaagccca gcatgaccct ggagcccaac aaggacctgc ggccagggga
1251    cacggtgacc atcacgtgct ccagctaccg ggctaccct gaggctgagg
1301    tgttctggca ggatgggcag ggtgtgcccc tgactggcaa cgtgaccacg
1351    tcgcagatgg ccaacgagca gggcttgttt gatgtgcaca gcgtcctgcg
1401    ggtggtgctg ggtgcgaatg cacctacag ctgcctggtg cgcaaccccg
1451    tgctgcagca ggatgcgcac ggctctgtca ccatcacagg gcagcctatg
1501    acattccccc cagaggccct gtgggtgacc gtggggctgt ctgtctgtct
1551    cattgcactg ctggtggccc tggctttcgt gtgctggaga aagatcaaac
1601    agagctgtga ggaggagaat gcaggagctg aggaccagga tggggaggga
1651    gaaggctcca agacagccct gcagcctctg aaacactctg acagcaaaga
1701    agatgatgga caagaaatag cctgaccatg aggaccaggg agctgctacc
1751    cctccctaca gctcctaccc tctggctgca atggggctgc actgtgagcc
1801    ctgccccaa cagatgcatc ctgctctgac aggtgggctc cttctccaaa
1851    ggatgcgata cacagaccac tgtgcagcct atttctcca atggacatga
1901    ttcccaagtc atcctgctgc ctttttctt atagacacaa tgaacagacc
1951    acccacaacc ttagttctct aagtcatcct gcctgctgcc ttatttcaca
2001    gtacatacat ttcttaggga cacagtacac tgaccacatc accaccctct
2051    tcttccagtg ctgcgtggac catctggctg cctttttct ccaaaagatg
```

FIG. 7B (CON'T)

```
2101  caatattcag actgactgac cccctgcctt atttcaccaa agacacgatg
2151  catagtcacc ccggccttgt ttctccaatg gccgtgatac actagtgatc
2201  atgttcagcc ctgcttccac ctgcatagaa tcttttcttc tcagacaggg
2251  acagtgcggc ctcaacatct cctggagtct agaagctgtt tcctttcccc
2301  tccttcctcc tcttgctcta gccttaatac tggccttttc cctccctgcc
2351  ccaagtgaag acagggcact ctgcgccac  cacatgcaca gctgtgcatg
2401  gagacctgca ggtgcacgtg ctggacacg  tgtggttccc ccctggccca
2451  gcctcctctg cagtgcccct ctccctgcc  catcctcccc acggaagcat
2501  gtgctggtca cactggttct ccaggggtct gtgatggggc cctgggggt
2551  cagcttctgt ccctctgcct tctcacctct ttgttccttt cttttcatgt
2601  atccattcag ttgatgttta ttgagcaact acagatgtca gcactgtgtt
2651  aggtgctggg ggcctgcgt  gggaagataa agttcctccc tcaaggactc
2701  cccatccagc tgggagacag acaactaact acactgcacc ctgcggtttg
2751  caggggggctc ctgcctggct ccctgctcca cacctcctct gtggctcaag
2801  gcttcctgga tacctcaccc ccatcccacc cataattctt acccagagca
2851  tggggttggg gcggaaacct ggagagaggg acatagcccc tcgccacggc
2901  tagagaatct ggtggtgtcc aaaatgtctg tccaggtgtg ggcaggtggg
2951  caggcaccaa ggccctctgg acctttcata gcagcagaaa aggcagagcc
3001  tggggcaggg cagggccagg aatgctttgg ggacaccgag gggactgccc
3051  cccacccca  ccatggtgct attctgggc  tggggcagtc ttttcctggc
3101  ttgcctctgg ccagctcctg gcctctggta gagtgagact tcagacgttc
3151  tgatgccttc cggatgtcat ctctccctgc cccaggaatg gaagatg
```

FIG. 7C

```
  1    ccggggtacc atgatcttcc tcctgctaat gttgagcctg gaattgcagc
 51    ttcaccagat agcagcttta ttcacagtga cagtccctaa ggaactgtac
101    ataatagagc atggcagcaa tgtgaccctg aatgcaact ttgacactgg
151    aagtcatgtg aaccttggag caataacagc cagtttgcaa aaggtggaaa
201    atgatacatc cccacaccgt gaaagagcca ctttgctgga ggagcagctg
251    cccctaggga aggcctcgtt ccacatacct caagtccaag tgagggacga
301    aggacagtac caatgcataa tcatctatgg ggtcgcctgg gactacaagt
351    acctgactct gaaagtcaaa gcttcctaca ggaaaataaa cactcacatc
401    ctaaaggttc cagaaacaga tgaggtagag ctcacctgcc aggctacagg
451    ttatcctctg gcagaagtat cctggccaaa cgtcagcgtt cctgccaaca
501    ccagccactc caggacccct gaaggcctct accaggtcac cagtgttctg
551    cgcctaaagc cacccctgg cagaaacttc agctgtgtgt tctggaatac
601    tcacgtgagg gaacttactt tggccagcat tgaccttcaa agtcagatgg
651    aacccaggac ccatccaact tggctgcttc acattttcat cccctcctgc
701    atcattgctt tcattttcat agccacagtg atagccctaa gaaaacaact
751    ctgtcaaaag ctgtattctt caaagacac aacaaaaaga cctgtcacca
801    caacaaagag ggaagtgaac agtgctatct gatctagagc gc
```

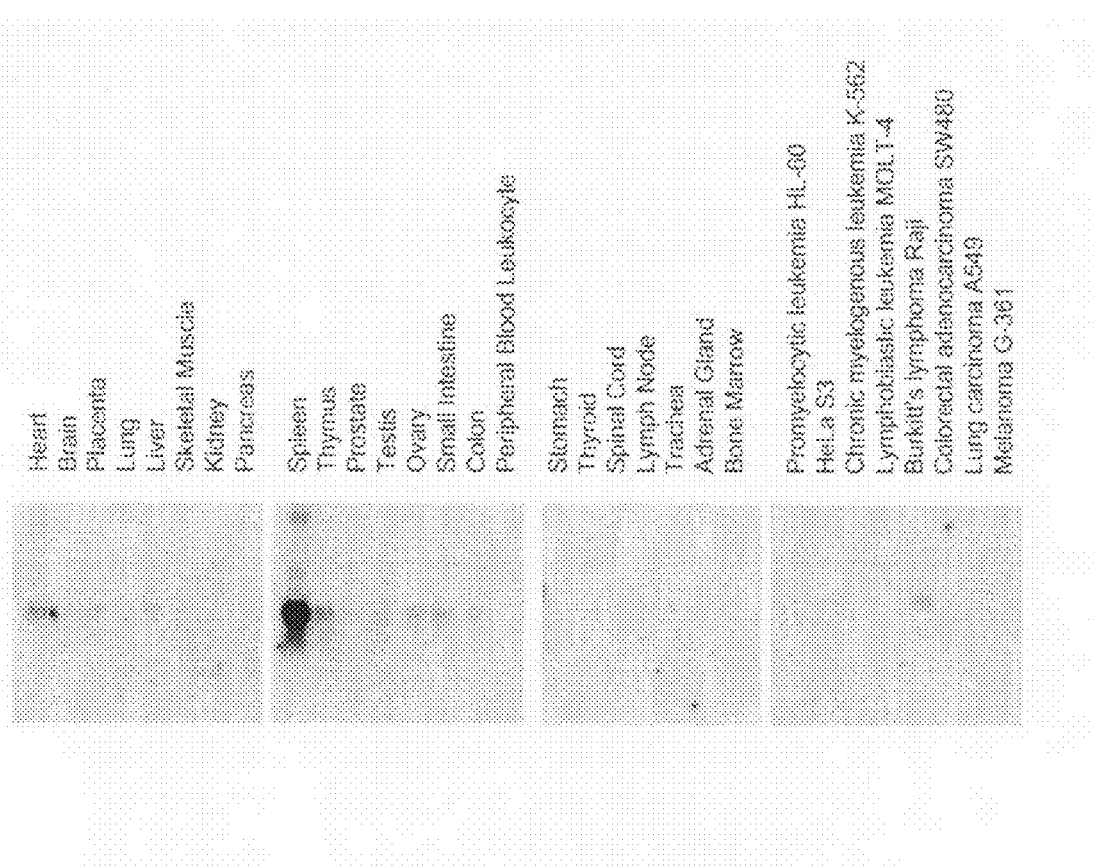

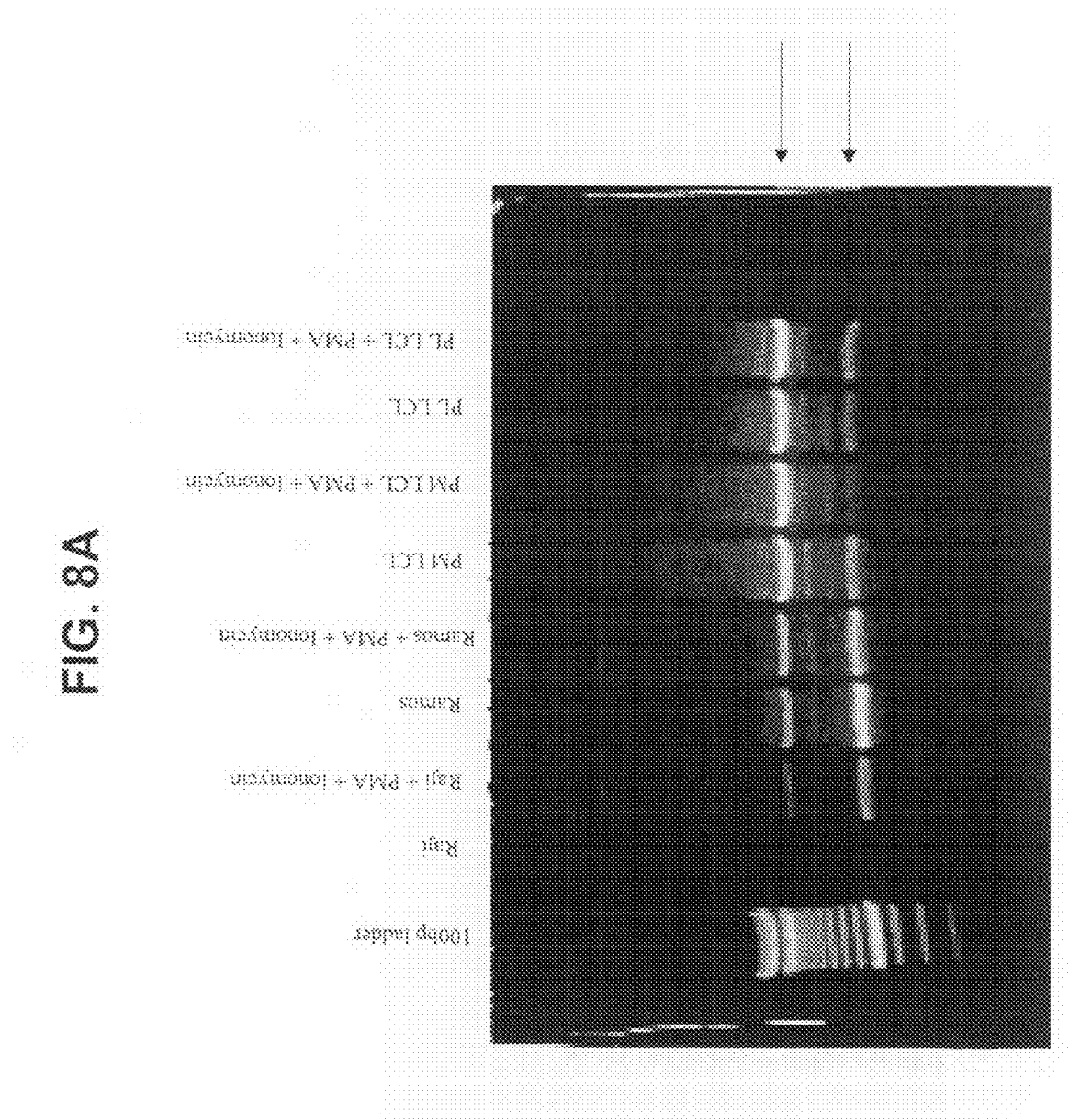

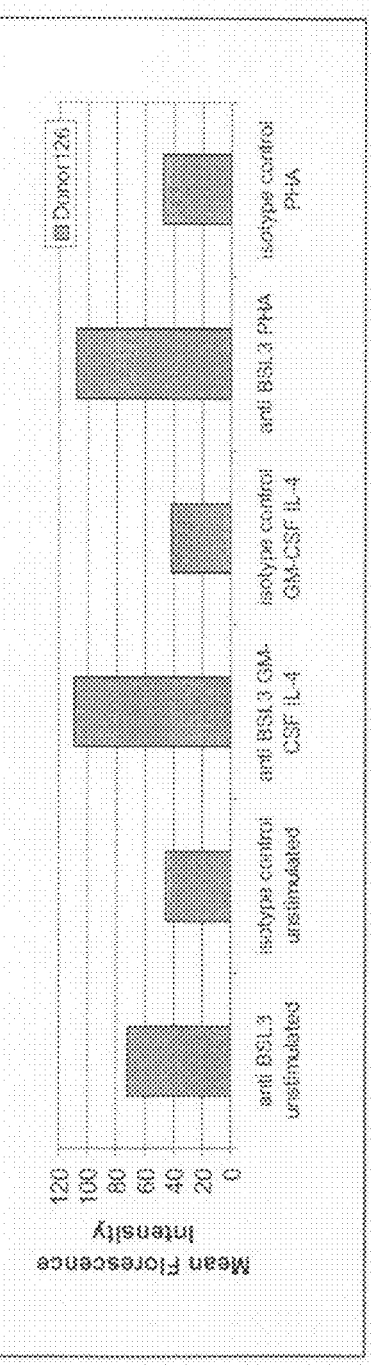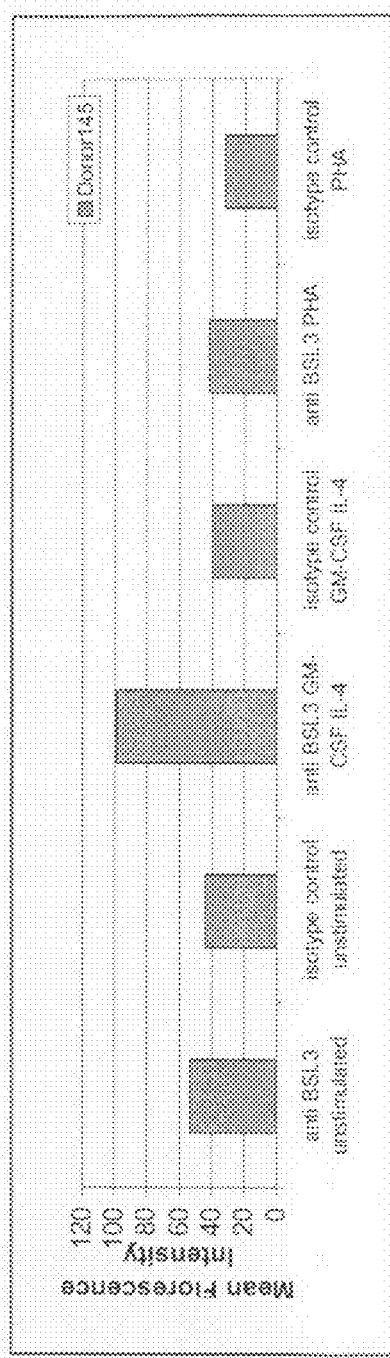

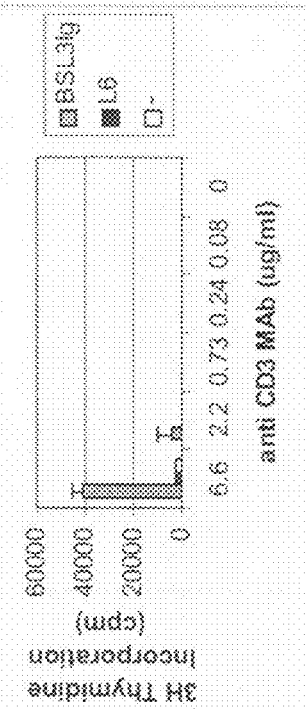
FIG. 10D
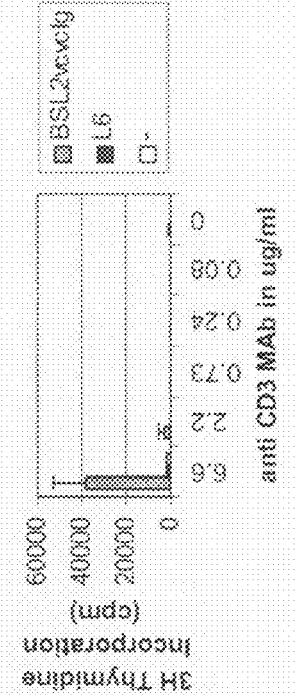
FIG. 10F
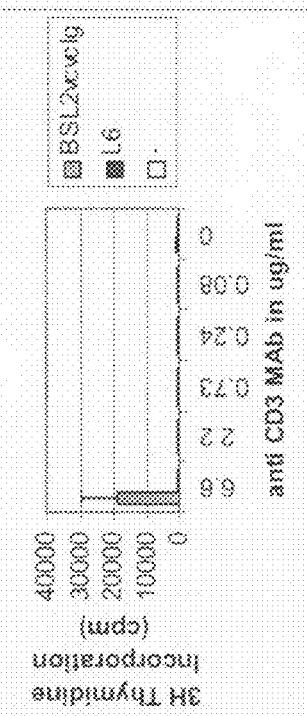
FIG. 10C
FIG. 10E

SEQUENCE LISTING

<160> NUMBER OF SEQ ID NOS: 94

<210> SEQ ID NO 1
<211> LENGTH: 1604
<212> TYPE: DNA
<213> ORGANISM: Homo sapiens

<400> SEQUENCE: 1

```
acgcgggggt gccgcgcggc cccagttctg cgcagcttcc cgaggctccg caccagccgc      60
gcttctgtcc gcctgcaggg cattccagaa agatgaggat atttgctgtc tttatattca     120
tgacctactg gcatttgctg aacgcattta ctgtcacggt tcccaaggac ctatatgtgg     180
tagagtatgg tagcaatatg acaattgaat gcaaattccc agtagaaaaa caattagacc     240
tggctgcact aattgtctat tgggaaatgg aggataagaa cattattcaa tttgtgcatg     300
gagaggaaga cctgaaggtt cagcatagta gctacagaca gagggcccgg ctgttgaagg     360
accagctctc cctgggaaat gctgcacttc agatcacaga tgtgaaattg caggatgcag     420
gggtgtaccg ctgcatgatc agctatggtg gtgccgacta caagcgaatt actgtgaaag     480
tcaatgcccc atacaacaaa atcaaccaaa gaattttggt tgtggatcca gtcacctctg     540
aacatgaact gacatgtcag gctgagggct acccccaagcc cgaagtcatc tggacaagca     600
gtgaccatca agtcctgagt ggtaagacca ccaccaccaa ttccaagaga gaggagaagc     660 tttttcaatgt gaccagcaca ctgagaatca acacaacaac taatgagatt ttctactgca     720
cttttaggag attagatcct gaggaaaaacc atacagctga attggtcatc ccagaactac     780
```

```
ctctggcaca tcctccaaat gaaaggactc acttggtaat tctgggagcc atcttattat      840
gccttggtgt agcactgaca ttcatcttcc gtttaagaaa agggagaatg atggatgtga      900
aaaaatgtgg catccaagat acaaactcaa agaagcaaag tgatacacat ttggaggaga      960
cgtaatccag cattggaact tctgatcttc aagcagggat tctcaacctg tggtttaggg     1020
gttcatcggg gctgagcgtg acaagaggaa ggaatgggcc cgtgggatgc aggcaatgtg     1080
ggacttaaaa ggcccaagca ctgaaaatgg aacctgcgaa agcagaggag gagaatgaag     1140
aaagatggag tcaaacaggg agcctggagg gagaccttga tactttcaaa tgcctgaggg     1200
gctcatcgac gcctgtgaca gggagaaagg atacttctga acaaggagcc tccaagcaaa     1260
tcatccattg ctcatcctag gaagacgggt tgagaatccc taatttgagg gtcagttcct     1320
gcagaagtgc cctttgcctc cactcaatgc ctcaatttct tttctgcatg actgagagtc     1380
tcagtgttgg aacgggacag tatttatgta tgagttttc ctatttattt tgagtctgtg     1440
aggtcttctt gtcatgtgag tgtggttgtg aatgatttct tttgaagata tattgtagta     1500
gatgttacaa ttttgtcgcc aaactaaact tgctgcttaa tgatttgctc acatctagta     1560
aaacatggag tattcaaaaa aaaaaaaaaa aaaaaaaaa aaaa                       1604

<210> SEQ ID NO 2
<211> LENGTH: 290
<212> TYPE: PRT
<213> ORGANISM: Homo sapiens

<400> SEQUENCE: 2

Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
             20                  25                  30

Gly Ser Asn Met Thr Ile Glu Cys Lys Phe Pro Val Glu Lys Gln Leu
         35                  40                  45

Asp Leu Ala Ala Leu Ile Val Tyr Trp Glu Met Glu Asp Lys Asn Ile
     50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
```

```
              225                 230                 235                 240
Leu Val Ile Leu Gly Ala Ile Leu Leu Cys Leu Gly Val Ala Leu Thr
                    245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 3
<211> LENGTH: 3600
<212> TYPE: DNA
<213> ORGANISM: Homo sapiens

<400> SEQUENCE: 3
```

| | | | | | |
|---|---|---|---|---|---|
| acgcggggt | gccgcgcggc | cccagttctg | cgcagcttcc | cgaggctccg | caccagccgc | 60 |
| gcttctgtcc | gcctgcaggg | cattccagaa | agatgaggat | atttgctgtc | tttatattca | 120 |
| tgacctactg | gcatttgctg | aacgcattta | ctgtcacggt | tcccaaggac | ctatatgtgg | 180 |
| tagagtatgg | tagcaatatg | acaattgaat | gcaaattccc | agtagaaaaa | caattagacc | 240 |
| tggctgcact | aattgtctat | tgggaaatgg | aggataagaa | cattattcaa | tttgtgcatg | 300 |
| gagaggaaga | cctgaaggtt | cagcatagta | gctacagaca | gagggcccgg | ctgttgaagg | 360 |
| accagctctc | cctgggaaat | gctgcacttc | agatcacaga | tgtgaaattg | caggatgcag | 420 |
| ggtgtaccg | ctgcatgatc | agctatggtg | gtgccgacta | caagcgaatt | actgtgaaag | 480 |
| tcaatgcccc | atacaacaaa | atcaaccaaa | gaattttggt | tgtggatcca | gtcacctctg | 540 |
| aacatgaact | gacatgtcag | gctgagggct | accccaaggc | cgaagtcatc | tggacaagca | 600 |
| gtgaccatca | agtcctgagt | ggtaagacca | ccaccaccaa | ttccaagaga | gaggagaagc | 660 |
| ttttcaatgt | gaccagcaca | ctgagaatca | acacaacaac | taatgagatt | ttctactgca | 720 |
| cttttaggag | attagatcct | gaggaaaacc | atacagctga | attggtcatc | ccagaactac | 780 |
| ctctggcaca | tcctccaaat | gaaaggactc | acttggtaat | tctgggagcc | atcttattat | 840 |
| gccttggtgt | agcactgaca | ttcatcttcc | gtttaagaaa | agggagaatg | atggatgtga | 900 |
| aaaaatgtgg | catccaagat | acaaactcaa | agaagcaaag | tgatacacat | ttggaggaga | 960 |
| cgtaatccag | cattggaact | tctgatcttc | aagcagggat | tctcaacctg | tggtttaggg | 1020 |
| gttcatcggg | gctgagcgtg | acaagaggaa | ggaatgggcc | cgtgggatgc | aggcaatgtg | 1080 |
| ggacttaaaa | ggcccaagca | ctgaaaatgg | aacctgcgaa | agcagaggag | gagaatgaag | 1140 |
| aaagatggag | tcaaacaggg | agcctggagg | gagaccttga | tactttcaaa | tgcctgaggg | 1200 |
| gctcatcgac | gcctgtgaca | gggagaaagg | atacttctga | caaggagcc | tccaagcaaa | 1260 |
| tcatccattg | ctcatcctag | gaagacgggt | tgagaatccc | taatttgagg | gtcagttcct | 1320 |
| gcagaagtgc | cctttgcctc | cactcaatgc | ctcaatttct | tttctgcatg | actgagagtc | 1380 |
| tcagtgttgg | aacggacag | tatttatgta | tgagttttc | ctatttattt | tgagtctgtg | 1440 |
| aggtcttctt | gtcatgtgag | tgtggttgtg | aatgatttct | tttgaagata | tattgtagta | 1500 |
| gatgttacaa | ttttgtcgcc | aaactaaact | tgctgcttaa | tgattgctc | acatctagta | 1560 |
| aaacatggag | tatttgtaag | gtgcttggtc | tcctctataa | ctacaagtat | acattggaag | 1620 |
| cataaagatc | aaaccgttgg | ttgcatagga | tgtcaccttt | atttaaccca | ttaatactct | 1680 |
| ggttgaccta | atcttattct | cagacctcaa | gtgtctgtgc | agtatctgtt | ccatttaaat | 1740 |

```
atcagcttta caattatgtg gtagcctaca cacataatct catttcatcg ctgtaaccac    1800
cctgttgtga taaccactat tattttaccc atcgtacagc tgaggaagca aacagattaa    1860
gtaacttgcc caaaccagta aatagcgagac ctcagactgc cacccactgt ccttttataa   1920
tacaatttac agctatattt tactttaagc aattcttta ttcaaaaacc atttattaag     1980
tgcccttgca atatcaatcg ctgtgccagg cattgaatct acagatgtga gcaagacaaa    2040
gtacctgtcc tcaaggagct catagtataa tgaggagatt aacaagaaaa tgtattatta   2100
caatttagtc cagtgtcata gcataaggat gatgcgaggg gaaaacccga gcagtgttgc    2160
caagaggagg aaataggcca atgtggtctg ggacggttgg atatacttaa acatcttaat   2220
aatcagagta atttttcattt acaaagagag gtcggtactt aaaataaccc tgaaaaataa  2280
cactggaatt cctttctag cattatattt attcctgatt tgcctttgcc atataatcta    2340
atgcttgttt atatagtgtc tggtattgtt taacagttct gtcttttcta tttaaatgcc   2400
actaaatttt aaattcatac ctttccatga ttcaaaattc aaaagatccc atgggagatg   2460
gttggaaaat ctccacttca tcctccaagc cattcaagtt tcctttccag aagcaactgc   2520
tactgccttt cattcatatg ttcttctaaa gatagtctac atttggaaat gtatgttaaa   2580
agcacgtatt tttaaaattt ttttcctaaa tagtaacaca ttgtatgtct gctgtgtact   2640
ttgctatttt tatttatttt agtgtttctt atatagcaga tggaatgaat ttgaagttcc   2700
cagggctgag gatccatgcc ttcttttgttt ctaagttatc tttcccatag cttttcatta 2760
tctttcatat gatccagtat atgttaaata tgtcctacat atacatttag acaaccacca   2820
tttgttaagt atttgctcta ggacagagtt tggatttgtt tatgtttgct caaaaggaga   2880
cccatgggct ctccagggtg cactgagtca atctagtcct aaaaagcaat cttattatta   2940
actctgtatg acagaatcat gtctggaact tttgttttct gctttctgtc aagtataaac   3000
ttcactttga tgctgtactt gcaaaatcac atttttcttc tggaaattcc ggcagtgtac   3060
cttgactgct agctaccctg tgccagaaaa gcctcattcg ttgtgcttga accctttgaat 3120 gccaccagct gtcatcacta cacagccctc ctaagaggct tcctggaggt ttcgagattc   3180
agatgccctg ggagatccca gagtttcctt tccctcttgg ccatattctg gtgtcaatga   3240
caaggagtac cttggctttg ccacatgtca aggctgaaga aacagtgtct ccaacgagc   3300 tccttgttat ctgtttgtac atgtgcattt gtacagtaat tggtgtgaca gtgttctttg   3360
tgtgaattac aggcaagaat tgtggctgag caaggcacat agtctactca gtctattcct   3420
aagtcctaac tcctccttgt ggtgttggat ttgtaaggca ctttatccct tttgtctcat   3480
gtttcatcgt aaatggcata ggcagagatg atacctaatt ctgcatttga ttgtcacttt   3540
ttgtacctgc attaatttaa taaaatattc ttatttattt tgttacttgg taaaaaaaaa   3600
```

<210> SEQ ID NO 4
<211> LENGTH: 1443
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 4

```
atgcccatgg ggtctctgca accgctggcc accttgtacc tgctggggat gctggtcgct      60
tcctgcctcg gaactagtgt tcccaaggac ctatatgtgg tagagtatgg tagcaatatg     120
acaattgaat gcaaattccc agtagaaaaa caattagacc tggctgcact aattgtctat    180
```

-continued

```
tgggaaatgg aggataagaa cattattcaa tttgtgcatg agaggaaga cctgaaggtt      240 cagcatagta gctacagaca gagggcccgg ctgttgaagg accagctctc cctgggaaat    300
gctgcacttc agatcacaga tgtgaaattg caggatgcag gggtgtaccg ctgcatgatc    360
agctatggtg gtgccgacta caagcgaatt actgtgaaag tcaatgcccc atacaacaaa    420
atcaaccaaa gaattttggt tgtggatcca gtcacctctg aacatgaact gacatgtcag    480
gctgagggct accccaaggc cgaagtcatc tggacaagca gtgaccatca agtcctgagt    540
ggtaagacca ccaccaccaa ttccaagaga gaggagaagc ttttcaatgt gaccagcaca    600
ctgagaatca acacaacaac taatgagatt ttctactgca ctttaggag attagatcct    660 gaggaaaacc atacagctga attggtcatc ccagaactac ctctggcaca tcctccaaat    720
gaaaggactc gaggagatcc cgaggagccc aaatcttgtg acaaaactca cacatgccca    780
ccgtgcccag cacctgaact cctgggggga ccgtcagtct tcctcttccc cccaaaaccc    840
aaggacaccc tcatgatctc ccggacccct gaggtcacat gcgtggtggt ggacgtgagc    900
cacgaagacc ctgaggtcaa gttcaactgg tacgtggacg gcgtggaggt gcataatgcc    960
aagacaaagc cgcgggagga gcagtacaac agcacgtacc gtgtggtcag cgtcctcacc    1020
gtcctgcacc aggactggct gaatggcaag gagtacaagt gcaaggtctc caacaaagcc    1080
ctcccagccc ccatcgagaa aaccatctcc aaagccaaag gcagccccg agaaccacag    1140 gtgtacaccc tgcccccatc ccgggatgag ctgaccaaga accaggtcag cctgacctgc    1200
ctggtcaaag gcttctatcc cagcgacatc gccgtggagt gggagagcaa tgggcagccg    1260
gagaacaact acaagaccac gcctcccgtg ctggactccg acggctcctt cttcctctac    1320
agcaagctca ccgtggacaa gagcaggtgg cagcagggga acgtcttctc atgctccgtg    1380
atgcatgagg ctctgcacaa ccactacacg cagaagagcc tctccctgtc tccgggtaaa    1440
tga                                                                   1443
```

<210> SEQ ID NO 5
<211> LENGTH: 480
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 5

```
Met Pro Met Gly Ser Leu Gln Pro Leu Ala Thr Leu Tyr Leu Leu Gly
  1               5                  10                  15

Met Leu Val Ala Ser Cys Leu Gly Thr Ser Val Pro Lys Asp Leu Tyr
             20                  25                  30

Val Val Glu Tyr Gly Ser Asn Met Thr Ile Glu Cys Lys Phe Pro Val
         35                  40                  45

Glu Lys Gln Leu Asp Leu Ala Ala Leu Ile Val Tyr Trp Glu Met Glu
     50                  55                  60

Asp Lys Asn Ile Ile Gln Phe Val His Gly Glu Glu Asp Leu Lys Val
 65                  70                  75                  80

Gln His Ser Ser Tyr Arg Gln Arg Ala Arg Leu Leu Lys Asp Gln Leu
                 85                  90                  95

Ser Leu Gly Asn Ala Ala Leu Gln Ile Thr Asp Val Lys Leu Gln Asp
            100                 105                 110

Ala Gly Val Tyr Arg Cys Met Ile Ser Tyr Gly Gly Ala Asp Tyr Lys
        115                 120                 125
```

```
Arg Ile Thr Val Lys Val Asn Ala Pro Tyr Asn Lys Ile Asn Gln Arg
    130                 135                 140

Ile Leu Val Val Asp Pro Val Thr Ser Glu His Glu Leu Thr Cys Gln
145                 150                 155                 160

Ala Glu Gly Tyr Pro Lys Ala Glu Val Ile Trp Thr Ser Ser Asp His
                165                 170                 175

Gln Val Leu Ser Gly Lys Thr Thr Thr Thr Asn Ser Lys Arg Glu Glu
            180                 185                 190

Lys Leu Phe Asn Val Thr Ser Thr Leu Arg Ile Asn Thr Thr Thr Asn
        195                 200                 205

Glu Ile Phe Tyr Cys Thr Phe Arg Arg Leu Asp Pro Glu Glu Asn His
    210                 215                 220

Thr Ala Glu Leu Val Ile Pro Glu Leu Pro Leu Ala His Pro Pro Asn
225                 230                 235                 240

Glu Arg Thr Arg Gly Asp Pro Glu Glu Pro Lys Ser Cys Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480

<210> SEQ ID NO 6
<211> LENGTH: 3197
<212> TYPE: DNA
<213> ORGANISM: Homo sapiens

<400> SEQUENCE: 6
attcggctcg agggcgactg agccaggctg ggccgcgtcc ctgagtccca gagtcggcgc      60
ggcgcggcag gggcagcctt ccaccacggg gagcccagct gtcagccgcc tcacaggaag     120
```

```
atgctgcgtc ggcggggcag ccctggcatg ggtgtgcatg tgggtgcagc cctgggagca    180
ctgtggttct gcctcacagg agccctggag gtccaggtcc ctgaagaccc agtggtggca    240
ctggtgggca ccgatgccac cctgtgctgc tccttctccc ctgagcctgg cttcagcctg    300
gcacagctca acctcatctg gcagctgaca gataccaaac agctggtgca cagctttgct    360
gagggccagg accagggcag cgcctatgcc aaccgcacgg ccctcttccc ggacctgctg    420
gcacagggca acgcatccct gaggctgcag cgcgtgcgtg tggcggacga gggcagcttc    480
acctgcttcg tgagcatccg ggatttcggc agcgctgccg tcagcctgca ggtggccgct    540
ccctactcga agcccagcat gaccctggag cccaacaagg acctgcggcc aggggacacg    600
gtgaccatca cgtgctccag ctaccagggc taccctgagg ctgaggtgtt ctggcaggat    660
gggcagggtg tgcccctgac tggcaacgtg accacgtcgc agatggccaa cgagcagggc    720
ttgtttgatg tgcacagcat cctgcgggtg gtgctgggtg caaatggcac ctacagctgc    780
ctggtgcgca accccgtgct gcagcaggat gcgcacagct ctgtcaccat cacaccccag    840
agaagcccca caggagccgt ggaggtccag gtccctgagg accggtggt ggccctagtg    900
ggcaccgatg ccaccctgcg ctgctccttc tcccccgagc ctggcttcag cctggcacag    960
ctcaacctca tctggcagct gacagacacc aaacagctgg tgcacagttt caccgaaggc    1020
cgggaccagg gcagcgccta tgccaaccgc acggccctct cccggacct gctggcacaa    1080
ggcaatgcat ccctgaggct gcagcgcgtg cgtgtggcgg acgagggcag cttcacctgc    1140
ttcgtgagca tccgggattt cggcagcgct gccgtcagcc tgcaggtggc cgctccctac    1200
tcgaagccca gcatgaccct ggagcccaac aaggacctgc ggccagggga cacggtgacc    1260
atcacgtgct ccagctaccg gggctaccct gaggctgagg tgttctggca ggatgggcag    1320
ggtgtgcccc tgactggcaa cgtgaccacg tcgcagatgg ccaacgagca gggcttgttt    1380
gatgtgcaca cgctcctgcg ggtggtgctg gtgcgaatg gcacctacag ctgcctggtg    1440
cgcaaccccg tgctgcagca ggatgcgcac ggctctgtca ccatcacagg gcagcctatg    1500
acattccccc cagaggccct gtgggtgacc gtggggctgt ctgtctgtct cattgcactg    1560
ctggtggccc tggctttcgt gtgctggaga aagatcaaac agagctgtga ggaggagaat    1620
gcaggagctg aggaccagga tgggagggga gaaggctcca agacagccct gcagcctctg    1680
aaacactctg acagcaaaga agatgatgga caagaaatag cctgaccatg aggaccaggg    1740
agctgctacc cctccctaca gctcctaccc tctggctgca atggggctgc actgtgagcc    1800
ctgcccccaa cagatgcatc ctgctctgac aggtgggctc cttctccaaa ggatgcgata    1860
cacagaccac tgtgcagcct tatttctcca atggacatga ttcccaagtc atcctgctgc    1920
cttttttctt atagacacaa tgaacagacc acccacaacc ttagttctct aagtcatcct    1980
gcctgctgcc ttatttcaca gtacatacat tcttaggga cacagtacac tgaccacatc    2040
accaccctct tcttccagtg ctgcgtggac catctggctg ccttttttct ccaaaagatg    2100
caatattcag actgactgac cccctgcctt atttcaccaa agacacgatg catagtcacc    2160
ccggccttgt ttctccaatg gccgtgatac actagtgatc atgttcagcc ctgcttccac    2220
ctgcatagaa tcttttcttc tcagacaggg acagtgcggc ctcaacatct cctggagtct    2280
agaagctgtt tcctttcccc tccttcctcc tcttgctcta gccttaatac tggccttttc    2340
cctccctgcc ccaagtgaag acagggcact ctgcgcccac cacatgcaca gctgtgcatg    2400
gagacctgca ggtgcacgtg ctggaacacg tgtggttccc cctggcccca gcctcctctg    2460
cagtgcccct ctcccctgcc catcctcccc acggaagcat gtgctggtca cactggttct    2520
```

```
ccaggggtct gtgatggggc ccctgggggt cagcttctgt ccctctgcct tctcacctct    2580 ttgttcctt cttttcatgt atccattcag ttgatgttta ttgagcaact acagatgtca    2640
gcactgtgtt aggtgctggg ggccctgcgt gggaagataa agttcctccc tcaaggactc    2700
cccatccagc tgggagacag acaactaact acactgcacc ctgcgtttg caggggctc     2760 ctgcctggct ccctgctcca cacctcctct gtggctcaag gcttcctgga tacctcaccc    2820
ccatcccacc cataattctt acccagagca tggggttggg gcggaaacct ggagagaggg    2880
acatagcccc tcgccacggc tagagaatct ggtggtgtcc aaaatgtctg tccaggtgtg    2940
ggcaggtggg caggcaccaa ggccctctgg acctttcata gcagcagaaa aggcagagcc    3000
tggggcaggg cagggccagg aatgctttgg ggacaccgag gggactgccc ccacccccca    3060
ccatggtgct attctggggc tggggcagtc ttttcctggc ttgcctctgg ccagctcctg    3120
gcctctggta gagtgagact tcagacgttc tgatgccttc cggatgtcat ctctccctgc    3180
cccaggaatg gaagatg                                                   3197
```

<210> SEQ ID NO 7
<211> LENGTH: 534
<212> TYPE: PRT
<213> ORGANISM: Homo sapiens

<400> SEQUENCE: 7

```
Met Leu Arg Arg Gly Ser Pro Gly Met Gly Val His Val Gly Ala
 1               5                  10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Ala
    65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
```

```
                   245                 250                 255
Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
            275                 280                 285

Asp Thr Lys Gln Leu Val His Ser Phe Thr Glu Gly Arg Asp Gln Gly
            290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
            325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
            355                 360                 365

Pro Asn Lys Asp Leu Arg Pro Gly Asp Thr Val Thr Ile Thr Cys Ser
            370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
            405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
            435                 440                 445

Ala His Gly Ser Val Thr Ile Thr Gly Gln Pro Met Thr Phe Pro Pro
            450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
            485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
            515                 520                 525

Asp Gly Gln Glu Ile Ala
            530

<210> SEQ ID NO 8
<211> LENGTH: 2097
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 8
atgctgcgtc ggcggggcag ccctggcatg ggtgtgcatg tgggtgcagc cctgggagca     60
ctgtggttct gcctcacagg agccctggag gtccaggtcc ctgaagaccc agtggtggca    120
ctggtgggca ccgatgccac cctgtgctgc tccttctccc tgagcctggc cttcagcctg    180
gcacagctca acctcatctg gcagctgaca gataccaaac agctggtgca cagctttgct    240
gagggccagg accagggcag cgcctatgcc aaccgcacgg ccctcttccc ggacctgctg    300
gcacagggca acgcatccct gaggctgcag cgcgtgcgtg tggcggacga gggcagcttc    360
```

-continued

```
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgctccag ctaccagggc taccctgagg ctgaggtgtt ctggcaggat     540
gggcagggtg tgccctgac tggcaacgtg accacgtcgc agatggccaa cgagcagggc      600
ttgtttgatg tgcacagcat cctgcgggtg gtgctgggtg caaatggcac ctacagctgc     660
ctggtgcgca acccgtgct gcagcaggat gcgcacagct ctgtcaccat cacacccag       720 agaagcccca caggagccgt ggaggtccag gtccctgagg accggtggt ggccctagtg      780 ggcaccgatg ccaccctgcg ctgctccttc tcccccgagc ctggcttcag cctggcacag    840
ctcaacctca tctggcagct gacagacacc aaacagctgg tgcacagttt caccgaaggc     900
cgggaccagg gcagcgccta tgccaaccgc acggccctct cccggacct gctggcacaa      960 ggcaatgcat ccctgaggct gcagcgcgtg cgtgtggcgg acgagggcag cttcacctgc    1020
ttcgtgagca tccgggattt cggcagcgct gccgtcagcc tgcaggtggc cgctccctac    1080
tcgaagccca gcatgaccct ggagcccaac aaggacctgc ggccagggga cacggtgacc    1140
atcacgtgct ccagctaccg ggctaccct gaggctgagg tgttctggca ggatgggcag     1200
ggtgtgcccc tgactggcaa cgtgaccacg tcgcagatgg ccaacgagca gggcttgttt    1260
gatgtgcaca gcatcctgcg ggtggtgctg ggtgcgaatg gcacctacag ctgcctggtg    1320
cgcaaccccg tgctgcagca ggatgcgcac ggctctgtca ccatcacagg gcagcctatg    1380
acattccccc cagaattcga gcccaaatct tgtgacaaaa ctcacacatg cccaccgtgc    1440
ccagcacctg aactcctggg gggaccgtca gtcttcctct tccccccaaa acccaaggac    1500
accctcatga tctcccggac ccctgaggtc acatgcgtgg tggtggacgt gagccacgaa    1560
gaccctgagg tcaagttcaa ctggtacgtg gacggcgtgg aggtgcataa tgccaagaca    1620
aagccgcggg aggagcagta caacagcacg taccgtgtgg tcagcgtcct caccgtcctg    1680
caccaggact ggctgaatgg caaggagtac aagtgcaagg tctccaacaa agccctccca    1740 gccccatcg agaaaaccat ctccaaagcc aaagggcagc cccgagaacc acaggtgtac     1800
accctgcccc catcccggga tgagctgacc aagaaccagg tcagcctgac ctgcctggtc    1860
aaaggcttct atcccagcga catcgccgtg gagtgggaga gcaatgggca gccggagaac    1920
aactacaaga ccacgcctcc cgtgctggac tccgacggct ccttcttcct ctacagcaag    1980
ctcaccgtgg acaagagcag gtggcagcag gggaacgtct tctcatgctc cgtgatgcat    2040
gaggctctgc acaaccacta cacgcagaag agcctctccc tgtctccggg taaatga       2097
```

<210> SEQ ID NO 9
<211> LENGTH: 698
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 9

```
Met Leu Arg Arg Arg Gly Ser Pro Gly Met Gly Val His Val Gly Ala
 1               5                  10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
```

-continued

```
                50                  55                  60
Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
                100                 105                 110

Arg Val Ala Asp Glu Gly Ser Phe Thr Cys Phe Val Ser Ile Arg Asp
                115                 120                 125

Phe Gly Ser Ala Ala Val Ser Leu Gln Val Ala Ala Pro Tyr Ser Lys
                130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Ile Leu
                195                 200                 205

Arg Val Val Leu Gly Ala Asn Gly Thr Tyr Ser Cys Leu Val Arg Asn
                210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
                275                 280                 285

Asp Thr Lys Gln Leu Val His Ser Phe Thr Glu Gly Arg Asp Gln Gly
                290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
                340                 345                 350

Ser Leu Gln Val Ala Ala Pro Tyr Ser Lys Pro Ser Met Thr Leu Glu
                355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
                420                 425                 430

Asn Gly Thr Tyr Ser Cys Leu Val Arg Asn Pro Val Leu Gln Gln Asp
                435                 440                 445

Ala His Gly Ser Val Thr Ile Thr Gly Gln Pro Met Thr Phe Pro Pro
                450                 455                 460

Glu Phe Glu Pro Lys Ser Cys Asp Lys Thr His Thr Cys Pro Pro Cys
465                 470                 475                 480
```

```
Pro Ala Pro Glu Leu Leu Gly Gly Pro Ser Val Phe Leu Phe Pro Pro
            485                 490                 495

Lys Pro Lys Asp Thr Leu Met Ile Ser Arg Thr Pro Glu Val Thr Cys
            500                 505                 510

Val Val Val Asp Val Ser His Glu Asp Pro Glu Val Lys Phe Asn Trp
            515                 520                 525

Tyr Val Asp Gly Val Glu Val His Asn Ala Lys Thr Lys Pro Arg Glu
            530                 535                 540

Glu Gln Tyr Asn Ser Thr Tyr Arg Val Val Ser Val Leu Thr Val Leu
545                 550                 555                 560

His Gln Asp Trp Leu Asn Gly Lys Glu Tyr Lys Cys Lys Val Ser Asn
            565                 570                 575

Lys Ala Leu Pro Ala Pro Ile Glu Lys Thr Ile Ser Lys Ala Lys Gly
            580                 585                 590

Gln Pro Arg Glu Pro Gln Val Tyr Thr Leu Pro Pro Ser Arg Asp Glu
            595                 600                 605

Leu Thr Lys Asn Gln Val Ser Leu Thr Cys Leu Val Lys Gly Phe Tyr
            610                 615                 620

Pro Ser Asp Ile Ala Val Glu Trp Glu Ser Asn Gly Gln Pro Glu Asn
625                 630                 635                 640

Asn Tyr Lys Thr Thr Pro Pro Val Leu Asp Ser Asp Gly Ser Phe Phe
            645                 650                 655

Leu Tyr Ser Lys Leu Thr Val Asp Lys Ser Arg Trp Gln Gln Gly Asn
            660                 665                 670

Val Phe Ser Cys Ser Val Met His Glu Ala Leu His Asn His Tyr Thr
            675                 680                 685

Gln Lys Ser Leu Ser Leu Ser Pro Gly Lys
            690                 695

<210> SEQ ID NO 10
<211> LENGTH: 951
<212> TYPE: DNA
<213> ORGANISM: Homo sapiens

<400> SEQUENCE: 10
atgctgcgtc ggcggggcag ccctggcatg ggtgtgcatg tgggtgcagc cctgggagca    60
ctgtggttct gcctcacagg agccctggag gtccaggtcc ctgaagaccc agtggtggca   120
ctggtgggca ccgatgccac cctgcgctgc tccttctccc ccgagcctgg cttcagcctg   180
gcacagctca acctcatctg cagctgacag acaccaaac agctggtgca cagtttcacc   240
gaaggccggg accagggcag cgcctatgcc aaccgcacgg ccctcttccc ggacctgctg   300
gcacaaggca atgcatccct gaggctgcag cgcgtgcgtg tggcggacga gggcagcttc   360
acctgcttcg tgagcatccg ggatttcggc agcgctgccg tcagcctgca ggtggccgct   420
ccctactcga agcccagcat gaccctggag cccaacaagg acctgcggcc aggggacacg   480
gtgaccatca cgtgctccag ctaccggggc taccctgagg ctgaggtgtt ctggcaggat   540
gggcagggtg tgcccctgac tggcaacgtg accacgtcgc agatggccaa cgagcagggc   600
ttgtttgatg tgcacagcgt cctgcgggtg gtgctgggtg cgaatggcac ctacagctgc   660
ctggtgcgca cccgtgctgc agcaggat gcgcacggct ctgtcaccat cacagggcag   720
cctatgacat ccccccagac ggccctgtgg tgaccgtgg ggtgtctgt ctgtctcatt   780
gcactgctgg tggccctggc tttcgtgtgc tggagaaaga tcaaacagag ctgtgaggag   840
```

```
gagaatgcag gagctgagga ccaggatggg gagggagaag gctccaagac agccctgcag    900
cctctgaaac actctgacag caaagaagat gatggacaag aaatagcctg a             951
```

<210> SEQ ID NO 11
<211> LENGTH: 316
<212> TYPE: PRT
<213> ORGANISM: Homo sapiens

<400> SEQUENCE: 11

```
Met Leu Arg Arg Arg Gly Ser Pro Gly Met Gly Val His Val Gly Ala
 1               5                  10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Arg Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Thr
 65                  70                  75                  80

Glu Gly Arg Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
           100                 105                 110

Arg Val Ala Asp Glu Gly Ser Phe Thr Cys Phe Val Ser Ile Arg Asp
       115                 120                 125

Phe Gly Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315
```

<210> SEQ ID NO 12
<211> LENGTH: 951
<212> TYPE: DNA
<213> ORGANISM: Homo sapiens

<400> SEQUENCE: 12

```
atgctgcgtc ggcggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc ctgagcctgg cttcagcctg     180
gcacagctca acctcatctg gcagctgaca gataccaaac agctggtgca cagctttgct     240
gagggccagg accagggcag cgcctatgcc aaccgcacgg ccctcttccc ggacctgctg     300
gcacaaggca atgcatccct gaggctgcag cgcgtgcgtg tggcggacga gggcagcttc     360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgctccag ctaccgggc taccctgagg ctgaggtgtt ctggcaggat     540
gggcagggtg tgcccctgac tggcaacgtg accacgtcgc agatggccaa cgagcagggc     600
ttgtttgatg tgcacagcgt cctgcgggtg gtgctgggtg cgaatggcac ctacagctgc     660
ctggtgcgca cccccgtgct gcagcaggat gcgcacggct ctgtcaccat cacagggcag     720
cctatgacat ccccccagat ggccctgtgg gtgaccgtgg ggctgtctgt ctgtctcatt     780
gcactgctgg tggccctggc tttcgtgtgc tggagaaaga tcaaacagag ctgtgaggag     840
gagaatgcag gagctgagga ccaggatggg gagggagaaa gctccaagac agccctgcag     900 cctctgaaaac actctgacag caaagaagat gatggacaag aaatagcctg a             951
```

<210> SEQ ID NO 13
<211> LENGTH: 316
<212> TYPE: PRT
<213> ORGANISM: Homo sapiens

<400> SEQUENCE: 13

```
Met Leu Arg Arg Arg Gly Ser Pro Gly Met Gly Val His Val Gly Ala
 1               5                  10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
         35                  40                  45

Cys Cys Ser Phe Ser Pro Glu Pro Gly Phe Ser Leu Ala Gln Leu Asn
     50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205
```

```
Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Ser Ser Lys Thr Ala Leu Gln Pro Leu Lys His
    290                 295                 300

Ser Asp Ser Lys Glu Asp Asp Gly Gln Glu Ile Ala
305                 310                 315

<210> SEQ ID NO 14
<211> LENGTH: 2435
<212> TYPE: DNA
<213> ORGANISM: Homo sapiens

<400> SEQUENCE: 14
gctttcgtca gttcctcaga actagttctg gtttgactca ctctcatgtt acggcaaacc      60
ttaagctgaa tgaacaactt ttcttctctt gaatatatct taacgccaaa ttttgagtgc     120
ttttttgtta cccatcctca tatgtcccag ctggaaagaa tcctgggttg gagctactgc     180
atgttgattg ttttgttttt ccttttggct gttcattttg gtggctacta taggaaaatc     240
taacacaaac agcaactgtt ttttgttgtt tactttttgca tctttacttg tggagctgtg     300
gcaagtcctc atatcaaata cagaacatga tcttcctcct gctaatgttg agcctggaat     360
tgcagcttca ccagatagca gctttattca cagtgacagt ccctaaggaa ctgtacataa     420
tagagcatgg cagcaatgtg accctggaat gcaactttga cactggaagt catgtgaacc     480
ttggagcaat aacagccagt ttgcaaaagg tggaaaatga tacatcccca caccgtgaaa     540
gagccacttt gctggaggag cagctgcccc tagggaaggc ctcgttccac atacctcaag     600
tccaagtgag ggacgaagga cagtaccaat gcataatcat ctatgggtc gcctgggact     660
acaagtacct gactctgaaa gtcaaagctt cctacaggaa aataaacact cacatcctaa     720
aggttccaga aacagatgag gtagagctca cctgccaggc tacaggttat cctctggcag     780
aagtatcctg gccaaacgtc agcgttcctg ccaacaccag ccactccagg acccctgaag     840
gcctctacca ggtcaccagt gttctgcgcc taaagccacc ccctggcaga aacttcagct     900
gtgtgttctg gaatactcac gtgagggaac ttactttggc cagcattgac cttcaaagtc     960
agatggaacc caggacccat ccaacttggc tgcttcacat tttcatcccc tcctgcatca    1020
ttgctttcat tttcatagcc acagtgatag ccctaagaaa acaactctgt caaaagctgt    1080
attcttcaaa agacacaaca aaaagacctg tcaccacaac aaagagggaa gtgaacagtg    1140
ctatctgaac ctgtggtctt gggagccagg gtgacctgat atgacatcta agaagcttc    1200
tggactctga acaagaattc ggtggcctgc agagcttgcc atttgcactt ttcaaatgcc    1260
tttgatgac ccagcacttt aatctgaaac ctgcaacaag actagccaac acctggccat    1320
gaaacttgcc ccttcactga tctggactca cctctggagc ctatggcttt aagcaagcac    1380
tactgcactt tacagaatta ccccactgga tcctggaccc acagaattcc ttcaggatcc    1440
ttcttgctgc cagactgaaa gcaaaaggaa ttatttcccc tcaagttttc taagtgattt    1500
```

-continued

```
ccaaaagcag aggtgtgtgg aaatttccag taacagaaac agatgggttg ccaatagagt   1560 tatttttttat ctatagcttc ctctgggtac tagaagaggc tattgagact atgagctcac   1620
agacagggct tcgcacaaac tcaaatcata attgacatgt tttatggatt actggaatct   1680
tgatagcata atgaagttgt tctaattaac agagagcatt taaatataca ctaagtgcac   1740
aaattgtgga gtaaagtcat caagctctgt ttttgaggtc taagtcacaa agcatttgtt   1800
ttaacctgta atggcaccat gtttaatggt ggttttttt ttgaactaca tctttccttt    1860
aaaaattatt ggtttctttt tatttgtttt taccttagaa atcaattata tacagtcaaa   1920
aatatttgat atgctcatac gttgtatctg cagcaatttc agataagtag ctaaaatggc   1980
caaagcccca aactaagcct ccttttctgg ccctcaatat gactttaaat ttgactttc   2040 agtgcctcag tttgcacatc tgtaatacag caatgctaag tagtcaaggc ctttgataat   2100
tggcactatg gaaatcctgc aagatcccac tacatatgtg tggagcagaa gggtaactcg   2160
gctacagtaa cagcttaatt ttgttaaatt tgttctttat actggagcca tgaagctcag   2220
agcattagct gacccttgaa ctattcaaat gggcacatta gctagtataa cagacttaca   2280
taggtgggcc taaagcaagc tccttaactg agcaaaattt ggggcttatg agaatgaaag   2340
ggtgtgaaat tgactaacag acaaatcata catctcagtt tctcaattct catgtaaatc   2400
agagaatgcc tttagaaatt accaaagtgt tccat                              2435
```

<210> SEQ ID NO 15
<211> LENGTH: 273
<212> TYPE: PRT
<213> ORGANISM: Homo sapiens

<400> SEQUENCE: 15

Met Ile Phe Leu Leu Met Leu Ser Leu Glu Leu Gln Leu His Gln
 1               5                  10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
    65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
               100                 105                 110

Lys Tyr Leu Thr Leu Lys Val Lys Ala Ser Tyr Arg Lys Ile Asn Thr
           115                 120                 125

His Ile Leu Lys Val Pro Glu Thr Asp Glu Val Glu Leu Thr Cys Gln
       130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Lys Arg Glu Val Asn Ser Ala
            260                 265                 270

Ile

<210> SEQ ID NO 16
<211> LENGTH: 1356
<212> TYPE: DNA
<213> ORGANISM: Artificial Sequence
<220> FEATURE:
<223> OTHER INFORMATION: Description of Artificial Sequence: Synthetic
      fusion construct

<400> SEQUENCE: 16
atgatcttcc tcctgctaat gttgagcctg gaattgcagc ttcaccagat agcagcttta        60
ttcacagtga cagtccctaa ggaactgtac ataatagagc atggcagcaa tgtgaccctg       120
gaatgcaact tgacactgg aagtcatgtg aaccttggag caataacagc cagttttgcaa       180
aaggtggaaa atgatacatc cccacaccgt gaaagagcca ctttgctgga ggagcagctg       240
cccctaggga aggcctcgtt ccacatacct caagtccaag tgagggacga aggacagtac       300
caatgcataa tcatctatgg ggtcgcctgg gactacaagt acctgactct gaaagtcaaa       360
gcttcctaca ggaaaataaa cactcacatc ctaaaggttc cagaaacaga tgaggtagag       420
ctcacctgcc aggctacagg ttatcctctg cagaagtat cctggccaaa cgtcagcgtt        480
cctgccaaca ccagccactc caggaccccct gaaggcctct accaggtcac cagtgttctg      540
cgcctaaagc caccccctgg cagaaacttc agctgtgtgg tctggaatac tcacgtgagg       600
gaacttactt tggccagcat tgaccttcaa agtcagatgg aacccaggac cgaattcgag       660
cccaaatctt gtgacaaaac tcacacatgc ccaccgtgcc cagcacctga actcctgggg       720
ggaccgtcag tcttcctctt ccccccaaaa cccaaggaca cctcatgat ctcccggacc        780
cctgaggtca catgcgtggt ggtggacgtg agccacgaag accctgaggt caagttcaac       840
tggtacgtgg acggcgtgga ggtgcataat gccaagacaa agccgcggga ggagcagtac       900
aacagcacgt accgtgtggt cagcgtcctc accgtcctgc accaggactg gctgaatggc       960
aaggagtaca agtgcaaggt ctccaacaaa gccctcccag cccccatcga gaaaaccatc      1020
tccaaagcca aagggcagcc ccgagaacca caggtgtaca ccctgccccc atcccgggat      1080
gagctgacca agaaccaggt cagcctgacc tgcctggtca aaggcttcta tcccagcgac      1140
atcgccgtgg agtgggagag caatgggcag ccggagaaca actacaagac cacgcctccc      1200
gtgctggact ccgacggctc cttcttcctc tacagcaagc tcaccgtgga caagagcagg      1260
tggcagcagg ggaacgtctt ctcatgctcc gtgatgcatg aggctctgca caaccactac      1320
acgcagaaga gcctctccct gtctccgggt aaatga                                1356

<210> SEQ ID NO 17
<211> LENGTH: 451
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 17

```
Met Ile Phe Leu Leu Leu Met Leu Ser Leu Glu Leu Gln Leu His Gln
  1               5                  10                  15

Ile Ala Ala Leu Phe Thr Val Thr Val Pro Lys Glu Leu Tyr Ile Ile
             20                  25                  30

Glu His Gly Ser Asn Val Thr Leu Glu Cys Asn Phe Asp Thr Gly Ser
         35                  40                  45

His Val Asn Leu Gly Ala Ile Thr Ala Ser Leu Gln Lys Val Glu Asn
     50                  55                  60

Asp Thr Ser Pro His Arg Glu Arg Ala Thr Leu Leu Glu Glu Gln Leu
 65                  70                  75                  80

Pro Leu Gly Lys Ala Ser Phe His Ile Pro Gln Val Gln Val Arg Asp
                 85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Val Trp Asn Thr His Val Arg Glu Leu Thr Leu Ala Ser Ile Asp
        195                 200                 205

Leu Gln Ser Gln Met Glu Pro Arg Thr Glu Phe Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 18
<211> LENGTH: 666
<212> TYPE: DNA
<213> ORGANISM: Homo sapiens

<400> SEQUENCE: 18
agcttttcaa tgtgaccagc acactgagaa tcaacacaac aactaatgag attttctact      60
gcacttttag gagattagat cctgaggaaa accatacagc tgaattggtc atcccagaac     120
tacctctggc acatcctcca aatgaaagga ctcacttggt aattctggga gccatcttat     180
tatgccttgg tgtagcactg acattcatct tccgtttaag aaaagggaga atgatggatg     240
tgaaaaaatg tggcatccaa atacaaact caaagaagca aagtgataca catttggagg      300
agacgtaatc cagcattgga acttctgatc ttcaagcagg gattctcaac ctgtggttta     360
ggggttcatc ggggctgagc gtgacaagag aaggaatgg gcccgtggga tgcaggcaat      420
gtgggactta aaaggcccaa gcactgaaaa tggaacctgg cgaaacagag aggagaatg      480
aagaaagatg gagtcaaaca gggagcctgg agggagacct tgatactttc aaatgcctga    540
ggggctcatc gacgcctgtg acagggagaa aggatacttc tgaacaagga gcctccaagc    600
aaatcatcca ttgctcatcc taggaagacg ggttgagaat ccctaatttg agggtcagtt    660
cctgca                                                                666

<210> SEQ ID NO 19
<211> LENGTH: 3197
<212> TYPE: DNA
<213> ORGANISM: Homo sapiens

<400> SEQUENCE: 19
attcggctcg agggcgactg agccaggctg ggccgcgtcc ctgagtccca gagtcggcgc      60
ggcgcggcag gggcagcctt ccaccacggg gagcccagct gtcagccgcc tcacaggaag     120
atgctgcgtc ggcggggcag ccctggcatg ggtgtgcatg tgggtgcagc cctgggagca     180
ctgtggttct gcctcacagg agccctggag gtccaggtcc ctgaagaccc agtggtggca     240
ctggtgggca ccgatgccac cctgtgctgc tccttctccc ctgagcctgg cttcagcctg     300
gcacagctca acctcatctg gcagctgaca gataccaaac agctggtgca gagctttgct     360
gagggccagg accagggcag cgcctatgcc aaccgcacgg ccctcttccc ggacctgctg     420
gcacagggca acgcatccct gaggctgcag cgcgtgcgtg tggcggacga gggcagcttc     480
acctgcttcg tgagcatccg ggatttcggc agcgctgccg tcagcctgca ggtggccgct     540
ccctactcga agcccagcat gaccctggag cccaacaagg acctgcggcc aggggacacg     600
gtgaccatca cgtgctccag ctaccagggc taccctgagg ctgaggtgtt ctggcaggat     660
gggcagggtg tgccctgac tggcaacgtg accacgtcgc agatggccaa cgagcagggc     720
ttgtttgatg tgcacagcat cctgcgggtg gtgctgggtg caaatggcac ctacagctgc     780
ctggtgcgca accccgtgct gcagcaggat gcgcacagct ctgtcaccat cacaccccag     840
```

```
agaagcccca caggagccgt ggaggtccag gtccctgagg acccggtggt ggccctagtg     900
ggcaccgatg ccaccctgcg ctgctccttc tcccccgagc ctggcttcag cctggcacag     960
ctcaacctca tctggcagct gacagacacc aaacagctgg tgcacagttt caccgaaggc    1020
cgggaccagg gcagcgccta tgccaaccgc acggccctct tcccggacct gctggcacaa    1080
ggcaatgcat ccctgaggct gcagcgcgtg cgtgtggcgg acgagggcag cttcacctgc    1140
ttcgtgagca tccgggattt cggcagcgct gccgtcagcc tgcaggtggc cgctccctac    1200
tcgaagccca gcatgaccct ggagcccaac aaggacctgc ggccagggga cacggtgacc    1260
atcacgtgct ccagctaccg gggctaccct gaggctgagg tgttctggca ggatgggcag    1320
ggtgtgcccc tgactggcaa cgtgaccacg tcgcagatgg ccaacgagca gggcttgttt    1380
gatgtgcaca gcgtcctgcg ggtggtgctg ggtgcgaatg cacctacag ctgcctggtg     1440
cgcaaccccg tgctgcagca ggatgcgcac ggctctgtca ccatcacagg gcagcctatg    1500
acattccccc cagaggccct gtgggtgacc gtggggctgt ctgtctgtct cattgcactg    1560
ctggtggccc tggcttttcgt gtgctggaga aagatcaaac agagctgtga ggaggagaat    1620
gcaggagctg aggaccagga tggggaggga gaaggctcca agacagccct gcagcctctg    1680
aaacactctg acagcaaaga agatgatgga caagaaatag cctgaccatg aggaccaggg    1740
agctgctacc cctccctaca gctcctaccc tctggctgca atgggctgc actgtgagcc     1800
ctgcccccaa cagatgcatc ctgctctgac aggtgggctc cttctccaaa ggatgcgata    1860
cacagaccac tgtgcagcct tatttctcca atggacatga ttcccaagtc atcctgctgc    1920
ctttttcctt atagacacaa tgaacagacc acccacaacc ttagttctct aagtcatcct    1980
gcctgctgcc ttatttcaca gtacatacat ttcttaggga cacagtacac tgaccacatc    2040
accaccctct tcttccagtg ctgcgtggac catctggctg ccttttttct ccaaaagatg    2100
caatattcag actgactgac ccctgccctt atttcaccaa agacacgatg catagtcacc    2160
ccggccttgt ttctccaatg gccgtgatac actagtgatc atgttcagcc ctgcttccac    2220
ctgcatagaa tcttttcttc tcagacaggg acagtgcggc ctcaacatct cctggagtct    2280
agaagctgtt tcctttcccc tccttcctcc tcttgctcta gccttaatac tggccttttc    2340
cctccctgcc ccaagtgaag acagggcact ctgcgcccac cacatgcaca gctgtgcatg    2400
gagacctgca ggtgcacgtg ctggaacacg tgtggttccc ccctggccca gcctcctctg    2460
cagtgccct ctcccctgcc catcctcccc acggaagcat gtgctggtca cactggttct     2520
ccagggggtct gtgatgggc ccctggggggt cagcttctgt ccctctgcct tctcacctct   2580
ttgttccttt cttttcatgt atccattcag ttgatgttta ttgagcaact acagatgtca    2640
gcactgtgtt aggtgctggg ggccctgcgt gggaagataa agttcctccc tcaaggactc    2700
cccatccagc tgggagacag acaactaact acactgcacc ctgcggtttg caggggctc     2760
ctgcctggct ccctgctcca cacctcctct gtggctcaag gcttcctgga tacctcaccc    2820
ccatcccacc cataattctt acccagagca tgggttggg gcggaaacct ggagagaggg     2880
acatagcccc tcgccacggc tagagaatct ggtggtgtcc aaaatgtctg tccaggtgtg    2940
ggcaggtggg caggcaccaa ggccctctgg acctttcata gcagcagaaa aggcagagcc    3000
tggggcaggg cagggccagg aatgctttgg ggacaccgag gggactgccc cccaccccca    3060
ccatggtgct attctgggc tggggcagtc ttttcctggc ttgcctctgg ccagctcctg     3120
gcctctggta gagtgagact tcagacgttc tgatgccttc cggatgtcat ctctccctgc    3180
```

```
cccaggaatg gaagatg                                                  3197
```

<210> SEQ ID NO 20
<211> LENGTH: 842
<212> TYPE: DNA
<213> ORGANISM: Homo sapiens

<400> SEQUENCE: 20

```
ccggggtacc atgatcttcc tcctgctaat gttgagcctg gaattgcagc ttcaccagat    60
agcagcttta ttcacagtga cagtccctaa ggaactgtac ataatagagc atggcagcaa   120
tgtgaccctg aatgcaact ttgacactgg aagtcatgtg aaccttggag caataacagc    180
cagtttgcaa aaggtggaaa atgatacatc cccacaccgt gaaagagcca ctttgctgga   240
ggagcagctg cccctaggga aggcctcgtt ccacatacct caagtccaag tgagggacga   300
aggacagtac caatgcataa tcatctatgg ggtcgcctgg gactacaagt acctgactct   360
gaaagtcaaa gcttcctaca ggaaaataaa cactcacatc ctaaaggttc cagaaacaga   420
tgaggtagag ctcacctgcc aggctacagg ttatcctctg gcagaagtat cctggccaaa   480
cgtcagcgtt cctgccaaca ccagccactc caggacccct gaaggcctct accaggtcac   540
cagtgttctg cgcctaaagc cacccctgg cagaaacttc agctgtgtgt tctggaatac   600
tcacgtgagg gaacttactt tggccagcat tgaccttcaa agtcagatgg aacccaggac   660
ccatccaact tggctgcttc acattttcat ccccctcctgc atcattgctt tcattttcat   720
agccacagtg atagccctaa gaaaacaact ctgtcaaaag ctgtattctt caaaagacac   780
aacaaaaaga cctgtcacca acaaagag ggaagtgaac agtgctatct gatctagagc    840
gc                                                                 842
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21

```
ggcataataa gatggctccc                                                20
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22

```
catgaactga catgtcaggc                                                20
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23

```
catttacaaa gagaggtcgg                                                20
```

<210> SEQ ID NO 24
<211> LENGTH: 22

```
<212> TYPE: DNA
<213> ORGANISM: Artificial Sequence
<220> FEATURE:
<223> OTHER INFORMATION: Description of Artificial Sequence: Primer

<400> SEQUENCE: 24
agggttattt taagtaccga cc                                              22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 25
ggaaatgtat gttaaaagca cg                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 26
ggcatggatc ctcagccctg gg                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 27
gagacccatg ggctctccag gg                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 28
gttcaagcac aacgaatgag gc                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 29
tggctttgcc acatgtcaag gc                                              22

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 30
```
tcaggtacta gtgttcccaa ggacctatat gtgg        34

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 31
gattcgagat ctcctcgagt cctttcattt ggaggatgtg cc        42

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 32
tcaggtacta gtgttcccaa ggaccatatg tgg        33

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 33
gattcgagat ctcctcgagt ctttcattgg ggatgtgcc        39

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 34
ggtgcacagc tttgctga        18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 35
gctgtgcacc agctgttt        18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 36
gctatgaaag gtccagag        18

<210> SEQ ID NO 37
<211> LENGTH: 18
<212> TYPE: DNA
<213> ORGANISM: Artificial Sequence

```
<220> FEATURE:
<223> OTHER INFORMATION: Description of Artificial Sequence: Primer

<400> SEQUENCE: 37
gaatctggtg gtgtccaa                                                 18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 38
ctctgtcacc atcacagg                                                 18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 39
ctctgtcacc atcacacc                                                 18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 40
gaaatcccgg atgctcac                                                 18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 41
accacacgtg ttccagca                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 42
tgctggaaca cgtgtggt                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 43
ggccctcagc aaagctgt                                                 18
```

```
<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 44
agctgtaggt gccattcg                                                 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 45
agggacctgg acctccac                                                 18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 46 tgggggaat gtcatagg                                                  18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 47
agcaggcagg atgactta                                                 18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 48
aacagaccac ccacaacc                                                 18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 49
gcaaatggca cctacagc                                                 18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Primer
```

<400> SEQUENCE: 50
tctggggtgt gatggtga                                         18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 51
atgaaaggtc cagagggc                                         18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 52
acccataatt cttaccca                                         18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 53
cacagctctg tttgatct                                         18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 54
ctcctaccct ctggctgc                                         18

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 55
atgctgcgtc ggcg                                             14

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 56
tcaggctatt tcttgtccat catc                                  24

<210> SEQ ID NO 57

```
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 57
gttttcccag tcacgac                                                  17

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 58
caggaaacag ctatgac                                                  17

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 59
tggtgcacag ctttgct                                                  17

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 60
tctgggggga atgtcat                                                  17

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 61
tggtgcacag ctttgct                                                  17

<210> SEQ ID NO 62
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 62
tctgggggga atgtcat                                                  17

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 63
```

```
gggggtaccat gctgcgtcgg cg                                           22

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 64
cggaattctg ggggaatgt catag                                          25

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 65
ggaattcgag cccaaatctt gtgacaa                                       27

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 66
gcgctctaga tcatttaccc ggagacagg                                     29

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 67
gaaggcctct accaggtc                                                 18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 68
ctttaggcgc agaacact                                                 18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 69
aagggtcagc taatgctc                                                 18

<210> SEQ ID NO 70
<211> LENGTH: 18
<212> TYPE: DNA
```

```
<213> ORGANISM: Artificial Sequence
<220> FEATURE:
<223> OTHER INFORMATION: Description of Artificial Sequence: Primer

<400> SEQUENCE: 70
tcagtttgca catctgta                                                 18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 71
tatgctatca agattcca                                                 18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 72
gtaaagtgca gtagtgct                                                 18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 73
tatgagctca cagacagg                                                 18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 74
aggttcagat agcactgt                                                 18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 75
acttatctga aattgctg                                                 18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 76
ttgatatgct catacgtt                                                 18
```

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 77
gaattctgtg ggtccagg                                              18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 78
catgtttaat ggtggttt                                              18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 79
aaagctgtat tcttcaaa                                              18

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 80
gaacactggt gacctggtag ag                                         22

<210> SEQ ID NO 81
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 81
ccggggtacc atgatcttcc tcctgctaat gttg                            34

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 82
gcgctctaga tcagatagca ctgttcactt ccc                             33

<210> SEQ ID NO 83
<211> LENGTH: 20
<212> TYPE: DNA
<213> ORGANISM: Artificial Sequence
<220> FEATURE:

```
<223> OTHER INFORMATION: Description of Artificial Sequence: Primer

<400> SEQUENCE: 83
tacaagcgaa ttactgtgaa                                                    20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 84
gatgtgccag aggtagttct                                                    20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 85
aatagagcat ggcagcaatg                                                    20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 86
ggcgacccca tagatgatta                                                    20

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 87
ccagtaagtg cgggtcat                                                      18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 88
ttcacctacg gaaacctt                                                      18

<210> SEQ ID NO 89
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 89
ccggggtacc atgatcttcc tcctgctaat gttg                                    34
```

```
<210> SEQ ID NO 90
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 90
cggaattcgg tcctgggttc catctg                                        26

<210> SEQ ID NO 91
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 91
cgggattcat gatcttcctc ctgctaatgt t                                  31

<210> SEQ ID NO 92
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 92
gcgctctaga tcatttaccc ggagacagg                                     29

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      Epitope tag

<400> SEQUENCE: 93

His His His His His His
 1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      Epitope tag

<400> SEQUENCE: 94

Asp Tyr Lys Asp Asp Asp Asp Lys
 1               5
```

BSL3 POLYPEPTIDES

RELATED APPLICATIONS

This application is a divisional application of non-provisional application U.S. Ser. No. 10/994,824, filed Nov. 22, 2004, now U.S. Pat. No. 7,279,567, which claims benefit to non-provisional application U.S. Ser. No. 09/875,338, filed Jun. 6, 2001, now U.S. Pat. No. 6,965,018, which claims benefit to provisional application U.S. Ser. No. 60/209,811, filed Jun. 6, 2000, and provisional application U.S. Ser. No. 60/272,107, filed Feb. 28, 2001, which are incorporated by reference in their entirety.

FIELD OF THE INVENTION

The present invention relates to isolated nucleic acids encoding B7-related polypeptides, including BSL1, BSL2, and BSL3, which modulate cells that are important for immune and inflammatory responses, such as T-cells. Also related are expression vectors and fusion constructs comprising nucleic acids encoding B7-related polypeptides. The present invention further relates to isolated B7-related polypeptides, isolated fusion proteins comprising B7-related polypeptides, and antibodies that are specifically reactive with B7-related polypeptides, or portions thereof. In addition, the present invention relates to methods of isolating and identifying the corresponding counter-receptor(s) of the B7-related polypeptides, utilizing B7-related polypeptides, or fusion proteins. Also related are methods of immunomodulation of a subject by the administration of compositions of the B7-related polypeptides, fusion proteins, cognate antibodies, or portions or derivatives thereof. The present invention further relates to methods of immunomodulation of animal or human subjects by the administration of compositions of genetically engineered vectors comprising the B7-related polypeptide expression cassettes as disclosed herein.

BACKGROUND OF THE INVENTION

The primary response of T-cells, involving T-cell activation, expansion, and differentiation is essential for the initiation of an immune response to a foreign antigen. The activation of T-cells by antigen presenting cells (APCs) requires at least two separate signals (K. E. Hellstrom et al. (1996) *Cancer Chemother. Pharmacol.* 38:S40-1; N. K. Damle et al. (1992) *J. Immunol.* 148:1985-92; J. M. Green et al. (1994) *Eur. J. Immunol.* 24:265-72; E. C. Guinan et al. (1994) *Blood* 84:3261-82; J. W. Hodge et al. (1995) *Cancer Res.* 55:3598-603). The first signal causes T-cell entry into the cell cycle, and is mediated by foreign antigens presented by the major histocompatibility complex (MHC). The second signal, termed costimulation, causes cytokine production and T-cell proliferation, but is neither antigen-specific, nor MHC restricted (R. H. Schwartz (1990) *Science* 248:1349-1356).

Costimulation is believed to be mediated by one or more distinct cells surface molecules expressed by APCs (M. K. Jenkins et al. (1988) *J. Immunol.* 140:3324-3330; P. S. Linsley et al. (1991) *J. Exp. Med.* 173:721-730; C. D. Gimmi, et al. (1991) *Proc. Natl. Acad. Sci. USA* 88:6575-6579; J. W. Young et al. (1992) *J. Clin. Invest.* 90:229-237; L. Koulova et al. (1991) *J. Exp. Med.* 173:759-762; H. Reiser et al. (1992) *Proc. Natl. Acad. Sci. USA* 89:271-275; G. A. van-Seventer et al. (1990) *J. Immunol.* 144:4579-4586; J. M. LaSalle et al. (1991) *J. Immunol.* 147:774-80; M. I. Dustin et al. (1989) *J. Exp. Med.* 169:503; R. J. Armitage et al. (1992) *Nature* 357:80-82; Y. Liu et al. (1992) *J. Exp. Med.* 175:437-445). Considerable evidence suggests that B7, an APC cell-surface protein, is one such costimulatory molecule (P. S. Linsley et al. (1991) *J. Exp. Med.* 173:721-730; C. D. Gimmi et al. (1991) *Proc. Natl. Acad. Sci. USA* 88:6575-6579; L. Koulova et al. (1991) *J. Exp. Med.* 173:759-762; H. Reiser et al. (1992) *Proc. Natl. Acad. Sci. USA* 89, 271-275; P. S. Linsley et al. (1990) *Proc. Natl. Acad. Sci. USA* 87:5031-5035; G. J. Freeman et al. (1991) *J. Exp. Med.* 174:625-631).

B7 has been shown to bind to two counter-receptors (ligands) expressed on T-cells, termed CD28 and CTLA-4. B7 binding to CD28 induces T-cells to proliferate and secrete IL-2 (P. S. Linsley et al. (1991) *J. Exp. Med.* 173, 721-730; C. D. Gimmi et al. (1991) *Proc. Natl. Acad. Sci. USA* 88:6575-6579; C. B. Thompson et al. (1989) *Proc. Natl. Acad. Sci. USA* 86:1333-1337; C. H. June et al. (1990) *Immunol. Today* 11:211-6; F. A. Harding et al. (1992) *Nature* 356:607-609), allowing full T-cell activation. Conversely, B7 binding to CTLA-4 mediates T-cell down-regulation. The importance of the B7:CD28/CTLA-4 costimulatory pathway has been demonstrated in vitro and in several in vivo model systems. Blockade of this pathway results in the development of antigen specific tolerance in murine and humans systems (F. A. Harding et al. (1992) *Nature* 356:607-609; D. J. Lenschow et al. (1992) *Science* 257:789-792; L. A. Turka et al. (1992) *Proc. Natl. Acad. Sci. USA* 89:11102-11105; C. D. Gimmi et al. (1993) *Proc. Natl. Acad. Sci. USA* 90:6586-6590). Conversely, the ectopic expression of B7 in B7 negative murine tumor cells induces T-cell mediated specific immunity accompanied by tumor rejection and long lasting protection to tumor challenge (L. Chen et al. (1992) *Cell* 71:1093-1102; S. E. Townsend et al. (1993) *Science* 259:368-370; S. Baskar et al. (1993) *Proc. Natl. Acad. Sci. USA* 90:5687-5690). Therefore, manipulation of the B7:CD28/CTLA-4 pathway offers great potential to stimulate or suppress immune responses in humans.

In addition to the previously characterized B7 molecule (referred to hereafter as B7-1) B7-1-like molecules have been identified (see, e.g., M. Azuma et al. (1993) *Nature* 366:76-79; C. Chen et al. (1994) *J. Immunol.* 152:4929-36; R. H. Reeves et al. (1997) *Mamm. Genome* 8:581-582; K. Ishikawa et al. (1998) *DNA Res.* 5:169-176; U.S. Pat. No. 5,942,607 issued Aug. 24, 1999 to Freeman et al.). In particular, PD-L1 and PD-L2 have been identified as inhibitors of T-cell activation (G. J. Freeman et al. (2000) *J. Exp. Med.* 192:1027-1034; Y. Latchman et al., (2001) *Nature Immunology* 2:261-268), whereas B7-H1, B7-H3, and B7-DC have been described as co-stimulators of T-cell proliferation (H. Dong et al. (1999) *Nature Medicine* 5:1365-1369; A. I. Chapoval (2001) *Nature Immunology* 2:269-274; Tseng et al. (2001) *J. Exp. Med.* 193(7):839-45).

Thus, there is a growing family of factors related to B7-1, which modulate T-cell activation (reviewed by J. Henry et al. (1999) *Immunol. Today* 20:285-288). The identification, isolation, and characterization of B7-related factors are therefore important goals for the further understanding of T-cell activation and function in both normal and disease states in animals, particularly humans. Accordingly, the present invention discloses the discovery and characterization of three B7-related factors, termed BSL1, BSL2, and BSL3. Also disclosed are various assays and treatments utilizing the BSL1, BSL2, and BSL3 factors.

SUMMARY OF THE INVENTION

It is an object of the present invention to provide isolated nucleic acids encoding B7-related polypeptides that modulate inflammatory and immune responses, including T-cell activation. B7-related polypeptides within the scope of the invention include counter-receptors on the surface of APCs capable of binding CD28 and/or CD28-related ligand(s). Specifically, B7-related polypeptides include the BSL1, BSL2, and BSL3 polypeptides, and soluble fragments or derivatives thereof. More specifically, the 87-related nucleic acid is:

i) a nucleic acid molecule comprising at least a fragment of a nucleotide sequence encoding a BSL1 (SEQ ID NO:2), BSL2 (SEQ ID NO:7, 11, or 13), or BSL3 (SEQ ID NO:15) polypeptide;

ii) a nucleic acid molecule comprising a nucleotide sequence encoding a polypeptide that shares moderate to substantial sequence homology with a BSL1 (SEQ ID NO:2), BSL2 (SEQ ID NO:7, 11, or 13), or BSL3 (SEQ ID NO:15) polypeptide;

iii) a nucleic acid molecule capable of hybridizing to the BSL1 (SEQ ID NO:1 or 3), BSL2 (SEQ ID NO:6, 10, or 12), or BSL3 (SEQ ID NO:14) nucleotide sequences, or fragments thereof, under appropriate conditions (e.g., moderate or high stringency hybridization conditions);

iv) a nucleic acid molecule which differs from the nucleotide sequence of BSL1 (SEQ ID NO:1 or 3), BSL2 (SEQ ID NO:6, 10, or 12), or BSL3 (SEQ ID NO:14) due to degeneracy in the genetic code, or recombinant or synthetic modifications; or v) a nucleic acid molecule that shares at least substantial homology with the nucleic acid, sequence set forth in SEQ ID NO:1, 3, 6, 10, 12, or 14.

In addition, nucleic acid probes useful for assaying a biological sample for the presence of APCs expressing the BSL1, BSL2, and BSL3 factors are encompassed by the present invention.

It is another object of the present invention to provide vectors (e.g., expression vectors) and fusion constructs comprising nucleic acids encoding B7-related polypeptides. Expression vectors direct the synthesis of the corresponding polypeptides or peptides in a variety of hosts, particularly eukaryotic cells, such as mammalian and insect cell culture, and prokaryotic cells, such as *Escherichia coli*. Expression vectors within the scope of the invention comprise a nucleic acid sequence encoding at least one B7-related polypeptide as described herein, and a promoter operatively linked to the nucleic acid sequence. In one embodiment, the expression vector comprises a DNA sequence encoding the extracellular domain of BSL1 (SEQ ID NO:2), BSL2 (SEQ ID NO:7, 11, or 13), or BSL3 (SEQ ID NO:15) fused to a DNA sequence encoding the Fc region human immunoglobulin G1 (IgG1). Such expression vectors can be used to transform or transfect host cells to thereby produce polypeptides or peptides, including fusion proteins or peptides encoded by nucleic acid molecules as described herein.

It is yet another object of the present invention to provide isolated B7-related polypeptides, including the BSL1, BSL2, and BSL3 polypeptides, or portions or derivatives thereof. Preferred B7-related polypeptides comprise the amino acid sequences of the BSL1 (SEQ ID NO:2), BSL2 (SEQ ID NO:7, 11, or 13), or BSL3 (SEQ ID NO:15) polypeptides, or portions thereof. Such polypeptides comprise at least a portion of the mature forms of the BSL1, BSL2, and BSL3 polypeptides, and preferably comprise soluble forms of these polypeptides. Also encompassed by the present invention are polypeptides that share moderate to substantial homology with the amino acid sequence set forth in SEQ ID NO:2, 7, 11, 13, or 15, which are naturally occurring isoforms of the BSL1, BSL2, or BSL3 polypeptides, or modified recombinant polypeptides.

It is still another object of the present invention to provide isolated fusion proteins comprising the B7-related polypeptides, or portions or derivatives thereof, as disclosed herein. In one aspect, the fusion protein comprises an extracellular domain portion of a B7-related polypeptide fused to another polypeptide that alters the solubility, purification, binding affinity, and/or valency of the B7-related polypeptide. Preferably, a DNA molecule encoding an extracellular domain portion of the BSL1, BSL2, or BSL3 polypeptides can be joined to DNA encoding the Fc region of human IgG1 to form DNA fusion products that encode the BSL1-Ig, BSL2-Ig, or BSL3-Ig fusion proteins.

It is a further object of the present invention to provide methods of isolating and identifying the corresponding counter-receptor(s) of the B7-related polypeptides, utilizing the isolated B7-related polypeptides, fusion proteins, or cognate antibodies disclosed herein. In one embodiment, isolated BSL1, BSL2, or BSL3 polypeptides, or portions thereof, can be incubated with protein extracts obtained from immune or inflammatory response cells, such as T-cells, to form a BSL/receptor complex, and then incubated with anti-BSL antibodies to isolate the BSL/receptor complex. Alternatively, a fusion protein comprising the BSL1, BSL2, or BSL3 polypeptide can be incubated with protein extracts obtained from immune or inflammatory response cells, such as T-cells, and then incubated with antibodies that specifically react with the fusion protein. Receptors that bind to the B7-related polypeptides would be expected to have significant immunomodulatory activity.

It is another object of the present invention to provide diagnostic methods and kits utilizing the B7-related factors of the present invention, including nucleic acids, polypeptides, antibodies, or functional fragments thereof. Such factors can be used, for example, in diagnostic methods and kits for measuring expression levels of B7-related factors, and to screen for various B7-related diseases. In addition, the B7-related nucleic acids described herein can be used to identify chromosomal abnormalities affecting BSL1, BSL2, or BSL3, and to identify allelic variants or mutations of BSL1, BSL2, or BSL3 in an individual or population.

It is yet another object of the present invention to provide isolated antibodies, including monoclonal and polyclonal antibodies, that are specifically reactive with the B7-related polypeptides, fusion proteins, or portions or derivatives thereof, as disclosed herein. Preferably, monoclonal antibodies are prepared to be specifically reactive with the BSL1 (SEQ ID NO:2), BSL2 (SEQ ID NO:7, 11, or 13), or BSL3 (SEQ ID NO:15) polypeptides, or portions or derivatives thereof.

It is another object of the present invention to provide methods of immunomodulation of a human or animal subject by the administration of compositions of the B7-related polypeptides, fusion proteins, or portions or derivatives thereof, as disclosed herein. Such compositions would be expected to up-regulate or down-regulate the activities of immune or inflammatory response cells (e.g., T-cells). For example, B7-related polypeptides in a composition may interact with CD28 and thereby up-regulate immune cell activity. Alternatively, B7-related polypeptides in a composition may interact with CTLA-4 and thereby down-regulate immune cell activity. In one embodiment, compositions of BSL1-Ig, BSL2-Ig, and BSL3-Ig, fusion proteins are administered, e.g. via injection, to a subject to provide systemic immunosuppression or immunostimulation. Such compositions can be administered alone, or in combination with one or more immunomodulatory molecules.

It is still another object of the present invention to provide methods of immunomodulation of a human or animal subject by the administration of compositions of antibodies that are specifically reactive with the B7-related polypeptides, fusion proteins, or portions or derivatives thereof, as disclosed herein. Such compositions can be expected to block the co-stimulatory activities of the B7-related polypeptides, and to down-regulate immune or inflammatory response cells (e.g., T-cells), accordingly. In one embodiment, compositions of monoclonal antibodies that are specifically reactive with the BSL1 (SEQ ID NO:2), BSL2 (SEQ ID NO:7, 11, or 13), or BSL3 (SEQ ID NO:15) polypeptides, or fragments thereof, are administered, e.g., via injection, to a subject to provide immunosuppression or induced tolerance. Such compositions can be administered alone, or in combination with one or more immunomodulatory molecules. The methods of inducing tolerance described herein can be used prophylactically for preventing immune responses such as transplantation rejection (solid organ and bone marrow) and graft versus host disease, especially in autologous bone marrow transplantation. Such methods can also be useful therapeutically, in the treatment of autoimmune diseases, transplantation rejection, and established graft versus host disease in a subject.

It is a further object of the present invention to provide methods of the immunomodulation of a human or animal subject by the administration of compositions of genetically engineered vectors or cells comprising the B7-related polypeptide expression cassettes as disclosed herein. In a preferred embodiment, the cells are antigen presenting cells, such as a macrophages, which are transfected or transduced to allow expression of one or more of the B7-related polypeptides, including the BSL1 (SEQ ID NO:2), BSL2 (SEQ ID NO:7, 11, or 13), or BSL3 (SEQ ID NO:15) polypeptides, or fragments or derivatives thereof, and then introduced e.g., via transplantation, into the recipient. Consistent with the present invention, the genes encoding the BSL1, BSL2, or BSL3 polypeptides can be transfected or transduced alone, or in combination with genes encoding other immunomodulatory molecules.

Additional objects and advantages afforded by the present invention will be apparent from the detailed description and exemplification hereinbelow.

DESCRIPTION OF THE FIGURES

The appended drawings of the figures are presented to further describe the invention and to assist in its understanding through clarification of its various aspects. In the figures of the present invention, the nucleotide and amino acid sequences are represented by their one-letter abbreviations.

FIGS. 1A-1C illustrate the nucleotide and predicted amino acid sequence of BSL1. FIG. 1A shows the nucleotide sequence of BSL1 (SEQ ID NO:1) determined from the full-length clone isolated from a cDNA library prepared from human microvascular endothelial cells treated with TNF-alpha; nucleotides 1-92 contain the 5'-untranslated region; nucleotides 93-95 contain the translation initiation signal (ATG); nucleotides 93-962 encode the protein coding region; nucleotides 963-965 contain the translation termination signal (TAA); nucleotides 963-1576 contain the 3'-untranslated region; and nucleotides 1577-1605 contain the poly(A)$^+$ RNA tail. FIG. 1B shows the predicted amino acid sequence of BSL1 (SEQ ID NO:2); amino acids 1-240 contain the predicted extracellular domain (ECD). FIG. 1C shows the nucleotide sequence of BSL1 (SEQ ID NO:3) determined from the full-length clone isolated from a cDNA library prepared from GM-CSF/IL-4 differentiated human monocyte cells; nucleotides 1-92 contain the 5'-untranslated region; nucleotides 93-95 contain the translation initiation signal (ATG); nucleotides 93-962 contain the protein coding sequence; nucleotides 963-965 contain the translation stop signal (TAA); and nucleotides 963-3621 contain the 3'-untranslated region (unique sequence is shown in bold).

FIGS. 2A-2B illustrate the nucleotide and predicted amino acid sequence of the BSL1-Ig fusion construct. FIG. 2A shows the nucleotide sequence of the BSL1-Ig fusion construct (SEQ ID NO:4); nucleotides 1-72 encode the predicted CD5 signal sequence; nucleotides 73-78 contain the SpeI restriction site; nucleotides 78-729 encode the predicted BSL1 ECD; nucleotides 730-1440 encode the Fc portion of human IgG1; and nucleotides 1441-1443 contain the translation stop signal (TGA). FIG. 2B shows the BSL1-Ig predicted amino acid sequence (SEQ ID NO:5).

FIGS. 3A-3F illustrate the nucleotide and predicted amino sequences of the BSL2 clones. FIG. 3A shows the nucleotide sequence of the BSL2-4616811 clone (SEQ ID NO:6); nucleotides 1-12 include vector sequence; nucleotides 121-123 contain the translation initiation signal (ATG); between nucleotides 204-205 is the predicted signal peptide cleavage site; nucleotides 1516-1587 encode the predicted transmembrane domain; nucleotides 1723-1725 contain the translation termination signal (TGA). FIG. 3B shows the predicted amino acid sequence of the BSL2-4616811 clone (SEQ ID NO:7); amino acids (1-465) contain the predicted ECD. FIG. 3C shows the nucleotide sequence of the BSL2-L165-21 clone (SEQ ID NO:10); nucleotides 1-3 encode the translation initiation signal (ATG); between nucleotides 84-85 is the predicted signal peptide cleavage site; nucleotides 742-813 encode the predicted transmembrane domain; nucleotides 949-951 contain the translation termination signal (TGA). FIG. 3D shows the predicted amino acid sequence of the BSL2-L165-21 clone (SEQ ID NO:11); amino acids 1-247 contain the predicted ECD. FIG. 3E shows the nucleotide sequence of the BSL2-L165-35b clone (SEQ ID NO:12); nucleotides 1-3 encode the translation initiation signal (ATG); between nucleotides 84-85 is the predicted signal peptide cleavage site; nucleotides 742-813 encode the predicted transmembrane domain; nucleotides 949-951 contain the translation termination signal (TGA). FIG. 3F shows the predicted amino acid sequence of the BSL2-L165-35b clone (SEQ ID NO:13); amino acids 1-247 contain the predicted ECD.

FIGS. 4A-4B illustrate the nucleotide and predicted amino sequences of the of the BSL2-4616811-Ig fusion construct. FIG. 4A shows the nucleotide sequence of the BSL2-4616811-Ig clone (SEQ ID NO:8): nucleotides 1-3 contain the translation initiation signal (ATG); nucleotides 1-1394 encode the native BSL2-4616811 sequence; nucleotide 1395 is a silent mutation introduced to facilitate construction of the fusion protein; nucleotides 1396-2097 encode the Fc portion of human IgG1; nucleotides 2095-2097 contain the translation termination signal (TGA). FIG. 4B shows the predicted amino acid sequence of the BSL2-4616811-Ig fusion protein (SEQ ID NO:9); amino acids 1-465 of contain the native sequence of BSL2-4616811; amino acids 466-698 contain the Fc domain of human IgG.

FIGS. 5A-5B illustrate the nucleotide and predicted amino acid sequence of BSL3. FIG. 5A shows the nucleotide sequence of BSL3 (SEQ ID NO:14): nucleotides 1-326 contain 5' untranslated region; nucleotides 327-329 contain the translation initiation signal (ATG); nucleotides 981-1055 encode a predicted transmembrane domain; nucleotides 1146-1148 contain the translation termination signal (TGA)

FIG. 5B shows the BSL3 predicted amino acid sequence (amino acids 1-273) (SEQ ID NO:15); amino acids 1-219 contain the predicted ECD.

FIGS. 6A-6B illustrate the nucleotide and predicted amino sequences of the of the BSL3-Ig fusion construct. FIG. 6A shows the nucleotide sequence of BSL3-Ig (L232-6) (SEQ ID NO:16): nucleotides 1-3 contain the translation initiation signal (ATG); nucleotides 1-651 encode the native BSL3 sequence; nucleotides 652-654 encode an artificial sequence introduced during construction; nucleotides 655-1356 encode the Fc domain of human IgG. FIG. 6B shows the predicted amino acid sequence of BSL3-Ig (L232-6) (SEQ ID NO:17); amino acids 1-217 contain the native BSL3 sequence; amino acid 218 contains an artificial sequence introduced during construction; amino acids 219-451 contain the Fc domain of human IgG.

Figure 7F:
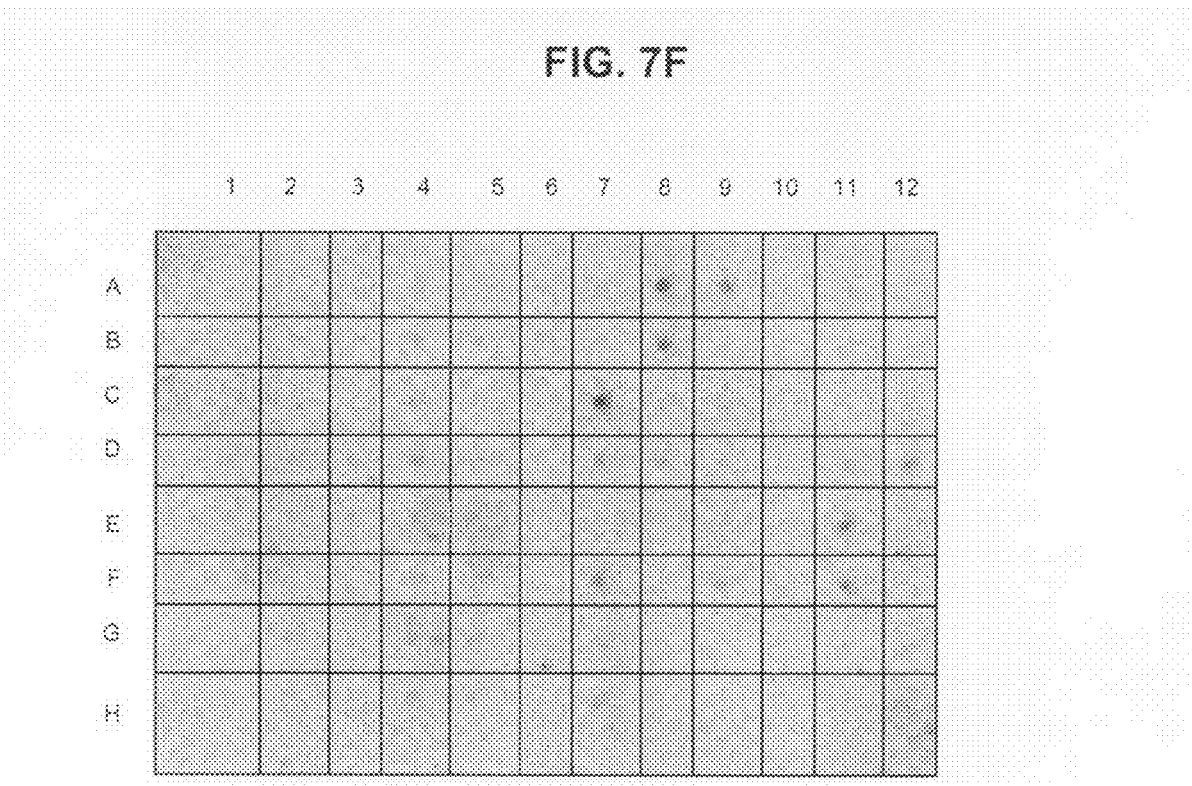
Figure 7G:
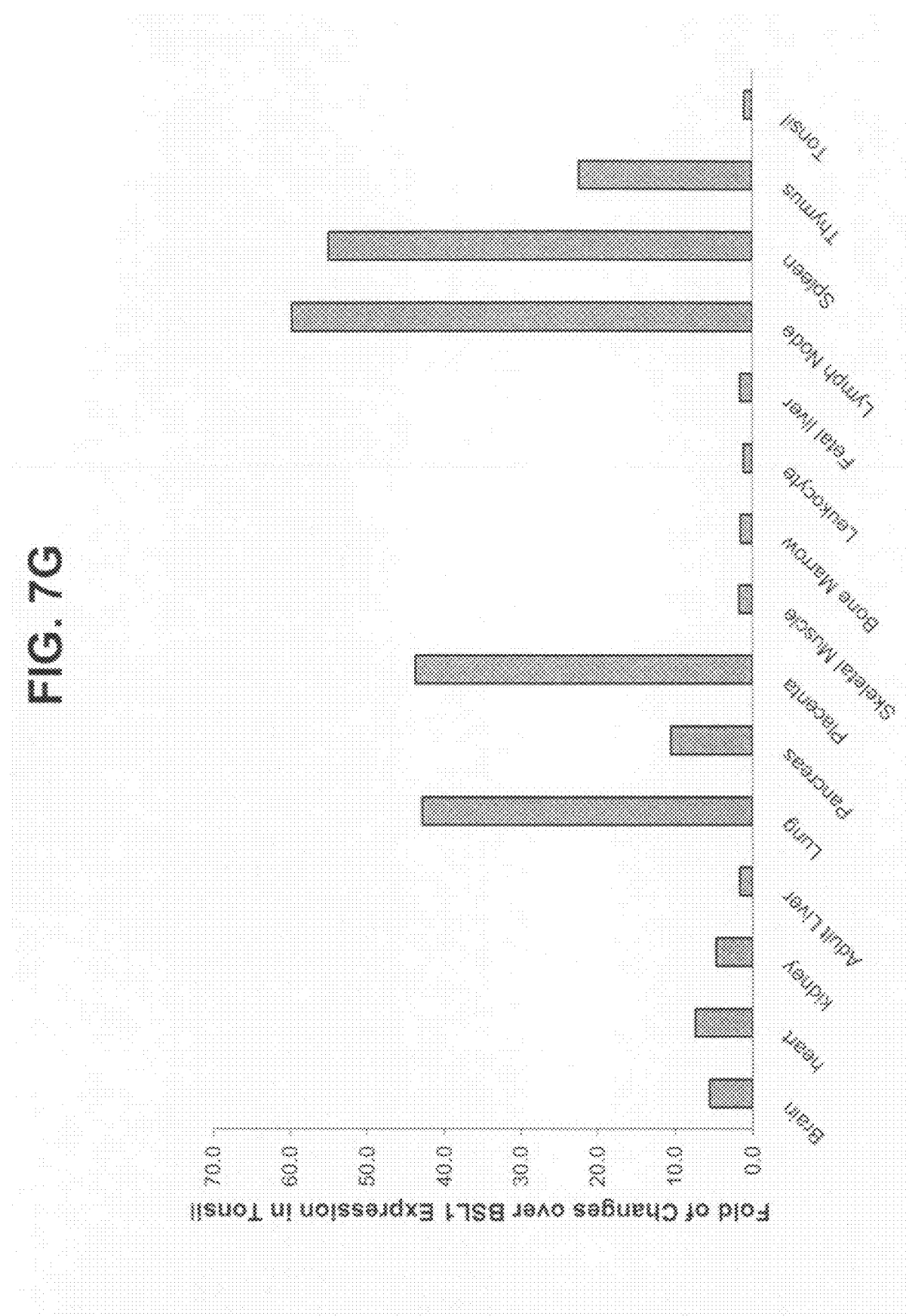

FIGS. 7A-7H illustrate the reagents and results of expression analysis performed for BSL1, BSL2, and BSL3. FIG. 7A shows the nucleotide sequence of the BSL1 probe (SEQ ID NO:18) used for northern blot analysis. FIG. 7B shows the nucleotide sequence of the BSL2 probe (SEQ ID NO:19) used for northern blot analysis. FIG. 7C shows the nucleotide sequence of the BSL3 probe (SEQ ID NO:20). FIG. 7D shows the levels of BSL1, BSL3, and BSL3 mRNA observed in various cell types as determined by northern blot analysis; "PBT" indicates peripheral blood T-cells; "CD3/CD28" indicates stimulation with anti-CD3 and anti-CD28 antibodies; "PMA" indicates stimulation with phorbol 12 myristate 13 acetate; "LPS" indicates stimulation with lipopolysaccharide; "PBM" indicates peripheral blood monocytes; "PHA" indicates stimulation with phytohemaglutinin; "GM-CSF/IL-4" indicates stimulation with GM-CSF and IL-4; "HMVEC" indicates human microvascular endothelial cells; "TNF-alpha" indicates stimulation with TNF-alpha; and "H292 (Starved) indicates serum starved H292 cells. FIG. 7E shows BSL3 expression levels in various tissue types as determined by northern analysis of commercially available blots using radiolabeled BSL3/KpnI+XbaI probe. FIG. 7F shows BSL3 expression levels in various tissue types as determined by hybridization analysis of commercially available microarrays using radiolabeled BSL3/KpnI+XbaI probe. FIG. 7G shows BSL1 expression levels in various tissue types as determined by quantitative PCR. FIG. 7H shows BSL3 expression levels in various tissue types as determined by quantitative PCR.

Figure 8C:
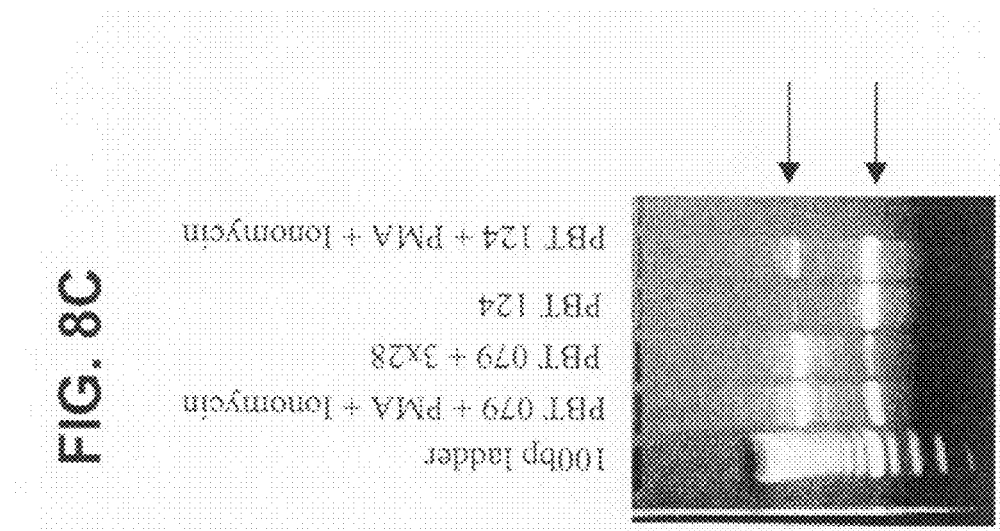
Figure 8B:
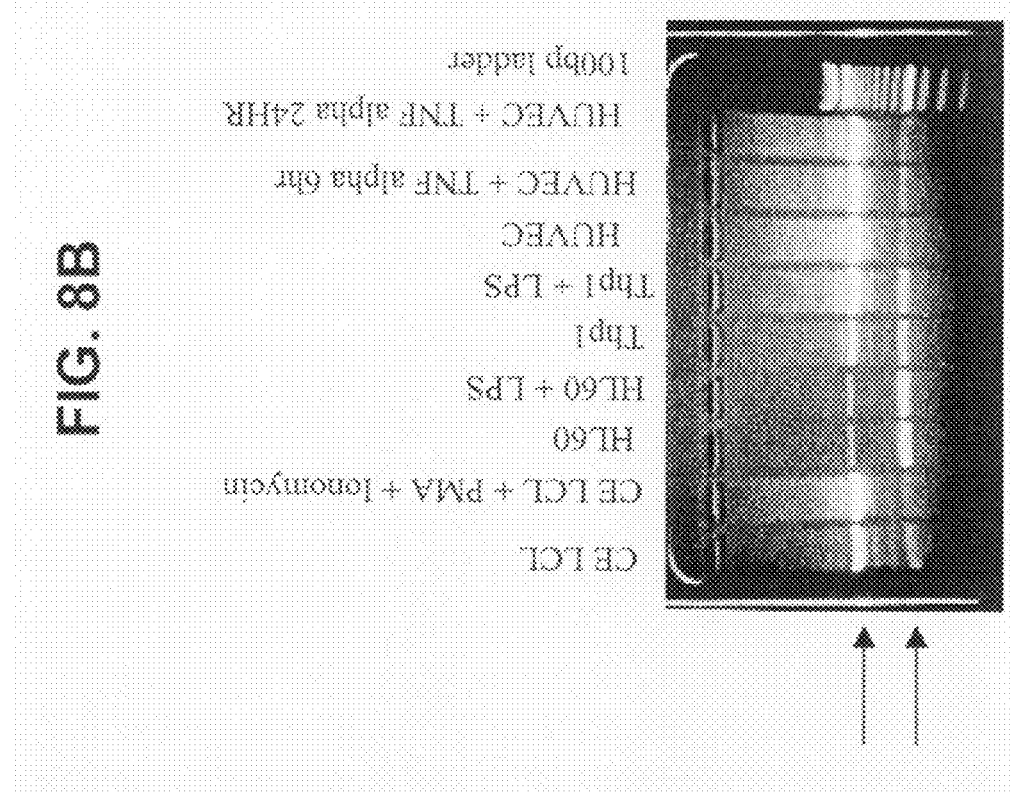
Figure 8E:
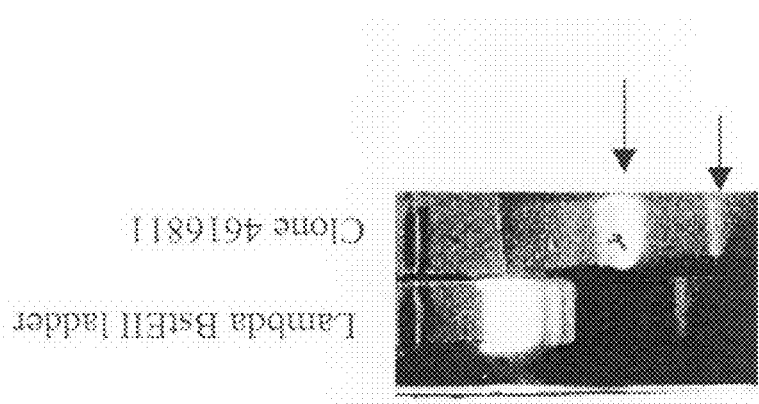
Figure 8D:
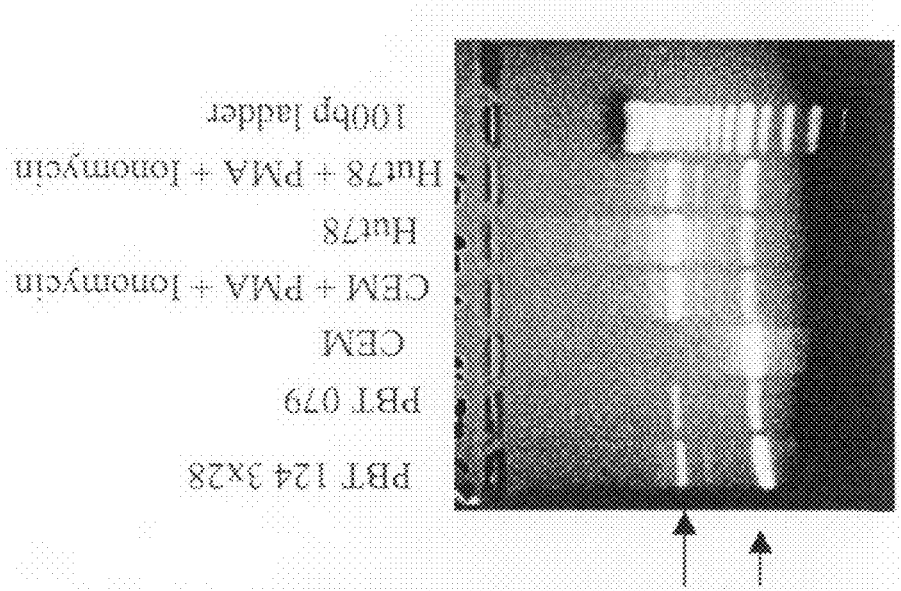

FIGS. 8A-8E illustrate the results of PCR analysis performed to determine the relative levels of the BSL2-4616811 or BSL2-L165-35b transcripts in various cell types, with or without stimulation. The top arrow points to the bands representing the BSL2-4616811 transcript; the bottom arrow points to the bands representing the BSL2-L165-35b transcript. FIG. 8A shows the results for Raji, Ramos, PM-LCL, and PL-LCL cell types, with or without PMA and ionomycin stimulation. FIG. 8B shows the results for CE-LCL cells, HL60, Thp1, and HUVEC cell types, with or without stimulation. FIG. 8C shows the results for peripheral blood T-cells with or without PMA and ionomycin stimulation. The results from cells isolated from two separate donors are shown (donor 079 and donor 124). FIG. 8D shows the results for CEM and HUT78 cells, with or without PMA and ionomycin stimulation. FIG. 8E shows the results of a PCR reaction using BSL2-4616811 plasmid as template. Lane 1: Lambda BstEII DNA ladder; lane 2: PCR product. The upper arrow points to the size of the predicted PCR product from the BSL2-4616811 transcript. The lower arrow points to the size of the predicted PCR product for the BSL2-L165-35b transcript. The results demonstrate that the forward primer preferentially binds the specific binding site in the first variable fold rather than for the homologous site in the second variable fold of BSL2-4616811.

Figure 9A:
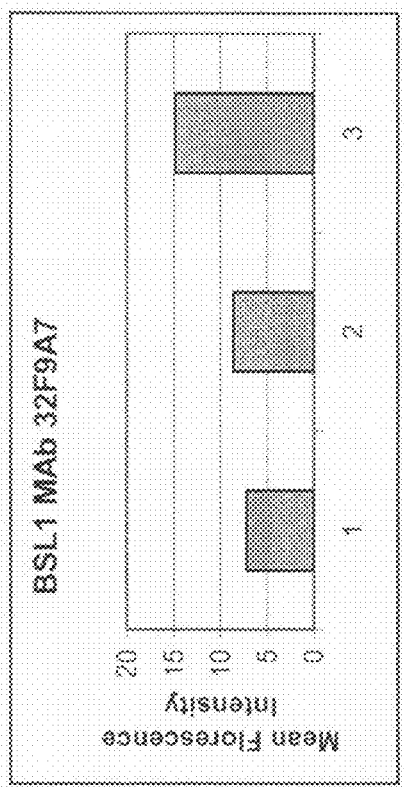
Figure 9B:
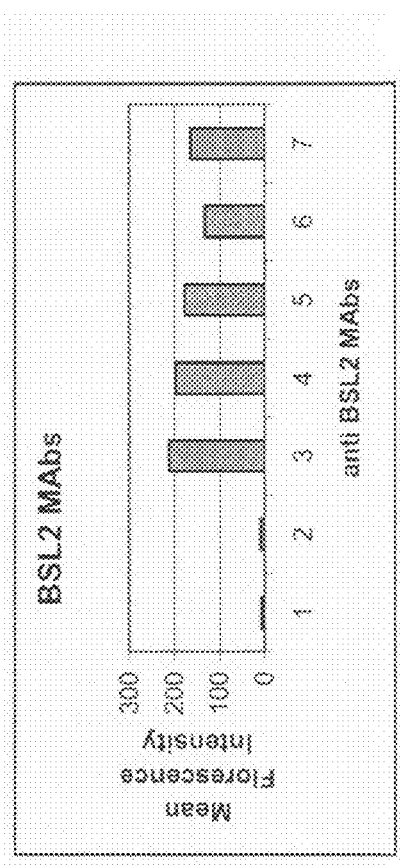
Figure 9C:
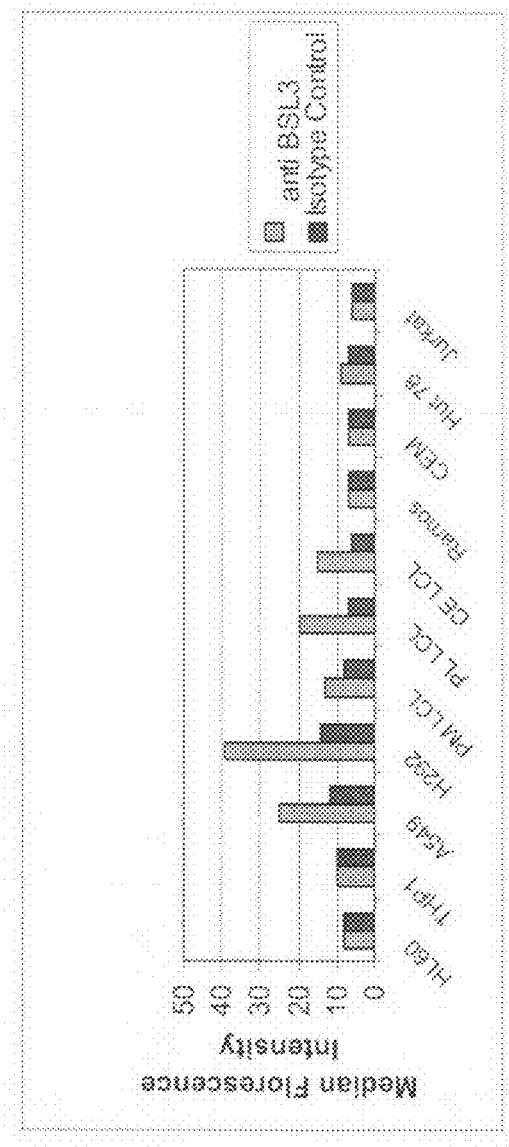
Figure 9D:
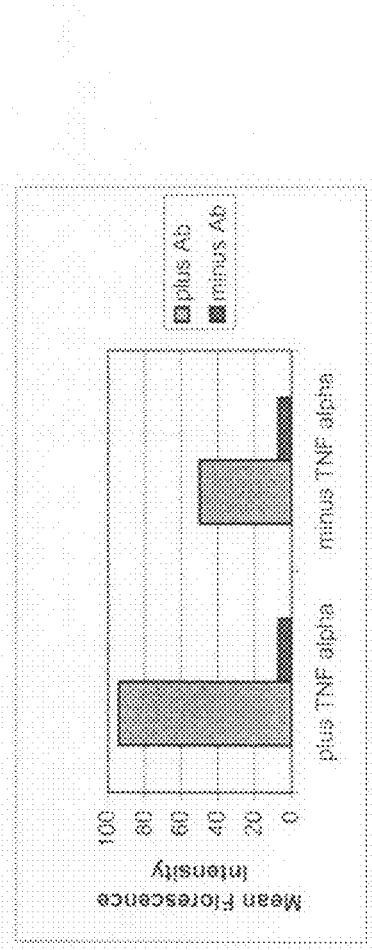

FIGS. 9A-9F illustrate the results of fluorescence activated cell sorting (FACS) performed using BSL1, BSL2, and BSL3 monoclonal antibodies. FIG. 9A shows FACS analysis of A549 epithelial lung cells using BSL1 monoclonal antibodies. Column 1: no monoclonal antibodies; column 2: isotype control; column 3: BSL1 hybridoma supernatant 32. FIG. 9B shows FACS analysis of A549 epithelial lung cells using BSL2-4616811 monoclonal antibodies. Column 1: no monoclonal antibodies; column 2: isotype control; column 3: BSL2 MAb 1F7G2; column 4: BSL2 Mab 2B10D7; column 5: BSL2 Mab 3E6D3; column 6: BSL2 Mab 4C2C6; column 7: BSL2 Mab 5D7E2. FIG. 9C shows FACS analysis of various cell types using BSL3 monoclonal antibodies. FIG. 9D shows FACS analysis of human umbilical vein endothelial cells (HUVEC) with or without TNF-alpha stimulation using BSL3 monoclonal antibodies. FIGS. 9E-9F shows FACS analysis of peripheral blood monocytes (PBMCs) with or without GM-CSF/IL4 or PHA stimulation using BSL3 monoclonal antibodies. FIG. 9E shows results from cells isolated from donor 126; FIG. 9F shows results from cells isolated from donor 145.

Figure 10A:
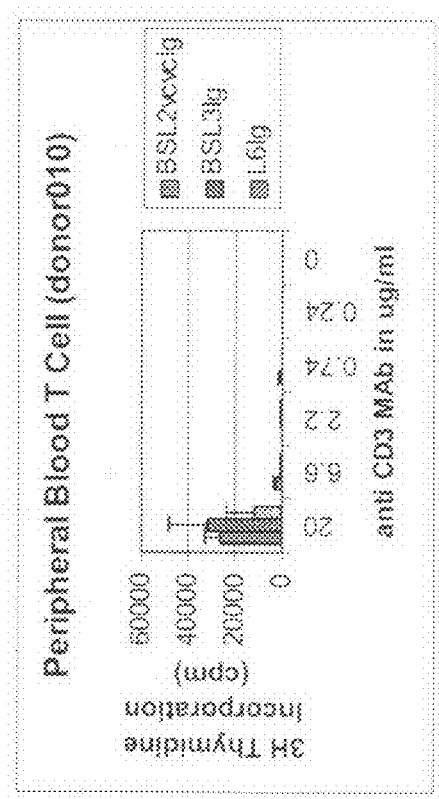
Figure 10B:
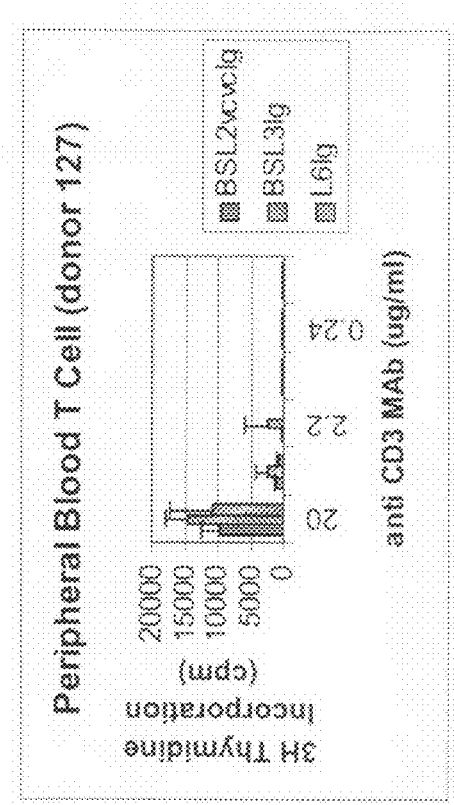
Figure 10H:
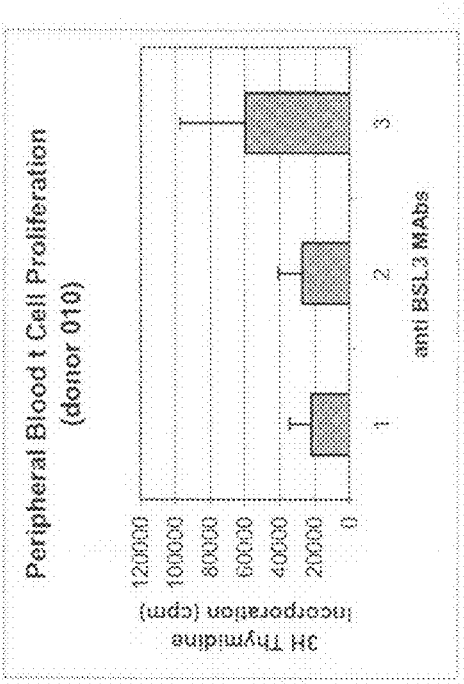
Figure 10J:
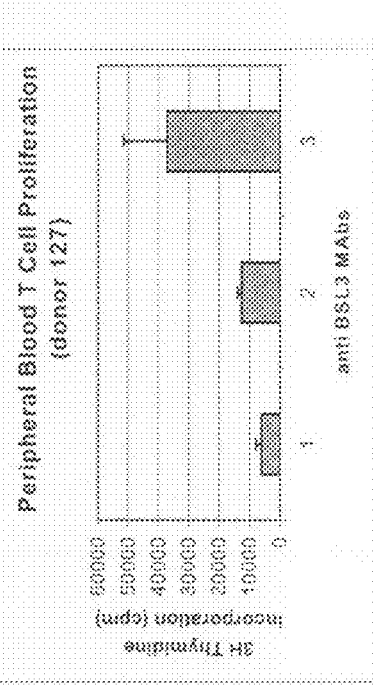
Figure 10G:
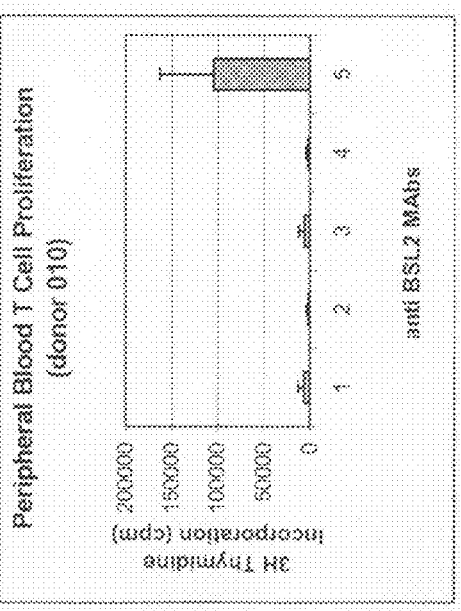
Figure 10I:
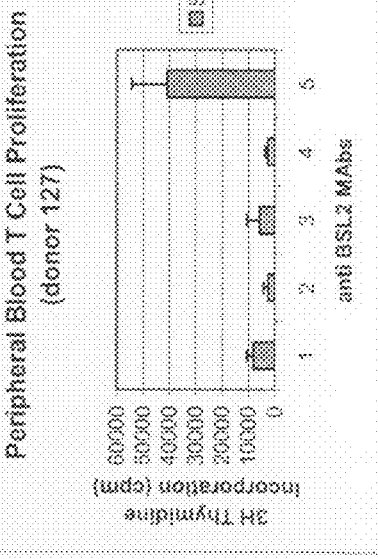

FIGS. 10A-10E illustrate co-stimulation of peripheral blood T-cells using BSL2-4616811-Ig (BSL2vcvclg) and BSL3-Ig fusion proteins in the presence of CD3 monoclonal antibody. The L6-Ig fusion protein is used as a negative control. FIG. 10A shows results from cells isolated from donor 010. FIG. 10B shows results from cells isolated from donor 127. FIGS. 10C-10D show results from cells isolated from donor 78. FIGS. 10E-10F show results from cells isolated from donor 124. FIGS. 10G-10J illustrate the blockade of co-stimulation of peripheral blood T-cells using BSL2 or BSL3 monoclonal antibodies. FIGS. 10G and 10I show the results from cells stimulated with CD3 monoclonal antibodies and BSL2-4616811-Ig (BSL2vcvclg) and blockaded with BSL2 monoclonal antibodies. Column 1: BSL2-1F7G2 MAb; column 2: BSL2-2B10D7 MAb; column 3: BSL2-3E6D3 MAb; column 4: BSL2-5D7E2 MAb; and column 5: isotype control antibody. FIG. 10G shows results from cells isolated from donor 010; FIG. 10I shows results from cells isolated from donor 127. FIGS. 10H and 10J show the results from cells stimulated with CD3 monoclonal antibodies and BSL3-Ig fusion protein and blockaded with BSL3 monoclonal antibodies. Column 1: BSL3-1A4A1 MAb; column 2: BSL3-2B6H7 MAb; and column 3: isotype control antibody. FIG. 10H shows results from cells isolated from donor 010; FIG. 10J shows results from cells isolated from donor 127.

DETAILED DESCRIPTION OF THE INVENTION

Identification of B7-Related Factors

In accordance with the methods of the present invention, three B7-related factors, designated BSL1, BSL2, and BSL3, have been identified and characterized. Such B7-related factors may provide a molecular basis for the activation of immune or inflammatory response cells, such as T-cells, at different times and in different illnesses and disease states. In addition, the disclosed B7-related factors can be utilized in the prevention or treatment certain diseases by modulating the activity of immune or inflammatory response cells, such as T-cells, using the methods described in detail herein: Such methods can be used as prophylaxis or treatments for cancers or immune-related disorders as detailed below.

Identification of B7-related genes from cDNA libraries: To identify B7-related factors, cDNA libraries can be constructed and analyzed using several well-established techniques. Messenger RNA can be obtained from cells expressing B7-1 and/or B7-related factors. For example, mRNA can be obtained from differentiated human peripheral blood mononuclear cells. Alternatively, mRNA can be obtained from various subsets of neoplastic B cells, including tumor cells isolated from patients with non-Hodgkin's lymphoma (L. Chaperot et al. (1999) *Exp. Hematol.* 27:479-88). Such cells are known to express B7-1 and, thus, may express B7-related factors, and can also serve as a source of the mRNA for construction of the cDNA library.

Total cellular mRNA can be isolated by a variety of techniques, e.g., guanidinium-thiocyanate extraction (J. M. Chirgwin et al. (1979) *Biochemistry* 18:5294-5299; Chomczynski et al. (1987) *Anal. Biochem.* 162:156-9). Following isolation, poly(A)$^+$ RNA can be purified using oligo(dT) cellulose. The purified poly(A)$^+$ RNA can then be used as a template for cDNA synthesis utilizing reverse transcriptase polymerase chain reaction (RT-PCR; see C. R. Newton et al. (1997) *PCR $2^{nd}$ Ed*, Scientific Publishers, Oxford, England). Following reverse transcription, the cDNA can be converted to double stranded DNA using conventional techniques (see H. Okayama et al. (1982) *Mol. Cell. Biol.* 2:161; U. Gubler et al. (1983) *Gene* 25:263).

Cloning of the double stranded cDNAs can be accomplished using techniques that are well known in the art (see J. Sambrook et al. (1989) *Molecular Cloning, A Laboratory Manual*, Cold Spring Harbor Press, Plainview, N.Y.; F. M. Ausubel et al. (1989) *Current Protocols in Molecular Biology*, John Wiley & Sons, New York, N.Y.). The use of synthetic adaptors prior to cloning is particularly preferred, since it obviates the need for cleavage of the cDNA with one or more restriction enzymes (see, for example, E. C. Bottger (1989) *Biotechniques* 7:925-6, 928-90). Using this method, non-self complementary, kinased adaptors can be added to the DNA prior to ligation with the vector. Virtually any adaptor can be employed.

A cDNA library sequence can be expressed when placed in the sense orientation in a vector that supplies an appropriate promoter. Vectors may also include an origin of replication and various enhancer sequences, splice acceptor/donor sequences, and polyadenylation sequences. Vectors may further include a marker that allows for selection of cells containing the vector construct. Markers may be an inducible or non-inducible gene and will generally allow for positive selection under induction, or without induction, respectively. Examples of marker genes include neomycin, dihydrofolate reductase, glutamine synthetase, and the like. Notably, prepared cDNA libraries can be obtained from various commercial sources (e.g., Incyte Genomics, Inc., St. Louis, Mo.; Stratagene, La Jolla, Calif.)

The cDNA library can be used to clone B7-related factors utilizing expression cloning techniques (see B. Seed et al. (1987) *Proc. Natl. Acad. Sci. USA* 84:3365-3369; A. Aruffo et al. (1987) *Proc. Natl. Acad. Sci. USA* 84:8573-8577). In one embodiment, plasmid DNA is introduced into a cell line by known methods of transfection (e.g., DEAE-Dextran) and allowed to replicate and express the cDNA inserts. B7-1 antigen is depleted from the transfected cells using an anti-B7-1 monoclonal antibody (e.g., 133 and B1.1) and anti-murine IgG and IgM coated immunomagnetic beads. Transfectants expressing B7-related factors are positively selected by incubation with CTLA-4-Ig and CD28-Ig followed by panning with anti-human Ig immunoglobulin. After panning, episomal DNA is recovered from the panned cells and transfected into a competent bacterial host, preferably *Escherichia coli* (*E. coli*). Plasmid DNA is subsequently reintroduced into the cell line and the cycle of expression and panning repeated at least two times. Following the final panning cycle, plasmid DNA is prepared from individual colonies, transfected into the cell fine and analyzed for expression of the B7-related polypeptides by indirect immunofluorescence with CTLA-4-Ig and CD28-Ig. After cloning, plasmids are prepared from the clones strongly reactive with the CTLA-4-Ig, and then sequenced using conventional sequencing techniques (reviewed in G. W. Slater et al. (1998) *Electrophoresis* 19:1525-41).

Identification of B7-related genes in protein sequence databases: Alternatively, B7-related factors can be identified by screening available sequence databases. The polypeptide sequence encoded by a previously identified B7 factor (e.g., B7-1, B7-2, or B7-H1) or a B7-related factor disclosed herein (e.g., BSL1, BSL2, or BSL3), can be compared with the polypeptide sequences present in various protein databases. Publicly available protein sequence databases, e.g., GENBANK® GenPept, SWISS-PROT®, Protein Data Bank (PDB), Protein Information Resource (PIR), Human Uni-Gene (National Center for Biotechnology Information), can be used to determine if additional B7-related factors are present in mammalian, preferably human, species. Alternatively, privately owned protein sequence databases, e.g., the Incyte Genomics sequence database (Incyte Genomics), can be used to identify B7-related factors. Databases with relatively few redundant sequences, e.g., PIR or SWISS-PROT® databases, can be used to improve the statistical significance of a sequence match. However, databases which are more comprehensive and up-to-date, e.g., GENBANK®, GenPept, and Incyte Genomics sequence databases (Incyte Genomics), are preferred.

Any method known in the art can be used to align and compare the previously identified B7 factor sequence with the sequences present in the protein sequence databases. Preferably, the BLAST program is used (S. F. Altschul et al. (1990) *J. Mol. Biol.* 215:403-410; S. Karlin et al. (1990) *Proc. Natl. Acad. Sci. USA* 87:2264-68; S. Karlin et al. (1993) *Proc. Natl. Acad. Sci. USA* 90:58.73-7). BLAST identifies local alignments between the sequence of the previously identified protein and the protein sequences in the database, and predicts the probability of the local alignment occurring by chance. Although the original BLAST programs utilized ungapped local alignments, more recently developed BLAST programs such as WU-BLAST2/BLAST v2.0 (S. F. Altschul et al. (1996) Methods Enzymol. 266, 460-480) have been modified to incorporate gapped local alignments similar to SSEARCH (T. F. Smith et al. (1981) *J. Mol. Biol.* 147:195-197) and FASTA programs (W. R. Pearson (1990) *Methods Enzymol.* 183:63-98). In addition, position-specific-iterated BLAST (PSI-BLAST) programs have been developed to identify weak but biologically relevant sequence similarities (S. F. Altschul et al. (1997) *Nucleic Acids Res.* 25:3389-3402). Furthermore, pattern-hit-initiated BLAST (PHI-BLAST) programs have been designed to identify specific patterns or sequence motifs shared by distantly-related proteins (Z. Zhang et al. (1998) *Nucleic Acids Res.* 26:3986-3990). Specialized BLAST programs are also available for performing searches of, human, microbial, and malaria genome sequences, as well as searches for vector, immunoglobulin, and predicted human consensus sequences (National Center for Biotechnology Information (NCBI), Bethesda, Md.).

Both FASTA and BLAST programs identify very short exact sequence matches between the query sequence and the databases sequences, analyze the best short sequence matches ("hits") to determine if longer stretches of sequence similarity are present, and then optimize the best hits by dynamic programming (S. F. Altschul et al. (1990) *J. Mol. Biol.* 215:403-410; W. R. Pearson, supra). In contrast, the SSEARCH program compares the query sequence to all the sequences in the database via pair-wise sequence comparisons (T. F. Smith et al., supra). Thus, the SSEARCH program is considered more sensitive than the BLAST and FASTA programs, but it is also significantly slower. The BLAST and FASTA programs utilize several approximations to increase their searching speed, and utilize statistical parameters (see below) to increase sensitivity and selectivity to approximate the performance of the SSEARCH program. A particular sequence alignment program can be chosen based on the requirements of a sequence search, or individual preferences. In some cases, it may be necessary to use more than one search alignment program to confirm search alignment results or resolve ambiguous search results.

Typically, BLAST analysis employs (i) a scoring matrix (such as, e.g., BLOSSUM 62 or PAM 120) to assign a weighted homology value to each residue and (ii) a filtering program(s) (such as SEG or XNU) that recognizes and eliminates highly repeated sequences from the calculation. An appropriate homology cutoff is then determined by performing BLAST comparisons (using a particular scoring matrix and filtering program) between sequences that are known to be related. It will be understood that other appropriate scoring matrices and filtering programs may be used when the cutoff is calibrated as described herein. That is, the particular cutoff point may vary when different standard parameters are used, but it will correspond to the P(N) scores exhibited when highly related sequences are compared using those particular parameters.

B7-Related Nucleic Acids

One aspect of the present invention pertains to isolated nucleic acids having a nucleotide sequence such as BSL1 (SEQ ID NO:1 or 3), BSL2 (SEQ ID NO:6, 10, or 12), or BSL3 (SEQ ID NO:14), or fragments thereof. The nucleic acid molecules of the invention can be DNA or RNA. A preferred nucleic acid is a DNA encoding the human BSL1 (SEQ ID NO:2), BSL2 (SEQ ID NO:7, 11, or 13), or BSL3 (SEQ ID NO:15), or fragments or functional equivalents thereof. Such nucleic acids can comprise at least 15, 20, 25, 50, 60, 100, 200, 240, 255, 270, 300, 305, 310, 410, 500, 630, 700, or 1000 contiguous nucleotides.

The term "isolated" as used throughout this application refers to a B7-related nucleic acid, polypeptide, peptide, protein fusion, or antibody, that is substantially free of cellular material or culture medium. An isolated or substantially purified molecule contains less than about 50%, preferably less than about 25%, and most preferably less than about 10%, of the cellular components with which it was associated.

The term "functional equivalent" is intended to include nucleotide sequences encoding functionally equivalent B7-related factors. A functional equivalent of a B7-related protein includes fragments or variants that perform at least one characteristic function of the B7-related protein (e.g., ligand-binding, antigenic, intra-, or intercellular activity). For example, DNA sequence polymorphisms within the nucleotide sequence of a B7-related factor, especially those within the third base of a codon, may result in "silent" mutations, which do not affect the encoded amino acid sequence of the protein due to the degeneracy of the genetic code.

Preferred embodiments include an isolated nucleic acid sharing at least 60, 70, 80, 85, 90, 95, 97, 98, 99, 99.5, or 100% sequence identity with a polynucleotide sequence of BSL1 (SEQ ID NO:1 or 3), BSL2 (SEQ ID NO:6, 10, or 12), or BSL3 (SEQ ID NO:15). This polynucleotide sequence may be identical to the nucleotide sequences of BSL1 (SEQ ID NO:1 and 3), BSL2 (SEQ ID NO:6, 10, or 12), or BSL3 (SEQ ID NO:14), or may include up to a certain integer number of nucleotide alterations as compared to the reference sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing. Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and Sequence Analysis Primer, Gribskov, M. and Devereux, J., eds., M Stockton Press, New York, 1991; and Carillo, H., and Lipman, D., SIAM *J. Applied Math.*, 48:1073 (1988).

For nucleic acids, sequence identity can be determined by comparing a query sequences, to sequences in publicly available sequence databases (NCBI) using the BLASTN2 algorithm (S. F. Altschul et al., 1997, *Nucl. Acids Res.*, 25:3389-3402). The parameters for a typical search are: E=0.05, v=50, B=50, wherein E is the expected probability score cutoff, V is the number of database entries returned in the reporting of the results, and B is the number of sequence alignments returned in the reporting of the results (S. F. Altschul et al., 1990, *J. Mol. Biol.*, 215:403-410).

In another approach, nucleotide sequence identity can be calculated using the following equation: % identity=(number of identical nucleotides)/(alignment length in nucleotides) *100. For this calculation, alignment length includes internal gaps but not terminal gaps. Alternatively, nucleotide sequence identity can be determined experimentally using the specific hybridization conditions described below.

In accordance with the present invention, nucleic acid alterations are selected from the group consisting of at least one nucleotide deletion, substitution, including transition and transversion, insertion, or modification (e.g., via RNA or DNA analogs, dephosphorylation, methylation, or labeling). Alterations may occur at the 5' or 3' terminal positions of the reference nucleotide sequence or anywhere between those terminal positions, interspersed either individually among the nucleotides in the reference sequence or in one or more contiguous groups within the reference sequence. Alterations of a nucleic acid sequence of BSL1 (SEQ ID NO:1 and 3), BSL2 (SEQ ID NO:6, 10, or 12), or BSL3 (SEQ ID NO:14) may create nonsense, missense, or frameshift mutations in the coding sequence, and thereby alter the polypeptide encoded by the nucleic acid.

Also encompassed by the present invention are splice variants derived from the BSL1 (SEQ ID NO:1 and 3), BSL2 (SEQ ID NO:6, 10, or 12), or BSL3 (SEQ ID NO:14) nucleic acid sequences. As used herein, the term "splice variant" refers to variant B7-related nucleic acids and polypeptides produced by differential processing of the primary transcript(s) of genomic DNA. An alternate splice variant may comprise, for example, any one of the sequences of BSL2 (SEQ ID NO:6, 10, or 12) disclosed herein. Alternate splice variants can also comprise other combinations of introns/exons of BSL1, BSL2, or BSL3, which can be determined by those of skill in the art. Alternate splice variants can be determined experimentally, for example, by isolating and analyzing cellular RNAs (e.g., Southern blotting or PCR), or by screening cDNA libraries using the B7-related nucleic acid probes or primers described herein. In another approach, alternate splice variants can be predicted using various methods, computer programs, or computer systems available to practitioners in the field.

General methods for splice site prediction can be found in Nakata, 1985, *Nucleic Acids Res.* 13:5327-5340. In addition, splice sites can be predicted using, for example, the GRAIL™ (E. C. Uberbacher and R. J. Mural, 1991, *Proc. Natl. Acad. Sci. USA*, 88:11261-11265; E. C. Uberbacher, 1995, *Trends Biotech.*, 13:497-500; http://grail.lsd.ornl.gov/grailexp); GenView (L. Milanesi et al., 1993, *Proceedings of the Second International Conference on Bioinformatics, Supercomputing, and Complex Genome Analysis*, H. A. Lim et al. (eds), World Scientific Publishing, Singapore, pp. 573-5881); SpliceView; and HSPL (V. V. Solovyev et al., 1994, *Nucleic Acids Res.* 22:5156-5163; V. V. Solovyev et al., 1994, "The Prediction of Human Exons by Oligonucleotide Composition and Discriminant Analysis of Spliceable Open Reading Frames," R. Altman et al. (eds), *The Second International conference on Intelligent systems for Molecular Biology*, AAAI Press, Menlo Park, Calif., pp. 354-362; V. V. Solovyev et al., 1993, "Identification Of Human Gene Functional Regions Based On Oligonucleotide Composition," L. Hunter et al. (eds), *In Proceedings of First International conference on Intelligent System for Molecular Biology*, Bethesda, pp. 371-379) computer systems.

Additionally, computer programs such as GeneParser (E. E. Snyder and G. D. Stormo, 1995, *J. Mol. Biol.* 248: 1-18; E. E. Snyder and G. D. Stormo, 1993, *Nucl. Acids Res.* 21(3): 607-613; http://mcdb.colorado.edu/~eesnyder/GeneParser.html); MZEF (M. Q. Zhang, 1997, *Proc. Natl. Acad. Sci. USA*, 94:565-568; http://argon.cshl.org/genefinder); MORGAN (S. Salzberg et al., 1998, *J. Comp. Biol.* 5:667-680; S. Salzberg et al. (eds), 1998, *Computational Methods in Molecular Biology*, Elsevier Science, New York, N.Y., pp. 187-203); VEIL (J. Henderson et al., 1997, *J. Comp. Biol.* 4:127-141); GeneScan (S. Tiwari et al., 1997, *CABIOS (BioInformatics)* 13: 263-270); GeneBuilder (L. Milanesi et al., 1999, *Bioinformatics* 15:612-621); Eukaryotic GeneMark (J. Besemer et al., 1999, *Nucl. Acids Res.* 27:3911-3920); and FEXH (V. V. Solovyev et al., 1994, *Nucleic Acids Res.* 22:5156-5163). In addition, splice sites (i.e., former or potential splice sites) in cDNA sequences can be predicted using, for example, the RNASPL (V. V. Solovyev et al., 1994, *Nucleic Acids Res.* 22:5156-5163); or INTRON (A. Globek et al., 1991, INTRON version 1.1 manual, Laboratory of Biochemical Genetics, NIMH, Washington, D.C.) programs.

The present invention also encompasses naturally-occurring polymorphisms of BSL1 (SEQ ID NO:1 and 3), BSL2 (SEQ ID NO:6, 10, or 12), or BSL3 (SEQ ID NO:14). As will be understood by those in the art, the genomes of all organisms undergo spontaneous mutation in the course of their continuing evolution generating variant forms of gene sequences (Gusella, 1986, *Ann. Rev. Biochem.* 55:831-854). Restriction fragment length polymorphisms (RFLPs) include variations in DNA sequences that alter the length of a restriction fragment in the sequence (Botstein et al., 1980, *Am. J. Hum. Genet.* 32, 314-331 (1980). RFLPs have been widely used in human and animal genetic analyses (see WO 90/13668; WO 90/11369; Donis-Keller, 1987, *Cell* 51:319-337; Lander et al., 1989, *Genetics* 121: 85-99). Short tandem repeats (STRs) include tandem di-, tri- and tetranucleotide repeated motifs, also termed variable number tandem repeat (VNTR) polymorphisms. VNTRs have been used in identity and paternity analysis (U.S. Pat. No. 5,075,217; Armour et al., 1992, *FEBS Lett.* 307:113-115; Horn et al., WO 91/14003; Jeffreys, EP 370,719), and in a large number of genetic mapping studies.

Single nucleotide polymorphisms (SNPs) are far more frequent than RFLPS, STRs, and VNTRs. SNPs may occur in protein coding (e.g., exon), or non-coding (e.g., intron, 5'UTR, 3'UTR) sequences. SNPs in protein coding regions may comprise silent mutations that do not alter the amino acid sequence of a protein. Alternatively, SNPs in protein coding regions may produce conservative or non-conservative amino acid changes, described in detail below. In some cases, SNPs may give rise to the expression of a defective or other variant protein and, potentially, a genetic disease. SNPs within protein-coding sequences can give rise to genetic diseases, for example, in the β-globin (sickle cell anemia) and CFTR (cystic fibrosis) genes. In non-coding sequences, SNPs may also result in defective protein expression (e.g., as a result of defective splicing). Other single nucleotide polymorphisms have no phenotypic effects.

Single nucleotide polymorphisms can be used in the same manner as RFLPs and VNTRs, but offer several advantages. Single nucleotide polymorphisms tend to occur with greater frequency and are typically spaced more uniformly throughout the genome than other polymorphisms. Also, different SNPs are often easier to distinguish than other types of polymorphisms (e.g., by use of assays employing allele-specific hybridization probes or primers). In one embodiment of the present invention, a BSL1, BSL2, or BSL3 nucleic acid contains at least one SNP. Various combinations of these SNPs are also encompassed by the invention. In a preferred aspect, a B7-related SNP is associated with a immune system disorder, such as the disorders described in detail herein.

Further encompassed by the present invention are nucleic acid molecules that share moderate homology with the BSL1 (SEQ ID NO:1 and 3), BSL2 (SEQ ID NO:6, 10, or 12), or BSL3 (SEQ ID NO:14) nucleic acid sequences, and hybridize to the BSL1, BSL2, or BSL3 nucleic acid molecules under moderate stringency hybridization conditions. More preferred are nucleic acid molecules that share substantial homology with the BSL1, BSL2, or BSL3 nucleic acid sequences and hybridize to the BSL1, BSL2, or BSL3 nucleic acid molecules under high stringency hybridization conditions. As used herein, the phrase "moderate homology" refers to sequences which share at least 60% sequence identity with a reference sequence (e.g., BSL1, BSL2 or BSL3), whereas the phrase "substantial homology" refers to sequences that share at least 90% sequence identity with a reference sequence. It is recognized, however, that polypeptides and the nucleic acids encoding such polypeptides containing less than the above-described level of homology arising as splice variants or that are modified by conservative amino acid substitutions (or substitution of degenerate codons) are contemplated to be within the scope of the present invention.

The phrase "hybridization conditions" is used herein to refer to conditions under which a double-stranded nucleic acid hybrid is formed from two single nucleic acid strands, and remains stable. As known to those of skill in the art, the stability of the hybrid sequence is reflected in the melting temperature ($T_m$) of the hybrid (see F. M. Ausubel et al., Eds, (1995) *Current Protocols in Molecular Biology*, John Wiley and Sons, Inc., New York, N.Y.). The $T_m$ decreases approximately 0.5° C. to 1.5° C. with every 1% decrease in sequence homology. In general, the stability of a hybrid sequence is a function of the length and guanine/cytosine content of the hybrid, the sodium ion concentration, and the incubation temperature. Typically, the hybridization reaction is initially performed under conditions of low stringency, followed by washes of varying, but higher, stringency. Reference to hybridization stringency relates to such washing conditions.

In accordance with the present invention, "high stringency" conditions can be provided, for example, by hybridization in 50% formamide, 5×Denhardt's solution, 5×SSPE, and 0.2% SDS at 42° C., followed by washing in 0.1×SSPE and 0.1% SDS at 65° C. By comparison, "moderate stringency" can be provided, for example, by hybridization in 50% formamide, 5×Denhardt's solution, 5×SSPE, and 0.2% SDS at 42° C., followed by washing in 0.2×SSPE and 0.2% SDS at 65° C. In addition, "low stringency" conditions can be provided, for example, by hybridization in 10% formamide, 5×Denhardt's solution, 6×SSPE, and 0.2% SDS at 42° C., followed by washing in 1×SSPE and 0.2% SDS at 50° C. It is understood that these conditions may be varied using a variety of buffers and temperatures well known to those skilled in the art.

In a preferred embodiment of the present invention, the nucleic acid is a DNA molecule encoding at least a portion of the B7-related factor. A nucleic acid molecule encoding a novel B7-related factor can be obtained from mRNA present in activated B lymphocytes. It may also be possible to obtain nucleic acid molecules encoding B7-related factors from B cell genomic DNA. Thus, a nucleic acid encoding a B7-related factor can be cloned from either a cDNA or a genomic library in accordance with the protocols described in detail herein. Nucleic acids encoding novel B7-related factors can also be cloned from genomic DNA or cDNA using established polymerase chain reaction (PCR) techniques (see K. Mullis et al. (1986) *Cold Spring Harbor Symp. Quant. Biol.* 51:260; K. H. Roux (1995) *PCR Methods Appl.* 4:S185) in accordance with the nucleic acid sequence information provided herein. The nucleic acid molecules of the invention, or fragments thereof, can also be chemically synthesized using standard techniques. Various methods of chemically synthesizing polydeoxynucleotides are known, including solid-phase synthesis which, like peptide synthesis, has been fully automated in commercially available DNA synthesizers (see, for example, U.S. Pat. No. 4,598,049 to Itakura et al.; U.S. Pat. No. 4,458,066 to Caruthers et al.; U.S. Pat. Nos. 4,401,796 and 4,373,071 to Itakura).

It will be appreciated by one skilled in the art that variations in one or more nucleotides (up to about 3-4% of the nucleotides) of the nucleic acid molecules encoding novel B7-related factors may exist among individuals within a population due to natural allelic variation. Any and all such nucleotide variations and resulting amino acid polymorphisms are within the scope of the invention. Furthermore, there may be one or more isoforms or related, cross-reacting family members of the B7-related factors described herein. Such isoforms or family members are defined as polypeptides that are related in function and amino acid sequence to a B7-related factor (e.g., BSL1, BSL2, or BSL3), but encoded by genes at different loci. In addition, it is possible to modify the DNA sequence of B7-related factors using genetic techniques to produce proteins or peptides with altered amino acid sequences.

DNA sequence mutations can be introduced into a nucleic acid encoding a B7-related factor by any one of a number of methods, including those for producing simple deletions or insertions, systematic deletions, insertions or substitutions of clusters of bases or substitutions of single bases, to generate desired variants. Mutations of the B7-related nucleic acid molecule to generate amino acid substitutions or deletions are preferably obtained by site-directed mutagenesis. Site directed mutagenesis systems are well known in the art, and can be obtained from commercial sources (see, for example, Amersham Pharmacia Biotech, Inc., Piscataway, N.J.). Guidance in determining which amino acid residues may be substituted, inserted, or deleted without abolishing biological or immunological activity may be found using computer programs well known in the art, for example, DNASTAR software (DNASTAR, Inc., Madison, Wis.). Mutant forms of the BSL1, BSL2, or BSL3 nucleic acid molecules are considered within the scope of the present invention, where the expressed polypeptide or peptide is capable modulating the activity of immune or inflammatory cells (e.g., T-cells).

A fragment of the nucleic acid molecule encoding a novel B7-related factor is defined as a nucleotide sequence having fewer nucleotides than the nucleotide sequence encoding the entire amino acid sequence of the B7-related factor. Nucleic acid fragments which encode polypeptides which retain the ability to bind to their natural ligand(s) on immune or inflammatory response cells, such as T-cells, and either amplify or block immune responses (as evidenced by, for example, lymphokine production and/or T-cell proliferation by T-cells that have received a primary activation signal) are considered within the scope of the invention. For example, nucleic acid fragments that encode polypeptides or peptides of a B7-related factor that retain the ability of the polypeptides or peptides to bind CD28 and/or CD28-related ligand(s) and deliver a co-stimulatory signal to T-cells are within the scope of the invention. Generally, the nucleic acid molecule encoding a fragment of a B7-related factor will be selected from the coding sequence for the mature protein. However, in some instances it may be desirable to select all or part of a fragment or fragments from the coding region that includes the leader sequence.

In one embodiment of the present invention, a nucleic acid molecule corresponding to a fragment of a BSL1, BSL2, or BSL3 nucleic acid sequence can be used as a probe for assaying a biological sample for the expression of one or more B7-related factors, or as a primer for DNA sequencing or PCR amplification. Preferably, such fragments are at least 8 contiguous nucleotides in length, more preferably at least 12 contiguous nucleotides in length, even more preferably at least 15 contiguous nucleotides in length, and even more preferably at least 20 contiguous nucleotides in length. Nucleic acid molecules within the scope of the invention may also contain linker sequences, modified restriction endonuclease sites, and other sequences useful for molecular cloning, expression, or purification of recombinant protein or fragments thereof. Nucleic acid molecules in accordance with the present invention may also be conjugated with radioisotopes, or chemiluminescent, fluorescent, or other labeling compounds (e.g., digoxigenin). In addition, the nucleic acid molecules of the present invention may be modified by nucleic acid modifying enzymes, for example, kinases or phosphatases. These and other modifications of nucleic acid molecules are well known in the art.

In addition, a nucleic acid molecule that encodes a B7-related factor, or a biologically active fragment thereof, can be ligated to a heterologous sequence to encode a fusion protein (also called a chimeric protein). For example, it may be useful to construct a nucleic acid encoding a fusion protein comprising a B7-related factor and the Fc domain of human IgG as described herein. The resulting BSL1-Ig, BSL2-Ig, and BSL3-Ig fusion proteins can then be expressed in host cells, and used to prepare pharmaceutical compositions useful for immunomodulation (see below). Fusion proteins comprising B7-related polypeptides can also be used for the isolation and purification of B7-related polypeptides or antibodies (see below). In addition, fusion proteins can be used to identify cellular ligands or binding partners for BSL1, BSL2, or BSL3 (see below).

B7-Related Nucleic Acid Expression Vectors

Another aspect of the present invention pertains to expression vectors comprising a nucleic acid encoding at least one B7-related factor, as described herein, operably linked to at least one regulatory sequence. "Operably linked" is intended to mean that the nucleotide acid sequence is linked to a regulatory sequence in a manner that allows expression of the nucleotide sequence. Regulatory sequences are known in the art and are selected to direct expression of the desired protein in an appropriate host cell. Accordingly, the term regulatory sequence includes promoters, enhancers and other expression control elements (see D. V. Goeddel (1990) *Methods Enzymol.* 185:3-7). It should be understood that the design of the expression vector may depend on such factors as the choice of the host cell to be transfected and/or the type of polypeptide desired to be expressed.

Appropriate host cells for use with the present invention include bacteria, fungi, yeast, plant, insect, and animal cells, especially mammalian and human cells. Preferred replication and inheritance systems include M13, ColE1, SV40, baculovirus, lambda, adenovirus, CEN ARS, 2 μm ARS and the like. Several regulatory elements (e.g., promoters) have been isolated and shown to be effective in the transcription and translation of heterologous proteins in the various hosts. Such regulatory regions, methods of isolation, manner of manipulation, etc. are known in the art. Non-limiting examples of bacterial promoters include the β-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac, UV5 promoters. Non-limiting examples of yeast promoters include the 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH1) promoter. Suitable promoters for mammalian cells include, without limitation, viral promoters, such as those from Simian Virus 40 (SV40), Rous sarcoma virus (RSV), adenovirus (ADV), and bovine papilloma virus (BPV).

Eukaryotic cells may also require terminator sequences, polyadenylation sequences, and enhancer sequences that modulate gene expression. Sequences that cause amplification of the gene may also be desirable. These sequences are well known in the art. Furthermore, sequences that facilitate secretion of the recombinant product from cells, including, but not limited to, bacteria, yeast, and animal cells, such as secretory signal sequences and/or preprotein or proprotein sequences, may also be included. Such sequences are well described in the art.

Suitable expression vectors include, but are not limited to, pUC, pBluescript (Stratagene), pET (Novagen, Inc., Madison, Wis.), and pREP (Invitrogen) plasmids. Vectors can contain one or more replication and inheritance systems for cloning or expression, one or more markers for selection in the host, e.g. antibiotic resistance, and one or more expression cassettes. The inserted coding sequences can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

In one embodiment, the expression vector comprises a nucleic acid encoding at least a portion of the BSL1, BSL2, or BSL3 polypeptide. In another embodiment, the expression vector comprises a DNA sequence encoding the B7-related factor and a DNA sequence encoding another B7-related factor or a heterologous polypeptide or peptide. Such expression vectors can be used to transfect host cells to thereby produce polypeptides or peptides, including fusion proteins or peptides encoded by nucleic acid molecules as described below.

Isolation of B7-Related Polypeptides

Yet another aspect of the present invention pertains to methods of isolating B7-related polypeptides and related peptides. As used herein, the terms "protein" and "polypeptide" are synonymous. Peptides are defined as fragments or portions of proteins or polypeptides, preferably fragments or portions having the same or equivalent function or activity as the complete protein. Both naturally occurring and recombinant forms of the B7-related polypeptides or peptides may be used in assays and treatments according to the present invention. Methods for directly isolating and purifying polypeptides or peptides from natural sources such as cellular or extracellular lysates are well known in the art (see E. L. V. Harris and S. Angel, Eds. (1989) *Protein Purification Methods: A Practical Approach*, IRL Press, Oxford, England). Such methods include, without limitation, preparative disc-gel electrophoresis, isoelectric focusing, high-performance liquid chromatography (HPLC), reversed-phase HPLC, gel filtration, ion exchange and partition chromatography, and countercurrent distribution, and combinations thereof. Naturally occurring polypeptides can be purified from many possible sources, for example, plasma, body cells and tissues, or body fluids.

To produce recombinant B7-related polypeptides or peptides, DNA sequences encoding the B7-related polypeptides or peptides are cloned into a suitable vector for expression in intact host cells or in cell-free translation systems (see J. Sambrook et al., supra). Prokaryotic and eukaryotic vectors and host cells may be employed. The particular choice of a vector, host cell, or translation system is not critical to the practice of the invention. DNA sequences can be optimized, if desired, for more efficient expression in a given host organism. For example, codons can be altered to conform to the preferred codon usage in a given host cell or cell-free translation system using techniques routinely practiced in the art.

For some purposes, it may be preferable to produce peptides or polypeptides in a recombinant system wherein the peptides or polypeptides carry additional sequence tags to facilitate purification. Such markers include epitope tags and protein tags. Non-limiting examples of epitope tags include c-myc, hemagglutinin (HA), polyhistidine (6×-HIS) (SEQ ID NO:93), GLU-GLU, and DYKDDDDK (SEQ ID NO:94) (FLAG®) epitope tags. Epitope tags can be added to peptides by a number of established methods. DNA sequences of epitope tags can be inserted into peptide coding sequences as oligonucleotides or through primers used in PCR amplification. As an alternative, peptide-coding sequences can be cloned into specific vectors that create fusions with epitope tags; for example, pRSET vectors (Invitrogen Corp., San Diego, Calif.). Non-limiting examples of protein tags include glutathione-S-transferase (GST), green fluorescent protein (GFP), and maltose binding protein (MBP). Protein tags are attached to peptides or polypeptides by several well-known methods. In one approach, the coding sequence of a polypeptide or peptide can be cloned into a vector that creates a fusion between the polypeptide or peptide and a protein tag of interest. Suitable vectors include, without limitation, the exemplary plasmids, pGEX (Amersham Pharmacia Biotech, Inc., Piscataway, N.J.), pEGFP (CLONTECH Laboratories, Inc., Palo Alto, Calif.), and pMAL™ (New England BioLabs, Inc., Beverly, Mass.). Following expression, the epitope or protein tagged polypeptide or peptide can be purified from a crude lysate of the translation system or host cell by chromatography on an appropriate solid-phase matrix. In some cases, it may be preferable to remove the epitope or protein tag (i.e., via protease cleavage) following purification.

Suitable cell-free, expression systems for use in accordance with the present invention include rabbit reticulocyte lysate, wheat germ extract, canine pancreatic microsomal membranes, *E. coli* S30 extract, and coupled transcription/translation systems (Promega Corp., Madison, Wis.). These systems allow the expression of recombinant polypeptides or peptides upon the addition of cloning vectors, DNA fragments, or RNA sequences containing coding regions and appropriate promoter elements.

Host cells for recombinant cloning vectors include bacterial, archebacterial, fungal, plant, insect and animal cells, especially mammalian cells. Of particular interest are *E. coli, B. subtilis, S. aureus, S. cerevisiae, S. pombe, N. crassa*, SF9, C129, 293, NIH 3T3, CHO, COS, and HeLa cells. Such cells can be transformed, transfected, or transduced, as appropriate, by any suitable method including electroporation, CaCl$_2$-, LiCl-, LiAc/PEG-, spheroplasting-, Ca-Phosphate, DEAE-dextran, liposome-mediated DNA uptake, injection, microinjection, microprojectile bombardment, or other established methods.

In order to identify host cells that contain the expression vector, a gene that contains a selectable marker is generally introduced into the host cells along with the gene of interest. Preferred selectable markers include those that confer resistance to drugs, such as G418, hygromycin, methotrexate, or ampicillin. Selectable markers can be introduced on the same plasmid as the gene of interest. Host cells containing the gene of interest are identified by drug selection, as cells that carry the drug-resistance marker survive in growth media containing the corresponding drug.

The surviving cells can be screened for production of recombinant B7-related polypeptides, or peptides or fusions thereof. In one embodiment, the recombinant polypeptides are secreted to the cell surface, and can be identified by cell, surface staining with ligands to the B cell antigens (e.g., CD28-Ig). In another embodiment, the recombinant polypeptides are retained in the cytoplasm of the host cells, and can be identified in cell extracts using anti-B7-related polypeptide antibodies. In yet another embodiment, soluble recombinant polypeptides are secreted into the growth media, and can be identified by screening the growth media with anti-B7-related polypeptide antibodies. A soluble, secreted recombinant B7-polypeptide includes the extracellular domain of the polypeptide, or any fragment thereof, that does not include the cytoplasmic and/or transmembrane regions. The cell-surface and cytoplasmic recombinant B7-related polypeptides can be isolated following cell lysis and extraction of cellular proteins, while the secreted recombinant B7-related polypeptides can be isolated from the cell growth media by standard techniques (see I. M. Rosenberg, Ed. (1996) *Protein Analysis and Purification: Benchtop Techniques*, Birkhauser, Boston, Cambridge, Mass.).

Antibody-based methods can used to purify natural or recombinantly produced B7-related polypeptides or peptides. Antibodies that recognize these polypeptides, or peptides derived therefrom, can be produced and isolated using methods known and practiced in the art (see below). B7-related polypeptides or peptides can then be purified from a crude lysate by chromatography on antibody-conjugated solid-phase matrices (see E. Harlow and D. Lane, 1999, *Using Antibodies: A Laboratory Manual*, Cold Spring Harbor Laboratory, Cold Spring Harbor, N.Y.). Other purification methods known and used in the art may also be employed.

It is noted that transfected host cells that express B7-related factors (e.g., BSL1, BSL2, and/or BSL3) or portions thereof on the surface of the cell are within the scope of this invention. For example, a tumor cell such as a sarcoma, melanoma, leukemia, lymphoma, carcinoma, or neuroblastoma can be transfected with an expression vector directing the expression of at least one B7-related factor on the surface of the tumor cell. Such transfected tumor cells can be used to treat tumor immunity as described in detail herein.

B7-Related Polypeptides

A further aspect of the present invention pertains to isolated B7-related polypeptides. The present invention encompasses the BSL1 (SEQ ID NO:2), BSL2 (SEQ ID NO:7, 11, or 13), or BSL3 (SEQ ID NO:15) polypeptides, and fragments and functional equivalents thereof. Such polypeptides can comprise at least 5, 12, 20, 30, 50, 100, 170, 200, 210, 300, or 500 contiguous amino acid residues. Preferred are polypeptides that share moderate homology with BSL1 (SEQ ID NO:2), BSL2 (SEQ ID NO:7, 11, or 13), or BSL3 (SEQ ID NO:15) polypeptides. More preferred are polypeptides that share substantial homology with BSL1 (SEQ ID NO:2), BSL2 (SEQ ID NO:7, 11, or 13), or BSL3 (SEQ ID NO:15).

The term "functional equivalent" is intended to include proteins which differ in amino acid sequence from a given B7-related polypeptide, such as sequence of BSL1 (SEQ ID NO:2), BSL2 (SEQ ID NO:7, 11, or 13), or BSL3 (SEQ ID NO:15) polypeptide, but where such differences result in a modified protein which performs at least one characteristic function of the B7-related polypeptide (e.g., ligand-binding, antigenic, intra- or intercellular activity). For example, a functional equivalent of a BSL1, BSL2, or BSL3 polypeptide may have a modification such as a substitution, addition or deletion of an amino acid residue which is not directly involved in the function of this polypeptide the ability of these polypeptides to co-stimulate T-cell proliferation). In addition, non-naturally occurring analogs of B7-related polypeptides capable of binding CD28 and/or CD28-related ligand(s) are considered functional equivalents. Various modifications of the B7-related polypeptides to produce functional equivalents of these polypeptides are described in detail herein.

It is also possible to modify the structure of a B7-related polypeptide for such purposes as increasing solubility, enhancing therapeutic or prophylactic efficacy (reactivity), or stability (e.g., shelf life ex vivo and resistance to proteolytic degradation in vivo). Such modified proteins are considered functional equivalents of the B7-related polypeptides as defined herein. Preferably, the B7-related polypeptides are modified so that they retain the ability to co-stimulate T-cell proliferation. Those residues shown to be essential to interact with the CD28 or CD28-related ligands on T-cells can be modified by replacing the essential amino acid with another, preferably similar amino acid residue (a conservative substitution) whose presence is shown to enhance, diminish, but not eliminate, or not effect receptor interaction. In addition, those amino acid residues that are not essential for receptor interaction can be modified by being replaced by another amino acid whose incorporation may enhance, diminish, or not effect reactivity. For example, a B7-related polypeptide can be modified by substitution of cysteine residues with other amino acids, such as alanine, serine, threonine, leucine, or glutamic acid, to prevent dimerization via disulfide linkages. In addition, the amino acid side chains of a B7-related polypeptide of the invention can be chemically modified. Also, a B7-related polypeptide can be modified by cyclization of the amino acid sequence.

In order to enhance stability and/or reactivity, the B7-related polypeptides can be altered to incorporate one or more polymorphisms in the amino acid sequence. Additionally, D-amino acids, non-natural amino acids, or non-amino acid analogs can be substituted or added to produce a modified polypeptide. Furthermore, the B7-related polypeptides disclosed herein can be modified using polyethylene glycol (PEG) according to known methods (Wie et al., supra) to produce a protein conjugated with PEG. In addition, PEG can be added during chemical synthesis of the protein. Other possible modifications include reduction/alkylation (Tarr (1986) *Methods of Protein Microcharacterization*, J. E. Silver, Ed., Humana Press, Clifton, N.J., pp. 155-194); acylation (Tarr, supra); chemical coupling to an appropriate carrier (Mishell and Shiigi, Eds. (1980) *Selected Methods in Cellular Immunology*, W H Freeman, San Francisco, Calif.; U.S. Pat. No. 4,939,239; or mild formalin treatment (Marsh (1971) *Int. Arch. of Allergy and Appl. Immunol.* 41:199-215) of the B7-related polypeptide.

Modified polypeptides can have conservative changes, wherein a substituted amino acid has similar structural or chemical properties, e.g., replacement of leucine with isoleucine. More infrequently, a modified polypeptide can have non-conservative changes, e.g., substitution of a glycine with a tryptophan. Guidance in determining which amino acid residues can be substituted, inserted, or deleted without abolishing biological or immunological activity can be found using computer programs well known in the art, for example, DNASTAR software (DNASTAR, Inc., Madison, Wis.)

As non-limiting examples, conservative substitutions in the B7-related amino acid sequence can be made in accordance with the following table:

| Original Residue | Conservative Substitution(s) |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunogenicity can be made by selecting substitutions that are less conservative than those shown in the table, above. For example, non-conservative substitutions can be made which more significantly, affect the structure of the polypeptide in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Preferred polypeptide embodiments further include an isolated polypeptide comprising an amino acid sequence sharing at least 60, 70, 80, 85, 90, 95, 97, 98, 99, 99.5 or 100% identity with an amino acid sequence of BSL1 (SEQ ID NO:2), BSL2 (SEQ ID NO:7, 11, or 13), or BSL3 (SEQ ID NO:15). This polypeptide sequence may be identical to the sequence of BSL1 (SEQ ID NO:2), BSL2 (SEQ ID NO:7, 11, or 13), or BSL3 (SEQ ID NO:15), or may include up to a certain integer number of amino acid alterations as compared to the reference sequence Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, *Bioinformatics: Sequence and Genome Analysis*, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch, 1970, *J Mol. Biol.* 48:443-453; 2) BLOSSUM62 comparison matrix from Hentikoff and Hentikoff, 1992, *Proc. Natl. Acad. Sci. USA* 89:10915-10919; 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)*100. For this calculation, alignment length includes internal gaps but does not include terminal gaps.

In accordance with the present invention, polypeptide sequences may be identical to the sequence of BSL1 (e.g., SEQ ID NO:2), BSL2 (e.g., SEQ ID NO:7, 11, or 13), or BSL3 (e.g., SEQ ID NO:15), or may include up to a certain integer number of amino acid alterations. Polypeptide alterations are selected from the group consisting of at least one amino acid deletion, substitution, including conservative and non-conservative substitution, or insertion. Alterations may occur at the amino- or carboxy-terminal positions of the reference polypeptide sequence or anywhere between those terminal positions, interspersed either individually among the amino acids in the reference sequence or in one or more contiguous groups within the reference sequence. In specific embodiments, polypeptide variants may be encoded by BSL1, BSL2, or BSL3 nucleic acids comprising single nucleotide polymorphisms and/or alternate splice variants. Polypeptides may also be modified by, for example, phosphorylation, sulfation, or acylation. They may also be modified with a label capable of providing a detectable signal, either directly or indirectly, including, but not limited to, radioisotopes and fluorescent compounds.

The invention also relates to isolated, synthesized and/or recombinant portions or fragments of a BSL1 (e.g., SEQ ID NO:2), BSL2 (e.g., SEQ ID NO:7, 11, or 13), or BSL3 (e.g., SEQ ID NO:15) protein or polypeptide as described herein. Polypeptide fragments (i.e., peptides) can be made which have full or partial function on their own, or which when mixed together (though fully, partially, or nonfunctional alone), spontaneously assemble with one or more other polypeptides to reconstitute a functional protein having at least one functional characteristic of a BSL1, BSL2, or BSL3 protein of this invention. In addition, B7-related polypeptide fragments may comprise, for example, one or more domains of the polypeptide (e.g., the transmembrane or extracellular domain) disclosed herein.

The polypeptides of the present invention, including function-conservative variants, may be isolated from wild-type or mutant cells (e.g., human cells or cell lines), from heterologous organisms or cells (e.g., bacteria, yeast, insect, plant, and mammalian cells), or from cell-free translation systems (e.g., wheat germ, microsomal membrane, or bacterial extracts) in which a protein-coding sequence has been introduced and expressed. Furthermore, the polypeptides may be part of recombinant fusion proteins. The polypeptides can also, advantageously, be made by synthetic chemistry. Polypeptides may be chemically synthesized by commercially available automated procedures, including, without limitation, exclusive solid phase synthesis, partial solid phase methods, fragment condensation or classical solution synthesis. Both the naturally occurring and recombinant forms of the polypeptides of the invention can advantageously be used to screen compounds for binding activity. The polypeptides of the invention also find use as therapeutic agents as well as antigenic components to prepare antibodies as described in detail herein.

Antibodies to B7-Related Polypeptides

Another aspect of the present invention encompasses antibodies that specifically recognize B7-related polypeptides or peptides, preferably the BSL1, BSL2, or BSL3 polypeptides, or fragments derived therefrom. As used herein, "antibody" refers to intact molecules as well as fragments thereof, such as Fab, F(ab)$_2$, and Fv, which are capable of binding an epitopic determinant. Antibodies that bind to a B7-related polypeptide, preferably the BSL1 (SEQ ID NO:2), BSL2 (SEQ ID NO:7, 11, or 13), or BSL3 (SEQ ID NO:15) polypeptide, can be prepared using the isolated B7-related polypeptide or peptide fragments as the immunogen or immunizing antigen by methods known in the art (see I. Lefkovits, Ed., (1996) *Immunology Methods Manual* Academic Press, Inc., San Diego, Calif.). As will be appreciated by those having skill in the art, the immunogen can be conjugated to a carrier protein, if desired, to increase immunogenicity, particularly, if a small peptide is used. Commonly used carriers that are routinely used chemically coupled to peptides include serum albumins, e.g., bovine, sheep, goat, or fish serum albumin, thyroglobulin, and keyhole limpet hemocyanin. The coupled immunogen-carrier is then used to immunize a recipient animal (e.g., mouse, rat, sheep, goat, or rabbit).

The term "antigenic determinant" refers to that fragment of a molecule (i.e., an epitope) that makes contact with a particular antibody. When the B7-polypeptide or peptide fragment is used to immunize a host animal, numerous regions of the polypeptide or peptide fragment may induce the production of antibodies which bind specifically to a given region or three-dimensional structure on the polypeptide or peptide. Such regions or structures are referred to as antigenic determinants or epitopes. An antigenic determinant may compete with the intact antigen (i.e., the immunogen used to elicit the immune response) for binding to an antibody. Preferred are those antigenic determinants that are specific for the BSL1 (SEQ ID NO:2), BSL2 (SEQ ID NO:7, 11, or 13), or BSL3 (SEQ ID NO:15) polypeptide or peptide. B7-related polypeptide- or peptide-derived immunogens can be obtained using techniques as described above. For example, B7-related polypeptide or peptide fragments can be isolated from natural or recombinant sources and purified by excising the polypeptides or peptide fragments from gels, particularly SDS-PAGE gels.

BSL1-, BSL2-, or BSL3-specific antibodies according to the present invention include polyclonal and monoclonal antibodies. The antibodies can be elicited in an animal host by immunization with B7-related polypeptide-derived immunogenic components or can be formed by in vitro immunization (sensitization) of immune cells. The immunogenic components used as immunogens to elicit the production of antibodies can be isolated from plasma, recombinantly produced, or chemically synthesized. The antibodies can also be produced in recombinant systems programmed with appropriate antibody-encoding DNA. Alternatively, the antibodies can be constructed by biochemical reconstitution of purified heavy and light chains. The antibodies include hybrid antibodies, chimeric antibodies, humanized antibodies (see, for example, U.S. Pat. No. 5,585,089 to C. J. Queen et al.) and univalent antibodies. Also included are Fab fragments, Fab' and F(ab)$_2$ fragments of antibodies. Notably, antibodies that specifically recognize either the secreted, cell surface form, or the cytoplasmic, soluble form of a B7-related factor can be isolated.

Hybridomas that produce monoclonal antibodies against the immunogenic components of the invention can be produced by well-known techniques. Hybridomas can be produced by the fusion of an immortalized cell line with a B-lymphocyte that produces the desired antibody. Alternatively, non-fusion techniques for generating immortal antibody-producing cell lines are possible, and are within the purview of the present invention (see Casali et al. (1986) *Science* 234: 476). Immortalized cell lines are typically transformed mammalian cells, particularly myeloma cells of rodent, bovine, and human origin. Most frequently, rat or mouse myeloma cell lines are employed as a matter of convenience and availability. Standard procedures can be used to select hybridomas, such as HAT (hypoxanthine-aminopterin-thymidine) selection. Hybridomas that secrete desired monoclonal antibodies can be selected by assaying the cells' culture medium by standard immunoassays, such as immunoblotting, ELISA (enzyme-linked immunosorbent assay; E. Engvall et al. (1971) *Immunochemistry*, 8:871-4; and D. J. Reen (1994) *Methods Mol. Biol.* 32:461-6), RIA (radioimmunoassay), or comparable assays. Antibodies can be recovered from the medium using standard protein purification techniques (see Tijssen (1985) *Practice and Theory of Enzyme Immunoassays*, Elsevier, Amsterdam).

In one embodiment, antibodies that react with a B7-related polypeptide or peptide fragment are used in accordance with the present invention to identify or isolate a B7-related polypeptide or peptide fragment in a biological sample. To isolate a B7-related polypeptide from a sample, antibodies that specifically recognize and bind to a B7-related polypeptide or peptide fragment are conjugated to a solid support, the antibody-conjugated solid support is incubated with the sample or an aliquot of the sample, and the polypeptide or peptide that binds to the antibodies is eluted from the solid support. To detect a B7-related polypeptide or peptide fragment in a sample, the sample is incubated with antibodies that specifically recognize and bind to a B7-related polypeptide or peptide fragment under conditions that allow the antibodies to bind to the polypeptide or peptide fragment, and the binding of the antibodies to the B7-related polypeptide or peptide fragment is determined.

Assays Utilizing B7-Related Nucleic Acids or Polypeptides

Expression analysis of B7-related factors: Several well-established techniques can be used to determine the expression levels, patterns, and cell-type specificity of the B7-related factors. For example, mRNA levels can be determined utilizing northern blot analysis (J. C. Alwine et al. (1977) *Proc. Natl. Acad. Sci. USA* 74:5350-5354; I. M. Bird (1998) *Methods Mol. Biol.* 105:325-36), whereby poly(A)$^+$ RNA is isolated from cells, separated by gel electrophoresis, blotted onto a support surface (e.g., nitrocellulose or Immobilon-Ny+ (Millipore Corp., Bedford, Mass.)), and incubated with a labeled (e.g., fluorescently labeled or radiolabeled) oligonucleotide probe that is capable of hybridizing with the mRNA of interest. Alternatively, mRNA levels can be determined by quantitative (for review, see W. M. Freeman et al. (1999) *Biotechniques* 26:112-122) or semi-quantitative RT-PCR analysis (Ren et al. *Mol. Brain Res.* 59:256-63). In accordance with this technique, poly(A)$^+$ RNA is isolated from cells, used for cDNA synthesis, and the resultant cDNA is incubated with PCR primers that are capable of hybridizing with the template and amplifying the template sequence to produce levels of the PCR product that are proportional to the cellular levels of the mRNA of interest. Another technique, in situ hybridization, can also be used to determine mRNA levels (reviewed by A. K. Raap (1998) *Mutat. Res.* 400:287-298). In situ hybridization techniques allow the visual detection of mRNA in a cell by incubating the cell with a labeled (e.g., fluorescently labeled or digoxigenin labeled) oligonucleotide probe that hybridizes to the mRNA of interest, and then examining the cell by microscopy.

Chromosomal mapping of B7-related genes: The chromosomal location of B7-related genes can be determined by various techniques known in the art. For example, high-resolution chromosomal banding can be used (reviewed by M. Ronne (1990) *In Vivo* 4:337-65). High-resolution banding techniques utilize elongated chromosomes from cells at early mitotic stages, which have been synchronized using DNA-synthesis inhibitors (e.g., methotrexate or thymidine) or DNA-binding agents (e.g., ethidium bromide). However, these techniques can only be used to map a gene to a relatively large region of a chromosome (~3 Mb). For more accurate gene mapping, fluorescence in situ hybridization (FISH) techniques can be used. In particular, high-resolution FISH techniques (A. Palotie et al. (1996) *Ann. Med.* 28:101-106) utilize free chromatin, DNA fibers, or mechanically-stretched chromosomes to map gene sequences ranging from several kilobases to 300 kb in size. Alternatively, the chromosomal location of a gene can be determined from the appropriate genome database, for example, the *Homo sapiens* genome database available at the Entrez Genome website (National Center for Biotechnology Information, Bethesda, Md.)

Identification of T-cell ligands: The B7-related polypeptides or peptides disclosed herein can be used to identify their cognate ligands on immune or inflammatory response cells, such as T-cells (i.e., CD28- or CTLA-4-related ligands). Candidate ligands, or fragments derived therefrom, can be identified and analyzed by many well-known methods in the art (see T. E. Creighton, Ed., 1997, *Proteins Structure: A Practical Approach*, IRL Press at Oxford Press, Oxford, England). For example, T-cell ligands that bind to the B7-related polypeptides or peptides can be identified from extracts or lysates obtained from animal, preferably human, immune or inflammatory response cells (e.g., T-cells). The proteins obtained from these sources can be separated into bands using sodium dodecylsulfate-polyacrylamide gel electrophoresis (SDS-PAGE) and transferred by electroblotting, for example, onto a suitable solid-phase support or membrane (e.g., nitrocellulose or polyvinylidene fluoride (PVDF)). The solid-phase support or membrane can then be incubated with a labeled form of a B7-related polypeptide or peptide, e.g., BSL1, BSL2, or BSL3 proteins that correspond to bands that exhibit specific binding with the labeled B7-related polypeptide or peptide can then be identified, isolated, purified, and analyzed by amino acid analysis and/or Edman degradation to determine the amino acid sequence of peptides derived therefrom.

As an alternative approach, a fusion protein comprising a B7-related polypeptide can be attached to a solid support and incubated with extracts obtained from cells, such as CHO or COS cells, that are transfected with an appropriate cDNA library. For example, a cDNA library can be constructed from resting or activated immortal human T-cell lines, such as CEM, HUT78, or Jurkat cell lines, or from resting or activated human T-cells derived from peripheral blood, tonsil, spleen, thymus or other specialized lymphoid tissues. Such cells can be activated by the addition of anti-CD3 and anti-CD28 monoclonal antibodies, phytohemaglutinin (PHA), or phorbol 12-myristate-13-acetate (PMA) with ionomycin. The cDNA library construct can contain a removable epitope tag (see above) that is different from the fusion protein, and will facilitate purification of the library expression product(s) that associate with the fusion protein. The isolated library expression product(s) can then be isolated and characterized. In addition, a fusion protein comprising a B7-related polypeptide can be attached to a solid support (e.g., a column comprising beads that specifically bind to the fusion protein) and incubated with lysates obtained from cells, such as T-cells, that are enriched for integral membrane proteins. The cellular proteins that associate with the fusion protein can be isolated and then characterized using MALDI-TOF analysis (Matrix Assisted Laser Desorption Ionization Time Of Flight Analysis; reviewed by Yates J R 3rd. (1998) *J. Mass Spectrom.* 33:1-19; P. Chaurand et al. (1999) *J. Am. Soc. Mass Spectrom.* 10:91-103). Fusion proteins can include, for example, FLAG®- (B. L. Brizzard et al. (1994) *Biotechniques* 16:730-735), 6×-HIS, and GST-tagged fusion proteins (see above), which can be attached to solid supports that are conjugated with anti-FLAG® antibodies, nickel, or glutathione molecules, respectively. Methods of producing and purifying such fusion proteins are well known in the art.

Another suitable ligand-binding assay is the yeast two-hybrid system (Fields et al. (1989) *Nature* 340:245-246; U.S. Pat. No. 5,283,173). The two-hybrid system relies on the reconstitution of transcription activation activity by association of the DNA-binding and transcription activation domains of a transcriptional activator through protein-protein interaction. The yeast GAL4 transcriptional activator may be used in this way, although other transcription factors have been used and are well known in the art. To carryout the two-hybrid assay, the GAL4 DNA-binding domain and the GAL4 transcription activation domain are expressed, separately, as fusions to potential interacting polypeptides. For example, one fusion protein can comprise a B7-related polypeptide fused to the GAL4 DNA-binding domain. The other fusion protein can comprise, for example, a T-cell cDNA library encoded polypeptide fused to the GAL4 transcription activation domain. If the two, coexpressed fusion proteins interact in the nucleus of a host cell, a reporter gene (e.g. LacZ) is activated to produce a detectable phenotype. The host cells that show two-hybrid interactions can be used to isolate the containing plasmids containing the cDNA library sequences. These plasmids can be analyzed to determine the nucleic acid sequence and predicted polypeptide sequence of the candidate T-cell ligand.

Related, in vivo, methods such as the three-hybrid (Licitra et al. (1996) *Proc. Natl. Acad. Sci. USA* 93:12817-12821), and reverse two-hybrid (Vidal et al. (1996) *Proc. Natl. Acad. Sci. USA* 93:10315-10320) systems may serve as alternative approaches. Commercially available two-hybrid systems such as the CLONTECH MATCHMAKER™ systems and protocols (CLONTECH, Palo Alto, Calif.) may be also be used. (See also, A. R. Mendelsohn et al. (1994) *Curr. Op. Biotech.* 5:482; E. M. Phizicky et al. (1995) *Microbiological Rev.* 59:94; M. Yang et al. (1995) *Nucleic Acids Res.* 23:1152; S. Fields et al. (1994) *Trends Genet.* 10:286; and U.S. Pat. Nos. 6,283,173 and 5,468,614).

Ligand sequence(s) obtained from ligand-binding assay(s) can be compared with subject sequences in available databases such as, without limitation, GenPept, SWISS-PROT®, and Incyte Genomics databases (Incyte Genomics). These databases, which contain previously identified and annotated sequences, may be searched for the full-length polypeptide and gene sequence using, for example, BLAST analysis (see above). In cases where the full-length sequences of the ligands are not available, extended or overlapping partial clones may be obtained by techniques conventionally known and practiced in the art. Non-limiting examples of such techniques include hybridization to plasmid or phage libraries of genomic DNA or cDNA; PCR from the same libraries using B7-related factor primer pairs; or hybridization or PCR directly to genomic DNA or cDNA. These clones may then be sequenced and assembled into full-length genes using the fragment sequence alignment program (PHRAP; Nickerson et al. (1997) *Nucleic Acids Res.* 25:2745-2751).

Assays for B7-related factor activity: Screening the fragments, mutants or variants for those which retain characteristic B7-related polypeptide activity as described herein can be accomplished using one or more of several different assays. For example, appropriate cells, such as CHO cells, can be transfected with the cloned variants and then analyzed for cell surface phenotype by indirect immunofluorescence and flow cytometry. Cell surface expression of the transfected cells is evaluated using a monoclonal antibody specifically reactive with a cell surface form of a B7-related factor (see above). Production of secreted forms of the B7-related factors can be evaluated by immunoprecipitation using a monoclonal antibody specifically reactive with a B7-related factor.

Other, more preferred, assays take advantage of the functional characteristics of the B7-related factors. As previously set forth, the binding of the B7-related factors to its T-cell ligand(s) causes the cells to produce increased levels of lymphokines, particularly of interleukin-2. Thus, B7-related factor function can be assessed by measuring the synthesis of lymphokines, such as interleukin-2 or other novel and as yet undefined cytokines, and/or assaying for T-cell proliferation by $CD28^+$T-cells that have received a primary activation signal. Any one of several conventional assays for interleukin-2 can be employed (see C. B. Thompson (1989) *Proc. Natl. Acad. Sci. USA* 86:1333).

The same basic functional assays can also be used to screen for B7-related polypeptides, peptides, fusion proteins, or antibodies that block T-cell activation. The ability of such proteins to block the normal costimulatory signal and induce a state of anergy can be determined using subsequent attempts at stimulation of the T-cells with antigen presenting cells that express cell surface B cell activation antigen B7 and present antigen. If the T-cells are unresponsive to the activation attempts, as determined by IL-2 synthesis and T-cell proliferation, a state of anergy has been induced and can be determined by methods known in the art (see R. H. Schwartz (1990) *Science* 248:1349-1356).

Modulators of B7-Related Factors

The BSL1, BSL2, and BSL3 polypeptides, polynucleotides, variants, or fragments thereof, can be used to screen for test agents (e.g., agonists, antagonists, or inhibitors) that modulate the levels or activity of the corresponding B7-related polypeptide. In addition, B7-related molecules can be used to identify endogenous modulators that bind to BSL1, BSL2, or BSL3 polypeptides or polynucleotides in the cell. In one aspect of the present invention, the full-length BSL1 (e.g., SEQ ID NO:2), BSL2 (e.g., SEQ ID NO:7, 11, or 13), or BSL3 (e.g., SEQ ID NO:15) polypeptide is used to identify modulators. Alternatively, variants or fragments of a BSL1, BSL2, or BSL3 polypeptide are used. Such fragments may comprise, for example, one or more domains of the B7-related polypeptide (e.g., the extracellular and transmembrane domains) disclosed herein. Of particular interest are screening assays that identify agents that have relatively low levels of toxicity in human cells. A wide variety of assays may be used for this purpose, including in vitro protein-protein binding assays, electrophoretic mobility shift assays, immunoassays, and the like.

The term "modulator" as used herein describes any test agent, molecule, protein, peptide, or compound with the capability of directly or indirectly altering the physiological function, stability, or levels of the BSL1, BSL2, and BSL3 polypeptide. Modulators that bind to the B7-related polypeptides or polynucleotides of the invention are potentially useful in diagnostic applications and/or pharmaceutical compositions, as described in detail herein. Test agents useful as modulators may encompass numerous chemical classes, though typically they are organic molecules, preferably small organic compounds having a molecular weight of more than 50 and less than about 2,500 daltons. Such molecules can comprise functional groups necessary for structural interaction with proteins, particularly hydrogen bonding, and typically include at least an amine, carbonyl, hydroxyl or carboxyl group, preferably at least two of the functional chemical groups. Test agents which can be used as modulators often comprise cyclical carbon or heterocyclic structures and/or aromatic or polyaromatic structures substituted with one or more of the above functional groups. Test agents can also comprise biomolecules including peptides, saccharides, fatty acids, steroids, purines, pyrimidines, derivatives, structural analogs, or combinations thereof.

Test agents finding use as modulators may include, for example, 1) peptides such as soluble peptides, including Ig-tailed fusion peptides and members of random peptide libraries (see, e.g., Lam et al. (1991) *Nature* 354:82-84; Houghten et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang et al., (1993) *Cell* 72:767-778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules.

Test agents and, modulators can be obtained from a wide variety of sources including libraries of synthetic or natural compounds. Synthetic compound libraries are commercially available from, for example, Maybridge. Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Natural compound libraries comprising bacterial, fungal, plant or animal extracts are available from, for example, Pan Laboratories (Bothell, Wash.). In addition, numerous means are available for random and directed synthesis of a wide variety of organic compounds and biomolecules, including expression of randomized oligonucleotides.

Alternatively, libraries of natural compounds in the form of bacterial, fungal, plant and animal extracts can be readily produced. Methods for the synthesis of molecular libraries are readily available (see, e.g., DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233). In addition, natural or synthetic compound libraries and compounds can be readily modified through conventional chemical, physical and biochemical means (see, e.g., Blondelle et al. (1996) *Trends in Biotech.* 14:60), and may be used to produce combinatorial libraries. In another approach, previously identified, pharmacological agents can be subjected to directed or random chemical modifications, such as aceylation, alkylation, esterification, amidification, and the analogs can be screened for BSL1-, BSL2-, and BSL3-modulating activity.

Numerous methods for producing combinatorial libraries are known in the art, including those involving biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer, or small molecule libraries of compounds (K. S. Lam, 1997, *Anticancer Drug Des.* 12:145).

Libraries may be screened in solution (e.g., Houghten, (1992) *Biotechniques* 13:412-421), or on beads (Lam, (1991) *Nature* 354:82-84), chips (Fodor, (1993) *Nature* 364:555-556), bacteria or spores (Ladner U.S. Pat. No. 5,223,409), plasmids (Cull et al. (1992) *Proc. Natl. Acad. Sci. USA* 89:1865-1869), or on phage (Scott and Smith, (1990) *Science* 249:386-390; Devlin, 1990, *Science* 249:404-406; Cwirla et al. (1990) *Proc. Natl. Acad. Sci. USA* 97:6378-6382; Felici, (1991) *J. Mol. Biol.* 222:301-310; Ladner, supra).

Where the screening assay is a binding assay, a BSL1, BSL2, and BSL3 polypeptide, polynucleotide, analog, or fragment thereof, may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin; digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc., that are used to facilitate optimal protein-protein binding and/or reduce non-specific or background interactions. Reagents that improve the efficiency of the assay, such as protease inhibitors, nuclease inhibitors, anti-microbial agents, etc., may be used. The components are added in any order that produces the requisite binding. Incubations are performed at any temperature that facilitates optimal activity, typically between 4° and 40° C. Incubation periods are selected for optimum activity, but may also be optimized to facilitate rapid high-throughput screening. Normally, between 0.1 and 1 hr (hour) will be sufficient. In general, a plurality of assay mixtures is run in parallel with different agent concentrations to obtain a differential response to these concentrations. Typically, one of these concentrations serves as a negative control, i.e. at zero concentration or below the level of detection.

To perform cell-free screening assays, it may be desirable to immobilize either the BSL1, BSL2, or BSL3 polypeptide, polynucleotide, or fragment to a surface to facilitate identification of modulators that bind to these molecules, as well as to accommodate automation of the assay. For example, a fusion protein comprising a BSL1, BSL2, or BSL3 polypeptide and an affinity-tag can be produced as described in detail herein. In one embodiment, a GST-fusion protein comprising a BSL1, BSL2, or BSL3 polypeptide is adsorbed onto glutathione sepharose beads (Sigma Chemical, St. Louis, Mo.) or glutathione-derivatized microtiter plates. Cell lysates (e.g., containing $^{35}$S-labeled polypeptides) are added to the polypeptide-coated beads under conditions to allow complex formation (e.g., at physiological conditions for salt and pH). Following incubation, the polypeptide-coated beads are washed to remove any unbound polypeptides, and the amount of immobilized radiolabel is determined. Alternatively, the complex is dissociated and the radiolabel present in the supernatant is determined. In another approach, the beads are analyzed by SDS-PAGE to identify BSL1-, BSL2-, or BSL3-binding polypeptides.

Various binding assays can be used to identify agonist or antagonists that alter the function or levels of the BSL1, BSL2, or BSL3 polypeptide. Such assays are designed to detect the interaction of test agents with BSL1, BSL2, or BSL3 polypeptides, polynucleotides, functional equivalents, or fragments thereof. Interactions may be detected by direct measurement of binding. Alternatively, interactions may be detected by indirect indicators of binding, such as stabilization/destabilization of protein structure, or activation/inhibition of biological function. Non-limiting examples of useful binding assays are detailed below.

Modulators that bind to BSL1, BSL2, or BSL3 polypeptides, polynucleotides, functional equivalents, or fragments thereof, can be identified using real-time Bimolecular Interaction Analysis (BIA; Sjolander et al. (1991) *Anal. Chem.* 63:2338-2345; Szabo et al. (1995) *Curr. Opin. Struct. Biol.* 5:699-705; e.g., BIAcore™; LKB Pharmacia, Sweden). Modulators can also be identified by scintillation proximity assays (SPA, described in U.S. Pat. No. 4,568,649). Binding assays using mitochondrial targeting signals (Hurt et al. (1985) *EMBO J.* 4:2061-2068; Eilers and Schatz, (1986) *Nature* 322:228-231) a plurality of defined polymers synthesized on a solid substrate (Fodor et al. (1991) *Science* 251:767-773) may also be employed.

Two-hybrid systems may be used to identify modulators (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO 94/10300). Alternatively, three-hybrid (Licitra et al. (1996) *Proc. Natl. Acad. Sci. USA* 93:12817-12821), and reverse two-hybrid (Vidal et al. (1996) *Proc. Natl. Acad. Sci. USA* 93:10315-10320) systems may be used. Commercially available two-hybrid systems such as the CLONTECH MATCH-MAKER™ systems and protocols (CLONTECH Laboratories, Inc., Palo Alto, Calif.) are also useful (see also, A. R. Mendelsohn et al. (1994) *Curr. Op. Biotech.* 5:482; E. M. Phizicky et al. (1995) *Microbiological Rev.* 59:94; M. Yang et al. (1995) *Nucleic Acids Res.* 23:1152; S. Fields et al. (1994) *Trends Genet.* 10:286; and U.S. Pat. Nos. 6,283,173 and 5,468,614).

Several methods of automated assays have been developed in recent years so as to permit screening of tens of thousands of test agents in a short period of time. High-throughput screening methods are particularly preferred for use with the present invention. The binding assays described herein can be adapted for high-throughput screens, or alternative screens may be employed. For example, continuous format high throughput screens (CF-HTS) using at least one porous matrix allows the researcher to test large numbers of test agents for a wide range of biological or biochemical activity (see U.S. Pat. No. 5,976,813 to Beutel et al.). Moreover, CF-HTS can be used to perform multi-step assays.

Diagnostics

According to another embodiment of the present invention, the B7-related polynucleotides, or fragments thereof, may be used for diagnostic purposes. The B7-related polynucleotides that may be used include oligonucleotide sequences, complementary RNA and DNA molecules, and PNAs. The polynucleotides may be used to detect and quantify levels of BSL1, BSL2, and BSL3 mRNA in biological samples in which expression (or under- or overexpression) of BSL1, BSL2, and BSL3 polynucleotide may be correlated with disease. The diagnostic assay may be used to distinguish between the absence, presence, increase, and decrease of the expression of BSL1, BSL2, and BSL3, and to monitor regulation of BSL1, BSL2, and BSL3 polynucleotide levels during therapeutic treatment or intervention.

In one aspect, PCR probes can be used to detect B7-related polynucleotide sequences, including BSL1, BSL2, and BSL3 genomic DNA sequences and BSL1-, BSL2-, and BSL3-related nucleic acid sequences. The specificity of the probe, whether it is made from a highly specific region, e.g., at least 8 to 10 or 12 or 15 contiguous nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding the B7-related polypeptide, alleles thereof, or related sequences.

Probes may also be used for the detection of BSL1-, BSL2-, and BSL3-related sequences, and should preferably contain at least 60%, preferably greater than 90%, identity to the BSL1, BSL2, and BSL3 polynucleotide, or a complementary sequence, or fragments thereof. The probes of this invention may be DNA or RNA, the probes may comprise all or a fragment of the nucleotide sequence of BSL1 (SEQ ID NO:2), BSL2 (SEQ ID NO:7, 11, or 13), or BSL3 (SEQ ID NO:15), or a complementary sequence thereof, and may include promoter, enhancer elements, and introns of the naturally occurring BSL1, BSL2, or BSL3 polynucleotide.

Methods for producing specific probes for B7-related polynucleotides include the cloning of nucleic acid sequences of BSL1 (SEQ ID NO:2), BSL2 (SEQ ID NO:7, 11, or 13), or BSL3 (SEQ ID NO:15), or a fragment thereof, into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of detector/reporter groups, e.g., radionucleotides such as $^{32}P$ or $^{35}S$, or enzymatic labels, such as alkaline phosphatase coupled to the Probe via avidin/biotin coupling systems, and the like.

A wide variety of labels and conjugation techniques are known and employed by those skilled in the art and may be used in various nucleic acid and amino acid assays. Means for producing labeled hybridization or PCR probes for detecting sequences related to polynucleotides encoding the BSL1, BSL2, or BSL3 polypeptide include oligo-labeling, nick translation, end-labeling, or PCR amplification using a labeled nucleotide. Alternatively, BSL1, BSL2, or BSL3 polynucleotide sequences, or any portions or fragments thereof, may be cloned into a vector for the production of an mRNA probe. Such vectors are known in the art, are commercially available, and may be used to synthesize RNA probes in vitro by addition of an appropriate RNA polymerase, such as T7, T3, or SP(6) and labeled nucleotides. These procedures may be conducted using a variety of commercially available kits (e.g., from Amersham Pharmacia Biotech, Inc., Piscataway, N.J.; Promega Corp., Madison Wis.; and U.S. Biochemical Corp., U.S. Biochemical Amersham, Cleveland, Ohio). Suitable reporter molecules or labels which may be used include radionucleotides, enzymes, fluorescent, chemiluminescent, or chromogenic agents, as well as substrates, cofactors, inhibitors, magnetic particles, and the like.

B7-related polynucleotide sequences, or fragments, or complementary sequences thereof, can be used in Southern or Northern analysis, dot blot, or other membrane-based technologies; in PCR technologies; or in dip stick, pin, ELISA or biochip assays utilizing fluids or tissues from patient biopsies to detect the status of, e.g., levels or overexpression of BSL1, BSL2, or BSL3, or to detect altered BSL1, BSL2, or BSL3 expression. Such qualitative or quantitative methods are well known in the art (G. H. Keller and M. M. Manak, 1993, *DNA Probes*, $2^{nd}$ Ed, Macmillan Publishers Ltd., England; D. W. Dieffenbach and G. S. Dveksler, 1995, *PCR Primer: A Laboratory Manual*, Cold Spring Harbor Press, Plainview, N.Y.; B. D. Hames and S. J. Higgins, 1985, *Gene Probes* 1, 2, IRL Press at Oxford University Press, Oxford, England).

BSL1, BSL2, and BSL3 oligonucleotides may be chemically synthesized, generated enzymatically, or produced from a recombinant source. Oligomers will preferably comprise two nucleotide sequences, one with a sense orientation (5'→3') and another with an antisense orientation (3'→5'), employed under optimized conditions for identification of a specific gene or condition. The same two oligomers, nested sets of oligomers, or even a degenerate pool of oligomers may be employed under less stringent conditions for detection and/or, quantification of closely related DNA or RNA sequences.

Methods suitable for quantifying the expression of B7-related factors include radiolabeling or biotinylating nucleotides, co-amplification of a control nucleic acid, and standard curves onto which the experimental results are interpolated (P. C. Melby et al. (1993) *J. Immunol. Methods* 159:235-244; and C. Duplaa et al. (1993) *Anal. Biochem.* 229-236). The speed of quantifying multiple samples may be accelerated by running the assay in an ELISA format where the oligomer of interest is presented in various dilutions and a spectrophotometric or colorimetric response gives rapid quantification.

In a particular aspect, a nucleic acid sequence complementary to a B7-related polynucleotide, or fragment thereof, may be useful in assays that detect diseases relating to aberrant immune responses, particularly those described herein. A BSL1, BSL2, and/or BSL3 polynucleotide can be labeled by standard methods; and added to a biological sample from a subject under conditions suitable for the formation of hybridization complexes. After a suitable incubation period, the sample can be washed and the signal is quantified and compared with a standard value. If the amount of signal in the test sample is significantly altered from that of a comparable negative control (normal) sample, the altered levels of BSL1, BSL2, and/or BSL3 nucleotide sequence can be correlated with the presence of the associated disease. Such assays may also be used to evaluate the efficacy of a particular prophylactic or therapeutic regimen in animal studies, in clinical trials, or for an individual patient.

To provide a basis for the diagnosis of a disease associated with altered expression of one or more B7-related factors, a normal or standard profile for expression is established. This may be accomplished by incubating biological samples taken from normal subjects, either animal or human, with a sequence complementary to a BSL1, BSL2, BSL3 polynucleotide, or a fragment thereof, under conditions suitable for hybridization or amplification. Standard hybridization may be quantified by comparing the values obtained from normal subjects with those from an experiment where a known amount of, a substantially purified polynucleotide is used. Standard values obtained from normal samples may be compared with values obtained from samples from patients who are symptomatic for the disease. Deviation between standard and subject (patient) values is used to establish the presence of the condition.

Once the disease is diagnosed and a treatment protocol is initiated, hybridization assays may be repeated on a regular basis to evaluate whether the level of expression in the patient begins to approximate that which is observed in a normal individual. The results obtained from successive assays may be used to show the efficacy of treatment over a period ranging from several days to months.

With respect to diseases involving a hyperactive or hypoactive immune response, the presence of an abnormal levels (decreased or increased) of B7-related transcript in a biological sample (e.g., body fluid, cells, tissues, or cell or tissue extracts) from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier, thereby preventing the development or further progression of the disease.

In one particular aspect, BSL1, BSL2, and BSL3 oligonucleotides may be used for PCR-based diagnostics. For example, PCR can be used to perform Genetic Bit Analysis (GBA) of BSL1, BSL2, and/or BSL3 in accordance with published methods (T. T. Nikiforov et al. (1994) *Nucleic Acids Res.* 22(20):4167-75; T. T. Nikiforov et al. (1994) *PCR Methods Appl.* 3(5):285-91). In PCR-based GBA, specific fragments of genomic DNA containing the polymorphic site(s) are first amplified by PCR using one unmodified and one phosphorothioate-modified primer. The double-stranded PCR product is rendered single-stranded and then hybridized to immobilized oligonucleotide primer in wells of a multiwell plate. Notably, the primer is designed to anneal immediately adjacent to the polymorphic site of interest. The 3' end of the primer is extended using a mixture of individually labeled dideoxynucleoside triphosphates. The label on the extended base is then determined. Preferably, GBA is performed using semi-automated ELISA or biochip formats (see, e.g., S. R. Head et al. (1997) *Nucleic Acids Res.* 25(24): 5065-71; T. T. Nikiforov et al. (1994) *Nucleic Acids Res.* 22(20):4167-75).

In another embodiment of the present invention, oligonucleotides, or longer fragments derived from at least one B7-related polynucleotide sequence described herein may be used as targets in a microarray (e.g., biochip) system. The microarray can be used to monitor the expression level of large numbers of genes simultaneously (to produce a transcript image), and to identify genetic variants, mutations, and polymorphisms. This information may be used to determine gene function, to understand the genetic basis of a disease, to diagnose disease, and to develop and monitor the activities of therapeutic or prophylactic agents. Preparation and use of microarrays have been described in WO 95/11995 to Chee et al.; D. J. Lockhart et al. (1996) *Nature Biotechnology* 14:1675-1680; M. Schena et al. (1996) *Proc. Natl. Acad. Sci. USA* 93:10614-10619; U.S. Pat. No. 6,015,702 to P. Lal et al.; J. Worley et al. (2000) *Microarray Biochip Technology*, M. Schena, ed., Biotechniques Book, Natick, Mass., pp. 65-86; Y. H. Rogers et al. (1999) *Anal. Biochem.* 266(1):23-30; S. R. Head et al. (1999) *Mol. Cell. Probes.* 13(2):81-7; S. J. Watson et al. (2000) *Biol. Psychiatry* 48(12):1147-56.

In one application of the present invention, microarrays containing arrays of B7-related polynucleotide sequences can be used to measure the expression levels of B7-related factors in an individual. In particular, to diagnose an individual with a condition or disease correlated with altered BSL1, BSL2, and/or BSL3 expression levels, a sample from a human or animal (containing, e.g., mRNA) can be used as a probe on a biochip containing an array of BSL1, BSL2, and/or BSL3 polynucleotides (e.g., DNA) in decreasing concentrations (e.g., 1 ng, 0.1 ng, 0.01 ng, etc.). The test sample can be compared to samples from diseased and normal samples. Biochips can also be used to identify BSL1, BSL2, and BSL3 mutations or polymorphisms in a population, including but not limited to, deletions, insertions, and mismatches. For example, mutations can be identified by: (i) placing B7-related polynucleotides of this invention onto a biochip; (ii) taking a test sample (containing, e.g., mRNA) and adding the sample to the biochip; (iii) determining if the test samples hybridize to the B7-related polynucleotides attached to the chip under various hybridization conditions (see, e.g., V. R. Chechetkin et al. (2000) *J. Biomol. Struct. Dyn.* 18(1):83-101). Alternatively microarray sequencing can be performed (see, e.g., E. P. Diamandis (2000) *Clin. Chem.* 46(10):1523-5).

In another embodiment of this invention, a B7-related nucleic acid sequence, or a complementary sequence, or fragment thereof, can be used as probes which are useful for mapping the naturally occurring genomic sequence. The sequences may be mapped to a particular chromosome, to a specific region of a chromosome, or to artificial chromosome constructions (HACs), yeast artificial chromosomes (YACs), bacterial artificial chromosomes (BACs), bacterial PI constructions, or single chromosome cDNA libraries (see C. M. Price (1993) *Blood Rev.*, 7:127-134 and by B. J. Trask (1991) *Trends Genet.* 7:149-154).

In a further embodiment of the present invention, antibodies which specifically bind to a BSL1, BSL2, or BSL3 polypeptide may be used for the diagnosis of conditions or diseases characterized by underexpression or overexpression of the BSL1, BSL2, or BSL3 polynucleotide or polypeptide, or in assays to monitor patients being treated with a BSL1, BSL2, or BSL3 polypeptide or peptide, or a BSL1, BSL2, or BSL3 agonist, antagonist, or inhibitor. The antibodies useful for diagnostic purposes may be prepared in the same manner as those for use in therapeutic methods, described herein. Diagnostic assays for a BSL1, BSL2, or BSL3 polypeptide include methods that utilize the antibody and a label to detect the protein in biological samples (e.g., human body fluids, cells, tissues, or extracts of cells or tissues). The antibodies may be used with or without modification, and may be labeled by joining them, either covalently or non-covalently, with a reporter molecule. A wide variety of reporter molecules that are known in the art may be used, several of which are described herein.

A number of fluorescent materials are known and can be utilized to label a B7-related polypeptide or antibodies that specifically bind thereto. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. B7-related polypeptides or antibodies thereto can also be labeled with a radioactive element or with an enzyme. The radioactive label can be detected by any of the currently available counting procedures. Preferred isotopes include $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Enzyme labels are likewise useful, and can be detected by any of the presently utilized calorimetric, spectrophotometric, fluorospectrophotometric, amperometric, or gasometric techniques. The enzyme can be conjugated by reaction with bridging molecules such as carbodiimides, diisocyanates, glutaraldehyde, and the like. Many enzymes, which can be used in these procedures, are known and can be utilized. Preferred are peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752; and 4,016,043).

Antibody-based diagnostics and their application are familiar to those skilled in the art and may be used in accordance with the present invention. As non-limiting examples, "competitive" (U.S. Pat. Nos. 3,654,090 and 3,850,752), "sandwich" (U.S. Pat. No. 4,016,043), and "double antibody," or "DASP" assays may be used. Several procedures including ELISA, RIA, and FACS for measuring B7-related polypeptide levels are known in the art and provide a basis for diagnosing altered or abnormal levels of B7-related polypeptide expression. Normal or standard values for B7-related polypeptide expression are established by incubating biological samples taken from normal subjects, preferably human, with antibody to the B7-related polypeptide under conditions suitable for complex formation. The amount of standard complex formation may be quantified by various methods; photometric means are preferred. Levels of the B7-related polypeptide expressed in the subject sample, negative control (normal) sample, and positive control (disease) sample are compared with the standard values. Deviation between standard and subject values establishes the parameters for diagnosing disease.

In another of its aspects, this invention relates to diagnostic kits for detecting B7-related polynucleotide(s) or polypeptide(s) as it relates to a disease or susceptibility to a disease, particularly the disorders of the immune system described herein. Such kits comprise one or more of the following:

(a) a B7-related polynucleotide, preferably the nucleotide sequence of BSL1 (SEQ ID NO:1 or 3), BSL2 (SEQ ID NO:6, 10, or 12), or BSL3 (SEQ ID NO:14), or a fragment thereof; or (b) a nucleotide sequence complementary to that of (a); or (c) a B7-related polypeptide, preferably the polypeptide of BSL1 (SEQ ID NO:2), BSL2 (SEQ ID NO:7, 11, or 13), or BSL3 (SEQ ID NO:15), or a fragment thereof; or (d) an antibody to a B7-related polypeptide, preferably to the polypeptide of BSL1 (SEQ ID NO:2), BSL2 (SEQ ID NO:7, 11, or 13), or BSL3 (SEQ ID NO:15), or an antibody bindable fragment thereof. It will be appreciated that in any such kits, (a), (b), (c), or (d) may comprise a substantial component and that instructions for use can be included. The kits may also contain peripheral reagents such as buffers, stabilizers, etc.

The present invention also includes a test kit for genetic screening that can be utilized to identify mutations in B7-related factors. By identifying patients with mutated BSL1, BSL2, and/or BSL2 DNA and comparing the mutation to a database that contains known mutations in BSL1, BSL2, and BSL3, and a particular condition or disease, identification and/or confirmation of, a particular condition or disease can be made. Accordingly, such a kit would comprise a PCR-based test that would involve transcribing the patients mRNA with a specific primer, and amplifying the resulting cDNA using another set of primers. The amplified product would be detectable by gel electrophoresis and could be compared with known standards for BSL1, BSL2, and/or BSL3. Preferably, this kit would utilize a patient's blood, serum, or saliva sample, and the DNA would be extracted using standard techniques. Primers flanking a known mutation Would then be used to amplify a fragment of BSL1, BSL2, and/or BSL3. The amplified piece would then be sequenced to determine the presence of a mutation.

Therapeutics

Pharmaceutical compositions: The present invention contemplates compositions comprising a B7-related nucleic acid, polypeptide, antibody, ligand, modulator (e.g., agonist, antagonist, or inhibitor), or fragments or functional variants thereof, and a physiologically acceptable carrier, excipient, or diluent as described in detail herein. The present invention further contemplates pharmaceutical compositions useful in practicing the therapeutic methods of this invention. Preferably, a pharmaceutical composition includes, in admixture, a pharmaceutically acceptable excipient (carrier) and one or more of a B7-related polypeptide, nucleic acid, ligand, modulator, antibody, or fragment or functional equivalent thereof, as described herein, as an active ingredient. Because B7-related polypeptides or peptides are naturally occurring cellular components, they may be administered to an individual's circulatory system with minimal risk of undesired immunological complications.

The preparation of pharmaceutical compositions that contain biological reagents as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof. In addition, if desired; the composition can contain minor amounts of auxiliary substances such as wetting or emulsifying agents, pH-buffering agents, which enhance the effectiveness of the active ingredient.

Pharmaceutical compositions can be produced and employed in treatment protocols according to established methods depending on the disorder or disease to be treated (see, for example, P. D. Mayne (1996) *Clinical Chemistry in Diagnosis and Treatment*, 6$^{th}$ ed., Oxford University Press, Oxford, England; Gilman et al., Eds. (1990) *Goodman and*

*Gilman's: The Pharmacological Basis of Therapeutics*, 8th ed., Pergamon Press; Avis et al., Eds. (1993) *Pharmaceutical Dosage Forms: Parenteral Medications*, Dekker, New York, N.Y.; and Lieberman et al., Eds. (1990) *Pharmaceutical Dosage Forms Disperse Systems*, Dekker, New York, N.Y.).

Pharmaceutical compositions may be produced as neutral or salt forms. Salts can be formed with many acids, including, but not limited to, hydrochloric, sulfuric, acetic, lactic, tartaric, malic and succinic acids. Compositions can take the form of solutions, suspensions, suppositories, tablets, pills, capsules, sustained release compounds, or powders. Such formulations can contain 10%-95% (w/w) of the active ingredient, preferably 25%-70% (w/w). If the active compound is administered by injection, for example, about 1 µg-3 mg and preferably from about 20 µg-500 µg of active compound (e.g., B7-related polypeptide) per dosage unit may be administered. Pharmaceutical preparations and compositions can also contain one or more physiologically acceptable carrier(s), excipient(s), diluent(s), disintegrant(s), lubricant(s), plasticizer(s), filler(s), colorant(s), dosage vehicle(s), absorption enhancer(s), stabilizer(s), or bacteriocide(s). The production and formulation of such compositions and preparations are carried out by methods known and practiced in the art.

Exemplary formulations are given below:

| Ingredient | mg/ml |
| --- | --- |
| Intravenous Formulation I: | |
| BSL1, BSL2, or BSL3 MAb | 5.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II: | |
| BSL1, BSL2, or BSL3 MAb | 5.0 |
| sodium bisulfite USP | 3.2 |
| disodium edetate USP | 0.1 |
| water for injection q.s.a.d. | 1.0 ml |
| Intravenous Formulation III | |
| BSL1, BSL2, or BSL3 protein, Ig-fusion protein, or agonist | 10.0 |
| sodium bisulfite USP | 3.2 |
| disodium edetate USP | 0.1 |
| water for injection q.s.a.d. | 1.0 ml |
| Intravenous Formulation IV | |
| BSL1, BSL2, or BSL3 protein, Ig-fusion protein, or agonist | 10.0 |
| dextrose USP | 45.0 |
| sodium bisulfite USP | 3.2 |
| edetate disodium USP | 0.1 |
| water for injection q.s.a.d. | 1.0 ml |

As used herein, "pg" means picogram, "ng" means nanogram, "µg" mean microgram, "mg" means milligram, "µl" mean microliter, "ml" means milliliter, and "l" means liter.

Following the preparation of pharmaceutical compositions, they may be placed in appropriate containers and labeled for the treatment of indicated conditions. Such labeling can include amount, frequency, and method of administration. Preparations may be administered systemically by oral or parenteral routes. Non-limiting parenteral routes of administration include subcutaneous, intramuscular, intraperitoneal, intravenous, transdermal, inhalation, intranasal, intra-arterial, intrathecal, enteral, sublingual, or rectal.

A therapeutically effective amount of a pharmaceutical composition containing one or more B7-related polypeptides, fusion proteins, peptide fragments, or antibodies that specifically react with these components is an amount sufficient to reduce, ameliorate, or eliminate a disease or disorder related to altered activation levels of immune or inflammatory response cells, such as T-cells. An effective amount can be introduced in one administration or over repeated administrations to an individual being treated. Therapeutic administration can be followed by prophylactic administration, after treatment of the disease. A prophylactically effective amount is an amount effective to prevent disease and will depend upon the specific illness and subject. The therapeutically effective dose may be estimated initially, for example, either in cell culture assays or in animal models, usually mice, rats, rabbits, dogs, sheep, goats, pigs, or non-human primates. The animal model may also be used to determine the maximum tolerated dose and appropriate route of administration. Such information can then be used to determine useful doses and routes for administration in humans.

Administration of the therapeutic compositions of the present invention to a subject can be carried out using known procedures, at dosages and for periods of time effective to achieve the desired result. For example, a therapeutically active amount B7-related polypeptides, fusion proteins, peptides, or antibodies that react with these components may vary according to factors such as the age, sex, and weight of the individual, and the ability of the treatment to elicit a desired response in the individual. Dosages may be adjusted to provide the optimum therapeutic response. For example, several sequential doses may be administered daily or the dose may be proportionally reduced as indicated by the exigencies of the therapeutic situation.

Gene transfer therapy: In addition, host cells that are genetically engineered to carry the gene encoding a B7-related polypeptide, fusion protein, or peptide fragment comprising a fragment of the BSL1 (SEQ ID NO:2), BSL2 (SEQ ID NO:7, 11, or 13), or BSL3 (SEQ ID NO:15) polypeptide sequence, can be introduced into an individual in need of immunomodulation. Following, expression and production of the B7-related polypeptide or peptide by the host cell, the so-produced B7-related polypeptide, fusion protein, or peptide can act to bind CD28 and/or CD28-related ligand(s) to modulate the activation of immune or inflammatory response cells (e.g., T-cells) in the recipient. Host cells may be genetically engineered by a variety of molecular techniques and methods known to those having skill in the art, for example, transfection, infection, or transduction. Transduction as used herein commonly refers to cells that have been genetically engineered to contain a foreign or heterologous gene via the introduction of a viral or non-viral vector into the cells. Transfection more commonly refers to cells that have been genetically engineered to contain a foreign gene harbored in a plasmid, or non-viral vector. Host cells can be transfected or transduced by different vectors and thus can serve as gene delivery vehicles to transfer the expressed products into muscle.

Although viral vectors are preferred for gene transfer therapies, cells can be genetically engineered to contain nucleic acid sequences encoding the desired gene product(s) by various methods known in the art. For example, cells can be genetically engineered by fusion, transfection, lipofection mediated by the use of liposomes, electroporation, precipitation with DEAE-Dextran or calcium phosphate, particle bombardment (biolistics) with nucleic acid-coated particles (e.g., gold particles), microinjection, or genetically engineered microorganisms (K. Yazawa et al. (2000) *Cancer Gene Ther.* 7:269-274). Vectors for introducing heterologous (i.e., foreign) nucleic acid (DNA or RNA) into muscle cells for the expression of active bioactive products are well known in the art. Such vectors possess a promoter sequence, preferably a promoter that is cell-specific and placed upstream of the sequence to be expressed. The vectors may also contain, optionally, one or more expressible marker genes for expression as an indication of successful transfection and expression of the nucleic acid sequences contained in the vector. In addition, vectors can be optimized to minimize undesired immunogenicity and maximize long-term expression of the desired gene product(s) (see Nabel (1999) *Proc. Natl. Acad. Sci. USA* 96:324-326). Moreover, vectors can be chosen based on cell-type that is targeted for treatment. For example, vectors for the treatment of tumor or cancer cells have been described (P. L. Hallenbeck et al. (1999) *Hum. Gene Ther.* 10:1721-1733; T. Shibata et al. (2000) *Gene Ther.* 7:493-498; M. Puhlmann et al. (2000) *Cancer Gene Ther.* 7:66-73; N. Krauzewicz et al. (2000) *Adv. Exp. Med. Biol.* 465:73-82).

Illustrative examples of vehicles or vector constructs for transfection or infection of the host cells include replication-defective viral vectors, DNA virus or RNA virus (retrovirus) vectors, such as adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors will normally be substantially free of any prokaryotic DNA and may comprise a number of different functional nucleic acid sequences. An example of such functional sequences may be a DNA region comprising transcriptional and translational initiation and termination regulatory sequences, including promoters (e.g., strong promoters, inducible promoters, and the like) and enhancers which are active in the host cells. Also included as part of the functional sequences is an open reading frame (polynucleotide sequence) encoding a protein of interest. Flanking sequences may also be included for site-directed integration. In some situations, the 5'-flanking sequence will allow homologous recombination, thus changing the nature of the transcriptional initiation region, so as to provide for inducible or noninducible transcription to increase or decrease the level of transcription, as an example.

In general, the encoded and expressed B7-related factor may be intracellular, i.e., retained in the cytoplasm, nucleus, or an organelle of a cell, or may be secreted by the cell. For secretion, the natural signal sequence present in the B7-related structural gene may be retained. When the polypeptide or peptide is a fragment of a B7-related factor that is larger, a signal sequence may be provided so that, upon secretion and processing at the processing site, the desired protein will have the natural sequence. Specific examples of coding sequences of interest for use in accordance with the present invention include the BSL1 (SEQ ID NO:2), BSL2 (SEQ ID NO:7, 11, or 13), or BSL3 (SEQ ID NO:15) polypeptide coding sequences. As previously mentioned, a marker may be present for selection of cells containing the vector construct. The marker may be an inducible or non-inducible gene and will generally allow for positive selection under induction, or without induction, respectively. Examples of marker genes include neomycin, dihydrofolate reductase, glutamine synthetase, and the like.

The vector employed will generally also include an origin of replication and other genes that are necessary for replication in the host cells, as routinely employed by those having skill in the art. As an example, the replication system comprising the origin of replication and any proteins associated with replication encoded by a particular virus may be included as part of the construct. The replication system must be selected so that the genes encoding products necessary for replication do not ultimately transform the cells. Such, replication systems are represented by replication-defective adenovirus (see G. Acsadi et al. (1994) *Hum. Mol. Genet.* 3:579-584) and by Epstein-Barr virus. Examples of replication defective vectors, particularly, retroviral vectors that are replication defective, are BAG, (see Price et al. (1987) *Proc. Natl. Acad. Sci. USA,* 84:156; Sanes et al. (1986) *EMBO J.,* 5:3133). It will be understood that the final gene construct may contain one or more genes of interest, for example, a gene encoding a bioactive metabolic molecule. In addition, cDNA, synthetically produced DNA or chromosomal DNA may be employed utilizing methods and protocols known and practiced by those having skill in the art.

According to one approach for gene therapy, a vector encoding a B7-related factor is directly injected into the recipient cells (in vivo gene therapy). Alternatively, cells from the intended recipients are explanted, genetically modified to encode a B7-related factor, and reimplanted into the donor (ex vivo gene therapy). An ex vivo approach provides the advantage of efficient viral gene transfer, which is superior to in vivo gene transfer approaches. In accordance with ex vivo gene therapy, the host cells are first infected with engineered viral vectors containing at least one B7-related gene encoding a B7-related gene product, suspended in a physiologically acceptable carrier or excipient such as saline or phosphate buffered saline, and the like, and then administered to the host. The desired gene product is expressed by the injected cells, which thus introduce the gene product into the host. The introduced gene products can thereby be utilized to treat or ameliorate a disorder that is related to altered levels of the activation of immune or inflammatory response cells (e.g., T-cells).

Methods of immunomodulation: In accordance with the present invention, the BSL1, BSL2, and BSL3 nucleic acid and polypeptide sequences can be used in the development of therapeutic reagents having the ability to either up-regulate (amplify) or down-regulate (suppress) immune responses (e.g., T-cell activation). In particular, B7-related polypeptides may interact with CD28 and thereby up-regulate immune cell activity. Alternatively, B7-related polypeptides may interact with CTLA-4 and thereby down-regulate immune cell activity. For example, soluble, dimeric forms of the B7-related polypeptides that bind to the CD28 and/or CD28-related ligand(s) but fail to provide a costimulatory signal to T-cells, can be used to block T-cell activation, and thereby provide a specific means by which to induce tolerance in a subject. Similarly, antibodies directed against one or more B7-related factors can be used to block the interaction between the B7-related factors and their cognate ligand(s), thereby preventing the activation of immune or inflammatory response cells (e.g., T-cells). In addition, fusion proteins comprising at least a fragment of a B7-related factor fused to at least the Fc domain of an IgG molecule can be used to up- or down-regulate cells expressing the cognate ligand(s) of the B7-related factor (e.g., T-cells). Furthermore, antisense or triplex oligonucleotides that bind to the nucleotide sequence of one or more B7-related factors can be used to decrease the expression these factors. In contrast, cell surface, multivalent forms of B7-related factors that bind to CD28 and/or CD28-related ligand(s) and provide a costimulatory signal to immune or inflammatory response cells, such as T-cells, can be used to increase the activation of these cells. It is also possible to utilize more than one B7-related factor, fusion protein, antibody, or therapeutically active fragments thereof, in order to up-regulate or down-regulate the activity of immune or inflammatory cells (e.g., T-cells) in an animal or human subject.

More specifically, given the structure and function of the B7-related factors disclosed herein, it is possible to up-regulate or down-regulate the function of a B7-related factor in a number of ways. Down-regulating or preventing one or more B7-related factor functions (i.e., preventing high level lymphokine synthesis by activated T-cells) should be useful in treating autoimmune diseases, such as rheumatoid arthritis, multiple sclerosis, Lupus erythematosus, Hashimoto's thyroiditis, primary mixedema, Graves' disease, pernicious anemia, autoimmune atrophic gastritis, insulin dependent diabetes mellitus, good pasture's syndrome, myasthenia gravis, pemphigus, Crohn's disease, sympathetic opthalmia, autoimmune uveitis, autoimmune hemolytic anemis, idiopathic thrombocytopenia, primary biliary cirrhosis, ulcerative colitis, Sjogren's syndrome, polymyositis and mixed connective tissue disease. B7-related factors may also be down-regulated for the treatment of inflammation related to psoriasis, chronic obstructive pulmonary disease, asthma, and atherosclerosis. In addition, B7-related factors may be down-regulated for the treatment of tissue, bone marrow, and organ transplantation, and graft versus host disease. For example, blockage of T-cell function should result in reduced tissue destruction in tissue transplantation. Typically, in tissue transplants, rejection of the transplant is initiated by its recognition as foreign material, followed by an immune reaction that destroys the transplant. The B7-related molecules of the present invention can also be used to treat or prevent cancers as described in detail below.

The B7-related nucleic acid molecules provided by the present invention can be used to design therapeutics to block the function of one or more B7-related factors. In particular, antisense or triplex oligonucleotides can be administered to prevent the expression of the BSL1, BSL2, and/or BSL3 factors. For example, an oligonucleotide (e.g., DNA oligonucleotide) that hybridizes to the BSL1, BSL2, and/or BSL3 mRNA can be used to target the mRNA for RnaseH digestion. Alternatively, an oligonucleotide that hybridizes to the translation initiation site of the BSL1 (SEQ ID NO:1 or 3), BSL2 (SEQ ID NO:6, 10, or 12), or BSL3 (SEQ ID NO:14) mRNA be used to prevent translation of the mRNA. In another approach, oligonucleotides that bind to the double-stranded DNA of the BSL1, BSL2, and/or BSL3 gene(s) can be administered. Such oligonucleotides can form a triplex construct and prevent the unwinding and transcription of the DNA encoding the targeted B7-related factor. In all cases, the appropriate oligonucleotide can be synthesized, formulated as a pharmaceutical composition, and administered to a subject. The synthesis and utilization of antisense and triplex oligonucleotides have been previously described (e.g., H. Simon et al. (1999) *Antisense Nucleic Acid Drug Dev.* 9:527-31; F. X. Barre et al. (2000) *Proc. Natl. Acad. Sci. USA* 97:3084-3088; R. Elez et al. (2000) *Biochem. Biophys. Res. Commun.* 269:352-6; E. R. Sauter et al. (2000) *Clin. Cancer Res.* 6:654-60).

In the context of this invention, antisense oligonucleotides are naturally-occurring oligonucleotide species or synthetic species formed from naturally-occurring subunits or their close homologs. Antisense oligonucleotides may also include moieties that function similarly to oligonucleotides, but have non-naturally-occurring portions. Thus, antisense oligonucleotides may have altered sugar moieties or inter-sugar linkages. Exemplary among these are phosphorothioate and other sulfur containing species which are known in the art.

In preferred embodiments, at least one of the phosphodiester bonds of the antisense oligonucleotide has been substituted with a structure that functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

Antisense oligonucleotides may also include species that include at least some modified base forms. Thus, purines and pyrimidines other than those normally found in nature may be so employed. Similarly, modifications on the furanosyl portions of the nucleotide subunits may also be effected, as long as the essential tenets of this invention are adhered to. Examples of such modifications are 2'-O-alkyl- and 2'-halogen-substituted nucleotides. Some non-limiting examples of modifications at the 2' position of sugar moieties which are useful in the present invention include OH, SH, $SCH_3$, F, $OCH_3$, OCN, $O(CH_2)_nNH_2$ and $O(CH_2)_nCH_3$, where n is from 1 to about 10. Such antisense oligonucleotides are functionally interchangeable with natural oligonucleotides or synthesized oligonucleotides, which have one or more differences from the natural structure. All such analogs are comprehended by this invention so long as they function effectively to hybridize with BSL1, BSL2, or BSL3 DNA or RNA to inhibit the function thereof.

For antisense therapeutics, the oligonucleotides in accordance with this invention preferably comprise from about 3 to about 50 subunits. It is more preferred that such oligonucleotides and analogs comprise from about 8 to about 25 subunits and still more preferred to have from about 12 to about 20 subunits. As defined herein, a "subunit" is a base and sugar combination suitably bound to adjacent subunits through phosphodiester or other bonds.

Antisense oligonucleotides can be produced by standard techniques (see, e.g., Shewmaker et al., U.S. Pat. No. 5,107, 065). The oligonucleotides used in accordance with this invention may be conveniently and routinely made through the well-known technique of solid phase synthesis. Equipment for such synthesis is available from several vendors, including PE Applied Biosystems (Foster City, Calif.). Any other means for such synthesis may also be employed, however, the actual synthesis of the oligonucleotides is well within the abilities of the practitioner. It is also will known to prepare other oligonucleotide such as phosphorothioates and alkylated derivatives.

The oligonucleotides of this invention are designed to be hybridizable with BSL1, BSL2, or BSL3 RNA (e.g., mRNA) or DNA. For example, an oligonucleotide (e.g., DNA oligonucleotide) that hybridizes to B7-related mRNA can be used to target the mRNA for RnaseH digestion. Alternatively, an oligonucleotide that hybridizes to the translation initiation site of B7-related mRNA can be used to prevent translation of the mRNA. In another approach, oligonucleotides that bind to the double-stranded DNA of BSL1, BSL2, or BSL3 can be administered. Such oligonucleotides can form a triplex construct and inhibit the transcription of the DNA encoding BSL1, BSL2, or BSL3 polypeptides. Triple helix pairing prevents the double helix from opening sufficiently to allow the binding of polymerases, transcription factors, or regulatory molecules. Recent therapeutic advances using triplex DNA have been described (see, e.g., J. E. Gee et al. (1994) *Molecular and Immunologic Approaches*, Futura Publishing Co., Mt. Kisco, N.Y.).

As non-limiting examples, antisense oligonucleotides may be targeted to hybridize to the following regions: mRNA cap region; translation initiation site; translational termination site; transcription initiation site; transcription termination site; polyadenylation signal; 3' untranslated region; 5' untranslated region; 5' coding region; mid coding region; and 3' coding region. Preferably, the complementary oligonucleotide is designed to hybridize to the most unique 5' sequence in BSL1, BSL2, or BSL3, including any of about 15-35 nucleotides spanning the 5' coding sequence. Appropriate oligonucleotides can be designed using OLIGO software (Molecular Biology Insights, Inc., Cascade, Colo.).

In accordance with the present invention, the antisense oligonucleotide can be synthesized, formulated as a pharmaceutical composition, and administered to a subject. The synthesis and utilization of antisense and triplex oligonucleotides have been previously described (e.g., H. Simon et al. (1999) *Antisense Nucleic Acid Drug Dev.* 9:527-31; F. X. Barre et al. (2000) *Proc. Natl. Acad. Sci. USA* 97:3084-3088; R. Elez et al. (2000) *Biochem. Biophys. Res. Commun.* 269:352-6; E. R. Sauter et al. (2000) *Clin. Cancer Res.* 6:654-60). Alternatively, expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express nucleic acid sequence that is complementary to the nucleic acid sequence encoding a BSL1, BSL2, or BSL3 polypeptide. These techniques are described both in Sambrook et al. (1989) and in Ausubel et al. (1992). For example, BSL1, BSL2, or BSL3 expression can be inhibited by transforming a cell or tissue with an expression vector that expresses high levels of untranslatable sense or antisense sequences. Even in the absence of integration into the DNA, such vectors may continue to transcribe RNA molecules until they are disabled by endogenous nucleases. Transient expression may last for a month or more with a non-replicating vector, and even longer if appropriate replication elements included in the vector system.

Various assays may be used to test the ability of specific antisense oligonucleotides to inhibit BSL1, BSL2, or BSL3 expression. For example, mRNA levels can be assessed northern blot analysis (Sambrook et al. (1989); Ausubel et al. (1992); J. C. Alwine et al. (1977) *Proc. Natl. Acad. Sci. USA* 74:5350-5354; I. M. Bird (1998) *Methods Mol. Biol.* 105: 325-36), quantitative or semi-quantitative RT-PCR analysis (see, e.g., W. M. Freeman et al. (1999) *Biotechniques* 26:112-122; Ren et al. (1998) *Mol. Brain Res.* 59:256-63; J. M. Cale et al. (1998), *Methods Mol. Biol.* 105:351-71), or in situ hybridization (reviewed by A. K. Raap (1998) *Mutat. Res.* 400:287-298). Alternatively, antisense oligonucleotides may be assessed by measuring levels of BSL1, BSL2, or BSL3 polypeptide, e.g., by western blot analysis, indirect immunofluorescence, immunoprecipitation techniques (see, e.g., J. M. Walker (1998) *Protein Protocols on CD-ROM*, Humana Press, Totowa, N.J.).

The B7-related polypeptide sequences provided by the present invention may also be useful in the design of therapeutic agents to block or enhance the activity of immune response cells (e.g., T-cells). For example, a fusion protein comprising the soluble portion of a B7-related polypeptide conjugated with the Fc domain of human IgG can be constructed by standard recombinant techniques, described above. The BSL1-Ig, BSL2-Ig, and/or BSL3-Ig, fusion proteins can be prepared as a pharmaceutical composition and administered to a subject. The BSL1-Ig, BSL2-Ig, and/or BSL3-Ig fusion proteins can be used to target specific T-cells for destruction, thereby reducing overall T-cell activation. Such treatment methods can be modeled on animal experiments, which utilize CTLA-4-Ig to prevent cardiac allograft rejection (Turka et al., supra). It will be understood by a person skilled in the art that such methods may be adapted for use in humans, and for use with other conditions, including various transplants and autoimmune diseases. Alternatively, the BSL1-Ig, BSL2-Ig, and/or BSL3-Ig fusion proteins can be used to enhance T-cell activation. For example, BSL2-Ig and BSL3-Ig fusion proteins can be used as co-stimulatory molecules as disclosed in detail herein.

As an alternative approach, antibodies that specifically react with B7-related polypeptides or peptides can be used to block the activity of immune or inflammatory response cells (e.g., T-cells). Antibodies or related antibody fragments that bind to peptides or polypeptides comprising the BSL1 (SEQ ID NO:2), BSL2 (SEQ ID NO:7, 11, or 13), or BSL3 (SEQ ID NO:15) sequences can be formulated as pharmaceutical compositions and administered alone or in combination to a subject. Such antibodies can then inhibit the interaction of the B7-related polypeptides with CD28 and/or CD28-related ligands, and thereby prevent T-cell activation. Treatments utilizing antibodies directed against B7-related factors may be modeled on animal experiments, which use antibodies against CD28, B7-1, or B7-2 (D. J. Lenshow et al. (1995) Transplantation 60:1171-1178; Y. Seko et al. (1998) *Circ. Res.* 83:463-469; A. Haczku et al. (1999) *Am. J. Respir. Crit. Care Med.* 159:1638-1643). One skilled in the art may adapt such methods for use in humans, and for use with various conditions involving inflammation or transplantation.

It is noted that antibody-based therapeutics produced from non-human sources can cause an undesired immune response in human subjects. To minimize this problem, chimeric antibody derivatives can be produced. Chimeric antibodies combine a non-human animal variable region with a human constant region. Chimeric antibodies can be constructed according to methods known in the art (see Morrison et al. (1985) *Proc. Natl. Acad. Sci. USA* 81:6851; Takeda et al. (1985) Nature 314:452; U.S. Pat. No. 4,816,567 of Cabilly et al.; U.S. Pat. No. 4,816,397 of Boss et al.; European Patent Publication EP 171496; EP 0173494; United Kingdom Patent GB 2177096B). In addition, antibodies can be further "humanized" by any of the techniques known in the art, (e.g., Teng et al. (1983) *Proc. Natl. Acad. Sci. USA* 80:7308-7312; Kozbor et al. (1983) *Immunology Today* 4: 7279; Olsson et al. (1982) Meth. Enzymol. 92:3-16; International Patent Application No. WO 92/06193; EP 0239400). Humanized antibodies can be also be obtained from commercial sources (e.g., Scotgen Limited, Middlesex, Great Britain). Immunotherapy with a humanized antibody may result in increased long-term effectiveness for the treatment of chronic disease situations or situations requiring repeated antibody treatments.

In yet another approach, an isolated ligand of a B7-related factor can be used to down-regulate the activity of immune or inflammatory response cells (e.g., T-cells). For example, a soluble fusion protein comprising a B7-related factor, ligand can be produced, isolated, and used to produce a pharmaceutical composition in accordance with the methods described in detail herein. This pharmaceutical composition can then be administered to a subject to bind to one or more endogenous B7-related factor(s) and block the activation of immune or inflammatory response cells (e.g., T-cells) as previously described.

Up-regulation of a B7-related factor function may also be useful in therapy. Because viral infections are cleared primarily by cytotoxic T-cells, an increase in cytotoxic activity would be therapeutically useful in situations where more rapid or thorough clearance of an infective viral agent would be beneficial to an animal or human subject. Notably, B7-1 acts to increase the cytotoxicity of T-cells though interactions with its cognate ligand(s). Thus, soluble active forms of B7-related polypeptides can be administered for the treatment of local or systemic viral infections, such as immunodeficiency (e.g., HIV); papilloma (e.g., HPV), herpes (e.g., HSV), encephalitis, influenza (e.g., human influenza virus A), and common cold (e.g., human rhinovirus) viral infections. For example, pharmaceutical formulations of active multivalent B7-related factors can be administered topically to treat viral skin diseases such as herpes lesions or shingles, or genital warts. Alternatively, pharmaceutical compositions of active, multivalent B7-related factors can be administered systemically to treat systemic viral diseases such as AIDS, influenza, the common cold, or encephalitis.

In addition, modulation of B7-related factor function may be useful in the induction of tumor immunity. For example, tumor cells (e.g., sarcoma, melanoma, lymphoma, leukemia, neuroblastoma, or carcinoma cells) can be genetically engineered to carry a nucleic acid encoding at least a fragment of at least one B7-related factor, such as BSL1 (SEQ ID NO:2), BSL2 (SEQ ID NO:7, 11, or 13), or BSL3 (SEQ ID NO:15), and then administered to a subject to traverse tumor-specific tolerance in the subject. Notably, ectopic expression of B7-1 in B7 negative murine tumor cells has been shown to induce T-cell mediated specific immunity accompanied by tumor rejection and prolonged protection to tumor challenge in mice (L. Chen et al., supra; S. Townsend et al., supra; S. Baskar et al., supra). Tumor or cancer cell gene therapy treatments utilizing B7-related factors may be modeled on animal experiments (see K. Dunussi-Joannopoulos et al. (1997) *J. Pediatr. Hematol. Oncol.* 19:356-340; K. Hiroishi et al. (1999) *Gene Ther.* 6:1988-1994; B. K. Martin et al. (1999) *J. Immunol.* 162:6663-6670; M. Kuiper et al. (2000) *Adv. Exp. Med. Biol.* 465:381-390), or human phase I trial experiments (H. L. Kaufman et al. (2000) *Hum. Gene Ther.* 11:1065-1082), which use B7-1 or B7-2 for gene transfer therapy. It will be understood that such methods may be adapted for use with various tumor or cancer cells. Additionally, tumor immunity may be achieved by administration of a B7-related fusion protein that directly stimulates the immune cells (see e.g., International Patent Application No. WO 01/21796 to V. Ling et al.).

Pharmacogenetics: The B7-related polypeptides and polynucleotides of the present invention are also useful in pharmacogenetic analysis, i.e., the study of the relationship between an individual's genotype and that individual's response: to a therapeutic composition or drug. See, e.g., Eichelbaum, M. (1996) *Clin. Exp. Pharmacol. Physiol.* 23(10-11):983-985, and Linder, M. W. (1997) *Clin. Chem.* 43(2):254-266. The genotype of the individual can determine the way a therapeutic acts on the body or the way the body metabolizes the therapeutic. Further, the activity of drug metabolizing enzymes affects both the intensity and duration of therapeutic activity. Differences in the activity or metabolism of therapeutics can lead to severe toxicity or therapeutic failure. Accordingly, a physician or clinician may consider applying knowledge obtained in relevant pharmacogenetic studies in determining whether to administer a B7-related polypeptide, polynucleotide, functional equivalent, fragment, or modulator, as well as tailoring the dosage and/or therapeutic or prophylactic treatment regimen with a B7-related polypeptide, polynucleotide, functional equivalent, fragment, or modulator.

In general, two types of pharmacogenetic conditions can be differentiated. Genetic conditions can be due to a single factor that alters the way the drug act on the body (altered drug action), or a factor that alters the way the body metabolizes the drug (altered drug metabolism). These conditions can occur either as rare genetic defects or as naturally occurring polymorphisms. For example, glucose-6-phosphate dehydrogenase deficiency (G6PD) is a common inherited enzymopathy which results in hemolysis after ingestion of oxidant drugs (anti-malarials, sulfonamides, analgesics, nitrofurans) and consumption of fava beans.

The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. The gene coding for CYP2D6 is highly polymorphic and several mutations have been identified in PM, which all lead to the absence of functional CYP2D6. Poor metabolizers quite frequently experience exaggerated drug response and side effects when they receive standard doses. If a metabolite is the active therapeutic moiety, PM show no therapeutic response. This has been demonstrated for the analgesic effect of codeine mediated by its CYP2D6-formed metabolite morphine. At the other extreme, ultra-rapid metabolizers fail to respond to standard doses. Recent studies have determined that ultra-rapid metabolism is attributable to CYP2D6 gene amplification.

By analogy, genetic polymorphism or mutation may lead to allelic variants of BSL1, BSL2, and/or BSL3 in the population which have different levels of activity. The BSL1, BSL2, and/or BSL3 polypeptides or polynucleotides thereby allow a clinician to ascertain a genetic predisposition that can affect treatment modality. Thus, in a BSL-based treatment, polymorphism or mutation may give rise to individuals that are more or less responsive to treatment. Accordingly, dosage would necessarily be modified to maximize the therapeutic effect within a given population containing the polymorphism. As an alternative to genotyping, specific polymorphic polypeptides or polynucleotides can be identified.

To identify genes that predict drug response, several pharmacogenetic methods can be used. One pharmacogenomics approach, "genome-wide association", relies primarily on a high-resolution map of the human genome. This high-resolution map shows previously identified gene-related markers (e.g., a "bi-allelic" gene marker map which consists of 60,000-100,000 polymorphic or variable sites on the human genome, each of which has two variants). A high-resolution genetic map can then be compared to a map of the genome of each of a statistically significant number of patients taking part in a Phase II/III drug trial to identify markers associated with a particular observed drug response or side effect. Alternatively, a high-resolution map can be generated from a combination of some 10 million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In this way, treatment regimens can be tailored to groups of genetically similar individuals, taking into account traits that may be common among such genetically similar individuals. See, e.g., D. R. Pfost et al. (2000) *Trends Biotechnol.* 18(8):334-8.

As another example, the "candidate gene approach", can be used. According to this method, if a gene that encodes a drug target is known, all common variants of that gene can be fairly easily identified in the population and it can be determined if having one version of the gene versus another is associated with a particular drug response.

As yet another example, a "gene expression profiling approach", can be used. This method involves testing the gene expression of an animal treated with a drug (e.g., a B7-related polypeptide, polynucleotide, functional equivalent, fragment, or modulator) to determine whether gene pathways related to toxicity have been turned on.

Information obtained from one of the pharmacogenetics approaches described herein can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a B7-related polypeptide, polynucleotide, functional equivalent, fragment, or modulator.

B7-related polypeptides or polynucleotides are also useful for monitoring therapeutic effects during clinical trials and other treatment. Thus, the therapeutic effectiveness of an agent that is designed to increase or decrease gene expression, polypeptide levels, or activity can be monitored over the course of treatment using the B7-related polypeptides or polynucleotides. For example, monitoring can be performed by: (i) obtaining a pre-administration sample from a subject prior to administration of the agent; (ii) detecting the level of expression or activity of the polypeptide in the pre-administration sample; (iii) obtaining one or more post-administration samples from the subject; (iv) detecting the level of expression or activity of the polypeptide in the post-administration samples; (v) comparing the level of expression or activity of the polypeptide in the pre-administration sample with the polypeptide in the post-administration sample or samples; and (vi) increasing or decreasing the administration of the agent to the subject accordingly.

Animal Models

B7-related polynucleotides can be used to generate genetically altered non-human animals or human cell lines. Any non-human animal can be used; however typical animals are rodents, such as mice, rats, or guinea pigs. Genetically engineered animals or cell lines can carry a gene that has been altered to contain deletions, substitutions, insertions, or modifications of the polynucleotide sequence (e.g., exon sequence). Such alterations may render the gene nonfunctional, (i.e., a null mutation) producing a "knockout" animal or cell line. In addition, genetically engineered animals can carry one or more exogenous or non-naturally occurring genes, e.g., "transgenes" or "orthologs", that are derived from different organisms (e.g., humans), or produced by synthetic or recombinant methods. Genetically altered animals or cell lines can be used to study. BSL1, BSL2, or BSL3 function, regulation, and to develop treatments for BSL1-, BSL2-, or BSL3-related diseases. In particular, knockout animals and cell lines can be used to establish animal models and in vitro models for analysis of BSL1-, BSL2-, or BSL3-related diseases. In addition, transgenic animals expressing human BSL1, BSL2, or BSL3 can be used in drug discovery efforts.

A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA.

As used herein, the term "ortholog" denotes a gene or polypeptide obtained from one species that has homology to an analogous gene or polypeptide from a different species. For example, the human BSL3 (SEQ ID NO:15) and mouse AF142780 polypeptides are orthologs.

Transgenic animals can be selected after treatment of germline cells or zygotes. For example, expression of an exogenous BSL1, BSL2, or BSL3 gene or a variant can be achieved by operably linking the gene to a promoter and optionally an enhancer, and then microinjecting the construct into a zygote (see, e.g., Hogan et al. (1994) *Manipulating the Mouse Embryo, A Laboratory Manual*, Cold Spring Harbor Laboratory, Cold Spring, Harbor, N.Y.). Such treatments include insertion of the exogenous gene and disrupted homologous genes. Alternatively, the gene(s) of the animals may be disrupted by insertion or deletion mutation of other genetic alterations using conventional techniques (see, e.g., Capecchi, (1989) *Science*, 244:1288; Valancuis et al. (1991) *Mol. Cell. Biol.*, 11:1402; Hasty et al. (1991) *Nature*, 350:243; Shinkai et al. (1992) *Cell*, 68:855; Mombaerts et al. (1992) *Cell*, 68:869; Philpott et al. (1992) *Science*, 256:1448; Snouwaert et al. (1992) *Science*, 257:1083; Donehower et al. (1992) *Nature*, 356:215).

In one aspect of the invention, BSL1, BSL2, or BSL3 knockout mice can be produced in accordance with well-known methods (see, e.g., M. R. Capecchi, (1989) *Science*, 244:1288-1292; P. Li et al. (1995) *Cell* 80:401-411; L. A. Galli-Taliadoros et al. (1995) *J. Immunol. Methods* 181(1):1-15; C. H. Westphal et al. (1997) *Curr. Biol.* 7(7):530-3; S. S. Cheah et al. (2000) *Methods Mol. Biol.* 136:455-63). The human BSL1, BSL2, and BSL3 clones can be used isolate murine homologs. A murine homologs can then be used to prepare a murine BSL1, BSL2, or BSL3 targeting construct that can disrupt BSL1, BSL2, or BSL3 in the mouse by homologous recombination at the corresponding chromosomal locus. The targeting construct can comprise a disrupted or deleted murine BSL1, BSL2, or BSL3 sequence that inserts in place of the functioning fragment of the native mouse gene. For example, the construct can contain an insertion in the murine BSL1, BSL2, or BSL3 protein-coding region.

Preferably, the targeting construct contains markers for both positive and negative selection. The positive selection marker allows the selective elimination of cells that lack the marker, while the negative selection marker allows the elimination of cells that carry the marker. In particular, the positive selectable marker can be an antibiotic resistance gene, such as the neomycin resistance gene, which can be placed within the coding sequence of murine BSL1, BSL2, or BSL3 to render it non-functional, while at the same time rendering the construct selectable. The herpes simplex virus thymidine kinase (HSV tk) gene is an example of a negative selectable marker that can be used as a second marker to eliminate cells that carry it. Cells with the HSV tk gene are selectively killed in the presence of gangcyclovir. As an example, a positive selection marker can be positioned on a targeting construct within the region of the construct that integrates at the BSL1, BSL2, or BSL3 locus. The negative selection marker can be positioned on the targeting construct outside the region that integrates at the BSL1, BSL2, or BSL3 locus. Thus, if the entire construct is present in the cell, both positive and negative selection markers will be present. If the construct has integrated into the genome, the positive selection marker will be present, but the negative selection marker will be lost.

The targeting construct can be employed, for example, in embryonal stem cell (ES). ES cells may be obtained from pre-implantation embryos cultured in vitro (M. J. Evans et al. (1981) *Nature* 292:154-156; M. O. Bradley et al. (1984) *Nature* 309:255-258; Gossler et al. (1986) *Proc. Natl. Acad. Sci. USA* 83:9065-9069; Robertson et al. (1986) *Nature* 322: 445-448; S. A. Wood et al. (1993) *Proc. Natl. Acad. Sci. USA* 90:4582-4584). Targeting constructs can be efficiently introduced into the ES cells by standard techniques such as DNA transfection or by retrovirus-mediated transduction. Following this, the transformed ES cells can be combined with blastocysts from a non-human animal. The introduced ES cells colonize the embryo and contribute to the germ line of the resulting chimeric animal (R. Jaenisch, (1988) *Science* 240:1468-1474). The use of gene-targeted ES cells in the generation of gene-targeted transgenic mice has been previously described (Thomas et al. (1987) *Cell* 51:503-512) and is reviewed elsewhere (Frohman et al. (1989) *Cell* 56:145-147; Capecchi, 1989, *Trends in Genet.* 5:70-76; Baribault et al. (1989) *Mol. Biol. Med.* 6:481-492; Wagner, (1990) *EMBO J.* 9:3025-3032; Bradley et al. (1992) *Bio/Technology* 10: 534-539).

Several methods can be used to select homologously recombined murine ES cells. One method employs PCR to screen pools of transformant cells for homologous insertion, followed by screening individual clones (Kim et al. (1988) *Nucleic Acids Res.* 16:8887-8903; Kim et al. (1991) *Gene* 103:227-233). Another method employs a marker gene is constructed which will only be active if homologous insertion occurs, allowing these recombinants to be selected directly (Sedivy et al. (1989) *Proc. Natl. Acad. Sci. USA* 86:227-231). For example, the positive-negative selection (PNS) method can be used as described above (see, e.g., Mansour et al. (1988) *Nature* 336:348-352; Capecchi, 1989, *Science* 244: 1288-1292; Capecchi, (1989) *Trends in Genet.* 5:70-76). In particular, the PNS method is useful for targeting genes that are expressed at low levels.

The absence of functional BSL1, BSL2, or BSL3 in the knockout mice can be confirmed, for example, by RNA analysis, protein expression analysis, and functional studies. For RNA analysis, RNA samples are prepared from different organs of the knockout mice and the BSL1, BSL2, or BSL3 transcript is detected in Northern blots using oligonucleotide probes specific for the transcript. For protein expression detection, antibodies that are specific for the BSL1, BSL2, or BSL3 polypeptide are used, for example, in flow cytometric analysis, immunohistochemical staining, and activity assays. Alternatively, functional assays are performed using preparations of different cell types collected from the knockout mice.

Several approaches can be used to produce transgenic mice. In one approach, a targeting vector is integrated into ES cell by homologous recombination, an intrachromosomal recombination event is used to eliminate the selectable markers, and only the transgene is left behind (A. L. Joyner et al. (1989) *Nature* 338(6211):153-6; P. Hasty et al. (1991) *Nature* 350(6315):243-6; V. Valancius and O, Smithies, (1991) *Mol. Cell. Biol.* 11(3):1402-8; S. Fiering et al. (1993) *Proc. Natl. Acad. Sci. USA* 90(18):8469-73). In an alternative approach, two or more strains are created; one strain contains the gene knocked-out by homologous recombination, while one or more strains contain transgenes. The knockout strain is crossed with the transgenic strain to produce new line of animals in which the original wild-type allele has been replaced (although not at the same site) with a transgene. Notably, knockout and transgenic animals can be produced by commercial facilities (e.g., The Lerner Research Institute, Cleveland, Ohio; B&K Universal, Inc., Fremont, Calif.; DNX Transgenic Sciences, Cranbury, N.J.; Incyte Genomics, Inc., St. Louis, Mo.).

Transgenic animals (e.g., mice) containing a nucleic acid molecule which encodes human BSL1, BSL2, or BSL3, may be used as in vivo models to study the effects of altered expression, of BSL1, BSL2, or BSL3. Such animals can also be used in drug evaluation and discovery efforts to find compounds effective to inhibit or modulate the activity of BSL1, BSL2, or BSL3, such as for example compounds for treating immune system disorders, diseases, or conditions. One having ordinary skill in the art can use standard techniques to produce transgenic animals which produce human BSL1, BSL2, or BSL3 polypeptide, and use the animals in drug evaluation and discovery projects (see, e.g., U.S. Pat. No. 4,873,191 to Wagner; U.S. Pat. No. 4,736,866 to Leder).

In another embodiment of the present invention, the transgenic animal can comprise a recombinant expression vector in which the nucleotide sequence that encodes human BSL1, BSL2, or BSL3 is operably linked to a tissue specific promoter whereby the coding sequence is only expressed in that specific tissue. For example, the tissue specific promoter can be a mammary: cell specific promoter and the recombinant protein so expressed is recovered from the animal's milk.

In yet another embodiment of the present invention, a BSL1, BSL2, or BSL3 "knockout" can be produced by administering to the animal antibodies (e.g., neutralizing antibodies) that specifically recognize an endogenous BSL1, BSL2, or BSL3 polypeptide. The antibodies can act to disrupt function of the endogenous BSL1, BSL2, or BSL3 polypeptide, and thereby produce a null phenotype. In one specific example, a murine BSL1, BSL2, or BSL3 polypeptide or peptide can be used to generate antibodies. These antibodies can then be given to a mouse to knockout the function of the corresponding mouse protein.

In addition, non-mammalian organisms may be used to study BSL1, BSL2, or BSL3, and their related diseases. For example, model organisms such as *C. elegans, D. melanogaster*, and *S. cerevisiae* may be used. BSL1, BSL2, or BSL3 homologues can be identified in these model organisms, and mutated or deleted to produce a BSL1-, BSL2-, or BSL3-deficient strain. Human BSL1, BSL2, or BSL3 can then be tested for the ability to "complement" the deficient strain. BSL1-, BSL2-, or BSL3-deficient strains can also be used for drug screening. The study of BSL1, BSL2, or BSL3 homologs can facilitate the understanding of the biological function corresponding human gene, and assist in the identification of binding proteins (e.g., agonists and antagonists).

EXAMPLES

The examples as set forth herein are meant to exemplify the various aspects of the present invention and are not intended to limit the invention in any way.

Example 1

Identification of BSL1

Preparation of Monocytes: Human Monocytes were Obtained from peripheral blood mononuclear cells by elutriation. The elutriation buffer contained 1 liter RPMI (GibcoBRL/Life Technologies Inc., Rockville, Md.; Cat. #11875-

085) with 2.5 mM EDTA and 10 µg/ml polymyxin B. The buffer was prepared 1 day prior to the elutriation procedure, and stored at room temperature. For the elutriation procedure, 225 ml EDTA whole blood/donor was obtained and prepared. Twenty milliliters of elutriation buffer was added to twelve 50 ml centrifuge tubes, and the 225 ml blood was divided equally among the tubes. Twelve milliliters of ficoll solution (lymphocyte separation medium) was used to underlay the mixture in each tube (AccuPrep Lymphocytes, Accurate Scientific Co.; Cat. # 1053980). The tubes were centrifuged at 1800 rpm for 25 min (minutes).

Sheep's red blood cells were prepared by the following procedure. Twelve milliliters of Sheep Blood Alsever's (SRBC; Colorado Serum Co., Denver, Colo.; Cat. # CS1112) was resuspended, and centrifuged at 2000 rpm for 10 min. The top coating of the SRBC pellet was removed, and the pellet was washed 2 times with elutriation buffer. Following each wash, the pellet was centrifuged at 2200 rpm for 8 min. After the second wash, the pellet was resuspended in 5 ml elutriation buffer and refrigerated.

Following centrifugation, the supernatant of the ficoll underlay tubes was aspirated to leave behind approximately 5 ml of the interface layer. The interface layer was then carefully removed to a new tube, without disturbing the red cell pellet in each tube. The interface layers of two 50 ml tubes was combined and transferred to a new 50 ml tube, resulting in a total of six 50 ml tubes. Elutriation buffer was added to each tube to bring final volume to 50 ml per tube. The tubes were centrifuged at 1800 rpm for 10 min, and the supernatant was removed. The peripheral blood monocytes from each donor was combined and divided between two tubes, and resuspended in 40 ml elutriation buffer per tube. The tubes were centrifuged at 1500 rpm for 10 min, the supernatant was aspirated, and the pellet was resuspended in 30 ml elutriation buffer per tube.

Following this step, 3 ml of washed SRBC was added to each tube, and the mixture was centrifuged at 1000 rpm for 5 min. The pellet was incubated on ice for at least 1 hr, and each pellet was gently resuspended by inverting the tubes. Twelve milliliters of ficoll was used to underlay the mixture in each tube. The tubes were centrifuged at 2500 rpm for 20 min, and the interface layers were removed to new tubes as previously described. The interface layers were then resuspended in 10 ml elutriation buffer and stored on ice until the start of the elutriation procedure.

Elutriation of monocytes: Elutriation was performed as follows. The elutriation pump speed was set to ~65 ml/min, and the storage ethanol was removed from the feed lines for the pump. The feed lines, chambers, and rotor were washed with ~100 ml distilled water. Pump speed was reduced to 50 ml/min, and elutriation buffer was passed through the feed lines, chamber, and rotor. The feed lines were checked for the presence of bubbles, and any bubbles were removed. The centrifuge speed was then set at 1950±1 rpm, and the pump was calibrated at 15 ml/min. The pump speed was then reduced to 11 ml/min and the stopcock to the chamber was closed.

To load cells, the loading syringe stopcock was closed and the outlet pipet was placed in the 50 ml sample tube labeled as 11 ml/min fraction. The cells were mixed and added to the loading syringe. The stopcock of the loading syringe was opened and the feeding tube was rinsed with 10 ml elutriation buffer. When ~0.5 ml cells remained in the syringe, elutriation buffer was added and this step was repeated one more time. Following this step, the loading syringe stopcock was closed and the chamber stopcock was opened.

Fifty milliliter fractions were collected at 11 (2 fractions), 14, 16, and 36 (2 fractions) ml/min pump speeds, and then placed on ice. In accordance with previous observations, the monocytes were predicted to be in the 36 ml/min fraction. The monocyte fraction was centrifuged at 1800 rpm for 8 min, and the cells were resuspended in 10 ml 25% Fetal Bovine Serum/RPMI with 1 µg/ml polymyxin B. The cells were counted and stored on ice until use.

Cell culture conditions: The isolated peripheral blood monocytes were resuspended in RPMI 1640 medium containing 10% fetal bovine serum (Hyclone, Logan, Utah) supplemented with penicillin/streptomycin, 2 mM glutamine, 1% non-essential amino acids, 1 mM sodium pyruvate, and IL-4 (75 ng/ml) and GM-CSF (15 ng/ml) cytokines (each from GibcoBRL). The cell suspension ($5 \times 10^5$ cells/ml) was transferred to tissue culture flasks and incubated in chambers containing 5% $CO_2$ at 37° C. for 7 days. Following the incubation period, the cell cultures were pipetted vigorously to remove cells from the flask. The human monocytic cell line THP1 was grown at 37 C and 5% $CO_2$ to a final concentration of $5 \times 10^5$ cells/ml in RPMI 1640 medium containing 10% fetal bovine serum supplemented with penicillin/streptomycin and 2 mM glutamine.

Poly(A)$^+$ RNA isolation: GM-CSF/IL-4 differentiated human peripheral blood mononuclear cells ($2 \times 10^8$ cells) and THP1 human monocytes ($2 \times 10^8$ cells) were washed twice with PBS (GibcoBRL) at 4° C. Poly(A)$^+$ RNA was isolated directly using the FAST TRACK™ 2.0 kit (Invitrogen Corp., Carlsbad, Calif.).

Subtraction library construction: A cDNA subtraction library was made using the CLONTECH PCR-Select™ cDNA Subtraction Kit (CLONTECH, Palo Alto, Calif.). Manufacturer's protocols were followed using 2.0 µg of GM-CSF/IL-4 differentiated human peripheral blood monocyte poly (A)$^+$ RNA as the tester sample and 2.0 µg of resting THP1 monocyte poly(A)$^+$ RNA as the driver sample. Ten secondary PCRs were combined and run on a 1.2% agarose gel. Fragments ranging from approximately 0.3 kb to 1.5 kb were gel purified using the QIAGEN gel extraction kit (QIAGEN, Valencia, Calif.) and inserted into the TA CLONING® vector, pCR2.1 (Invitrogen). TOP10F' competent *E. coli* (Invitrogen) were transfected and plated onto Lauria-Bertani (LB) plates containing 50 µg/ml ampicillin. Approximately 300 clones were isolated and grown in LB broth containing similar concentrations of ampicillin. Plasmids were isolated using QIAGEN miniprep spin (QIAGEN) and sequenced using ABI cycle sequencers (ABI PRISM®, PE Applied Biosystems).

Full-length cloning: To clone the 5' and 3' ends of BSL1, the SMART™ RACE (rapid amplification of cDNA ends) cDNA Amplification kit (CLONTECH) was used according to the manufacturer's directions. The 5' and 3' RACE libraries were constructed using 1.0 µg of poly(A)$^+$ RNA template obtained from human microvascular endothelial cell treated with TNF-alpha for 1 hr. The 5'-RACE-PCR mixture contained 1.5 µl of 5'-RACE ready cDNA, 0.4 µM JNF 155 primer (5'-GGCATAATAAGATGGCTCCC-3') (SEQ ID NO:21), 1× Universal Primer Mix (UPM), 200 µM dNTP, 1× Advantaq Plus PCR buffer (CLONTECH), and 1× Advantaq Plus Polymerase (CLONTECH) in a total volume of 25 µl. The 3'-RACE-PCR mixture contained the same buffer conditions, 3'-RACE ready cDNA, and 0.4 µM JNF 154 primer (5'-CATGAACTGACATGTCAGGC-3') (SEQ ID NO:22). Both reactions were incubated using a traditional touchdown PCR approach: 5 cycles of incubation at 94° C. for 30 sec (seconds), 65° C. for 30 sec, and 72° C. for 3 min; 5 cycles of incubation at 94° C. for 30 sec, 63° C. for 30 sec, and 72° C.

for 3 min; and 15 cycles of incubation at 94° C. for 30 sec, 62° C. for 30 sec, and 72° C. for 3 min.

The PCR products were isolated by electrophoresis using a 2.0% agarose gel, and DNA was visualized by ethidium bromide staining. An 888-bp fragment from the 5'-RACE reaction and a 1,110-bp fragment from the 3'-RACE reaction were purified using the QIAGEN gel extraction kit and resuspended in 10 μl distilled water. Six microliters of each fragment was ligated into pCR2.1-TA CLONING® vector (Invitrogen), and the ligation mixture was used to transfect TOP10F' ultracompetent E. coli cells (Invitrogen). Transfected cells were plated onto LB plates supplemented with 50 μg/ml ampicillin, 40 mg/ml X-gal, and 100 mM IPTG. Colonies were isolated and grown overnight at 37° C. in 4 ml of LB-broth supplemented with 50 μg/ml ampicillin. Plasmids were isolated using the QIAGEN miniprep spin kit (QIAGEN), resuspended in 30 μl distilled water, and sequenced using an ABI cycle sequencer (ABI PRISM®, PE Applied Biosystems).

To generate the full-length clone, JNF155RACE5.1, JNF154RACE3.2, and pCR2.1 were ligated together. JNF155RACE5.1 was doubly digested with XhoI and HindIII. JNF154RACE3.2 was doubly digested with HindIII and EcoRI. The TA CLONING® vector (Invitrogen) was digested with XhoI and EcoRI. Each fragment was purified using the QIAGEN gel extraction kit and resuspended in water. One microliter of each digested fragment was ligated together in the same reaction using T4 DNA ligase. The ligation mixture was used to transfect TOP10F' E. coli ultracompetent cells, plated onto LB plates containing 50 μg/ml ampicillin, 40 mg/ml X-gal, and 100 mM IPTG. Colonies were isolated from the plates, and grown in LB broth containing 50 μg/ml ampicillin overnight at 37° C. Plasmids containing full-length BSL1 were purified using the QIAGEN miniprep spin kit (QIAGEN), and sequenced (ABI cycle sequencer; PE Applied Biosystems). The plasmid carrying DNA encoding the full-length BSL1 sequence (pTADV: BSL1) was deposited with the American Type Culture Collection (ATCC, 10801 University Blvd., Manassas, Va. 20110-2209 USA), under ATCC Designation No. PTA-1989, on Jun. 6, 2000.

Example 2

Characterization of BSL1

Sequence analysis of the BSL1 clones: The full-length BSL1 nucleotide and predicted amino acid sequence was determined from a clone isolated from TNF-alpha treated human microvascular endothelial cell cDNA subtraction library (FIGS. 1A and 1B) and a clone isolated from a GM-CSF/IL-4 differentiated human monocyte cDNA library (FIG. 1C). The sequencing primers for the BSL1 clones are shown in Table 1.

TABLE 1

| Primer | Sequence | SEQ ID NO: |
|---|---|---|
| JNF 292 forward | CATTTACAAAGAGAGGTCGG | 23 |
| JNF 298 reverse | AGGGTTATTTTAAGTACCGACC | 24 |
| JNF 293 forward | GGAAATGTATGTTAAAAGCACG | 25 |
| JNF 297 reverse | GGCATGGATCCTCAGCCCTGGG | 26 |
| JNF 294 forward | GAGACCCATGGGCTCTCCAGGG | 27 |
| JNF 296 reverse | GTTCAAGCACAACGAATGAGGC | 28 |
| JNF 295 forward | TGGCTTTGCCACATGTCAAGGC | 29 |

Both BSL1 clones had identical coding sequences, however, the clone obtained from the differentiated human monocyte cDNA library contained a different sequence in the 3' untranslated region of the BSL1 gene (FIG. 2B; see bold text). The nucleotide and predicted amino acid sequences of BSL1 are shown in FIGS. 1A-1C.

EST clones encoding BSL1 were identified from public) (GENBANK®) and private (Incyte Genomics) databases, and are shown in Table 2.

TABLE 2

| Clone ID | Database | Tissue | Length (bp) | Position (1-3797) |
|---|---|---|---|---|
| AI733919 | GENBANK ® | Ovary tumor | 429 | 401-829 |
| AA292201 | GENBANK ® | Ovary tumor | 430 | 401-830 |
| AA399416 | GENBANK ® | Ovary tumor | 325 | 506-830 |
| 3166966H1 | Incyte | CD4+ T lymphos t/CD3, CD28 Ab's | 197 | 415-611 |
| 4415633H1 | Incyte | Peripheral Blood Monocytes, t/anti-IL-10, LPS | 253 | 542-794 |
| AA368815 | GENBANK ® | Placenta, fetal | 55 | 998-1052 |
| 5611256H1 | Incyte | Peripheral Blood Monocytes, t/anti-IL-10, LPS, SUB | 254 | 1005-1258 |
| 5048659F6 | Incyte | Placenta, fetal | 332 | 1016-1347 |
| 3680369H1 | Incyte | Lung, aw/asthma | 240 | 1203-1442 |
| AI202916 | GENBANK ® | Germ cell tumor, pool, SUB | 259 | 1381-1639 |
| AA373164 | GENBANK ® | Lung fibroblast line, HSC172, fetal | 274 | 1416-1689 |
| 4354914H1 | Incyte | Fat, auxiliary, aw/breast adenoCA | 288 | 1449-1736 |
| AA037078 | GENBANK ® | Fibroblasts, senescent | 365 | 1529-1893 |
| 171033R6 | Incyte | Bone Marrow | 273 | 1785-2057 |
| R30906/ R30861* | GENBANK ® | Placenta, neonatal | 1932 | 1867-3798 |

*Full-length sequence not known.

It is noted that the BSL1 coding sequence and predicted amino acid sequence have also been identified as B7-H1 and PD-L1 (H. Dong et al. (1999) *Nature Med.* 5:1365-9; GenPept Accession No. NP_054862; G. J. Freeman et al. (2000) *J. Exp. Med.* 192:1027-1034). In addition, a murine homolog of B7-H1 has been identified (H. Tamura et al. (2001) *Blood* 97:1809-1816). Notably, the mouse and human B7-H1 factors have been described as costimulatory molecules (H. Dong et al. (1999) *Nature Med.* 5:1365-9; H. Tamura et al. (2001) *Blood* 97:1809-1816), whereas PD-L1 has been described as an inhibitor of T-cell proliferation (G. J. Freeman et al. (2000) *J. Exp. Med.* 192:1027-1034).

Chromosomal Mapping: BSL1 was previously mapped utilizing radiation hybrid mapping (T. Ishida et al. (1999) *CytoGenet. Cell Genet.* 85:232-6). Analysis of NCBI's Genemap '99 using GENBANK® EST AA399416 indicated that the BSL1 gene was linked to chromosome 9p24 with the order of AFM274xe1-stSG46389 (BSL1)-AFM242xh6.

BSL1 expression analysis: BSL1 expression patterns were determined by northern blot analysis of several cell types, including resting peripheral blood T-cells, peripheral blood T-cells stimulated with anti-CD3/anti-CD28 antibodies, peripheral blood T-cells stimulated with phorbol 12 myristate 13 acetate (PMA), peripheral blood T-cells stimulated with phytohemaglutinin (PHA), resting THP1 monocytes, THP1 stimulated with lipopolysacharide (LPS), resting peripheral blood monocytes, resting peripheral blood monocytes stimulated with PHA, resting peripheral blood monocytes stimulated with GM-CSF and IL-4, RAJI B cells, RAMOS B cells, resting human microvascular endothelial cells (HMVEC), HMVEC stimulated with TNF-alpha, and serum starved H292 human lung epithelial cells.

Cell culture conditions: Peripheral blood T-cells were grown in RPMI 1640 (Hyclone) with 10% human serum at 37° C. and 5% $CO_2$ for 48 hr. Peripheral blood T-cells stimulated with anti-CD3 and anti-CD28 antibodies were grown in RPMI 1640 with 10% human serum at 37° C. and 5% $CO_2$ for 24-72 hr in the presence of 1 anti-CD3 monoclonal antibodies (P. S. Linsley et al. (1993) *Ann. Rev. Immunol.* 11:191-212) and 1 µg/ml anti-CD28 monoclonal antibodies (Linsley et al., supra). Peripheral blood T-cells stimulated with PMA and ionomycin were grown in RPMI 1640 (Hyclone) with 10% human serum at 37° C. and 5% $CO_2$ for 48 hr in the presence of 30 ng/ml PMA with 1 µM ionomycin. Peripheral blood T-cells stimulated with PHA were grown in RPMI 1640 (Hyclone) with 10% human serum at 37° C. and 5% $CO_2$ for 48 hr in the presence of 3 µg/ml PHA. THP1 cells obtained from an immortal human monocytic cell line were grown in RPMI 1640 (Hyclone) with 10% fetal bovine serum at 37° C. and 5% $CO_2$ with or without 100 ng/ml LPS for 2 hr. Peripheral blood monocytes were grown in RPMI 1640 (Hyclone) with 25% fetal bovine serum in teflon plates at 37° C. and 5% $CO_2$ with or without 1 µg/ml PHA or 15 ng/ml GM-CSF with 75 ng/ml IL-4 for 7 days. RAJI and RAMOS cells obtained from immortal human B cell lines were grown in RPMI 1640 (Hyclone) with 10% fetal bovine serum at 37° C. and 5% $CO_2$. HMVEC were grown in DMEM with 10% fetal bovine serum at 37° C. and 5% $CO_2$ with or without 10 ng/ml TNF-alpha for 1-24 hr. H292 cells obtained from an immortal human lung epithelial cell line were grown in RPM 1640 (Hyclone) with 10% fetal bovine serum at 37° C. and 5% $CO_2$, and then grown in serum free medium for 16 hr prior to harvest.

Northern blot analysis: For northern blot analysis, 0.5 µg of total poly(A)$^+$ RNA obtained from each cell type was separated on a 1.2% agarose gel containing 3% formaldehyde, and transferred to a HYBOND®-N+ nylon membrane (Amersham) overnight using 20×SSC as transfer buffer. The membrane was then auto-crosslinked, washed with 4×SSPE, and allowed to air-dry. The membrane was then prehybridized at 65° C. in ExpressHyb solution (CLONTECH) for 1 hr, and then hybridized with a [$^{32}$P]dCTP-radiolabeled (NEN, Boston, Mass.) random primed BSL1 cDNA probe. The probe was obtained from a 666 by BSL1 HindIII/PstI fragment (FIG. 6A), which was purified using the NUCTRAP® purification column (Stratagene), and radiolabeled to have a specific activity of $2.0 \times 10^6$ cpm/ml. Following hybridization, the membrane was washed in 2.0×SSC with 0.05% SDS at 65° C., and exposed to film for 72 hr at −70° C.

A 3.8 kb BSL1 mRNA transcript was detected in several cell types. In particular, high levels of BSL1 mRNA were detected in peripheral blood monocytes stimulated with PHA, and in HMVEC stimulated with TNF-alpha (FIG. 7D). Moderate levels of BSL1 mRNA were detected in peripheral blood T-cells following stimulation with anti-CD3 and anti-CD28 monoclonal antibodies for 72 hr (FIG. 7D). Moderate levels of BSL1 mRNA were also observed in THP1 cells stimulated with LPS (FIG. 7D). However, BSL1 mRNA was not detected in resting THP1 cells, resting BJAB cells, LPS-activated BJAB cells, resting peripheral blood T-cells, PBT-activated peripheral blood T-cells, or GM-CSF/IL-4-activated peripheral blood monocytes (FIG. 7D). In addition, BSL1 mRNA was not detected in resting RAJI cells, resting RAMOS cells, or serum starved H292 cells (FIG. 7D).

BSL1-Ig fusion construct: The DNA fragment corresponding to the BSL1 predicted extracellular domain (ECD; amino acids 23-290) was amplified by PCR utilizing full-length BSL1-pCR2.1 as a template, and oligonucleotide primers that hybridize to the 5' and 3' ends of the BSL1 ECD: JNF 184 forward primer 5'-TCAGGTACTAGTGTT CCCAAGGACCTATATGTGG-3') (SEQ ID NO:30); and JNF 185 reverse primer (5'-GATTCGAGATCTCCTCGAGTCCTTTCATTTGGAGGATGTGC C-3' (SEQ ID NO:31). PCR was performed using ~100 ng template DNA, 0.4 μM of each primer, 200 μM dNTP, 1× ADVANTAGE® 2 PCR buffer, and 1× ADVANTAGE® 2 Polymerase (CLONTECH) in a total volume of 50 μl. The PCR mixture was incubated at 94° C. for 30 sec, 62° C. for 30 sec, and 72° C. for 1 min, and this was repeated for 30 cycles. The PCR products were separated by gel electrophoresis on a 1.2% agarose gel, and the DNA was visualized by ethidium bromide staining. A 680-bp fragment corresponding to the BSL1 ECD was purified from the agarose gel using the QIAGEN gel extraction kit (QIAGEN), and the resuspended in 32 μl distilled water.

The BSL1 ECD fragment was then digested using SpeI and BglII restriction endonucleases and directionally cloned into SpeI/BamHI-digested PD19 vector using 5 U/μl T4 DNA ligase (GibcoBRL). The ligation mixture was used to transfect DH5 alpha competent *E. coli* cells (GibcoBRL), and transfected cells were plated onto Lauria-Bertani (LB) plates containing 50 μg/ml ampicillin. Plates were incubated overnight at 37° C., and colonies were isolated and grown overnight at 37° C. in LB broth containing 50 μg/ml ampicillin. Plasmids were isolated using the QIAGEN miniprep spin kit, resuspended in 50 μl distilled water, and sequenced using ABI cycle sequencer (PE Biosystems, Foster City, Calif.). Primer sequences were as follows: sense JNF 184 (5'-TCAGGTACTAG TGTTCCCAAGGACCATATGTGG-3') (SEQ ID NO:32) and anti-sense JNF 185 (5'-GATTCGAGATCTCCTCGAGTCTTTCATTGGGGATGTGCC-3') (SEQ ID NO:33).

The plasmid carrying DNA encoding BSL1-Ig (pD19:BSL1Ig) was deposited with the American Type Culture Collection (ATCC, 10801 University Blvd., Manassas, Va.

20110-2209 USA), under ATCC Designation No. PTA-1992, on Jun. 6, 2000. The nucleotide and predicted amino acid sequence of BSL1-Ig is shown in FIGS. 2A and 2B.

BSL1 monoclonal antibodies: The BSL1-Ig fusion protein was purified by affinity purification as described for BSL3-Ig, below. The purified fusion protein was then used to immunize mice using the protocol described for BSL3-Ig. Following this, hybridoma cell lines were constructed and BSL1 monoclonal antibodies (MAbs) were isolated as described for BSL3, below. In addition, BSL1 MAbs were screened for specificity by whole cell ELISA. For whole cell ELISA, COS cells were transiently transfected with full length BSL1 (L156-3). Cells were lifted with VERSENE® on day 4 following transfection. Cells were washed twice in PBS and resuspended in PBS with 10% FBS at a concentration of $5.0 \times 10^6$ cells/ml. Then, 50 µl of cells were added to each well of a Falcon 3911 96-well plate and incubated on ice for 30 min. Next, 50 µl supernatant from the putative BSL1 hybridomas was added per well and incubated on ice 30 min. Cells were washed twice in PBS. Cells were then resuspended in goat anti-mouse HRP-conjugated secondary antibodies (Amersham Cat. # NA9310) diluted 1:1000 in PBS. Cells were incubated on ice for 30 min, washed twice in PBS, and resuspended in 125 µl PBS. Following this, cells were transferred to a fresh plate. Cells were washed in PBS and resuspended in 25 µl PBS. Next, 125 µl Peroxidase solution B (KPL, Gaithersburg, Md.; Cat. #50-65-00) with TMB peroxidase substrate (KPL Cat. # 50-76-01) was added. Color was allowed to develop. Cells were pelleted, and 100 µl supernatant was transferred to an IMMULON® 2 plate. The signal was quenched with 100 µl 1 N sulfuric acid, and the plates were read at $OD_{450}/OD_{630}$.

Example 3

Identification of BSL2

Database searches: BSL2 was identified by BLAST and FASTA analysis of the Incyte Genomics sequence databases (Incyte Genomics) utilizing the B7-1 or B7-2 amino acid sequences as query sequences. For BLAST analysis, the BLOSSUM-62 scoring matrix was used (S. Henikoff et al. (1992) *Proc. Natl. Acad. Sci. USA* 89:10915-10919), and the remaining parameters were set to the default designations. For FASTA analysis, all the parameters were set to the default designations (W. R. Pearson et al. (1988) *Proc. Natl. Acad. Sci. USA* 85:2444-2448). The sequence database searches, identified two Incyte Genomics 'templates': 252899.6 and the potential splice variant 252899.8 (Incyte Genomics templates are consensus EST sequences that are considered to represent mRNA transcripts).

Sequence analysis of the BSL2 clone: Incyte Genomics template 252899.8 was used to identify Incyte Genomics clone 4616811. Incyte Genomics clone 4616811 belongs to Incyte Genomics Library ID No. BRAYDIT01, which was originally constructed using poly(A)+ RNA from diseased hypothalamus tissue. Incyte Genomics clone 4616811 was obtained from Incyte Genomics and used for sequence analysis (ABI cycle sequencer, PE Biosystems) with the primers shown in Table 3.

TABLE 3

| Clone | Primer | Sequence | SEQ ID NO: |
|---|---|---|---|
| 4616811 | 392.423 | GGTGCACAGCTTTGCTGA | 34 |
| 4616811 | 392.415 | GCTGTGCACCAGCTGTTT | 35 |
| 4616811 | 392.439 | GCTATGAAAGGTCCAGAG | 36 |
| 4616811 | 392.499 | GAATCTGGTGGTGTCCAA | 37 |
| 4616811 | 392.1716 | CTCTGTCACCATCACAGG | 38 |
| 4616811 | 392.852 | CTCTGTCACCATCACACC | 39 |
| 4616811 | 392.523 | GAAATCCCGGATGCTCAC | 40 |
| 4616811 | 392.766A | ACCACACGTGTTCCAGCA | 41 |
| 4616811 | 392.766B | TGCTGGAACACGTGTGGT | 42 |
| 4616811 | 392.383 | GGCCCTCAGCAAAGCTGT | 43 |
| 4616811 | 392.1448 | AGCTGTAGGTGCCATTCG | 44 |
| 4616811 | 392.892 | AGGGACCTGGACCTCCAC | 45 |
| 4616811 | 392.1528 | TGGGGGGAATGTCATAGG | 46 |
| 4616811 | 392.1215 | AGCAGGCAGGATGACTTA | 47 |
| 4616811 | 392.1242 | AACAGACCACCCACAACC | 48 |
| 6487516 | 314.570 | GCAAATGGCACCTACAGC | 49 |
| 6487516 | 314.634 | TCTGGGGTGTGATGGTGA | 50 |
| 6487516 | 314.450 | ATGAAAGGTCCAGAGGGC | 51 |
| 6487516 | 314.584 | ACCCATAATTCTTACCCA | 52 |
| 6487516 | 314.824 | CACAGCTCTGTTTGATCT | 53 |
| 6487516 | 314.644 | CTCCTACCCTCTGGCTGC | 54 |

Notably, the predicted amino acid sequence of Incyte Genomics clone 4616811 contained 2 sets of V/C (variable/constant domain) folds, whereas typical B7-related amino acid sequences contain only 1 set of V/C folds. SEQWEB® Gap (Genetics Computer Group) analysis indicated that the BSL2-4616811 sequence shared less than 50% sequence identity with B7-1, B7-2, BSL1/B7-H1 nucleotide sequences, while the BSL2-4616811 amino acid sequence shared less than 35% sequence identity with the B7-1, B7-2, and BSL1/B7-H1 amino acid sequences. A sequence similar to BSL2-4616811 has been identified as an amyloid precursor protease in International Patent Application No. WO 00/68266 to G. W. Becker et al.

The nucleotide and predicted amino acid sequences of Incyte Genomics clone 4616811 (BSL2-4616811) are shown in FIGS. 3A and 3B. The plasmid carrying DNA encoding BSL2-4616811 (pINCY:BSL2-4616811) was deposited with the American Type Culture Collection (ATCC, 10801 University Blvd., Manassas, Va. 20110-2209 USA), under ATCC Designation No. PTA-1993, on Jun. 6, 2000.

Full-length cloning: To verify the sequence of Incyte Genomics clone 4616811, PCR primers were designed to amplify the nucleotide sequence from the predicted translation start codon to the predicted translation stop codon of the clone: forward primer BSL2-7 (5'-ATGCTGCGTCGGCG-3') (SEQ ID NO:55); reverse primer BSL2-8 (5'-TCAGGC-TATTTCTTGTCCATCATC-3') (SEQ ID NO:56).

A HMVEC library was constructed utilizing the SMART™ RACE cDNA Amplification Kit (CLONTECH) according to manufacturer's instructions, using poly(A)+

RNA obtained from human microvascular endothelial cells treated with TNF-alpha for 1 hr as the RACE reaction template. The PCR mixture included 1 µl PCR-ready HMVEC library, 5 µl PCR buffer (GibcoBRL), 1.5 µl 50 mM MgCl$_2$, 1 µl 10 mM dNTPs (Boehringer Mannheim Biochemicals/ Roche Molecular Biochemicals, Indianapolis, Ind.), 25 pMol BSL2-7 primer, 25 pMol BSL2-8 primer, and 1 µl CLONTECH ADVANTAGE® Enzyme mix in a total volume of 50 µl. PCR was performed in a PE Biosystems Thermal Cycler model 9700. The PCR mixture was incubated at 94° C. for 1 min, followed by 35 cycles of incubation at 94° C. for 30 sec, 60° C. for 30 sec, and 72° C. for 45 sec, followed by incubation at 72° C. for 10 min.

One microliter of the PCR mixture was ligated directly into pCR2.1 (Invitrogen) according to the manufacturer's directions. One half of the ligation mixture was used to transfect MAX-EFFICIENCY® DH5 alpha *E coli* cells (GibcoBRL) in accordance with the manufacturer's directions. Transfected cells were plated onto LB agar plates with 100 µg/ml ampicillin and 30 µg/ml X-gal and incubated at 37° C. overnight. White colonies were isolated and grown overnight at 37° C. in 5 ml LB broth containing 100 µg/ml ampicillin.

Plasmid DNA was isolated from the bacterial culture using Spin Miniprep kit (QIAGEN) according to the manufacturer's directions. DNA was digested with EcoRI to release the cloned insert, and the digestion mixture was analyzed by electrophoresis on a 1% agarose gel. Insert fragments larger than 700 by were sequenced using the vector-specific M13 (5'-GTTTTCCCAGTCACGAC-3') (SEQ ID NO:57) and M13 reverse (5'-CAGGAAACAGCTATGAC-3') (SEQ ID NO:58) sequencing primers (ABI cycle sequencer, PE Applied Biosystems).

Sequence analysis indicated that two splice variants of BSL2 had been cloned: BSL2-L165-21 and BSL2-L165-35b. The BSL2-L165-21 and BSL2-L165-35b splice variants encoded amino acid sequences that each contained one V/C fold and were ~95% identical to one another. SEQWEB® Gap analysis (Genetics Computer Group) also indicated that the BSL2-L165-21 and BSL2-L165-35b nucleotide sequences shared less than 50% sequence identity with B7-1, B7-2, and BSL1/B7-H1 nucleotide sequences, while the BSL2-L165-21 and BSL2-L165-35b amino acid sequences shared less than 35% sequence identity with the B7-1, B7-2, and BSL1/B7-H1 amino acid sequences.

Sequence analysis further indicated that the amino acid and nucleotide sequences of BSL2-L165-21 shared less than 99% sequence identity with the PRO352 amino acid and nucleotide sequences, respectively, reported in International Patent Application No. WO 99/46281 to K. P. Baker et al. The amino acid and nucleotide sequences of BSL2-L165-35b shared less than 99.5% sequence identity with the PRO352 amino acid and nucleotide sequences, respectively.

Amino acid sequence alignments using GCG Gap program (GCG, Madison, Wis.) indicated that the longest stretch of identical amino acid residues shared by BSL2-L165-21 and PRO352 was 88 contiguous amino acids in length. The longest stretch of identical amino acid residues shared by BSL2-L165-35b and PRO352 was 168 contiguous amino acids in length. The longest stretch of identical amino acids shared by BSL2-4616811 and PRO352 was 206 contiguous amino acids in length.

Nucleotide sequence alignments indicated that the longest stretch of identical bases shared by BSL2-L165-21 and PRO352 was 254 contiguous nucleotides in length. The longest stretch of identical bases shared by BSL2-L165-35b and PRO352 was 305 contiguous nucleotides in length. The longest stretch of identical bases shared by BSL2-4616811 and PRO352 was 302 contiguous nucleotides in length. Notably, BSL2-L165-35b has also been identified as B7-H3, a costimulatory molecule for T-cell activation (A. I. Chapoval et al. (2001) *Nature Immunology* 2:269-274).

The nucleotide and predicted amino acid sequences of the BSL2-L165-21 splice variant are shown in FIGS. 3C and 3D, while the nucleotide and predicted amino acid sequences of BSL2-L165-35b are shown in FIGS. 3E and 3F. The plasmid carrying DNA encoding BSL2-L165-21 (pCR2.1:BSL2-L165-21) was deposited with the American Type Culture Collection (ATCC, 10801 University Blvd., Manassas, Va. 20110-2209 USA), under ATCC Designation No. PTA-1987, on Jun. 6, 2000. In addition, the plasmid carrying DNA encoding BSL2-L165-35b (pCR2.1:BSL2-L165-35b) was deposited with the American Type Culture Collection (ATCC, 10801 University Blvd., Manassas, Va. 20110-2209 USA), under ATCC Designation No. PTA-1988, on Jun. 6, 2000.

Example 4

Characterization of BSL2

BSL2 expression analysis: BSL2 expression patterns were determined by northern blot analysis of various tissue and cell types, using the BSL2-4616811-derived probe shown in FIG. 6B, and the procedure described for BSL1 (see above). A 3.6 kb BSL2 mRNA transcript was detected in several cell types. In particular, high levels of BSL2 mRNA were detected in all HMVEC stimulated with TNF-alpha. Moderate levels of BSL2 mRNA were detected in resting THP1 cells, and THP1 cells activated with LPS (FIG. 7D). In contrast, low levels of BSL2 mRNA were detected in peripheral blood monocytes stimulated with PHA or GM-CSF/IL-4, and BSL2 mRNA was not detected in resting or stimulated peripheral blood T-cells, or in resting RAJI cells, resting RAMOS cells, or serum starved H292 cells (FIG. 7D).

PCR assay to determine relative abundance of BSL2-4616811 and BSL2-L165-35b: To determine whether BSL2-4616811 or BSL2-L165-35b was predominant species of BSL2, and whether predominance corresponded with cell type and/or stimulus type, the following experimental approach was used. Analysis, of the genomic sequence of BSL2 indicated that the sequence includes several exons separated by introns. It was presumed that a primary transcript was produced from this sequence, and the primary transcript was spliced to yield BSL2-4616811 mature RNA. Analysis of BSL2-4616811 sequence showed that it coded for the following: a 5' UTR, an initiating ATG, a signal peptide sequence, a variable Ig fold (v1), an Ig constant fold (c1), an Ig V fold (v2), an Ig C fold (c2), a short hinge a putative transmembrane domain, a short cytoplasmic tail, a stop codon, and a 3' UTR.

The BSL2-4616811 coding sequence appeared unique in the human genome, as the v1 and c1 (v1c1) sequence was about 95% identical to the v2 and c2 (v2c2) sequence at the amino acid level. Importantly, all of the structurally important residues were conserved in the v1c1 and v2c2 amino acid sequences, and most of the changes from v1c1 to v2c2 were conservative changes. Comparison of the BSL2-L165-21 and BSL2-L165-35b sequences (which contained only single V and C folds) to the BSL2-4616811 sequence indicated that in each case, a splicing event occurred which resulted in a shift from v1 to the exactly homologous place in v2. However, BSL2-L165-21 shifted from v1 to v2 at a different place than BSL2-L165-35b.

Despite the 96% identity between v1c1 and v2c2 at the nucleotide level, sequence comparison between the two regions using GCG Gap revealed one short region of relatively low homology. A forward primer designated BSL2-9 was designed to take advantage of this short region of low homology. BSL2-9 was designed to bind specifically to v1 (FIG. 8E demonstrates the specificity of the BSL2-9 primer). A reverse primer, BSL2-11 was designed to hybridize to the hinge sequence.

Notably, the BSL2-4616811 transcript contained both the BSL2-9 v1-binding site in v1 and the homologous site in v2. The BSL2-L165-35b transcript contained only the BSL2-9 v1 binding site. The BSL2-L165-21 transcript contained only the v2 site. Accordingly, PCR performed with primers BSL2-9 and BSL2-11 was expected to produce: 1) a PCR product of approximately 1150' bp, representing BSL2-4616811; or 2) a PCR product of about 550 bp, representing BSL2-L165-35b.

PCR was initially conducted with BSL2-4616811 plasmid to confirm the specificity of the BSL2-9 primer. PCR was performed using 2 µl 10 ng/µl BSL2-4616811 plasmid DNA, 5 µl PCR buffer (GibcoBRL), 1.5 µl of 25 mM $MgCl_2$ (GibcoBRL), 1 µl of 10 mM dNTPs (GibcoBRL), 2.5 µl of 10 pMol/µl BSL2-9 primer (5' TGGTGCACAGCTTTGCT 3') (SEQ ID NO:59), 2.5 µl of 10 pMol/µl BSL2-11 primer (5' TCTGGGGGGAATGTCAT 3') (SEQ ID NO:60), 0.5 µl of 5 U/µl GibcoBRL PLATINUM® Taq DNA polymerase (Cat. #10966-018), and 35 $dH_2O$. PCR was performed on a PE Biosystems 9700 using the following cycling conditions: 94° C. for 30 sec; followed by 35 cycles of 94° C. for 30 sec, 61° C. for 30 sec, 72° C. for 60 sec; followed by 72° C. for 10 min. Following this, 40 µl of the PCR reaction was run on a 1.2% agarose gel next to Lambda BstEII DNA ladder (New England Biolabs Beverly, Mass.; Cat. #301-4S). The 1150 by band was predominant, indicating that the BSL2-9 PCR primer was specific for the BSL2-4616811 sequence (FIG. 8E).

Raji, Ramos, PM-LCL, PL-LCL, and CE-LCL B-like cell lines; HL-60 and Thp1 monocytic like cell lines; and CEM and Hut78 T-like cell lines were grown in RPMI 1640 with 10% FBS and 1% GibcoBRL penicillin/streptomycin to a concentration of $5 \times 10^5$ cells/ml. The cultures were split and one-half of the B-like and T-like cell cultures were stimulated with 30 ng/ml PMA and 1 µM ionomycin for 24 hr. Monocytic cell lines were stimulated with 1 µg/ml LPS for 24 hr. Early passage HUVEC were grown to 90% confluence, and one-half of the culture was stimulated with 10 ng/ml TNFα, and harvested at 6 or 24 hr. Unstimulated HUVEC were harvested at 24 hr.

Peripheral blood T-cells from two donors were purified as described, above. Cells were added ($1 \times 10^6$ cells/ml) to RPMI 1640 with 10% human serum and 1% GibcoBRL penicillin/streptomycin. Cells were then incubated at 37° C. and 5% $CO_2$ for 72 hr. T75 flasks were coated with 1 µg/ml CD3 Mab G19.4 (described herein) in PBS for 4 hr at 37° C. The flask was washed twice with PBS, and cells were added ($1 \times 10^5$ cells/ml) in RPMI 1640 with 10% human serum and 1% GibcoBRL penicillin/streptomycin. CD28 MAb 9.3 (previously described) was added to a final concentration of 1 µg/ml. Cells were grown at 37° C. and 5% $CO_2$ for 72 hr. Cells were added ($1 \times 10^6$ cells/ml) to RPMI 1640 with 10% human serum and 1% GibcoBRL penicillin/streptomycin. PMA was added to 30 ng/ml and ionomycin was added to 1 µM and incubated at 37° C. and 5% $CO_2$ for 48 hr. Proliferation of stimulated T-cells was confirmed visually. All cell types were pelleted and frozen on dry ice and stored at −70° C. until use.

Total RNA was prepared using the Invitrogen (Carlsbad, Calif.) SNAP total RNA isolation kit (Cat. # K1950-01) according to the manufacturer's instructions. First strand cDNA was produced using the GibcoBRL Superscript First-Strand Synthesis System for RT-PCR (Cat. # 11904-018) according to the manufacturer's instructions for oligo dT priming. PCR was performed using 2 µl first strand cDNA, 5 µl PCR buffer (GibcoBRL), 1.5 µl of 25 mM $MgCl_2$ (GibcoBRL), 1 µl of 10 mM dNTPs (GibcoBRL), 2.5 µl of 10 pMol/µl BSL2-9 primer (5' TGGTGCACAGCTTTGCT 3') (SEQ ID NO:61), 2.5 µl of 10 pMol/µl BSL2-11 primer (5' TCTGGGGGGAATGTCAT 3') (SEQ ID NO:62), 0.5 µl of 5 U/µl GibcoBRL PLATINUM® Taq DNA polymerase (Cat. #10966-018), and 35 µl $dH_2O$. PCR was performed on a PE Biosystems 9700 using the following cycling conditions: 94° C. for 30 sec; followed by 35 cycles of 94° C. for 30 sec, 61° C. for 30 sec, 72° C. for 60 sec; followed by 72° C. for 10 min. Following this, 40 µl of the PCR reaction was run on a 1.2% agarose gel.

PCR analysis indicated that certain cell types contained predominantly the BSL2-4616811 transcript, with or without stimulation. Unstimulated and stimulated PL-LCL cells showed higher levels of the BSL2-4616811 transcript than the than the BSL2-L165-35b transcript (FIG. 8A). Both unstimulated and stimulated HUVEC cells showed higher levels of the BSL2-4616811 transcript than the BSL2-L165-35b transcript (FIG. 8B).

In contrast, other cell types contained predominantly the BSL2-L165-35b transcript, with or without stimulation. Stimulated Raji cells, and unstimulated and stimulated Ramos cells showed higher levels of the BSL2-L165-35b transcript than the BSL2-4616811 transcript (FIG. 8A). Unstimulated and stimulated HL60 cells showed higher levels of the BSL2-L165-35b transcript than the BSL2-4616811 transcript (FIG. 8B).

In addition, certain cell types showed an increase in BSL2-4616811 transcript levels upon activation. Unstimulated PM-LCL cells showed higher levels of the BSL2-4616811 transcript, which increased relative to the BSL2-L165-35b transcript upon stimulation (FIG. 8A). Similarly, unstimulated CE-LCL cells showed higher levels of the BSL2-4616811 transcript, which increased relative to the BSL2-L165-35b transcript upon stimulation (FIG. 8B). Unstimulated Thp1 cells showed equivalent levels of the BSL2-4616811 and the BSL2-L165-35b transcript, however, levels of the BSL2-4616811 transcript increased upon stimulation (FIG. 8B). Unstimulated peripheral blood T cells from donor 079 showed predominantly BSL-L165-35b but shifted to predominantly BSL2-4616811 upon stimulation. Peripheral blood T cells from donor 124 showed a less dramatic shift from BSL2-L165-35b to BSL2-4616811 upon stimulation (FIG. 8C). Unstimulated CEM cells showed higher levels of the BSL2-L165-35b transcript, but levels of the BSL2-4616811 transcript increased upon activation (FIG. 8D).

Other cell types showed an increase in BSL2-L165-35b levels upon activation. Unstimulated HUT78 cells showed higher levels of the BSL2-4616811 transcript, but levels of the BSL2-L165-35b transcript increased upon activation (FIG. 8D). These results, coupled with the conservation of the amino acid sequences in all four Ig folds, the conservation of structurally important amino acid residues in all four Ig folds, and the conservative nature of the amino acid differences between v1c1 and v2c2, support a function for BSL2-4616811 (BSL2vcvc) which is distinct from BSL2-L165-35b and BSL2-L165-21 (BSL2vc).

To rule out the presence of PCR artifacts, the PCR product from HUVEC activated with TNFα for 24 hr was cloned using the Invitrogen Original TA CLONING® Kit (Cat. # K2000-01) according to the manufacturer's directions. The construct was used to transfect bacterial cells, and 25 white colonies were isolated and grown in LB with 100 μg/ml ampicillin. DNA preps were made and sequencing was performed. Of the clones, 10 clones did not contain insert, 3 clones did not produce readable sequence, 3 clones contained BSL2-related sequences with extensive deletions, and the remaining 9 clones produced sequence consistent with BSL2-4616811.

It was noted that no PCR product corresponding to BSL2-4616811 or BSL2-L165-35b was observed in unstimulated Raji cells. To confirm this result, PCR was repeated for unstimulated and unstimulated Raji cells as previously described. Again, no PCR product was detected for the unstimulated Raji cells. Following this, PCR was performed using G3PDH primers with template isolated from unstimulated and stimulated Raji cells. Cycling conditions were identical to those described above, except the annealing temperature was 55° C., and the extension time was 45 sec. Relatively equal amounts of G3PDH product was detected for both unstimulated and stimulated Raji cells. This provided further support for the observation that unstimulated Raji cells do not contain detectable BSL2 transcript.

BSL2-4616811-Ig fusion construct: To construct the BSL2-4616811-Ig plasmid, the BSL2-4616811 extracellular domain was PCR amplified from first strand cDNA (Gibco-BRL Cat. #11904-018). cDNA was prepared from RNA purified from THP1 cells stimulated with 100 ng/ml LPS for 2 hr. RNA was purified using Invitrogen FASTTRACK® 2.0 (Cat. #K1593-02). The PCR reaction included 1 μl cDNA; 5 μl GibcoBRL 10×PCR buffer; 1.5 μl 25 mM $MgCl_2$; 1 μl 10 mM dNTPs (Boehringer-Mannheim); 2.5 μl BSL2-L165:21-Ig-1 primer (10 μM/μl); 2.5 μl BSL2-L165-21-Ig-2 primer (10 pM/μl); 1 μl CLONTECH ADVANTAGE® polymerase (Cat. #8417-1); and 35.5 μl milliQ $H_2O$. The primers contained the following sequence: BSL2-L165-21-Ig-1: 5'gg ggt acc ATG CTG CGT CGG CG 3' (SEQ ID NO:63); BSL2-L165-21-Ig-2: 5'cg gaa ttc TGG GGG GAA TGT CAT AG 3' (SEQ ID NO:64). PCR samples were incubated at 94° C. for 1 min, followed by 35 cycles of incubation at 94° C. for 30 sec, 59° C. for 30 sec, and 72° C. for 45 sec, followed by incubation at 72° C. for 10 min.

Following this, 30 μl of the PCR reaction was run on a 1.2% agarose 0.5×TBE gel. A band of approximately 1100 by was excised and purified using QIAGEN Gel Extraction Kit (Cat. #28704). One microliter of the purified PCR product (L254) was ligated into pCR2.1 using the TA CLONING® kit (Invitrogen; Cat. # K2050-01). Five microliters of the ligation mixture was transfected into MAX-EFFICIENCY® DH5-alpha competent bacteria (GibcoBRL; Cat. #18258-012), and transfected cells were plated onto LB plates containing 100 μg/ml ampicillin and 800 μg X-Gal. White colonies were inoculated into 5 ml LB broth containing 100 μg/ml ampicillin, and grown at 37° C. for 18 hr. Plasmid DNA was purified with QIAGEN spin miniprep kit (Cat. #27106). Plasmid DNA was digested with KpnI and EcoRI. Plasmids containing inserts of about 1300 by were sequenced using Applied Biosystems automated DNA sequencers (ABI 3700 capillary array sequencers). L254-7 was determined to contain wild-type BSL2-4616811 sequence.

The Fc portion of human IgG1 was PCR amplified using 0.001 BSL1-Ig, described previously; 5 μl GibcoBRL PCR buffer; 1.5 μl 25 mM $MgCl_2$; 1 μl 10 mM dNTPs (Boehringer-Mannheim); 2.5 μl Ig-1 primer (10 pM/μl) 2.5 μl BSL1Ig-2 primer (10 pM/μl); 1 μl CLONTECH ADVANTAGE® polymerase; 36 μl $dH_2O$. The primers contained the following sequence: IgG-1: 5'g gaa ttc GAG CCC AAA TCT TGT GAC AA 3' (SEQ ID NO:65); BSL1Ig-2 gc gc tct aga TCA TTT ACC CGG AGA CAG G (SEQ ID NO:66). PCR samples were incubated at 94° C. for 1 min; followed by 25 cycles of incubation at 94° C. for 30 sec, 59° C. for 30 sec, and 72° C. for 30 sec; followed by incubation at 72° C. for 10 min.

Following this, 30 μl of the PCR reaction was run on a 1.2% agarose 0.5×TBE gel. A band of about 700 by was excised and purified using QIAGEN QIAQUICK® gel extraction kit. Two microliters of the purified fragment (L174) was ligated into pCR2.1 using the TA CLONING® kit (Invitrogen). Five microliters of the ligation mixture was transfected into GibcoBRL MAX-EFFICIENCY® DH5-alpha competent bacteria, and transfected cells were plated onto LB plates containing 100 μg/ml ampicillin and 800 μg X-gal. Plates were incubated for 18 hr at 37° C. White colonies were inoculated into 5 ml LB broth containing 100 μg/ml ampicillin and grown at 37° C. for 18 hr. Plasmid DNA was prepared using QIAGEN QIAPREP® spin miniprep kit. Plasmid DNA was digested with EcoRI and run on an agarose gel. Plasmids containing inserts of about 900 by were sequenced. L174-3 was determined to contain wild-type human IgG1 Fc sequence.

L174-3 was digested with EcoRI/XbaI and separated on a 1.2% agarose 0.5×TBE gel. A band of about 750 by was excised and purified using QIAGEN gel extraction kit. Ten microliters of the purified fragment was run on an agarose gel next to a standard to obtain an estimate of the concentration. Approximately 20 ng of the EcoRI/XbaI fragment was ligated (Ligation 200) into 40 ng of EcoRI/XbaI digested pcDNA3.1+ vector (Invitrogen) using GibcoBRL high concentration T4 DNA ligase (5 U/μl) diluted in GibcoBRL T4 DNA ligase buffer. Five microliters of the ligation mixture was transfected into MAX-EFFICIENCY® DH5-alpha competent bacteria (GibcoBRL), and transfected cells were plated onto LB plates containing 100 μg/ml ampicillin. Plates were incubated at 37° C. for 18 hr. Colonies were inoculated into LB broth containing 100 μg/ml ampicillin. Plasmid DNA was purified using QIAGEN spin miniprep kit and sequenced. The L200-1 sequence was determined to be identical to the L174-3 sequence.

The L254-7 BSL2-4146811 construct was digested with KpnI/EcoRI. A band of about 1300 by was excised from a 1.2% agarose 0.5×TBE gel and ligated into the L200-1 Fc construct digested with KpnI/EcoRI. Five microliters of the ligation reaction was transfected into MAX-EFFICIENCY® DH5-alpha cells and plated onto LB plates containing 100 μg/ml ampicillin. Colonies were grown, and plasmid DNA was purified as above. Plasmid DNA was digested with KpnI/XbaI and separated on an agarose gel as above. Plasmids containing a band of about 2 kb were sequenced as above. BSL2-4616811-Ig was determined to contain the wild-type BSL2-4616811 and human IgG1 sequences. The nucleotide and predicted amino acid sequence of BSL2-4616811-Ig is shown in FIGS. 4A and 4B.

BSL2 monoclonal antibodies: The BSL2-4616811-Ig fusion protein was purified by affinity purification as described for BSL3-Ig, below. The purified fusion protein was then used to immunize mice using the protocol described for BSL3-Ig, except that a fourth boost was used. Following this, hybridoma cell lines were constructed and BSL2 MAbs were isolated as described for BSL3, below.

Example 5

Identification of BSL3

Database searches: BSL3 was identified by BLAST and FASTA analysis of the Incyte Genomics sequence databases (Incyte Genomics) utilizing the B7-1 or B7-2 proteins as query sequences, and the parameters described for the BSL2 searches. The sequence database searches identified Incyte Genomics 'gene' 117327 (an Incyte Genomics gene is an EST sequence that is grouped with similar sequences, and considered to represent the product of a single genomic locus). The Incyte Genomics gene 17327 has since been renamed as. Incyte Genomics gene 899898. In a secondary screen, the BLAST and FASTA programs were used to search the Incyte Genomics sequence databases (Incyte Genomics) for sequences related to the mouse AF142780 gene (potential ortholog of the 117327 gene), using the previously described search parameters. These searches identified Incyte Genomics gene 143522.

The 143522 and 117327 genes were then used to identify Incyte Genomics clones 3844031 and 3207811, respectively. The 3844031 clone belongs to Incyte Genomics Library ID No. DENDTNT01, which was originally constructed utilizing poly(A)+ RNA isolated from untreated dendritic cells from peripheral blood. The 3207811 clone belongs to Incyte Genomics Library ID No. PENCNOT03, which was originally constructed utilizing poly(A)+ RNA isolated from corpus cavernosum tissue. The 3844031 and 3207811 clones were obtained from Incyte Genomics, and sequenced (ABI cycle sequencer, PE Biosystems) using the primers shown in Table 4.

TABLE 4

| Clone | Primer | Sequence | SEQ ID NO: |
|---|---|---|---|
| 3844031 | 316.491 | GAAGGCCTCTACCAGGTC | 67 |
| 3844031 | 316.512 | CTTTAGGCGCAGAACACT | 68 |
| 3844031 | 316.203 | AAGGGTCAGCTAATGCTC | 69 |
| 3844031 | 316.379 | TCAGTTTGCACATCTGTA | 70 |
| 3844031 | 316.1538 | TATGCTATCAAGATTCCA | 71 |
| 3844031 | 316.1839 | GTAAAGTGCAGTAGTGCT | 72 |
| 3844031 | 316.1601 | TATGAGCTCACAGACAGG | 73 |
| 3207811 | 315.560 | AGGTTCAGATAGCACTGT | 74 |
| 3207811 | 315.468 | ACTTATCTGAAATTGCTG | 75 |
| 3207811 | 315.493 | TTGATATGCTCATACGTT | 76 |
| 3207811 | 315.1011 | GAATTCTGTGGGTCCAGG | 77 |
| 3207811 | 315.601 | CATGTTTAATGGTGGTTT | 78 |
| 3207811 | 315.498 | AAAGCTGTATTCTTCAAA | 79 |

Full-length cloning of BSL3: To clone the 5' end of BSL3, the SMART™ RACE (rapid amplification of cDNA ends) cDNA Amplification kit (CLONTECH) was used according to the manufacturer's directions. The 5' RACE library was constructed using 1.0 µg of poly(A)+ RNA template obtained from human microvascular endothelial cell treated with TNF-alpha for 1 hr. The 5' RACE reaction, mixture contained 2 µl RACE-ready cDNA, 1×PCR buffer (GibcoBRL), 200 µM dNTP (Boehringer Mannheim), 1.5 mM $MgCl_2$, 1 µl CLONTECH ADVANTAGE® enzyme mix, 1× CLONTECH SMART™ primer, and 25 pMol BSL3 3' specific primer (BSL3-2 5'-GAACACTGGTGACCTGGTAGAG-3') (SEQ ID NO:80) in a total volume of The 5' RACE reaction was performed in a GENEAMP® PCR System 9700 machine (PE Applied Biosystems) using an initial denaturation step of incubation at 94° C. for 1 min, followed by 35 cycles of incubation at 94° C. for 30 sec, 62° C. for 30 sec, 72° C. for 30 sec, followed by incubation at 72° C. for 10 min.

The PCR products were analyzed by gel electrophoresis using a 1.2% agarose gel (GibcoBRL) with 0.5×TBE and 10 µg/ml ethidium bromide (Bio-Rad). An ~875 by fragment was excised from the gel and purified using the QIAGEN QIAQUICK® Gel Extraction kit according to the manufacturers directions. One microliter of the purified fragment was mixed with 2 µl pCR2.1 pTADV cloning vector (CLONTECH), 2 µl ligation cocktail (GibcoBRL), and 4 U T4 DNA ligase (GibcoBRL) in a total volume of 10 µl, and the ligation mixture was incubated at 14 C for 4 hr. Five microliters of the ligation mixture was used to transfect MAX-EFFICIENCY® DH5 alpha *E. coli* cells (GibcoBRL) according to the manufacturers directions, and transfected cells were plated onto LB plates containing 100 µg/ml ampicillin and 30 µg/ml X-gal. White colonies were picked and grown in 5 ml of LB broth containing 100 µg/ml of ampicillin. DNA was purified from the bacteria using the QIAPREP® Spin Miniprep Kit (QIAGEN). Plasmid DNA was digested with EcoRI and analyzed by agarose gel electrophoresis. Plasmid isolates containing an EcoRI fragment of approximately 900 by were retained for sequencing (ABI cycle sequencer, PE Biosystems). The sequence was analyzed by SEQWEB® Gap (Genetics Computer Group).

The 5' RACE library was then used as a template for PCR amplification. The PCR mixture contained 1 µg 5' RACE library template, 1×PCR buffer (GibcoBRL), 200 µM dNTP (Boehringer Mannheim), 1.5 mM $MgCl_2$, 1 µl CLONTECH ADVANTAGE® enzyme mix, 25 pMol forward primer (BSL3-3: 5'-CCGGGGTACCATGATCTTCCTCCT-GCTAATGTTG-3') (SEQ ID NO:81), and 25 pMol reverse primer (BSL3-4: 5'-GCGCTCTAGATCAGATAGCACTGT-TCACTTCCC-3') (SEQ ID NO:82) in a total volume of 50 PCR was performed in a GENEAMP® PCR System 9700 (PE Applied Biosystems): machine using an initial denaturation step of incubation at 94° C. for 1 min, followed by 30 cycles of incubation at 94° C. for 30 sec, 60° C. for 30 sec, 72° C. for 30 sec, and followed by incubation at 72° C. for 10 min.

An ~800 by BSL3 PCR product was obtained. To clone the BSL3 fragment, 1 µl of the PCR product was mixed with 2 µl pCR2.1 cloning vector (Invitrogen), 2 µl ligation buffer (GibcoBRL), 4 U T4 DNA ligase (GibcoBRL), and 4 µl $H_2O$. The ligation mixture was incubated at 14° C. for 4 hr, and 5 µl microliters of the mixture was used to transfect MAX-EFFICIENCY® DH5 alpha *E. coli* cells (GibcoBRL). Transfected cells were plated onto LB agar plates containing 100 µg/ml ampicillin and 30 µg/ml X-gal, and 18 white colonies were isolated and grown in 5 ml of LB broth containing 100 µg/ml of ampicillin. DNA was purified from the bacterial culture using the QIAPREP® Spin Miniprep Kit (QIAGEN) according to the manufacturer's directions. Plasmid DNA was digested with EcoRI and analyzed by agarose gel electrophoresis. Sixteen plasmid isolates contained EcoRI fragment of ~800 bp, and were retained for sequencing (ABI cycle sequencer, PE Biosystems) using the vector-specific M13 and M13 reverse primers (see above).

SEQWEB® Gap (Genetics Computer Group) analysis indicated the optimal alignment of the sequences of the BSL3

Incyte Genomics clones and the BSL3 5' RACE product. SEQWEB® Gap analysis (Genetics Computer Group) also indicated that the BSL3 nucleotide sequence shared less than 55% sequence identity with B7-1, B7-2, or BSL1/B7-H1 nucleotide sequences, while the BSL3 amino acid sequence shared less than 45% sequence identity with the B7-1, B7-2, and BSL1/B7-H1 amino acid sequences.

In addition, the BSL3 C-terminal amino acid sequence shared less than 98% identity to the amino acid sequence encoded by GENBANK®Accession No. AK001872, over a stretch of 174 amino acids. Amino acid sequence alignments using the GCG Gap program indicated that the longest stretch of identical residues shared by BSL3 and AK001872 was 99 contiguous amino acids in length. Nucleotide sequence alignments using GCG Gap indicated that the longest stretch of identical bases shared by BSL3 and AK001872 was 239' contiguous nucleotides in length. Notably, a mouse ortholog of BSL3 was identified from the GENBANK® Database (Accession No. AF142780). The BSL3 N-terminal amino acid sequence shared approximately 70% sequence identity with the amino acid sequence corresponding mouse AF142780, over a stretch of 250 amino acids. In addition, it was noted that BSL3 has also been identified as PD-L2, an apparent inhibitor of T-cell proliferation (Y. Latchman et al. (2001) *Nature Immunology* 2:261-268).

The nucleotide and predicted amino acid sequences of BSL3 are shown in FIGS. 5A and 5B. The plasmid carrying DNA encoding BSL3 (pCR2.1:BSL3) was deposited with the American Type Culture Collection (ATCC, 10801 University Blvd., Manassas, Va. 20110-2209 USA), under ATCC Designation No. PTA-1986, on Jun. 6, 2000.

The BSL1, BSL2, and BSL3 sequence information is summarized in Table 5.

TABLE 5

| BSL NO. | Sequence Name | Nucleic Acid (NA) SEQ ID NO: | NA FIG. NO. | Amino Acid (AA) SEQ ID NO: | AA FIG. NO. |
|---|---|---|---|---|---|
| 1 | BSL1 (TNF-α) | 1 | 1A | 2 | 1B |
| 1 | BSL1 (GM-CSF/IL-4) | 3 | 1C | 2 | 1B |
| 1 | BSL1-Ig | 4 | 2A | 5 | 2B |
| 2 | BSL2-4616811 | 6 | 3A | 7 | 3B |
| 2 | BSL2-L165-21 | 10 | 3C | 11 | 3D |
| 2 | BSL2-L165-35b | 12 | 3E | 13 | 3F |
| 2 | BSL2-4616811-Ig | 8 | 4A | 9 | 4B |
| 3 | BSL3-L143 | 14 | 5A | 15 | 5B |
| 3 | BSL3-L232-6-Ig | 16 | 6A | 17 | 6B |

Example 6

Characterization of BSL3

BSL3 expression analysis: BSL3 expression patterns were determined by northern blot analysis of various cell types, using the BSL3 probe shown in FIG. 7C, and the procedure described for BSL1. A 2.7 kb BSL3 mRNA transcript was detected in several cell types. In particular, high levels of BSL3 mRNA were detected in all HMVEC stimulated with TNF-alpha (FIG. 7D). Moderate levels of BSL3 mRNA were detected in peripheral blood monocytes stimulated with PHA or GM-CSF/IL-4 (FIG. 7D). However, or BSL3 mRNA was not detected in any of the remaining cell types (FIG. 7D).

In addition, multiple tissue northern blots and expression arrays were purchased from CLONTECH Laboratories and hybridized with $P^{32}$-labeled BSL3 probe. Briefly, a 900 by BSL3 fragment (BSL3/KpnI+XbaI) was isolated from clone L168-2 using KpnI and XbaI restriction endonucleases, run on a 1.2% agarose gel, and purified using the QIAGEN Gel Extraction Kit. Approximately 30 ng of BSL3/KpnI+XbaI was radiolabeled (6000 Ci/mmol $P^{32}$-dCTP) using the Random Primed DNA Labeling Kit (Roche, Indianapolis, Ind.). Unincorporated nucleotides were removed using NUC-TRAP® Probe Purification Columns (Stratgene, La Jolla, Calif.). Radiolabeled BSL3/KpnI+XbaI probe was added at a specific activity of $3.0 \times 10^6$ cpm/ml of ExpressHyb hybridization solution (CLONTECH) and incubated overnight at 65° C. Blots were washed with 0.1×SSC/0.1% SDS at 62° C. and exposed to film for 72 hr.

Northern blot analysis indicated that high levels of BSL3 transcript were present in spleen tissue; moderate levels of BSL3 transcript were present in thymus, testis, ovary, and small intestine tissues; and low levels of BSL3 transcript were present in heart, placenta, lung, liver, skeletal muscle, prostate, colon, lymph node, trachea, and adrenal gland tissues, and Burkitt's lymphoma Raji cell line (FIG. 7E). Microarray analysis indicated that high levels of BSL3 transcript were present in spleen tissue; moderate levels of BSL3 transcript were present in lung, liver, placenta, fetal spleen, lymph node, and fetal thymus tissues; and low levels of BSL3 transcript were present in heart, aorta, corpus callosum, left atrium, right atrium, jejunum, thymus, fetal liver, and mammary gland tissues (FIG. 7F).

Quantitative PCR: BSL1 and BSL3 expression patterns were determined by quantitative PCR. Human Multiple Tissue cDNA (MTC™) Panels (Cat. # PT3158-1) were purchased from CLONTECH. For each PCR reaction, 5 μl of cDNA was used. Human and murine BSL1 and BSL3 PCR primers were designed by Primer3 program (Whitehead Institute for Biomedical Research; Steve Rozen, Helen J. Skaletsky, 1998, Primer3) as shown in Table 6.

TABLE 6

| Primer | Sequence | SEQ ID NO: | nucleotides |
|---|---|---|---|
| human BSL1 forward | TACAAGCGAATTACTGTGAA | 83 | 459-479 |
| human BSL1 reverse | GATGTGCCAGAGGTAGTTCT | 84 | 773-793 |
| human BSL3 forward | AATAGAGCATGGCAGCAATG | 85 | 419-439; |
| human BSL3 reverse | GGCGACCCCATAGATGATTA | 86 | 634-654 |
| human 18s rRNA forward | CCAGTAAGTGCGGGTCAT | 87 | 7-25 |
| human 18s rRNA reverse | TTCACCTACGGAAACCTT | 88 | 196-214 |

SYBR® Green PCR Core Reagents (Cat. #4306736) were purchased from PE Applied Biosystem. Real-time PCR was performed on ABI PRISM® 5700 Sequence Detection System PE Applied Biosystem. PCR samples were incubated at 95° C. for 15 sec, 55° C. for 20 sec, and 75° C. for 1 min for 40 cycles. The BSL1 PCR product was 334 bp; the BSL3 PCR product was 235 bp; the 18S rRNA PCR was 207 bp. Following PCR and data collection, dissociation curve studies were performed. In addition, PCR samples were analyzed by agarose gel electrophoresis to confirm the size of the PCR product.

Data processing and presentation: For each PCR reaction, a threshold cycle number ($C_T$) was generated as a read-out by the real-time PCR machine. The data was processed according to the manual of ABI PRISM® 5700 Sequence Detection System. Briefly, the $C_T$ of BSL1 and BSL3 was normalized to the $C_T$ of 18S rRNA in the each sample. The data was then subtracted by the normalized $C_T$ in the sample showing lowest expression levels. For BSL1, lowest expression levels were found in tonsil tissue. For BSL3, the lowest expression levels were found in skeletal muscle. The final data was presented as the fold increase over the lowest expression levels.

Quantitative PCR indicated that high levels of BSL1 transcript were present in lymph node, spleen, lung, and placenta tissue; moderate levels of BSL1 transcript were present in thymus and pancreas tissue; and low levels of BSL1 transcript were present in heart, brain, kidney, adult liver, skeletal muscle, bone marrow, leukocyte, fetal liver, and tonsil tissue (FIG. 7G). For BSL3, high levels of transcript were present in lymph node and spleen tissue; and low levels of BSL3 transcript were present in thymus, lung, tonsil, heart, pancreas, placenta, kidney, bone marrow, fetal liver, and adult liver tissue (FIG. 7H).

BSL3-Ig (L232-6) fusion construct: The BSL3-Ig (L232-6) construct was made using the following procedure. The ECD of BSL3 was amplified by PCR using 0.01 µl pCR2.1: BSL3 (L143-4), described above; 5 GibcoBRL PCR buffer; 1.5 µl 25 mM MgCl$_2$; 1 µl 10 mM dNTPs; 2.5 µl BSL3-3 primer (10 µM/µl); 2.5 µl BSL3Ig-6 primer (10 µM/µl); 1 µl CLONTECH ADVANTAGE® polymerase; 36 µl dH$_2$O. The primers contained the following sequence: BSL3-3: 5'cc gg ggt acc ATG ATC TTC CTC CTG CTA ATG TTG 3' (SEQ ID NO:89); BSL3Ig-6: 5'cg gaa ttc GGT CCT GGG TTC CAT CTG 3' (SEQ ID NO:90). PCR samples were incubated at 94° C. for 1 min; followed by 20 cycles of incubation at 94° C. for 30 sec, 59° C. for 30 sec, and 72° C. for 30 sec; followed by incubation at 72° C. for 10 min.

Following this, 38 µl of the PCR product was digested with KpnI/EcoRI and run on a 1.2% agarose 0.5×TBE gel. A band of about 650 by was excised and purified with QIAGEN gel extraction kit. Ten microliters of the purified fragment was run on an agarose gel next to a size standard. Ten nanograms of fragment was ligated (L232) to 20 ng of KpnI/EcoRI digested L200-1 (described previously). Five microliters of the ligation mixture was transfected into GibcoBRL MAX-EFFICIENCY® DH5 alpha competent bacteria, and transfected cells were plated onto LB plates containing 100 µg/ml ampicillin. Plates were incubated at 37° C. for 18 hr. Colonies were inoculated into 5 ml of LB broth containing 100 µg/ml ampicillin and grown for 18 hr at 37° C. DNA was purified using QIAGEN spin miniprep kit and digested with PmeI. The digested samples were run on an agarose gel and plasmids that contained fragments of about 1500 by were sequenced. L232-6 was determined to have wild-type BSL3 sequence. The nucleotide and predicted amino acid sequence of BSL3-Ig (L232-6) is shown in FIGS. 6A and 6B.

BSL3-Ig (L275-1) fusion construct: The BSL3-Ig (L275-1) construct was made using the following procedure. BSL3-Ig was PCR amplified from L232-6 using 0.001 µl L232-6; 5 µl GibcoBRL PCR buffer; 1.5 µl 25 mM MgCl$_2$; 1 µl 10 mM Boehringer-Mannheim dNTPs; 2.5 µl BSL3-5 primer (10 µM/µl); 2.5 µl BSL1Ig-2 primer (10 µM/µl); 1 µl CLONTECH ADVANTAGE® polymerase; and 35.5 µl dH$_2$O. The primers contained the following sequence: BSL3-5: 5' cg gga ttc ATG ATC TTC CTC CTG CTA ATG TT 3' (SEQ ID NO:91); BSL11 g-2: 5' gc gc tct aga TCA TTT ACC CGG AGA CAG G 3' (SEQ ID NO:92). PCR samples were incubated at 94° C. for 1 min; followed by 20 cycles of incubation at 94° C. for 30 sec, 58° C. for 30 sec, and 72° C. for 1.5 min; followed by incubation at 72° C. for 10 min.

Following this, 2 µl of the PCR reaction was ligated (L262) into pCR2.1 using the TA CLONING® kit (Invitrogen). Five microliters of the ligation was transfected into MAX-EFFICIENCY® DH5 alpha competent cells (GibcoBRL), and transfected cells were plated onto LB plates containing 100 µg/ml ampicillin and 800 µg of X-Gal. Plates were incubated at 37° C. for 18 hr. White colonies were inoculated into 5 ml of LB broth containing 100 µg/ml ampicillin and grown at 37° C. for 18 hr. Plasmid DNA was purified using QIAGEN spin miniprep kit. Plasmid DNA was digested with BamHI/XbaI and analyzed on an agarose gel. Plasmids that contained an approximately 1300 by fragment were sequenced. L262-2 was determined to contain the wild-type BSL3 sequence.

L262-2 was digested with BamHI/XbaI and run on a 1.2% agarose 0.5×TBE gel. An approximately 1300 by fragment was purified using QIAGEN gel extraction kit. Ten nanograms of the purified fragment was ligated into 30 ng of BamHI/XbaI digested pD18 (related to pD16 and pD17 plasmids, described in U.S. Pat. No. 6,051,228). Five microliters of the ligation was transfected into GibcoBRL MAX-EFFICIENCY® DH5 alpha competent bacteria. Transfected cells were plated onto LB plates containing 100 µg/ml ampicillin, and grown at 37° C. for 18 hr. Colonies were inoculated into 5 ml of LB broth containing 100 µg/ml ampicillin and grown at 37° C. for 18 hr. Plasmid DNA was purified using QIAGEN spin miniprep kit. Plasmid DNA was digested with BamHI plus XbaI or HindIII, and the digested samples were analyzed on an agarose gel. As determined by restriction mapping, L275-1 through L275-9 contained the correct construction.

Purification of BSL3-Ig fusion protein: Purification of BSL3-Ig (human-IgG1) was accomplished by one-step affinity purification. Supernatant from transiently transfected COS cells expressing BSL3-Ig was applied to a Sepharose column of immobilized protein A. The column was washed with PBS until the absorbance at 280 nm reached the baseline level. Bound protein was eluted with Immuno Pure IgG Elution Buffer (Pierce Chemical, Rockford, Ill.; Cat. #21004). Fractions containing the bound protein were neutralized with ⅛ v/v of 3 M sodium phosphate, pH 7. The resulting preparation was dialyzed against PBS, filtered (0.2 µm). All buffers contained 0.02% w/v sodium azide.

Immunization with BSL3 polypeptide: For the initial immunization, mice between 1 and 3 months were used (BalbC; Harlan, Indianapolis, Ind.). RIBI adjuvant was prepared as follows. In one vial, 0.5 mg MPL (monophosphoryl lipid A; RIBI Immunochemical Research, Inc., Hamilton, Mont.); 0.5 mg TDM (synthetic trehalose dicorynomycolate; RIBI Immunochemical Research, Inc.); and 40 µl Squalene with 0.2% TWEEN® 80 were mixed together. The mixture was warmed to 40-45° C. for 5-10 min, and 2 ml of BSL3 polypeptide/PBS (125 µg/ml) was added. The solution was vortexed vigorously for several minutes. The solution was drawn into a syringe and injected immediately into the mice.

Dosages followed recommendations by RIBI Immunochemical Research, Inc. For the first injection, approximately 100 μg of BSL3 polypeptide was resuspended in 250 μl of 1×RIBI in PBS. The mixture was injected intraperitoneally with 21 gauge needle. For second and later injections, boosts were given at least 3 weeks apart. Injections were at half dose. At least 3 weeks following the third injection, once the titer reached an acceptable level (see below), the animal was given a final boost. For final injections, approximately 1 mg/ml of BSL3 polypeptide was resuspended in PBS (RIBI was omitted), and the mixture was administered intravenously via tail veins. Animals were harvested 3-4 days later.

To monitor titer levels, sera samples were taken before initial immunization (background) and 7-10 days after each immunization for titer monitoring. Titer levels were measured by ELISA. Sera was harvested by eye-bleed, or tail-bleed. Typically, 200 μl of blood was removed for sera testing.

Hybridoma cell lines: Hybridoma cell lines were constructed using the following reagents: Iscoves Modified Dulbecco's Medium (GibcoBRL; Cat. #12440-053); Fetal Bovine Serum (Hyclone; Cat. # A-1115L, Lot #11152564) heat inactivated for 30 min at 56° C.; L-Glutamine-200 mm, 100× (GibcoBRL; Cat. #25030-081); Penicillin/Streptomycin (GibcoBRL; Cat. #15140-122); ORIGEN Hybridoma Cloning Factor (Igen International, Inc., Gaithersburg, Md.; Cat. # IG50-0615, Lot #8077); HT Supplement 100× (GibcoBRL; Cat. #11067-030); HAT Supplement 100× (GibcoBRL; Cat. #31062-037); PEG 1500, (Boehringer Mannheim; Cat. #783 641); Red Blood Cell Lysing Buffer from Lab Services (Cat. #3KL-449); Trypane Blue; 70% Ethanol; Myeloma Cells (P3x) from ATCC.

The following equipment and supplies were used: laminar flow hood; $CO_2$ incubator; inverted microscope; 37° C. water bath; centrifuge; 96-well flat bottom tissue culture plates (Corning; Cat. #25860-96); Serological pipets and Integrid petri dishes (Falcon); 50 ml centrifuge tubes (Corning; Cat. #430921); 15 ml conical tubes (Falcon; Cat. #2096); autoclaved scissors and forceps; multichannel pipet; wide orifice 200 μl pipet tips (Denville Scientific, Inc., Metuchen, N.J.; Cat. # P1105-CP); sterile pipet tips (VWR, Buffalo Grove, Ill.; Cat. #53508-794).

HAT and HT medium were made as follows:

| HAT Medium | | HT Medium | |
|---|---|---|---|
| IMDM | 500 ml | IMDM | 500 ml |
| L-Glutamine | 2.5 ml | L-Glutamine | 2.5 ml |
| Pen/Strep | 5 ml | Pen/Strep | 5 ml |
| HAT Supplement | 5 ml | HT Supplement | 5 ml |
| Origen Hy. Clon. F. | 10% Final | Origen Hy. Clon. F. | 10% Final |

Mice were given a final boost 3-4 days prior to fusion in PBS intravenously or intraperitoneal. Myeloma cells were kept in exponential growth (log phase). The mice were euthanized, and the spleen from each mouse was aseptically harvested. The spleen was placed in a petri dish containing warm Iscoves solution without FBS. A spleen cell suspension was prepared and transferred to a centrifuge tube. HAT-sensitive myeloma cells were placed in a separate 50 ml centrifuge tube. Spleen cells and myeloma cells were centrifuged at 400×g for 5 min, and the supernatant was aspirated. The red blood cells from the spleen were lysed with 5 ml RBC Lysing Buffer for 1 min, and the tube was filled with SF media (hybridoma serum-free media; GibcoBRL; Cat. #12045-076). Splenocytes were washed with 50 ml SF media, and spleen cells and myeloma cells were centrifuged in separate centrifuge tubes at 400×g for 5 min. Spleen cells and myeloma cells were counted and resuspended in 25 ml with SF media. Myeloma cells were added to spleen cells to give a 1:4 ratio. The mixture was centrifuged at 400×g for 10 min to form a tight pellet, and all media solution was removed by aspiration.

For the cell fusion experiments, PEG, SF media, and HAT media were incubated at 37° C. One ml of 50% PEG was added to the cells for 1 min (PEG was added for 30 sec and cells were stirred for 30 sec). The PEG solution was added to the side of the tube, and the pellet was gently stirred. With stirring, 1 ml of SF media was added to the cells for 1 min, and 8 ml of SF media was added to the cells for 2 min. Cells were centrifuged at 400×g for 10 min, and the supernatant was aspirated. Cells were gently resuspended in 10 ml HAT selective media by aiming pipet directly at pellet and stirring. Additional HAT media was added to bring cell concentration to $5\times10^5$ cells/ml. Cells were aliquotted into 96-well tissue culture plates at $5\times10^4$ cells/well. After 3 days, HT media was added at 100 μl/well. Approximately 10 days later, clones were tested for antibody production. Positive clones were expanded to 1 well of 24-well plate. Positive clones were then re-tested, isotyped, and expanded to T25 (0.25 cm square tissue culture flask).

ELISA analysis: To test for positive clones, ELISA analysis was performed using the following reagents and supplies: carbonate/bicarbonate pH 9.6 (Sigma, St. Louis, Mo.; Cat. # C-3041) for coat; IMMULON® 2 ELISA plates (Dynex, Chantilly, Va.; Cat. # 0110103455); 10×PBS (GibcoBRL) made to 1× concentration; wash buffer comprising TWEEN® 20 (0.05% final concentration) in 1×PBS; block buffer/sample diluent comprising wash buffer with 5% NFM non-fat milk; and chromogen mixture comprising 50% TMB (Kirkegaard & Perry Labs Gaithersburg, Md.; Cat. # 50-76-01) and 50% peroxidase (Kirkegaard & Perry Labs Cat. # 50-65-00).

For ELISA, plates were coated with 75 μl/well (1 μg/ml) BSL3-Ig in carbonate/bicarbonate overnight at 4° C. Plates were washed with PBS TWEEN® 20 (using Skatron), and blocked with 300 μl block buffer for 45 min at room temperature. Plates were flicked dry and incubated with 75 μl/well sera diluted in blocking buffer (sera was diluted 1:50 for highest concentration and then serially diluted by factors of three) for 45 min at room temperature, and washed as before. Plates were then incubated with 75 μl/well anti-mouse IgG in blocking buffer (1:10000 dilution; HRP-labeled; Amersham Pharmacia Biotech, Piscataway, N.J.) for 45 min at room temperature, and washed as before. Following this, plates were incubated with 100 μl/well chromogen mixture, and incubated up to 15 min at room temperature. The signal was quenched with 100 μl 1N sulfuric acid, and samples were read at 450/630 nm. Using ELISA, supernatants from hybridomas were initially screened against BSL3-Ig fusion protein, and then screened against Ig protein alone. Hybridomas that produced antibodies that bound to BSL3-Ig, but not Ig, were designated as positive clones.

Subcloning: Positive clones from the initial fusion plate were expanded. Once growing, cells were put through two rounds of single cell cloning to ensure that they were monoclonal. Each hybridoma was plated in a 96-well tissue culture plate at a concentration of 0.5 cells/well or less. Once macroscopic colonies formed, supernatants were screened by ELISA. Positive clones from each hybridoma were titered by ELISA. The clones giving rise to the strongest signals were expanded and put through a second round of cloning. Positive clonesNO: were again screened by ELISA and titered. The clones giving rise to the strongest signal were expanded and frozen back.

Example 7

Assays Using BSL Monoclonal Antibodies

FACS Analysis of Lung Epithelial Cells Using BSL1 and BSL2 Monoclonal Antibodies: A549, a lung epithelium cell line was cultured in RPMI 1640 (GibcoBRL Cat. #11875-005) plus 10% FBS (Summit, Ft Collins, Colo.; Cat. # S-100-05) and 1% Penicillin-Streptomycin (GibcoBRL Cat. #15140-122) at 37° C. and 5% $CO_2$ to 90% confluence in a T75 flask (Becton Dickinson, Franklin Lakes, N.J.; Cat. #353111). Cells were lifted with VERSENE® (GibcoBRL Cat. #15040-066) and washed twice in RPMI 1640. Cells were added to a 96-well plate (Becton Dickinson Cat. #353077) ($2.5 \times 10^5$ cells per well), and centrifuged at 2000 RPM in a Beckman tabletop centrifuge. Next, cells were resuspended in RPMI 1640 or RPMI1640 with 1 µg negative control antibody (MAb 15E10AA3) or hybridoma supernatant, and incubated on ice for 30 min. Cells were then washed twice in RPMI 1640, and resuspended in goat anti-mouse anti-Fc FITC conjugated antibodies (BioSource, Camarillo Calif.; Cat. # AMI4408) diluted 1:50 in RPMI 1640. Following this, cells were incubated on ice for 30 min, washed twice in RPMI 1640, resuspended in RPMI 1640, and analyzed on a Becton Dickinson FACScan. FACS analysis indicated that BSL1 MAb 32F9A7 (FIG. 9A) and BSL2-4616811 (FIG. 9B) MAbs all bound to the A549 cells.

FACS Analysis of Various Cell Types Using BSL3 Monoclonal Antibodies: To determine whether BSL3 polypeptide was expressed on the surface of various cell types, cells were grown in media as shown in Table 7, below. HUT 78 was supplemented with 20% FBS (Summit Biotechnology, Ft Collins, Colo.; Cat. # S-100-05). All other cell lines were supplemented with 10% Summit FBS. In addition, all cell lines were supplemented with 1% penicillin/streptomycin (GibcoBRL; Cat. #15140-122). All cell lines were grown at 37° C. with 5% $CO_2$.

TABLE 7

| CELL LINE | ORIGIN | MEDIA |
| --- | --- | --- |
| HL60 | pre myeloid | RPMI 1640 |
| THP1 | monocytic | RPMI 1640 |
| A549 | lung epithelium | RPMI 1640 |
| H292 | lung epithelium | RPMI 1640 |
| PM LCL | B lineage | RPMI 1640 |
| PL LCL | B lineage | RPMI 1640 |
| CE LCL | B lineage | RPMI 1640 |
| Ramos | B lineage | RPMI 1640 |
| CEM | T lineage | RPMI 1640 |
| HUT 78 | T lineage | IMDM[1] |
| Jurkat | T lineage | RPMI 1640[2] |

[1]IMDM: GibcoBRL; Cat. # 12440-053
[2]RPMI 1640: GibcoBRL; Cat. # 11875-005

Cells were grown to about $5 \times 10^5$ cells/ml. Cells were washed twice in serum free RPMI 1640 and resuspended to give a final concentration of $2.5 \times 10^6$ cells/ml. Anti-BSL3 MAb 1A4A1 antibodies or isotype control MAb 15E10A3 antibodies were added to 5 µg/ml and incubated at 4° C. for 30 min. Cells were washed twice in serum free RPMI 1640 and resuspended in serum free RPMI 1640 plus 2% goat anti-mouse IgG conjugated to FITC (BioSource, Camarillo, Calif.; Cat. #AMI4408). Cells were incubated 30 min at 4° C. Cells were washed twice in serum free RPMI 1640 and analyzed on a Becton Dickenson FACScan (Becton Dickenson, Franklin Lakes, N.J.). BSL3 polypeptide was expressed on A549 (lung epithelium), H292 (lung epithelium), PM LCL (B lineage), PL LCL (B lineage), CE LCL (B lineage), and HUT78 (T lineage) cells (FIG. 9C).

FACS Analysis of Human Umbilical Vein Endothelial Cells Using BSL3 Monoclonal Antibodies: BSL3 monoclonal antibodies were used to measure BSL3 polypeptide levels on human umbilical vein endothelial cells with or without TNF-alpha stimulation. Human umbilical vein endothelial cells (HUVEC) were grown at 37° C. with 5% $CO_2$ in EGM media (Clonetics, Walkersville, Md.; Cat. # CC-4176) and grown to confluence. TNF-alpha was omitted or added to 10 ng/ml for 24 hr. Cells were lifted with VERSENE® (GibcoBRL; Cat. #15040-066) and prepared for flow cytometry using anti-BSL3 MAb 1A4A1 antibodies as described above. As a control, flow cytometry was performed without antibodies. The results indicated that BSL3 polypeptide levels increased on TNF-alpha stimulated HUVEC (FIG. 9D). This increase was not observed in unstimulated cells (FIG. 9D).

FACS Analysis of Human Peripheral Blood Monocytes using BSL3 Monoclonal Antibodies: BSL3 monoclonal antibodies were used to measure BSL3 polypeptide levels on human peripheral blood monocytes with or without GM-CSF IL-4 or PHA stimulation. Peripheral blood monocytes (PBMCs) were purified as follows. Blood samples were aliquoted equally among twelve 50 ml conical tubes. One volume of elutriation buffer (at room temperature) was added to each of the samples. Samples were underlayed with 10 ml LSM (lymphocyte separation mixture) ficoll solution, and centrifuged at 1800 rpm for 25 min. The upper layer of reddish material was removed and the LSM layer was transferred to a new tube (6 tubes per donor). Most of the PBMCs were observed on top of the LSM layer. Elutriation buffer (50 ml) was added to each tube, and the mixture was centrifuged at 1800 rpm for 8 min. The supernatant was aspirated, and the PBMCs were resuspended in 15 ml elutriation buffer. The mixture was transferred into 2 new 50 ml conical tubes. (45 ml total volume per tube), and centrifuged at 1000 rpm for 8 min. The supernatant was aspirated, and this process was repeated two more times.

PBMCs were resuspended in flasks containing RPMI 1640 with 2% FBS, and incubated at 37° C. with 5% $CO_2$ for one hr. Flasks were rocked once every 20 min. Flasks were washed gently (twice) with media to remove T-cells and B cells. Flasks were then washed vigorously with RPMI 1640 plus 10% FBS and 1% penicillin/streptomycin to obtain monocytes. PBMCs were washed twice in RPMI 1640 with 10% FBS and 1% penicillin/streptomycin. PBMCs were resuspended to $5 \times 10^6$ cells/ml, and transferred to flasks. PBMCs were incubated at 37° C. with 5% $CO_2$ without stimulation for four days. In parallel experiments, PBMCs were incubated with GM-CSF (15 ng/ml) and IL-4 (75 ng/ml) for four days, or PBMCs were incubated with PHA (1 µg/ml) for four days. Flasks were washed vigorously with RPMI 1640 to remove the monocytes. PBMCs were washed twice in RPMI 1640 examined by flow cytometry as described for the various cell lines, above. The results indicated that BSL3 polypeptide levels increased on GM-CSF IL4 or PHA stimulated cells (FIGS. 9E-9F). This increase was not observed in unstimulated cells (FIGS. 9E-9F).

Peripheral Blood T Cell Costimulation: 96-well plates (Becton Dickinson Cat. #353072) were coated with the indicated amount of anti-CD3 MAb G19.4 (described previously) in PBS (GibcoBRL Cat. #14190-144). Plates were incubated at 4° C. for 16 hr. Plates were washed twice in PBS. The following proteins were added: BSL2-4616811-Ig (20 µg/ml), BSL3-Ig (15 µg/ml), or Chi L6 (10 µg/ml) in PBS. Chi L6 is a protein fragment that comprises the Fc portion of human IgG, and is identical to the Fc portion used in the BSL fusion proteins, described above. Different concentrations of protein were used to give equivalent molarity. Plates were incubated at 37° C. for 4 hr. Plates were washed twice in PBS. Peripheral blood T-cells were purified as described, above. Cells were added ($5\times10^4$ cells per well) in RPMI with 10% human serum (Sigma Cat. # H-4522) and 1% penicillin/streptomycin. Cells were incubated at 37° C. and 5% $CO_2$ for 72 hr. During the last 8 hr, cells were incubated with an additional 50 µl of media containing 50 µl Ci/ml $^3$H-thymidine (NEN Cat. # NET-027). Cells were harvested on a Brandel cell harvester (Brandel, Gaithersburg, Md.) using Packard GF/C plates (Packard, Meriden, Conn.; Cat. #6005174), and the plates were air-dried overnight. After this, 50 µl Microscint 20 (Packard Cat. #6013621) was added, and the radiolabel was counted on a Packard Topcount NXT.

Blockade of Peripheral Blood T Cell Costimulation Using BSL2 and BSL3 Monoclonal Antibodies: 96-well plates (Becton Dickinson Cat. #353072) were coated with 20 µg/ml CD3 MAb G19.4 (previously described) in PBS (GibcoBRL Cat. #14190-144). Plates were incubated at 4° C. for 16 hr. Plates were washed twice in PBS. The following proteins were added: BSL2-4616811-Ig (20 µg/ml), BSL3-Ig (15 µg/ml), or (10 µg/ml) L6-Ig in PBS. Different concentrations of protein were used to give equivalent molarity. Plates were incubated at 37° C. for 4 hr. Plates were washed twice in PBS. Peripheral blood T-cells were purified as described, above. Cells were added ($5\times10^4$ cells per well) in RPMI with 10% human serum (Sigma Cat. # H-4522) and 1% GibcoBRL penicillin/streptomycin. Purified BSL2 or BSL3 MAbs or control isotype MAbs were added to a final concentration of 20 µg/ml. To assay co-stimulation, MAbs were omitted. Plates were incubated at 37° C. and 5% $CO_2$ for 72 hr. During the last eight hours, cells were incubated in an additional 50 µl of media with 50 µCi/ml $^3$H-thymidine (NEN Cat. # NET-027). The cells were harvested on a Brandel cell harvester using Packard GF/C plates (Cat. #6005174) the plates were air-dried overnight. Following this, 50 µl Microscint 20 (Packard Cat. #6013621) was added, and the radiolabel was counted on a Packard Topcount NXT.

The results indicated that BSL2-4616811-Ig and BSL3-Ig fusion proteins acted as co-stimulatory molecules for peripheral blood T-cells incubated with CD3 MAb G19.4 (FIGS. 10A-10F). This was confirmed with three separate peripheral blood T-cells donors: donor 010 (FIG. 10A); donor 127 (FIG. 10B); donor 078 (FIGS. 10C-10D); and donor 124 (FIGS. 10E-10F). The results further indicated that BSL2 and BSL3 MAbs blocked the co-stimulatory effect of the BSL2-4616811-Ig and BSL3-Ig fusion proteins, respectively (FIGS. 10G-10J). This was confirmed with two separate peripheral blood T-cells donors: donor 010 (FIGS. 10G-10H); and donor 127 (FIGS. 10I-10J).

As various changes can be made in the above compositions and methods without departing from the scope and spirit of the invention, it is intended that all subject matter contained in the above description, shown in the accompanying drawings, or defined in the appended claims be interpreted as illustrative, and not in a limiting sense.

The contents of all patents, patent applications, published articles, books, reference manuals, texts and abstracts cited herein are hereby incorporated by reference in their entirety to more fully describe the state of the art to which the present invention pertains.

What is claimed is:

1. An isolated polypeptide sequence comprising a sequence selected from the group consisting of:

(a) an isolated polypeptide sequence comprising amino acids 1 to 273 of SEQ ID NO:15; and (b) an isolated polypeptide sequence comprising amino acids 2 to 273 of SEQ ID NO:15.

2. The isolated polypeptide sequence of claim 1, wherein said polypeptide is (a).

3. The isolated polypeptide of claim 1, wherein said polypeptide is (b).

4. An isolated polypeptide sequence encoded by the cDNA clone contained in plasmid BSL3 in ATCC Deposit No. PTA-1986.

5. An isolated polypeptide produced by a method comprising:

(a) culturing an isolated recombinant host cell comprising a vector that comprises the coding region encoding the polypeptide of claim 1 under conditions such that said polypeptide is expressed; and (b) recovering said polypeptide.

6. The isolated polypeptide of claim 1 wherein said polypeptide further comprises a heterologous polypeptide.

7. The isolated polypeptide of claim 6 wherein said heterologous polypeptide is the Fc domain of human IgG.

8. An isolated polypeptide comprising a sequence selected from the group consisting of:
   (a) an isolated polypeptide sequence comprising amino acids 1 to 219 of SEQ ID NO:15;
   (b) an isolated polypeptide sequence comprising amino acids 2 to 219 of SEQ ID NO:15;
   (c) an isolated polypeptide sequence comprising amino acids 1 to 217 of SEQ ID NO:15; and
   (d) an isolated polypeptide sequence comprising amino acids 2 to 217 of SEQ ID NO:15.

9. The isolated polypeptide of claim 8, wherein said polypeptide is (a).

10. The isolated polypeptide of claim 8, wherein said polypeptide is (b).

11. The isolated polypeptide of claim 8, wherein said polypeptide is (c).

12. The isolated polypeptide of claim 8, wherein said polypeptide is (d).

13. An isolated polypeptide according to claim 8 further comprising the Fc domain of human IgG.

14. The isolated polypeptide according to claim 13, wherein said polypeptide is SEQ ID NO:16.

15. The isolated polypeptide according to claim 1, wherein said polypeptide contains one amino acid substitution.

16. The isolated polypeptide according to claim 8, wherein said polypeptide contains one amino acid substitution.

* * * * *

UNITED STATES PATENT AND TRADEMARK OFFICE
CERTIFICATE OF CORRECTION

PATENT NO. : 7,723,479 B2 Page 1 of 1
APPLICATION NO. : 11/900026
DATED : May 25, 2010
INVENTOR(S) : Glen Mikesell, Robert Peach and Han Chang It is certified that error appears in the above-identified patent and that said Letters Patent is hereby corrected as shown below:

Title Page item (75) Inventors:

Delete "Joshua N. Finger, Guchen Yang, Henry Shen"

Title Page Related U.S. Application Data

Item (62)

Delete "10/944,824"

Add "10/994,824"

Signed and Sealed this

Thirty-first Day of August, 2010

David J. Kappos
*Director of the United States Patent and Trademark Office*